United States Patent
Lee et al.

(10) Patent No.: US 12,421,556 B2
(45) Date of Patent: Sep. 23, 2025

(54) MATERIALS AND METHODS FOR STRATIFYING AND TREATING CANCERS

(71) Applicants: The Institute of Cancer Research:Royal Cancer Hospital, London (GB); The Royal Marsden NHS Foundation Trust, London (GB)

(72) Inventors: Alex Lee, London (GB); Paul Huang, London (GB); Maggie Cheang, London (GB); Robin Jones, London (GB)

(73) Assignees: The Institute of Cancer Research: Royal Cancer Hospital, London (GB); The Royal Marsden NHS Foundation Trust, London (GB)

( * ) Notice: Subject to any disclaimer, the term of this patent is extended or adjusted under 35 U.S.C. 154(b) by 145 days.

(21) Appl. No.: 16/637,975

(22) PCT Filed: Aug. 10, 2018

(86) PCT No.: PCT/EP2018/071758
§ 371 (c)(1),
(2) Date: Feb. 10, 2020

(87) PCT Pub. No.: WO2019/030379
PCT Pub. Date: Feb. 14, 2019

(65) Prior Publication Data
US 2021/0010085 A1    Jan. 14, 2021

(30) Foreign Application Priority Data

Aug. 10, 2017 (GB) ...................................... 1712871
May 31, 2018 (GB) ...................................... 1808941

(51) Int. Cl.
| | | |
|---|---|---|
| C12Q 1/6886 | (2018.01) | |
| A61K 31/506 | (2006.01) | |
| A61P 35/00 | (2006.01) | |
| C07K 16/28 | (2006.01) | |
| G06F 18/2413 | (2023.01) | |
| G16B 25/00 | (2019.01) | |
| G16B 40/00 | (2019.01) | |
| G16H 20/00 | (2018.01) | |

(52) U.S. Cl.
CPC .......... *C12Q 1/6886* (2013.01); *A61K 31/506* (2013.01); *A61P 35/00* (2018.01); *C07K 16/2863* (2013.01); *G06F 18/24137* (2023.01); *G16B 25/00* (2019.02); *G16B 40/00* (2019.02); *G16H 20/00* (2018.01); *C07K 2317/21* (2013.01); *C12Q 2600/106* (2013.01); *C12Q 2600/158* (2013.01)

(58) Field of Classification Search
CPC .......... C12Q 1/6886; C12Q 2600/106; C12Q 2600/158; A61K 31/506; A61P 35/00; C07K 16/2863; C07K 2317/21; G06F 18/24137; G16B 25/00; G16B 40/00; G16H 20/00
See application file for complete search history.

(56) References Cited

U.S. PATENT DOCUMENTS

| | | |
|---|---|---|
| 2011/0091524 A1 | 4/2011 | Wang et al. |
| 2015/0252435 A1 | 9/2015 | Chou et al. |
| 2015/0267259 A1 | 9/2015 | Kuznetsov et al. |

FOREIGN PATENT DOCUMENTS

| | | |
|---|---|---|
| WO | 2006/110581 A2 | 10/2006 |
| WO | 2007/109571 A2 | 9/2007 |
| WO | 2009/012140 A2 | 1/2009 |
| WO | 2013/075059 A1 | 5/2013 |
| WO | 2014/144121 A2 | 9/2014 |
| WO | 2014/144121 A9 | 9/2014 |
| WO | 2015/148904 A1 | 10/2015 |
| WO | 2017/085326 A1 | 5/2017 |

OTHER PUBLICATIONS

Harbig et al (Nucleic Acids Research, 2005, 33(3): 1-9.*
Pénzváltó et al. Identifying Resistance Mechanisms against Five Tyrosine Kinase Inhibitors Targeting the ERBB/RAS Pathway in 45 Cancer Cell Lines. PloS One 2013, vol. 8, issue 3, e59503, pp. 1-11 (Year: 2013).*
Teicher et al. Sarcoma Cell Line Screen of Oncology Drugs and Investigational Agents Identifies Paterns Associated with gene and microRNA Expression. Mol Cancer Ther 2015, 14(11), pp. 2452-2462 (Year: 2015).*
Chibon et al. Cancer gene expression signatures—The rise and fall? European Journal of Cancer 2013, 49, pp. 2000-2009 (Year: 2013).*
Takahashi et al. Analysis of Gene Expression Profiles of Soft Tissue Sarcoma Using a Combination of Knowledge-Based Filtering with Integration of Multiple Statistics. PloS One 2014, vol. 9, Issue 9, e106801, pp. 1-13 (Year: 2014).*
Yoon et al. Efficacy of Sunitinib and Radiotherapy in genetically engineered mouse model of soft tissue sarcoma. Int. J. Radiation Oncology Biol. Phys. 2009, vol. 74, No. 4, pp. 1207-1216 (Year: 2009).*
Shibasaki et al. Role of IL13RA2 in Sunitinib Resistance in Clear Cell Renal Cell Carcinoma. PLOS One 2015, 10(6): e0130980, pp. 1-20 (Year: 2015).*
Uramoto H. Which biomarker predicts benefit from EGFR-TKI treatment for patients with lung cancer? British Journal of Cancer 96:857-863. (Year: 2007).*

(Continued)

Primary Examiner — Olivia M. Wise
Assistant Examiner — Robert J. Kallal
(74) Attorney, Agent, or Firm — Howson & Howson, LLP; Kathleen D. Rigaut; Richard F. Kane

(57) ABSTRACT

Materials and methods for stratifying and treating cancers and to methods of identifying/selecting patients for treatment of cancer with tyrosine kinase inhibitors are disclosed. Gene expression profiles, TP53 mutations and FGFR1 and PDGFRA expression used to identify/select/stratify the cancers and patients are also disclosed.

16 Claims, 28 Drawing Sheets

Specification includes a Sequence Listing.

(56) References Cited

OTHER PUBLICATIONS

Davicioni E. Diagnostic and prognostic sarcoma signatures. Molecular Diagnosis and Therapy 12(6): 359-374. (Year: 2008).*
Dancsok AR. Advances in sarcoma diagnostics and treatment. Oncotarget 8(4): 7068-7093. (Year: 2017).*
Baird K. Gene expression profiling of human sarcomas: insights into sarcoma biology. Cancer Research 65(20: 9226-9235. (Year: 2005).*
International Search Report and Written Opinion, dated Oct. 18, 2018, issued in corresponding International Application No. PCT/EP2018/071758.
Cha, Kihoon et al., "Discovering gene expression signatures responding to tyrosine kinase inhibitor treatment in chronic myeloid leukemia," BMC Medical Genomics, vol. 9, No. S1, Aug. 2016, pp. 51-97.
Kim, T-M et al., "Gene expression signatures associated with the in vitro resistance to two tyrosine kinase inhibitors, nilotinib and imatinib," Blood Cancer Journal, vol. 1, No. 8, Aug. 2011, e32, pp. 1-9.
ThermoFisher Scientific. "Affymetrix Genechip bHuman Genome U133 plus 2.0 Array," GEO, 2002.
Sleijfer, S. et al., "Cytokine and angiogenic factors associated with efficacy and toxicity of pazopanib in advanced soft-tissue sarcoma: an EORTC-STBSG study," British Journal of Cancer, vol. 107, No. 4, Jul. 2012, pp. 639-645.
Patents Act 1977: Search Report under Section 17(5), dated May 11, 2018, issued in corresponding British Patent Application No. GB1712871.1.
Reiter, Andreas et al., "Tyrosine Kinases as Therapeutic Targets in BCR-ABL Negative Chronic Myeloproliferative Disorders," Current Drug Targets, vol. 8, No. 2, 2007, pp. 205-216.
Notice of Reasons for Rejection, mailed Aug. 16, 2022, issued in corresponding Japanese Patent Application No. 2020-529821.
Tran, Hai T. et al., "Prognostic or predictive plasma cytokines and angiogenic factors for patients treated with pazopanib for metastatic renal-cell cancer: a retrospective analysis of phase 2 and phase 3 trials," The Lancet: Oncology, vol. 13, No. 8, Aug. 2012, pp. 827-837.
Vincenzi, Bruno et al., "Olaratumab: PDGFR-α inhibition as a novel tool in the treatment of advanced soft tissue sarcomas," Critical Reviews in Oncology/Hemotology, vol. 118, Oct. 2017, pp. 1-6.
Eckstein, Niels et al., "Clinical pharmacology of tyrosine kinase inhibitors becoming generic drugs: the regulatory perspective, Journal of Experimental & Clinical Cancer Research," vol. 33, No. 1, Feb. 2014, 15.
Ayers, Mark et al., "IFN-γ-related mRNA profile predicts clinical response to PD-1 blockade," The Journal of Clinical Investigation, vol. 127, No. 8, Aug. 2017, pp. 2930-2940.
Balko, Justin M. et al., "Gene expression patterns that predict sensitivity to epidermal growth factor receptor tyrosine kinase inhibitors in lung cancer cell lines and human lung tumors," BMC Genomics, vol. 7, Nov. 2006, 289.
Kitagawa, Daisuke et al., "Activity-based kinase profiling of approved tyrosine kinase inhibitors," Genes to Cells, vol. 18, No. 2, Feb. 2013, pp. 110-122.
Ku, Xin et al., "New Affinity Probe Targeting VEGF Receptors for Kinase Inhibitor Selectivity Profiling by Chemical Proteomics," Journal of Proteome Research, vol. 13, No. 5, May 2014, pp. 2445-2452.
Kumar, Rakesh et al., "Pharmacokinetic-pharmacodynamic correlation from mouse to human with pazopanib, a multikinase angiogenesis inhibitor with potent antitumor and antiangiogenic activity," Molecular Cancer Therapeutics, vol. 6, No. 7, Jul. 2007, pp. 2012-2021.
Noujaim, J. et al., "Phosphoproteomics in translational research: a sarcoma perspective," Annals of Oncology, vol. 27, Jan. 2016, pp. 787-794.

Podar, Klaus et al., "The small-molecule VEGF receptor inhibitor pazopanib (GW786034B) targets both tumor and endothelial cells in multiple myeloma," PNAS, vol. 103, No. 51, Dec. 2006, pp. 19478-19483.
Delea, T. E. et al., "Cost-effectiveness of pazopanib in advanced soft-tissue sarcoma in Canada," Current Oncology, vol. 21, No. 6, Dec. 2014, pp. e748-e759.
Amdahl, Jordan et al., "Cost-Effectiveness of Pazopanib in Advanced Soft Tissue Sarcoma in the United Kingdom," Sarcoma, vol. 2014, Jun. 2014, 481071, pp. 1-14.
Kasper, B. et al., Long-term responders and survivors on pazopanib for advanced soft tissue sarcomas: subanalysis of two European Organisation for Research and Treatment of Cancer (EORTC) clinical trials 62043 and 62072, Annals of Oncology, vol. 25, No. 3, Mar. 2014, pp. 719-724.
Sleijfer, Stefan et al., "Pazopanib, a Multikinase Angiogenesis Inhibitor, in Patients With Relapsed or Refractory Advanced Soft Tissue Sarcoma: A Phase II Study From the European Organisation for Research and Treatment of Cancer—Soft Tissue and Bone Sarcoma Group (EORTC Study 62043)," Journal of Clinical Oncology, vol. 27, No. 19, Jul. 2009, pp. 3126-3132.
Stacchiotti, S. et al., "Preclinical and clinical evidence of activity of pazopanib in solitary fibrous tumour," European Journal of Cancer, vol. 50, No. Nov. 17, 2014, pp. 3021-3028.
Maruzzo, M. et al., "Pazopanibas first line treatment forsolitary fibrous tumours: the Royal Marsden Hospital experience," Clinical Sarcoma Research, (Feb. 2015) 5:5.
Kollar, A. et al., "Pazopanib in advanced vascular sarcomas: an EORTC Soft Tissue and Bone Sarcoma Group (STBSG) retrospective analysis," Acta Oncologica,(Sep. 2016) 56:1, 88-92.
Lipplaa, A. et al., "Efficacy of panzopanib and sunitinib in advanced axial chordoma: a single reference centre case series," Clin Sarcoma Res (Nov. 2016) 6:19.
Nakamura, T. et al., "The clinical outcome of pazopanib treatment in Japanese patients with relapsed soft tissue sarcoma: A Japan Musculoskeletal Oncology Group (JMOG) study," Cancer, (Apr. 2016) 122: 1408-1416.
Chibon, F. et al., "Validated prediction of clinical outcome in sarcomas and multiple types of cancer on the basis of a gene expression signature related to genome complexity," Nat Med (Jun. 2010) 16, 781-787.
Guo, X. et al., "Clinically Relevant Molecular Subtypes in Leiomyosarcoma," Clin Cancer Res, (Aug. 2015), 21(15).
Koehler, K. et al., "TP53 mutational status is predictive of pazopanib response in advanced sarcomas," Annals of Oncology, (Dec. 2015) 27: 539-543.
Fu, S. et al., "Phase I study of pazopanib and vorinostat: a therapeutic approach for inhibiting mutant p53-mediated angiogenesis and facilitating mutatnt p53 degradation," Annals of Oncology, (Feb. 2015), 26: 1012-1018.
Wong. J. et al.,"Dual Targeting of PDGFRalpha and FGFR1 Displays Synergistic Efficacy in Malignant Rhabdoid Tumors," Cell Reports, (Oct. 2016) 17, 1265-1275.
Altman, D. et al., "Reporting Recommendations for Tumor Marker Prognostic Studies (REMARK): Explanation and Elaboration," BMC Med. (May 2012) PLoS Med 9(5): e1001216.
Tusher, V. et al., "Significance analysis of micorarrays applied to the ionizing radiation response," PNAS, (Apr. 2001), vol. 98, No. 9.
Tibshirani, R. et al., "Diagnosis of multiple cancer types by shrunken centroids of gene expression," PNAS, (May 2002), vol. 99, No., 10, pp. 6567-6572.
Parker, J. et al., "Supervised Risk Predictor of Breast Cancer Based on Intrinsic Subtypes," J Clin Oncol (Feb. 2009), 27: 1160-1167.
Velghe, A. et al., "PDGFRA alterations in cancer: characterization of a gain-of-function V536E transmembrane mutant as well as loss-of-function and passenger mutations," Oncogene (Jun. 2013) 33, 2568-2576.
Corless, C. et al.,"PDGFRA Mutations in Gastrointestinal Stromal Tumors: Frequency, Spectrum and In Vitro Sensitivity to Imatinib," J Clin Oncol, (Sep. 2005) 23:5357-5364.
Ahmad, I. et al., "Mechanisms of FGFR-mediated carcinogenesis," Biochimica et Biophysica Acta1823 (Jan. 2012) 850-860.

(56) References Cited

OTHER PUBLICATIONS

Muller, P. et al., "Mutant p53 in Cancer: New Functions and Therapeutic Opportunities," Cancer Cell 25 (Mar. 2014).
Segal, N. et al., "Classification and Subtype Prediction of Adult Soft Tissue Sarcoma by Functional Genomics," AJP (Aug. 2003), vol. 163, No. 2.
Henderson, S. et al., "A molecular map of mesenchymal tumors," Genome Biology, (Aug. 2005), 6:R76.
Nielsen, T. et al., "Molecular characterisation of soft tissue tumours: a gene expression study," Lancet (Apr. 2002), 359:1301-07.
Van der Graaf, W. et al., "Pazopanib for metastatic soft-tissue sarcoma (PALETTE): a randomised, double-blind, placebo-controlled phase 3 trial," Lancet, (May 2012), 379: 1879-86.
Yoo, K. et al., "Efficacy of pazopanb monotherapy in patients who had been heavily pretreated for metastatic soft issue sarcoma: a retrospective case series," BMC Cancer (Mar. 2015) 15:154.
Ray-Coquard, I. et al., "Treatment patterns and survival in an exhaustive French cohort of pazopanib-eligible patients with metastatic soft tissue sarcoma (STS)," BMC Cancer (Feb. 2017) 17:111.
Linch, M. et al., "Systemic treatment of soft-tissue sarcoma—gold standard and novel therapies," Nat. Rev. Clin. Oncol. 11, 187-202 (Mar. 2014).
Lee, A. et al., "Phase III Soft Tissue Sarcoma Trials: Success or Failure?," Curr. Treat. Options in Oncol. (Mar. 2017) 18:19.
Tap, W. et al., "Olaratumab and doxorubicin versus doxorubicin alone for treatment of soft-tissue sarcoma: an open-label phase 1b and randomised phase 2 trial," Lancet (Jun. 2016); 388: 488-97.
Mir, O. et al., "Safety and efficacy of regoafenib in patients with advanced soft tissue sarcoma (REGOSARC): a randomised, double-blind, placebo-controlled, phase 2 trial," Lancet Oncol (Oct. 2016); 17: 1732-42.
Ho, T. et al.,"The impact of FGFR1 and FRS2alpha expression on sorafenib treatment in metastatic renal cell carcinoma," BMC Cancer (Apr. 2015)15: 304.
Mohindra, Nisha et al., "Targeted therapy and promising novel agents for the treatment of advanced soft tissue sarcomas," Expert Opinion on Investigational Drugs, vol. 24, No. 11, Aug. 8, 2015, pp. 1409-1418.

* cited by examiner

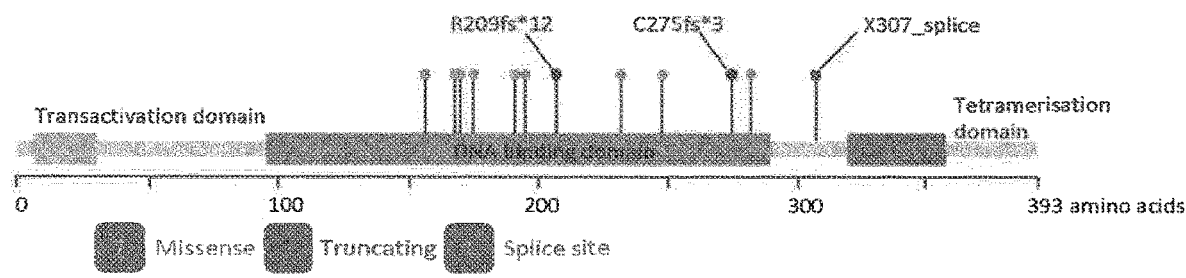

| Case ref. | Sub-type | Mutation type | Genomic change | Protein Change |
|---|---|---|---|---|
| PZP022 | Leiomyosarcoma | Missense | g.12457G>T | V157F |
| PZP015 | Solitary fibrous tumour | Missense | g.12491A>G | H168R |
| PZP060 | Leiomyosarcoma | Missense | g.12497G>A<br>g.12640G>A<br>g.12653A>G | T170M<br>P193S<br>I195T |
| PZP035 | Uterine Leiomyosarcoma | Missense | g.12512G>A | R175H |
| PZP028 | Spindle cell sarcoma | Missense | g.13331A>T | I232F |
| PZP003 | Uterine Leiomyosarcoma | Missense | g.13379C>T | R248W |
| PZP004 | Solitary fibrous tumour | Missense | g.13824C>T | R282W |
| PZP019 | Undifferentiated pleomorphic sarcoma | Splice donor site | g.13900G>T | X307_splice |
| PZP006 | Undifferentiated pleomorphic sarcoma | Inversion | g.13801_14073inv | C275fs*3 |
| PZP030 | Solitary fibrous tumour | Frameshift | g.12695_12696delGA | R209fs*12 |

Figure 8

| B | Assigned Subgroup A or C | Assigned Subgroup B | Total |
|---|---|---|---|
| LMS subtype I | 8 | 23 | 31 |
| LMS subtype II | 32 | 6 | 38 |
| Total | 40 | 29 | 69 |

| C | Assigned Subgroup A or C | Assigned Subgroup B | Total |
|---|---|---|---|
| LMS subtype I | 8 | 23 | 31 |
| LMS subtype III | 19 | 7 | 26 |
| Total | 27 | 30 | 57 |

SEQUENCE LISTING

<160> NUMBER OF SEQ ID NOS: 242

<210> SEQ ID NO 1
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 1
tgttgccaaa ctttgtcgca tgcataatgt atgatggagg cttggatggg aatatgctga    60
ttttgttctg cacttaaagg cttctcctcc tggagggctg                          100

<210> SEQ ID NO 2
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 2
cgaattctct ggtggttgag atcccgccat ttcggaatca gaggataacc agcccgttc     60 acgtcagttt ctacgtctgc aacgggaaga gaaagcgaag                          100

<210> SEQ ID NO 3
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 3
ccgtgccggc cacctgtgtg atcgcctgct acttttacga acgcctcaac atggattact    60
ggaagatcct ggcggcgcag cacaagtgca aaatgaacaa                          100

<210> SEQ ID NO 4
<211> LENGTH: 100
<212> TYPE: DNA
<213> ORGANISM: Artificial Sequence
<220> FEATURE:

```
<223> OTHER INFORMATION: Sarcoma centroid target sequence

<400> SEQUENCE: 4
gaggaggaat tctttccccg cctaacattt caagggacac aattcactcc aagtctcttc    60
cctttccaag ccgcttccga agtgctcccg gtgcccgcaa                         100

<210> SEQ ID NO 5
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 5
cctgcccgcg ctcaagacca tcgtcatcct gaccctgcgc aaggtggcgg gtgatgagct    60
gactgggctt tgctacgtgg ccagcacgga tgcagcagcg                         100

<210> SEQ ID NO 6
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 6
cagtgaagct gggtgcggtg gtgcactcct gtaaccctgg gactttggga agctgaggca    60
ggaagattga gcctaggagt tcgagactga cctgggcagc                         100

<210> SEQ ID NO 7
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 7
ttgaacactt cctctccaaa atgccagagg cggaggagaa caaacagatc atccgcaaac    60
acgcgcagac cttcgttgcc ctctgtgcca cagatgtgaa                         100

<210> SEQ ID NO 8
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 8
agccaggaac agaaacggct actgatggat ttggatattt ccatgaggac ggtggactgt    60
ccattcactg tcacctttta tggcgcactg tttcgggagg                         100

<210> SEQ ID NO 9
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 9
ggggagcagg gctcactcca gccacctgaa gtccaaaaag ggtcagtcta cctcccgcca    60
taaaaaactc atgttcaaga cagaagggcc tgactcagac                         100
```

```
<210> SEQ ID NO 10
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 10
ctgtctatct gggtctgcta acagactggg gtcaacgttt gcactatgac cttcagaaag    60
gcatttgggt tggaactgag tcccaagatg tgccctggga                        100

<210> SEQ ID NO 11
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 11
ccagcgtcct ttacttctcc tggcaccgct atgagcatgg gcgcttctgg cctttcctgc    60
gagagtcaga tgcagacgca gtggggcggg gacagggcct                        100

<210> SEQ ID NO 12
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 12
ttgaaaatcg gcccaagaag gagcaggttc tggaactgga gcgggagaat gaaatgctga    60
agaccaaaaa ccaggagctg cagtccatca tccaggccgg                        100

<210> SEQ ID NO 13
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 13
aagagttacc tcctccatct tactctgccc tatttgaaag tctcagggga gaaaagggaa    60
caagatgctg atccaacctg agtggagtca ggtgaggcat                        100

<210> SEQ ID NO 14
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 14
gcaccgtagc atgcagatgt caaggcagtt aggaagtaaa tggtgtcttg tagatatgtg    60
caaggtagca tgatgagcaa cttgagtttg ttgccactga                        100

<210> SEQ ID NO 15
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 15
```

```
cctccgtggg acattagaat caaatttcaa aaggcttctg tgagcagatg tacccttat      60 tggagagatg agggactggt actgcttaat cgactcagat                          100
```

<210> SEQ ID NO 16
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 16

```
aattgaagat ctagaactga aggaaagaga acttgatcag cagaagttgt ggctacagca    60
aagcatcaaa aatgtgatgg acgattccat taataataga                          100
```

<210> SEQ ID NO 17
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 17

```
ttccgaaaac caggccttat ctccaagacc agagatagtg gggagacttc ttggcttggt    60
gaggaaaagc ggacatcagc tggtcaaaca aactctctga                          100
```

<210> SEQ ID NO 18
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 18

```
ctccaagagg agcacacttt ggggagatgt cctggtttcc tgcctccatt tctctgggac    60
cgatgcagta tcagcagctc ttttccagat caaagaactc                          100
```

<210> SEQ ID NO 19
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 19

```
acagagaaaa gagagactta ttctggttgt tgctaataat gttaacctgc tatttatatt    60
ccagtgccct tcgcatggcg aagcaggggg gaaaagttat                          100
```

<210> SEQ ID NO 20
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 20

```
aatctccttc tctcggatca ttgtgatgga tgctggaacc tcagggtatg gagctcacat    60
cagttcatca tggtgggtgt tagagaattc ggtgacatgc                          100
```

<210> SEQ ID NO 21
<211> LENGTH: 100
<212> TYPE: DNA
<213> ORGANISM: Artificial Sequence

```
<220> FEATURE:
<223> OTHER INFORMATION: Sarcoma centroid target sequence

<400> SEQUENCE: 21
aaaaataaaa acccacaaaa atgttgaacc aaacctccct gctaatctcc atgcccacgt      60
tctttcccac cctgttccca gtcttctgac aaactgtgta                           100

<210> SEQ ID NO 22
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 22
tttgacaaca ttggctatgc ctggatcgcc atcttccagg tcatcacgct ggagggctgg      60
gtcgacatca tgtactttgt gatggatgct cattccttct                           100

<210> SEQ ID NO 23
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 23
ttaaaggaca gttgaaaagg gcaagaggaa accagggcag ttctagagga gtgctggtga      60
ctggatagca gttttaagtg gcgttcacct agtcaacacg                           100

<210> SEQ ID NO 24
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 24
acaccaacct ggagaagttc tcagatggtg ccttcctggg tgtaaccacg ctgaaacacg      60
tccatttgga gaacaaccgc ttgaaccagc taccctccaa                           100

<210> SEQ ID NO 25
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 25
accacacatc ccagcccaat ccaggtacgc acagacaggt tttcacataa atgcagccca      60
tttctccaga acccatttga ggggtggggg ggtgttaatt                           100

<210> SEQ ID NO 26
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 26
cacctcctct gttggagaag cagaccgtta ccaaagacgt cacagataag ccactagact      60
tgtcttctaa agtggtggat gtagatgctt ccaaagctga                           100
```

<210> SEQ ID NO 27
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 27
tccctctccg aggccgagaa gaccttctgt tcctgtaaat acagccagca agtgcaaact      60
gtgattttat tttccacgta ttcctgagga cggactggac                          100

<210> SEQ ID NO 28
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 28
agtgctcctg tgtgaccttc gccctgtgtc cttccatttc ctgtctttcc cgtccatcac      60
ccatcctaag cacttacgtg agtaaataat gcagctcaga                          100

<210> SEQ ID NO 29
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 29
aagagtcacc aaattttgag agttatactt gcttgtgtgc tcctggctgg caaggtcagc      60
ggtgtaccat tgacattgac gagtgtatct ccaagccctg                          100

<210> SEQ ID NO 30
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 30
ctttatggca ggggtggaag gaggtacatt taattcccac tgcctgcctt tggcaagccc      60
tgggttcttt gctccccata tagatgtcta agctaaaagc                          100

<210> SEQ ID NO 31
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 31
gtatctttgg gaagccatgt gtctggtttg tcgtgctggg acagtcatgg gactgcatct      60
tccgacttgt ccacagcaga tgaggacagt gagaattaag                          100

<210> SEQ ID NO 32
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 32

```
tatatgttct tcaacacatc agagctccga gaagcggtac ctgaacccgt gttgctctcc      60
cgggcagagc tgcgtctgct gaggctcaag ttaaaagtgg                          100

<210> SEQ ID NO 33
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 33
cggcacggtt tcgtggggac ccaggcttgc aaagtgacgg tcattttctc tttctttctc      60
cctcttgagt ccttctgaga tgatggctct gggcgcagcg                          100

<210> SEQ ID NO 34
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 34
gtggcgcccc aactcttcgc cagcatatca tcccggcagg cgataaacta cattcagttg      60
agtctgcaag actgggagga actggggtga taagaaatct                          100

<210> SEQ ID NO 35
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 35
tggctgtggg ttacactgcc ttcaatggcg tggacttcga gggcacgttc catgtgaaca      60
cggtcacgga tgacgactat gcgggcttca tctttggcta                          100

<210> SEQ ID NO 36
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 36
tgtggtctgc cagctaaagg tgaagatata ttcctccaat tcaggaccca cacgacggga      60
agacaagttc atgtactttg agttccctca gccgttacct                          100

<210> SEQ ID NO 37
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 37
atggccaagg atgtggacag agacaacaaa gggttcttca actgcgatgg tttcctggca      60
ctaatgggag tttaccatga gaaggcccag aaccaggaga                          100

<210> SEQ ID NO 38
<211> LENGTH: 100
<212> TYPE: DNA
```

```
<213> ORGANISM: Artificial Sequence
<220> FEATURE:
<223> OTHER INFORMATION: Sarcoma centroid target sequence

<400> SEQUENCE: 38
ctgaaagaga cggagctgag gaaggtgaag gtgcttggat ctggcgcttt tggcacagtc    60
tacaagggca tctggatccc tgatggggag aatgtgaaaa                          100

<210> SEQ ID NO 39
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 39
tccagcccgc cctgttgtct cctgccaagc agccgactat gagaacttct cttgcacttg    60
gagtcccagc cagatcagcg gtttaccccac ccgctacctc                         100

<210> SEQ ID NO 40
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 40
cataccatga ccggaagtca aaagttgacc tggataggct caatgatgat gccaagcgtt    60
acagttgcac tcccaggaat tactcggtca atataagaga                          100

<210> SEQ ID NO 41
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 41
cgtgtgctgg ggccctgctc tgagatcctc aagaggaaca ttcagcgtta caacagcttc    60
atctccctca ccgtctgagc acagctcccg ccctgcagcc                          100

<210> SEQ ID NO 42
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 42
ggggaacgtg atcctgctga acatggacgg caaagagctt tggaatctca gaatgcacaa    60
aaagaaagtg acgcatgtgg ccctgaaccc atgctgtgat                          100

<210> SEQ ID NO 43
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 43
ggcgtttgga atcgcattct cccagttaat tggcatgctg ctggcctgct gtctgtcccg    60
gttcatcacg gccaatcagt atgagatggt gtaaggagaa                          100
```

```
<210> SEQ ID NO 44
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 44
tgggtcatgt tgcagcagtc cgctgtgttc aatatgatgg caggagggtt gttagtggag     60
catatgattt tatggtaaag gtgtgggatc cagagactga                          100

<210> SEQ ID NO 45
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 45
accagtcggt gtacgtcata tccgaggaga aggatgagtg cgtcatagca actgaggtgt     60
aaaatggaag tgagatggca agactcccgt ttctcttaaa                          100

<210> SEQ ID NO 46
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 46
gctggagagg cggctaaggt gtttggaggc ttccaggtgg taccggctcc cgatggccag     60
tttgctttcc tcattcccaa cggggccttc gcgcacagcg                          100

<210> SEQ ID NO 47
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 47
ggatccaaac cttggctgct cctctgacac catcgaggtc tcctgcaact tcactcatgg     60
tggacagacg tgtctcaagc ccatcacggc ctccaaggtc                          100

<210> SEQ ID NO 48
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 48
tagtgcttgg tcgggtcttg gggtctggag cgtttgggaa ggtggttgaa ggaacagcct     60
atggattaag ccggtcccaa cctgtcatga aagttgcagt                          100

<210> SEQ ID NO 49
<211> LENGTH: 100
<212> TYPE: DNA
<213> ORGANISM: Artificial Sequence
<220> FEATURE:
<223> OTHER INFORMATION: Sarcoma centroid target sequence
```

```
<400> SEQUENCE: 49
agcctgcatc ccttcgcctg cagcctactt tggggaaata aagtgcctta ctgactgtag    60
ccattacagt atccaatgtc ttttgacagg tgcctgtcct                          100

<210> SEQ ID NO 50
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 50
agcctcagca gccgtcacag acagtgcgtt tcaaattgcc aatctggcag actgcccgca    60
gaatcattcc tcctcctcct cgtcctcctc aggggggagct                         100

<210> SEQ ID NO 51
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 51
cgggagagac tcgctcactc ccatgttggg tttgagacag acaccttttc tatttacctc    60
ctaatggcat ggagactctg agagcgaatt gtgtggagaa                          100

<210> SEQ ID NO 52
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 52
gcatctacta ccttgacaca gagtgttttc ccactagaag ctctgctctg ctctcctggc    60
ccaagtaggg gattccatgc cttcccttc atggtcttag                           100

<210> SEQ ID NO 53
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 53
ccctcgatca tatttcccct tggacacttg gttagacgcc ttccaggtca ggatgcacat    60
ttctggattg tggttccatg cagccttggg gcattatggg                          100

<210> SEQ ID NO 54
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 54
tcctggatag tttgcggctg agaatgcact tactggctca ttcagcgggt gccaaagcct    60
ttgtctgtga tcagtgcggt gcacagtttt cgaaggagga                          100

<210> SEQ ID NO 55
<211> LENGTH: 100
```

```
<212> TYPE: DNA
<213> ORGANISM: Artificial Sequence
<220> FEATURE:
<223> OTHER INFORMATION: Sarcoma centroid target sequence

<400> SEQUENCE: 55
gtattcatac agcactactt acttagagat gctactgtca gtgtcctcag ggctctacca    60
agacataatg cactggggta ccacatggtc catttcatgt                         100

<210> SEQ ID NO 56
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 56
gccttgtctc ttgggtctga gtcccttgct taagggattt tgaagtccta gttttcagct    60
tgcagagatt atgtctgaaa tgcctaatga gtcgcaggga                         100

<210> SEQ ID NO 57
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 57
atcaatgaca cagatgctaa tcctcgatac aagatcccag tggaagctga cttcctcttc    60
gcctattcca cggttccagg ctattactcg tggaggagcc                         100

<210> SEQ ID NO 58
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 58
gatcacctga ggacccgagc cattgatgga ctcggacgag accgggttcg agcactcagg    60
actgtgggtt tctgtgctgg ctggtcttct gctgggagcc                         100

<210> SEQ ID NO 59
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 59
cagcacagcg ctatggccgc gagctccgga ggatgagtga cgagtttgtg gactccttta    60
agaagggact tcctcgcccg aagagcgcgg gcacagcaac                         100

<210> SEQ ID NO 60
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 60
actgattata cctctagtat agatgtatgg tctgctggct gtgtgttggc tgagctgtta    60
```

-continued ctaggacaac caatatttcc aggggatagt ggtgtggatc					100

<210> SEQ ID NO 61
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 61
attatggatc tttgcataga atgtcaagct aaccaggcgt ccgctacttc agaagagtgt					60 actgtcgcat ggggagtctg taaccatgct tttcacttcc					100

<210> SEQ ID NO 62
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 62
gatggcttct atgaggctga gctctgcccg gaccgctgca tccacagttt ccagaacctg					60 ggaatccagt gtgtgaagaa gcgggacctg gagcaggcta					100

<210> SEQ ID NO 63
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 63
gaaactgggg ctcctccagg gtggcagcaa caataaatag acacgcacgg cagccacagc					60 ttgggtgtgt gttcatcctt gttaaaaaaa aaaaaaaaa					100

<210> SEQ ID NO 64
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 64
ttaaagatga gcgggtggca gcgacagagc caaaatcaga gctggaacct gaggagagag					60 tgttcaagaa ggaagtgtat cttcatacat caccacacct					100

<210> SEQ ID NO 65
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 65
aaatgggggg aaggtccaac ttaaccttat ggatttagtg tctgggattc cagcaactca					60 aagtcaaaaa attcaagagg tgggggagat cacaaacttg					100

<210> SEQ ID NO 66
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 66
ggatatgctt tcaatgggac aaagctggat gctgtttacc taaacaagaa taaatacctg    60
acagttattg acaaagatgc atttggagga gtatacagtg                          100

<210> SEQ ID NO 67
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 67
ctaagagcca tttaggggcc acttttgact agggattcag gctgcttggg ataaagatgc    60
aaggaccagg actccctcct cacctctgga ctggctagag                          100

<210> SEQ ID NO 68
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 68
cttcatcatg agttctgctg aatgccgcga tgggtcaggt aggggggaaa caggttggga    60
tgggatagga ctagcaccat tttaagtccc tgtcacctct                          100

<210> SEQ ID NO 69
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 69
gcatttggag tcctgctgta tgaaatgttg gctgggcagg caccctttga agggaggat     60 gaagatgaac tcttccaatc catcatggaa cacaacgtag                          100

<210> SEQ ID NO 70
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 70
agtccagaaa tcttcctgaa acgcccagtg gttgagggaa atcgttggag gttggactgc    60
attcttaaac gaaaagcaca acaaggagtg aggatcttca                          100

<210> SEQ ID NO 71
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 71
ccaactcgcc tgtggacggg gaggctctcc ctctctctca tcttacattt ctcaccctac    60
tctggatggt gtgtggtttt taaagaaggg ggctttcttt                          100

<210> SEQ ID NO 72

<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 72
ctgcgcaata gcccagaaga taagcgggcg ggcggtgaag agtcacagtt tgagatggac    60
atttaaagca ccagccatcg tgtggagcac taccaagggg                         100

<210> SEQ ID NO 73
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 73
gtgttggccg aggtcctcac gggcatccct gcaatggata acaaccgaag cccggtttac    60
ctgaaggact tactcctcag tgatattcca agcagcaccg                         100

<210> SEQ ID NO 74
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 74
atagtggtga ccctcaagac cagcttgcag tggcttatca tcttatcatt gacaatcgga    60
gaataatgaa ccaagccagt gagttctacc tcgcctctag                         100

<210> SEQ ID NO 75
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 75
gtggatgtaa aacccatttc acaagagaag attgagagtg agagagccct catcagccag    60
tgtggaaaac cagtggtaaa tgtcagctac aggccagctt                         100

<210> SEQ ID NO 76
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 76
acggaatgga cagccgacct cccatggcaa tttttgagtt gttggattac atagtcaacg    60
agcctcctcc aaaactgccc agtggagtgt tcagtctgga                         100

<210> SEQ ID NO 77
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 77
gtgagactcg cgccctccgg cacggaaaag gccaggcgac aggtgtcgct tgaaaagact    60

```
gggcttgtcc ttgctggtgc atgcgtcgtc ggcctctggg                              100

<210> SEQ ID NO 78
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 78
ccaatgtcca gatggccaga atgaatgtga tagttcagac caatgccttc cactgctcct      60
ttatgactgc acttctagcc agtagctctg cacaagttag                            100

<210> SEQ ID NO 79
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 79
agcagaagga agcactacag ttcgtaagga gatcatcagg aataagatca gagccattgg      60
gaagatggca cgggtctttt caattcttcg gcaagaaagt                            100

<210> SEQ ID NO 80
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 80
ccatgaattc ctatgaaatg cggaaggcat tagaagaagc aggtttcaag atgccctgtc      60
aactccacca agtcatcgtt gctcggtttg cagatgacca                            100

<210> SEQ ID NO 81
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 81
acactacaag aggtgaagat gacagtgcag gaagatcgaa agtgcgaatc tgacttacgc      60
cattattacg acagtaccat tgagttgtgc gtggggacc                             100

<210> SEQ ID NO 82
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 82
gatgggtgtt gctcccttat ccccaaatca ctctatacat ccaattcagg aaacaaacat      60
ggtggcaatt ctacacaaaa agagatgaga ttaacagtgc                            100

<210> SEQ ID NO 83
<211> LENGTH: 100
<212> TYPE: DNA
<213> ORGANISM: Artificial Sequence
<220> FEATURE:
```

<223> OTHER INFORMATION: Sarcoma centroid target sequence

<400> SEQUENCE: 83
tcattggtaa aggacgcagc tacaagggaa cagtatctat cactaagagt ggcatcaaat    60
gtcagccctg gagttccatg ataccacacg aacacagctt    100

<210> SEQ ID NO 84
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 84
catgattcag cgcaaggagt gggacttatc tgagtatagt tacaaggacc cagaggacca    60
aggaaacctc tatattgggt acacgatgca ggtaggcagc    100

<210> SEQ ID NO 85
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 85
ctttctacat agtgtccatg tgcgtcgcca gtagtgtcgg gagcaagttc agcaaaactc    60
aaacctttca gggttgtgga atcttgcagc ctgatccgcc    100

<210> SEQ ID NO 86
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 86
aggcaccacg taagacctcc tgcccttagc tctcttgctc accacccaag aacctcagga    60
cagaagcgag agcccattgc tcctgctcag ctcagcccgg    100

<210> SEQ ID NO 87
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 87
gacctccgcg ccgagcgctc cgtactcatc cccgagacct accaggccaa caattgccag    60
ggcgtgtgcg gctggcctca gtccgaccgc aacccgcgct    100

<210> SEQ ID NO 88
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 88
tgaaacaccc tgtggtagca gctttgctgt cttctacttc atcagcttct acatgctctg    60
tgccttcctg atcatcaacc tctttgtagc tgtcatcatg    100

```
<210> SEQ ID NO 89
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 89
gacacggacg aggacaagac gtcggtccac ttcgaggagg acttccacaa gctcagagaa      60
ctccagacca cagagctgaa gatgtgttcc ctggccgtga                          100

<210> SEQ ID NO 90
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 90
ttcgagcatc agtacgtcag tgccatcaag accctgtggg aggacccggg catccaggaa      60
tgctacgacc gcaggcgcga gtaccagctc tccgactctg                          100

<210> SEQ ID NO 91
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 91
tgatagtggg tgccccctac ttctttgagc gccaagaaga gctgggggt gctgtgtatg       60 tgtacttgaa ccaggggggt cactgggctg ggatctcccc                          100

<210> SEQ ID NO 92
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 92
ttgcttgtgg aggcgtggga ttccagtaat gacaccgttc aacctgacag tattattgaa      60
aaggcttctc actcgggcat gatcaacccc agccggcagt                          100

<210> SEQ ID NO 93
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 93
gccatgaatt tctcctactc gccgctgcta cgtgagttca ccaaggccac caacgtccgc      60
ctgcgcttcc tgcgtaccaa cacgctgctg ggccatctca                          100

<210> SEQ ID NO 94
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 94
```
caccggctca ttgatgacat ggtggctcag gtcctcaagt cttcgggtgg ctttgtgtgg    60
gcctgcaaga actatgacgg agatgtgcag tcagacatcc                         100

<210> SEQ ID NO 95
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 95
cagagcgtcc tgtgcggacc ggcagagaac aaatgccaag aactgttgtg caagtgtgac    60
caggagattg ctaactgctt agcccaaact gagtacaact                         100

<210> SEQ ID NO 96
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 96
agccgcgcgc tcagccggca actcagcagc ggggtctcgg agatccggca cactgcggac    60
cgctggcgcg tgtccctgga tgtcaaccac ttcgccccgg                         100

<210> SEQ ID NO 97
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 97
caagcggaaa ttgaagcaga taggtcttat cagcacagtc tccgcctcct ggattcagtg    60
tctcggcttc agggagtcag tgatcagtcc tttcaggtgg                         100

<210> SEQ ID NO 98
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 98
gggcctgtcc attgctgtgg agggtcctag caaagcggag attgcatttg aggatcgcaa    60
agatggctcc tgcggcgtct cctatgtcgt ccaggaacca                         100

<210> SEQ ID NO 99
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 99
atttggttcc cgatggccct gtgggagaac agatccgacg tatcctgaag ggaaagtcca    60
ttcagcagag agctccaccg tattagctcc attagcttgg                         100

<210> SEQ ID NO 100
<211> LENGTH: 100
<212> TYPE: DNA
<213> ORGANISM: Artificial Sequence

```
<220> FEATURE:
<223> OTHER INFORMATION: Sarcoma centroid target sequence

<400> SEQUENCE: 100
gggaatggac atgcattgcc tactcgcagc ttcgagatca gtgcattgtt gatgacatca      60
cttacaatgt gaacgacaca ttccacaagc gtcatgaaga                           100

<210> SEQ ID NO 101
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 101
ataaaggttt cgaaggcatc agcggacctc atgtcctact gtgaggaaca tgccaggagt      60 gacccttttgc tgataggaat accaacttca gaaaacccctt                         100

<210> SEQ ID NO 102
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 102
ccgcatctat tggcagcttt gttattgatc agaaactgct cgccgccgac ttggcttcca      60
gtctggctgc gggcaaccct tgagttttcg cctctgtcct                           100

<210> SEQ ID NO 103
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 103
ctgtggcttg ggacagatag aagggatggt tgggatact tcccaaaact ttttccaagt       60
caacttggtg tagccggttc cccggccacg actctgggca                           100

<210> SEQ ID NO 104
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 104
ctttctcttc ttgtttctcc tgcccactgc tgcagtaggg gaggagcaca gtttgtggct      60
tataggtgtt ggttttgggg gtgtgagtgt ttggggacg                            100

<210> SEQ ID NO 105
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 105
cgccaactga aaaagtggga aaggatgtct ggaggcgagg cgtcccatta cagaggaagg      60
agctcgctat ataagccagc caaagttggc tgcaccggcc                           100
```

<210> SEQ ID NO 106
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 106
aagcgcacat tcatgtgggc atttcttgcg agcctcgcag cctccggaag ctgtcgactt    60
catgacaagc attttgtgaa ctagggaagc tcagggggt                          100

<210> SEQ ID NO 107
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 107
cacttgggtg acggcagtcg atgcgttcac tccaatgtct gctgaggagt tatggtgaac    60
ccacaactta ggccctagcg gcagaaagga aaacctgaag                         100

<210> SEQ ID NO 108
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 108
gcgcttctga acgcgatcag aaagcttcat gtgggcaaag tcggggagaa cgggtatgtg    60
gagatagagg atgacattgg aaggagggca gaaatgaatg                         100

<210> SEQ ID NO 109
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 109
aaaccagtga gcagtatgaa tttgtgcacc atgctctgtg cctgtatgag agcagacttt    60
cagcagagac tgtccagtga gtcattgaag acttgtcaga                         100

<210> SEQ ID NO 110
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 110
ctttggagtc tgccgtgatg gcatcaaccg ctacgactgt gtctgccaac ctggcttcac    60
agggcccctt tgtaacgtgg agatcaatga gtgtgcttcc                         100

<210> SEQ ID NO 111
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 111

```
cccctcaggag ccctggagga gtgctatgtc acagaaattg accaagataa gtatgctgtg    60
cgcttcatcc ctcgggagaa tggcgtttac ctgattgacg                           100

<210> SEQ ID NO 112
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 112
gaataagcct tggaattaga tatggggcaa tgactgagcc ctgtctcacc catggattac    60
tccttactgt agggaatggc agtatggtag agggataaat                           100

<210> SEQ ID NO 113
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 113
cgataatcct ccgatcttca atcccaccac gtacaagggt caggtgcctg agaacgaggc    60
taacgtcgta atcaccacac tgaaagtgac tgatgctgat                           100

<210> SEQ ID NO 114
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 114
gacgggtaca ataacacact gtactgatgt cacaactttg caagctctgc cttgggttca    60
gcccatctgg gctcaaattc cagcctcacc actcacaagc                           100

<210> SEQ ID NO 115
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 115
atttagaaaa cttgaaagtc agcactaaag gatgggcaga ggttcaaccc acacctccac    60
tttgcttctg aaggcccatt cattagacca cttgtaaaga                           100

<210> SEQ ID NO 116
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 116
ctccccgtgt acatatactc ccggtttccc tgccctcca ttgcccttgg cttttctgg       60 tatgtgctgt gctccacgac caagccgaga aaggacctag                           100

<210> SEQ ID NO 117
<211> LENGTH: 100
<212> TYPE: DNA
```

```
<213> ORGANISM: Artificial Sequence
<220> FEATURE:
<223> OTHER INFORMATION: Sarcoma centroid target sequence

<400> SEQUENCE: 117
gaatgacagc tatcttcggt cgtccttgag gtcaacggca tcgtactgtt ccagggacag    60
tcggggccac aatgatgtgt atatttcgga gcatgttatg                         100

<210> SEQ ID NO 118
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 118
gagagtgtat cctgtgcccg atctacttgt cattgcagac aaatatgatc ctttcactac    60
gacaaatacc gaatgcctct gcataaaccc tggctctttt                         100

<210> SEQ ID NO 119
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 119
ataatgtaaa cgtcaatgca caaaatggat ttggaaggac tgcgctgcag gttatgaaac    60
ttggaaatcc cgagattgcc aggagactgc tacttagagg                         100

<210> SEQ ID NO 120
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 120
cgccagctga gccgagcggt agctggtctg gcgaggtttt atacacctga aagaagagaa    60
tgtcaagacg aagtagccgt ttacaagcta agcagcagcc                         100

<210> SEQ ID NO 121
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 121
ccagaagcct ctttcttgga cggatcctct ccttgacttc ctcagcctcc cgcctgctta    60
caactgccct gacctccttc tgtgccaaat atacataccc                         100

<210> SEQ ID NO 122
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 122
ctctctgtgt gacattacta tcactcagat gctggaggaa gattctaacc agggcacct     60 gattggtgat ttttccaagg tatgtgcgct gccaaccgtg                         100
```

<210> SEQ ID NO 123
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 123
gcaaagtgat tgactgtgac agttctgagg cctatgctaa tcattctagt tcatttatag     60
gctctgcttt gcaggatcaa gcctcaaggc tgggggttcc                          100

<210> SEQ ID NO 124
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 124
cgggacaaag ctggcctgaa tcattaatac gaaagactgg atatacccctg gaaagtctta    60 agccttgtct catggacctt caccagacct acctcaaagc                          100

<210> SEQ ID NO 125
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 125
caaaaccaat ctatgatgat gacccatctc ttgaaggtgg tgttaatggc aaaaatcttg     60
gccccataaa tgaatggtgg atcactggct ttgatggagg                          100

<210> SEQ ID NO 126
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 126
aaaagagtgc acgccagtat cacgtacagt tctttggtga cgccccagaa agagcttgga    60
tatttgagaa gagcctcgta gcttttgaag gagaaggaca                          100

<210> SEQ ID NO 127
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 127
ccagctccaa gccgtggact cttcggagaa ctttcagatc tcccttaaga gcaaacaagg    60
cccgatcgat gttttcctgt gccctgagga gaccgtaggt                          100

<210> SEQ ID NO 128
<211> LENGTH: 100
<212> TYPE: DNA
<213> ORGANISM: Artificial Sequence
<220> FEATURE:
<223> OTHER INFORMATION: Sarcoma centroid target sequence

```
<400> SEQUENCE: 128
tactctgatc tacgttgata aggaaattgg agaaccaggc acccgtgtgg ctgccaagga    60
tgtgctgaag ctggagtcta gaccttcaat caaagcatta                         100

<210> SEQ ID NO 129
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 129
acaggtggaa aggagatcac agagaaagtg attacagaca ttgccggggt aataccagct    60
gagaaaattg atggagtatt tgctgcctgt cagagtggct                         100

<210> SEQ ID NO 130
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 130
tttgtgcttc tcacctttgg gtgggatgcc ttgccagtgt gtcttacttg gttgctgaac    60
atcttgccac ctccgagtgc tttgtctcca ctcagtacct                         100

<210> SEQ ID NO 131
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 131
cagttatcct gtttgctcac aatgatctcg ttgacaaggt ccagcctggg gacagagtga    60
atgttacagg catctatcga gctgtgccta ttcgagtcaa                         100

<210> SEQ ID NO 132
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 132
ggggacagat ttgtgaccgg cgcggttttt gtcagcttac tccggccaaa aaagaactgc    60
acctctggag cggacttatt taccaagcat tggaggaata                         100

<210> SEQ ID NO 133
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 133
aaccagaggt tccagagagt aaccagaaac agtggcaatc taagagaaag tcagagtgta    60
ttaaccagaa tcctgctgca tcttcaaatc actggcagat                         100

<210> SEQ ID NO 134
<211> LENGTH: 100
```

```
<212> TYPE: DNA
<213> ORGANISM: Artificial Sequence
<220> FEATURE:
<223> OTHER INFORMATION: Sarcoma centroid target sequence

<400> SEQUENCE: 134
aacttgagga agagcaagca gtcagaccaa aatacctact gggtcgggaa gtcactggaa      60
acatgagagc catcctaatt gactggctag tacaggttca                          100

<210> SEQ ID NO 135
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 135
gctggcttat tagctgtaat ggcccagatg ggttgttacg tccctgctga agtgtgcagg      60
ctcacaccaa ttgatagagt gtttactaga cttggtgcct                          100

<210> SEQ ID NO 136
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 136
atgagacgaa gggggaggac aacattgact tcatgcccac catcttgtcg cgcttcgaca      60
tgatcttcat cgtcaaggat gagcacaatg aggagaggga                          100

<210> SEQ ID NO 137
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 137
aaacaaaagg ctgatgagga agagatgctt gataatctac cagaggctgg tgactccaga      60
gtacacaact caacacagaa aaggaaggcc agtcagctag                          100

<210> SEQ ID NO 138
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 138
ccgggagaat gacatcaaga gctactttgg ccgtaaggtg gccattgatg cctctatgag      60
catttatcag ttcctgattg ctgttcgcca gggtggggat                          100

<210> SEQ ID NO 139
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 139
agggtgatgg attggagttc aagagacact tcctgaagat taaagggaag ctgattgata      60
```

```
ttgtgagcag ccagaagatt tggcttcctg ccacatgatc                          100
```

<210> SEQ ID NO 140
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 140

```
gatgtgcaaa gcctgggata tagaagaact tgtcagcctg gggaagaaac taaaggcctg    60
tccatattac acagcccgag aactaataca agatgctgac                         100
```

<210> SEQ ID NO 141
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 141

```
atcccacata atcacaggaa acaagattcc actgagtggc ccagtaccta aggagctgga    60
tcagcagtcc accacaaaag cttctgttaa aagaccctac                         100
```

<210> SEQ ID NO 142
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 142

```
atcggagtgc cttttgcagg caaggatcaa agaggcaaag tgctcattta taatgggaac    60
aaagatggct taaacaccaa gccttcccaa gttctgcaag                         100
```

<210> SEQ ID NO 143
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 143

```
caaccatgtc tttcaaggat tacatccaag agaggagtga cccagtggag caaggcaaac    60
cagttatacc tgcagctgtg ctggccggct tcacaggaag                         100
```

<210> SEQ ID NO 144
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 144

```
tgggatttcc tgggcttaat ggattccaag gaattgaggg tcaaaagggt gacattggcc    60
tgccaggccc agatgttttc atcgatatag atggtgctgt                         100
```

<210> SEQ ID NO 145
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 145
cagaggactg tgtttcaca cgggcactaa gaactccttt atggctcttt atctttcaaa    60
aggacgtctg gtctttgcac tggggacaga tgggaaaaaa                         100

<210> SEQ ID NO 146
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 146
caaagtcttg aacgtggacc ccgacaatgt gaccttctgt gtgctggctg cgggtgagga    60
ggacgagggc gacatcgcgc tgcagatcca ttttacgctg                         100

<210> SEQ ID NO 147
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 147
cggatatcag catcctgtcc ttgcaggctt ctgaattccc ttctgagtta atgtcaaatg    60
acagcaaagc actgtgtggc tgaataagcg gtgttcatga                         100

<210> SEQ ID NO 148
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 148
tcttttgtaa gtgctacata aattggcctg gtatggctgc agtcctccgg ttgcatactg    60
gactcttcaa aaactgtttt gggtagctgc cacttgaaca                         100

<210> SEQ ID NO 149
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 149
acagtgatac acacacgtat ttaaggacta tccctgagac catccctctc attttggaaa    60
ctgctaggga gggaaccaac cacttaaaca agcgtggttt                         100

<210> SEQ ID NO 150
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 150
ggaacggcac tgttcacctt tatctgacca aaccgctcta cacgtcagca ccatctctgc    60
agcatctctg taggctcacc attaacaaat gtaccggtgc                         100

<210> SEQ ID NO 151

```
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 151
tattcggtcg ggagccatac caaaggatcc caaaatcttg gctgctcttg aagctgttgg      60
aaaatcagaa aatgatctgg aagggcggat agtttgtgtc                          100

<210> SEQ ID NO 152
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 152
cagacggtgg aggatggggt gtttgacatc cacttgtaat agatgctgtg gttggatcaa      60
ggactcattc ctgccttgga gaaaatactt caaccagagc                          100

<210> SEQ ID NO 153
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 153
ttgatggtgg catcaaacta ccgatttaaa actggaagtt gctggtactc aaaccaaaag      60
ttcatactct ggcgacacga agggtttcct ttgagcaacg                          100

<210> SEQ ID NO 154
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 154
caaaagacat cacaattagc aatgtgacca aggactcagt gatggtctcc tggagccctc      60
ctgttgcatc tttcgattac taccgagtat catatcgacc                          100

<210> SEQ ID NO 155
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 155
gttactccct acactgatgc aaggattaca gaaactgatg ccaaggggct gagtgagttc      60
aactacatgt tctgggggcc cggagataga tgactttgca                          100

<210> SEQ ID NO 156
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 156
gacacgagcc ttcctgacaa gtgtaactca ttcctacaca acaaggcgga gtggaggtgc      60
```

```
gaaattgagg caactcttga gaggctaaag aaactagagc                          100
```

<210> SEQ ID NO 157
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 157

```
gaaaggctca agttgcacca ggcagacaac agacatggaa ttcttatata tccagctgtt    60
agcaacaaaa caaaagtcaa atagcaaaca gcgtcacagc                          100
```

<210> SEQ ID NO 158
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 158

```
cgggaggaag caggacattg gagacatttt acagcaaatt atgaccatca cagaccagag    60
tttggatgag gcgcaggcca gaaaacatgc tttaaactgc                          100
```

<210> SEQ ID NO 159
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 159

```
gagcaaagag gtggccatcc gcatctttca gggctgccag tttcgctccg tggaggctgt    60
gcaggagatc acagagtatg ccaaaagcat tcctggtttt                          100
```

<210> SEQ ID NO 160
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 160

```
accctcgtca cataggctgg aaagatttca ccgcctacag atggcgtctc agccacaggc    60
caaagacggg tttcattaga gtggtgatgt atgaagggaa                          100
```

<210> SEQ ID NO 161
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 161

```
caaagccctc atcgacagaa acatccaggc caccctggaa agccagaaga aactcaactg    60
gtgtcgagaa gtccggaagc ttgtggcgct gaaaacgaac                          100
```

<210> SEQ ID NO 162
<211> LENGTH: 100
<212> TYPE: DNA
<213> ORGANISM: Artificial Sequence
<220> FEATURE:

<223> OTHER INFORMATION: Sarcoma centroid target sequence

<400> SEQUENCE: 162
cacagcagag tacagcacaa tccacagccc atcaacaccc attaaagatt cagattctga    60
tcgattgcgt cgaggttcag atgggaaatc acgtggacgg                          100

<210> SEQ ID NO 163
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 163
agtcaaaatc cgctctccat gcttactctt gacaccccat tgaagccact cattgtgtgt    60
gcgtctgggt gtgaagtcca gctccgtgtg gtcctgtgct                          100

<210> SEQ ID NO 164
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 164
tcggacaccg aggagaatgt caagaggcga acacacaacg tcttggagcg ccagaggagg    60
aacgagctaa aacggagctt ttttgccctg cgtgaccaga                          100

<210> SEQ ID NO 165
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 165
agggtatagc ttcccacact atggatttcc tacttatggt gggattactt tccatcctgg    60
aactactaaa tctaatgctg ggatgaagca tggaaccatg                          100

<210> SEQ ID NO 166
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 166
cagccatgaa gaaccaggtt gcaagattta atgacctcag gtttgtcggt cgaagtggaa    60
gagggaaaag cttcactctg accatcactg tcttcacaaa                          100

<210> SEQ ID NO 167
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 167
ttggcacaac aggaagctgt tgaaggagga tgttcccatc ttggtcagtc ctatgcggat    60
agagatgtct ggaagccaga accatgccaa atatgtgtct                          100

```
<210> SEQ ID NO 168
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 168
ggttcatgct accctgaagt cactcagtag tcagattgaa accatgcgca gccccgatgg      60
ctcgaaaaag cacccagccc gcacgtgtga tgacctaaag                           100

<210> SEQ ID NO 169
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 169
ggatgacttg aagggttcct tgaaagagga cctgacacag cacaagttca tttgtgaaca      60
gtgtgggaag tgcaagtgtg gagaatgcac tgctcccagg                           100

<210> SEQ ID NO 170
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 170
ggcgaggcca cggcttatgc aagcaaagat ctggaggagc agttacggtc tgtgtccagt      60
gtagatgaac tcatgactgt actctaccca gaatattgga                           100

<210> SEQ ID NO 171
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 171
cgtgctggaa atctgggatg cttccttctg ggttctgatt ctcagtgagt ggagcccatt      60
catccaggca ggtttccatg ctatgagtgg ccctttcgtt                           100

<210> SEQ ID NO 172
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 172
ggaggatgga ggagacggga catctttcac ctcaggctcc tggtagagaa gacaggggat      60
tctactctgt gcctcctgac tatgtctggc taagagattc                           100

<210> SEQ ID NO 173
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 173
```

```
cacataccaa cggcgaggat cacttcagct ctggcagttt ttggtagctc ttctggatga      60
cccttcaaat tctcatttta ttgcctggac tggtcgaggc                          100
```

<210> SEQ ID NO 174
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 174

```
accctggtcc tgacttccct ggaggagaag tattcctgtt gctgtcttca gtctcacaga      60
gaagctcctg ctacttcccc agctctcagt agtttagtac                          100
```

<210> SEQ ID NO 175
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 175

```
gggatggaag gctgtcttct tttgaggatg atcagagaac ttgggcatag gaacaatctg      60
gcagaagttt ccagaaggag gtcacttggc attcaggctc                          100
```

<210> SEQ ID NO 176
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 176

```
aaacagccac cacttctcct agaggagcca agccatctgt gaaatcagaa ttaagccctg      60
ttgccaggca gacatcccaa ataggtgggt caagtaaagc                          100
```

<210> SEQ ID NO 177
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 177

```
caaggttacc aactacctag actggattcg tgacaacatg cgaccgtgac caggaacacc      60
cgactcctca aaagcaaatg agatcccgcc tcttcttctt                          100
```

<210> SEQ ID NO 178
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 178

```
catctggagg caccatctca acgaagactg cgatctccca atgatgatat ttctggatac      60
aaagagaact acacaaggtg gctgtgttac tgcaacgtgc                          100
```

<210> SEQ ID NO 179
<211> LENGTH: 100
<212> TYPE: DNA
<213> ORGANISM: Artificial Sequence

```
<220> FEATURE:
<223> OTHER INFORMATION: Sarcoma centroid target sequence

<400> SEQUENCE: 179
aaatgaggaa gaccttcaga aggttgctga gtacaagact gggcctgtgc tggaacaccc    60
agattgtttc ccatgtcagg actgcagcag caaagccaat                         100

<210> SEQ ID NO 180
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 180
agttcgagga agacctaaac aacggtgtga caccgagaat ccttacacca aagctgatgg    60
gcgtggagac ggttgtgtga caatggtctg gatggaaagg                         100

<210> SEQ ID NO 181
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 181
gaacaagcac ttcggtcatc ccagtcaagc tgtttttgac gacgaagcag acaagaccgg    60
tgaactgagg gacagtgatt tcagtaatga acaattctcc                         100

<210> SEQ ID NO 182
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 182
gaagataatc tgtttcctaa gcaagaaata acaggaaaga tcccttatgc caggaggcct    60
gccatactca ggataagatc cttgaatatg aacttagtt                          100

<210> SEQ ID NO 183
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 183
ccggtgagct gactcctgag gaggaggccc agtacaaaaa ggctttctcc gcggttgaca    60
cggatggaaa cggcaccatc aatgcccagg agctgggcgc                         100

<210> SEQ ID NO 184
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 184
aagagtccgg cggcatctgt cttgtcccta ttcctgcagc ctgtgctgag ggtagcagtg    60
tatgagctac cagcgtgcat gtcagcgacc ctggcccgac                         100
```

```
<210> SEQ ID NO 185
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 185
agggtgatag tcaaattatg tattggtggg gctgggtacc aatgctgcag gtcaacagct      60
atgctggtag gctcctgcca gtgtggaacc actgactact                          100

<210> SEQ ID NO 186
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 186
gtcctgctgc ccgagccagg aactgtgtgt gttgcagggg ggcagtaact ccccaactcc      60
ctcgttaatc acaggatccc acgaatttag gctcagaagc                          100

<210> SEQ ID NO 187
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 187
ttgctttgac cactcttcct gagttcagtg gcactcaaca tgagtcaaga gcatcctgct      60
tctaccatgt ggatttggtc acaaggttta aggtgaccca                          100

<210> SEQ ID NO 188
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 188
gacgtccagt acgacctgta cttgaacgtt gccaacaggc gtcaacagta cgagtgtctt      60
cactacaaaa cggatgctca gggaacacgt atcgggtgtc                          100

<210> SEQ ID NO 189
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 189
ccggaccacc tcgtccctgt ggaaagacaa ggcagcagtg gaaatcaacg tggccgtgct      60
gcacagttac cagctagcca aagtcaccat cgtggaccac                          100

<210> SEQ ID NO 190
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 190
```
tgacaaacaa attcggtaca tcctcgacgg catctcagcc ctgagaaagg agacatgtaa    60
caagagtaac atgtgtgaaa gcagcaaaga ggcactggca                          100

<210> SEQ ID NO 191
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 191
ctggctactt caatcttgtt cggggaccac caacgcttga atatggctga aggatgccat    60
gtttgctcta aattaagaca gcattgatct cctggaggct                          100

<210> SEQ ID NO 192
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 192
tcatgtgtca taactcagtc aagctcagtg agcattctca gcacattgcc tcaacagctt    60
caaggtgagc cagctcaaga ctttgctctc caccaggcag                          100

<210> SEQ ID NO 193
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 193
tggccttgtg gataagggag agttgaccgt tttcatcctg gcctcctttt gctgtttgga    60
tgtttccacg ggtctcactt ataccaaagg gaaaactctt                          100

<210> SEQ ID NO 194
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 194
cacaacgaga ttctgagcaa cgcagactcg ctgtccactt tcgtctctga gcagcaaatg    60
gaaagccagg agccggcaga tttgacaggt gtcactgtac                          100

<210> SEQ ID NO 195
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 195
gaaagcctga agcactttgt ggcttccacg ggttcgtttc taggaagctt ttgctttacc    60
tggggaaacc ccaagctcta cagtgagaaa gttgtaaatt                          100

<210> SEQ ID NO 196
<211> LENGTH: 100
<212> TYPE: DNA

```
<213> ORGANISM: Artificial Sequence
<220> FEATURE:
<223> OTHER INFORMATION: Sarcoma centroid target sequence

<400> SEQUENCE: 196
actcagaaaa gccctgctgg atggtaaatc atggaatcca gaaggaacag tgggtacagg    60
atgcaattgg caggaagcaa catctatctg aagaggaaaa                        100

<210> SEQ ID NO 197
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 197
tcaaaagggg ggacatcctc aaggttttga acgaagaatg tgatcagaac tggtacaagg    60
cagagcttaa tggaaaagac ggcttcattc ccaagaacta                        100

<210> SEQ ID NO 198
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 198
gctgccacaa cttgtgtacc ttcagggatg gggctcttac tccctcctga ggccagctgc    60
tctaatatcg atggtcctgc ttgccagaga gttcctctac                        100

<210> SEQ ID NO 199
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 199
catactggta ctgctgtaat gagccaagtg gcagctaaaa gttggggtg ttctgcccag     60 tcccgtcatt ctgggctaga aggcagggga ccttggcatg                        100

<210> SEQ ID NO 200
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 200
tttctctcaa gtttcctgag tctccagaaa aacagcacta acgctggacc tgtctactct    60
cagaacccgg cacagattct ctcttgatct cctttggaa                         100

<210> SEQ ID NO 201
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 201
ctgctttcaa ctggtagttg tgggttgaag cactggacaa tgccacatac tttgtggatg    60
gtgtgggtct tggggtcat catcagcctc tccaaggaag                         100
```

<210> SEQ ID NO 202
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 202
aaaacatacc aattgttggc cagaagggaa gtctgggatc aaagtgcttt ggatgttggg      60
ttaacaatgc agctcctgga ctgcaacttc tcagatgaaa                          100

<210> SEQ ID NO 203
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 203
cggactctcc aaagcactgc gtgctgatga aaactactac aaggcccaga cccatggaaa      60
gtggcctgtc aagtggtacg ctccggaatg catcaactac                          100

<210> SEQ ID NO 204
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 204
cttggtaaga agccgggaac agacaacaga agtcatgaag cccaagtgaa atcaaaggtg      60
ctaaatggtc gcccaggaga catccgttgt gcttgcctgc                          100

<210> SEQ ID NO 205
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 205
cgaacaggac cagattttgt ttggagcctc agcatgccgg ggcccagatg atggagcata      60
acgggtccca gccaattgtg atgatccttt ttgctcattt                          100

<210> SEQ ID NO 206
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 206
gcttagcttt agaaacagtg caacactggt ctgctgttcc agtggtaagc tatgtcccag      60
gaatcagttt aaaagcacga cagtggatgc tgggtccata                          100

<210> SEQ ID NO 207
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 207
tgacactcat tgattctaaa gcatctttaa tctgccaggc ggagggggct ttgctggtct    60
ttcttggact attccagaga ggacaactgt catctgggaa                          100

<210> SEQ ID NO 208
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 208
gagtccacca ggctttaaca acaccgagag aacatgtgat aaagagttta ttatacggag    60
aacggctacc aatcgagttc tgaacgtcct ccgtcactgg                          100

<210> SEQ ID NO 209
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 209 gggggggaccc agcctgggac agacctgcgt gctgatcgtg atcttcacag tgctcctgca    60
gtctctctgt gtggctgtaa cttacgtgta ctttaccaac                          100

<210> SEQ ID NO 210
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 210
ctcatgcgag ccttcattga tgtgactgct gctgccgaaa atatcaggct gccaaatgca    60
ggcactcagg ttcgagtgac tgtgtttccc tcaaagactg                          100

<210> SEQ ID NO 211
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 211
cactactgtg cctttgagtc cggtggacga tgcctgcaac gtgaacatct tcgacgccat    60
cgcggagatt gggaaccagc tgtatttgtt caaggatggg                          100

<210> SEQ ID NO 212
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 212
cgtggatgag tgctgcttcc ggagctgtga tctaaggagg ctggagatgt attgcgcacc    60
cctcaagcct gccaagtcag ctcgctctgt ccgtgcccag                          100

<210> SEQ ID NO 213
<211> LENGTH: 100

```
<212> TYPE: DNA
<213> ORGANISM: Artificial Sequence
<220> FEATURE:
<223> OTHER INFORMATION: Sarcoma centroid target sequence

<400> SEQUENCE: 213
gtgctgctga aggtcatgga tgccaagcac aagaactgca tggagtcatt cctggaagca      60
gcgagcttga tgagccaagt gtcgtaccgg catctcgtgc                           100

<210> SEQ ID NO 214
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 214
atttggagaa tgttgagtcc ttcaagcaga ccgatgtcta ctccatggct ctggtgctct      60
gggaaatgac atctcgctgt aatgcagtgg gagaagtaaa                           100

<210> SEQ ID NO 215
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 215
aaagaggaaa tactccgcgt gcgcttgtag aagggagtc gtctccagct ccgaaccccg       60
gagtgttcat cagcggggaa tctggctccg aattctcttt                           100

<210> SEQ ID NO 216
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 216
tccaggccat ggagcgggtc agcgagaaca aggtgcgtcc tgtccacttc tggtttgcca      60
cgggcggcgc tggcttctgc atcagccgtg ggctggctct                           100

<210> SEQ ID NO 217
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 217
cagtggcact tggactgcaa tgctttacct tggacctgaa gaatgttacc tgtcaatggc      60
agcaacagga ccatgctagc tcccaaggct tcttctacca                           100

<210> SEQ ID NO 218
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 218
ccgccagcct cctgggtgga gatttgttca tgtcccactg gctacacggg ccagttctgt      60
```
gaatcctgtg ctccgggata caagagggag atgccacagg    100

<210> SEQ ID NO 219
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 219
aggagccagg gtcggattcc agttaaatgg atggcaattg aatccctttt tgatcatatc    60
tacaccacgc aaagtgatgt atggtctttt ggtgtcctgc    100

<210> SEQ ID NO 220
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 220
actcaagtcc ttacctcttc cggagatgta gcaaaacgca tggagtgtgt attgttccca    60
gtgacacttc agagagctgg tagttagtag catgttgagc    100

<210> SEQ ID NO 221
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 221
tcccaatttc aggctcaccc atgacatcag cctggaggag tttgaggatg aagacctctc    60
ggagatcact gatgagtgtg gcatcagctt acagtgcaaa    100

<210> SEQ ID NO 222
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 222
cgggcattcc tgaagctgac agcattcggg ccgagatgtc tcgctccgtg gccttagctg    60
tgctcgcgct actctctctt tctggcctgg aggctatcca    100

<210> SEQ ID NO 223
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 223 acgttttct aggtacagct cccaggaaca gctaggtggg aaagtcccat cactgaggga    60
gcctaaccat gtccctgaac aaaaattggg cactcatcta    100

<210> SEQ ID NO 224
<211> LENGTH: 100
<212> TYPE: DNA
<213> ORGANISM: Artificial Sequence
<220> FEATURE:
<223> OTHER INFORMATION: Sarcoma centroid target sequence

```
<400> SEQUENCE: 224
tagaacccat ggaaaactgg ctacagttga tgttgaattg ggaccctcag cagagaggag    60
gacctgttga ccttactttg aagcagccaa gatgttttgt                         100

<210> SEQ ID NO 225
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 225
gcggacctga agatgctcac aaaccacacc ttcatcaagc ggtccgaggt ggaagaagtg    60
gattttgccg gctggttgtg taaaaccctg cggctgaacc                         100

<210> SEQ ID NO 226
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 226
ccacagacat gcaccatata gaagagagtt tccaagaaat caaaagagcc atccaagcta    60
aggacacctt cccaaatgtc actatcctgt ccacattgga                         100

<210> SEQ ID NO 227
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 227
cagaaacatc ggatttgggg aacgcgtgtc aatcccttgt gccgcagggc tgggcgggag    60
agactgttct gttccttgtg taactgtgtt gctgaaagac                         100

<210> SEQ ID NO 228
<211> LENGTH: 100
<212> TYPE: DNA
<213> ORGANISM: Artificial Sequence
<220> FEATURE:
<223> OTHER INFORMATION: Sarcoma centroid target sequence

<400> SEQUENCE: 228
ttcattgatt acccaaagaa ggaggactac atcgtctacc tgggtcgctc aaggcttaac    60
tccaacacgc aagggagat gaagtttgag gtggaaaacc                          100

<210> SEQ ID NO 229
<211> LENGTH: 20
<212> TYPE: DNA
<213> ORGANISM: Artificial Sequence
<220> FEATURE:
<223> OTHER INFORMATION: TP53 primer

<400> SEQUENCE: 229
tctcatgctg gatccccact                                                20

<210> SEQ ID NO 230
<211> LENGTH: 20
<212> TYPE: DNA
```

```
<213> ORGANISM: Artificial Sequence
<220> FEATURE:
<223> OTHER INFORMATION: TP53 primer

<400> SEQUENCE: 230
agtcagagga ccaggtcctc                                          20

<210> SEQ ID NO 231
<211> LENGTH: 20
<212> TYPE: DNA
<213> ORGANISM: Artificial Sequence
<220> FEATURE:
<223> OTHER INFORMATION: TP53 primer

<400> SEQUENCE: 231
tgaggacctg gtcctctgac                                          20

<210> SEQ ID NO 232
<211> LENGTH: 20
<212> TYPE: DNA
<213> ORGANISM: Artificial Sequence
<220> FEATURE:
<223> OTHER INFORMATION: TP53 primer

<400> SEQUENCE: 232
agaggaatcc caaagttcca                                          20

<210> SEQ ID NO 233
<211> LENGTH: 20
<212> TYPE: DNA
<213> ORGANISM: Artificial Sequence
<220> FEATURE:
<223> OTHER INFORMATION: TP53 primer

<400> SEQUENCE: 233
tgttcacttg tgccctgact                                          20

<210> SEQ ID NO 234
<211> LENGTH: 20
<212> TYPE: DNA
<213> ORGANISM: Artificial Sequence
<220> FEATURE:
<223> OTHER INFORMATION: TP53 primer

<400> SEQUENCE: 234
ttaacccctc ctcccagaga                                          20

<210> SEQ ID NO 235
<211> LENGTH: 20
<212> TYPE: DNA
<213> ORGANISM: Artificial Sequence
<220> FEATURE:
<223> OTHER INFORMATION: TP53 primer

<400> SEQUENCE: 235
aggcgcactg gcctcatctt                                          20

<210> SEQ ID NO 236
<211> LENGTH: 20
<212> TYPE: DNA
<213> ORGANISM: Artificial Sequence
<220> FEATURE:
<223> OTHER INFORMATION: TP53 primer

<400> SEQUENCE: 236
tgtgcagggt ggcaagtggc                                          20
```

```
<210> SEQ ID NO 237
<211> LENGTH: 19
<212> TYPE: DNA
<213> ORGANISM: Artificial Sequence
<220> FEATURE:
<223> OTHER INFORMATION: TP53 primer

<400> SEQUENCE: 237
ttgggagtag atggagcct                                                19

<210> SEQ ID NO 238
<211> LENGTH: 20
<212> TYPE: DNA
<213> ORGANISM: Artificial Sequence
<220> FEATURE:
<223> OTHER INFORMATION: TP53 primer

<400> SEQUENCE: 238
agtgttagac tggaaacttt                                               20

<210> SEQ ID NO 239
<211> LENGTH: 20
<212> TYPE: DNA
<213> ORGANISM: Artificial Sequence
<220> FEATURE:
<223> OTHER INFORMATION: TP53 primer

<400> SEQUENCE: 239
caattgtaac ttgaaccatc                                               20

<210> SEQ ID NO 240
<211> LENGTH: 20
<212> TYPE: DNA
<213> ORGANISM: Artificial Sequence
<220> FEATURE:
<223> OTHER INFORMATION: TP53 primer

<400> SEQUENCE: 240
ggatgagaat ggaatcctat                                               20

<210> SEQ ID NO 241
<211> LENGTH: 20
<212> TYPE: DNA
<213> ORGANISM: Artificial Sequence
<220> FEATURE:
<223> OTHER INFORMATION: TP53 primer

<400> SEQUENCE: 241
agaccctctc actcatgtga                                               20

<210> SEQ ID NO 242
<211> LENGTH: 20
<212> TYPE: DNA
<213> ORGANISM: Artificial Sequence
<220> FEATURE:
<223> OTHER INFORMATION: TP53 primer

<400> SEQUENCE: 242
tgacgcacac ctattgcaag                                               20
```

MATERIALS AND METHODS FOR STRATIFYING AND TREATING CANCERS

CROSS-REFERENCE TO RELATED APPLICATIONS

The present application is a § 371 of International Patent Application No. PCT/EP2018/071758, filed Aug. 10, 2018, which claims priority from GB Application No. 1712871.1, filed Aug. 10, 2017 and GB Application No. 1808941.7, filed May 31, 2018. The entire disclosure of each of the aforesaid applications is incorporated by reference in the present application.

INCORPORATION-BY-REFERENCE OF MATERIAL SUBMITTED IN ELECTRONIC FORM

Incorporated herein by reference in its entirety is the Sequence Listing submitted via EFS-Web as a text file named SequenceListing.txt., created Sep. 10, 2020 and having a size of 68,024 bytes.

FIELD OF THE INVENTION

The present invention relates to materials and methods for stratifying and treating cancers and to methods of identifying/selecting patients for treatment of cancer with tyrosine kinase inhibitors.

BACKGROUND

Cancer is a complex and dynamic disease, and many different ways of analysing and classifying tumours have been developed with the aims of determining the prognosis for the patient, and informing treatment decisions.

Pazopanib is an oral multi-target tyrosine kinase inhibitor (TKI) with a clinical anti-tumour effect that is thought to be exerted through its selective inhibition of VEGFR-mediated angiogenesis as well as direct blockade of growth-promoting receptor tyrosine kinases (RTKs) that include platelet-derived growth factor receptors (PDGFRs), fibroblast growth factor receptors (FGFRs) and KIT[1-5]. Pazopanib is the first and currently only TKI licensed for the treatment of many subtypes of advanced soft tissue sarcoma (STS) This approval was based on the results of the PALETTE study that randomised 369 patients with pre-treated advanced STS to receive either pazopanib 800 mg once daily or placebo until disease progression[32]. After a median follow-up of 25 months, a clinically significant improvement in progression-free survival (PFS) was seen in the pazopanib arm (median PFS 4.6 v. 1.6 months; HR 0.31; 95% CI 0.24-0.40; p<0.0001). Despite this evidence of anti-tumour effect, no significant difference in overall survival (OS) was observed between pazopanib and placebo-treated patients. The failure of PFS gain to translate to OS benefit has adversely influenced cost assessment of pazopanib for this indication, leading to funding limitations in certain health economies worldwide[6,7].

The development of biomarkers capable of identifying patients most likely to benefit from a therapy is central to the notion of personalised cancer treatment. There is currently an unmet need for predictive biomarkers that are successful in prospectively selecting the subgroup of STS patients most likely to benefit from pazopanib, thus improving the clinical efficiency of the drug. The presence of such a patient subgroup was indicated in a pooled analysis of patients who received the drug within the PALETTE trial or its antecedent EORTC phase II study[8]. In this retrospective report of unblinded, patient-level data, 76 of 344 analysed patients (22%) experienced PFS greater than 6 months and OS greater than 18 months. No STS histological subtype was identified as being enriched in these outstanding responders. In the single arm phase II trial, prospective stratification of patients into one of four histotype-defined subgroups saw patients with adipocytic tumours fail to meet predefined efficacy cut-off, with a 12 week progression-free survival of 26%[9]. The leiomyosarcoma, synovial sarcoma and 'other' histotype subgroups, however, all showed sufficient evidence of pazopanib response, with these histological subtypes taken forward for phase III investigation. The efficacy of pazopanib in several of the rare STS subtypes encompassed within the heterogeneous 'other subtypes' subgroups has been further explored in a number of post-licensing retrospective series[10-14]. Whilst these studies provide further indication of pazopanib activity across a range of STS diagnoses, none of these rarer subtypes have been found to exhibit particular sensitivity relative to the general STS populations treated in phase II and III studies.

It is possible that there are aspects of tumour biology targeted by pazopanib that are shared by individual cases across different STS subtypes, presenting a potential avenue for biomarker discovery. This is supported by translational research that have identified genomic and gene expression signatures that are able to describe patient subgroups of distinct clinical phenotype both across and within STS subtypes[15,16]. In a 19 patient cohort of advanced STS treated with pazopanib or related TKIs, Koehler et al found that the presence of TP53 mutations was associated with significantly improved PFS compared to cases with TP53 wildtype tumours[17]. In a phase I trial of pazopanib in combination with the histone deacetylase inhibitor vorinostat, TP53 hotspot mutations were found in 3 of 11 tested sarcoma patients[18]. In this study, TP53 mutation was significantly associated with improved disease control and PFS across all tested patients, and also improved OS in a subset with either sarcoma or colorectal cancer. Meanwhile, our laboratory has recently shown that, in malignant rhabdoid tumour cells with basal pazopanib sensitivity, acquired drug resistance is mediated by modulation of PDGFRA and FGFR1 signalling[19].

It therefore remains a problem in the art to identify biomarkers for classifying and stratifying patients for susceptibility to pazopanib and other similar tyrosine kinase inhibitors, so that treatment can be tailored to these groups.

SUMMARY OF THE INVENTION

The present invention is based on research to identify biomarkers associated with successful treatment with tyrosine kinase inhibitors (TKI) such as Pazopanib.

In doing so, the inventors identified several biomarkers, which could be used independently or in combination to identify patients who would benefit from TKI treatment. The inventors identified biomarkers associated with longer progression-free survival (PFS) and overall survival (OS). In other words, the inventors identified biomarkers for subtypes of cancers which have greater or lesser sensitivity to TKIs such as Pazopanib.

In particular, three groups of biomarkers have been identified for stratifying cancers: 1) baseline expression, e.g. protein expression, of FGFR1 and PDGFRA, for example using immunohistochemistry (IHC), 2) TP53 mutational status, and 3) gene expression levels of genes (shown in List 1) involved in key oncogenic pathways for example as indicated by mRNA transcript abundance levels.

Accordingly, the invention relates to the use of one or more of these groups of biomarkers for stratifying cancers, and selecting or identifying cancers for treatment with TKIs such as Pazopanib.

The invention also relates to kits for testing and stratifying cancers, to methods for identifying patients for treatment, and to TKIs for use in methods of treatment of cancer.

The stratification of patients according to the invention involves determining the expression, e.g. protein expression, of FGFR1 and PDGFRA. In some cases, the method of the invention may include following the steps of a decision tree classifier, as depicted in FIG. 5 herein.

In addition, the inventors have identified a set of genes shown in table 5 that can be used to stratify PDGFRA-high/FGFR1-low IHC intrinsic resistant poor responder cases from other cases.

In addition, the inventors have developed a gene signature using the genes shown in table 4 that allows for the stratification of patients into the five distinct subgroups identified by the decision tree without the need to apply a decision tree workflow.

In a first aspect the invention provides a method of selecting an individual with cancer for treatment with a TKI. The method may comprise determining the expression levels of PDGFRA and FGFR1 as 'high'(Hi) or 'low' (Lo) in a sample of cancer cells from the individual, and selecting an individual for TKI treatment if they have PDGFRA-Hi/FGFR1-Hi PDGFRA-Lo/FGFR1-Lo, or PDGFRA-Lo/FGFR1-Hi expression levels. An individual may be selected for TKI treatment if they have PDGFRA-Lo and/or FGFR1-Hi expression levels. An individual may be selected for TKI treatment if they do not have PDGFRA-Hi/FGFR1-Lo expression levels.

Equally, an individual may be "deselected" for treatment with TKIs (for example selected as more appropriately treated with an alternative therapy choice, such as in one example an anti-PDGFRA antibody (e.g. olaratumab), binding fragment thereof or a pharmaceutical composition comprising said antibody or said binding fragment) if they have PDGFRA-Hi/FGFR1-Lo.

The expression levels of PDGFRA or FGFR1 determined may be the expression levels of FGFR1 and PDGFRA proteins. The expression levels may be determined to be 'high' if, using immunohistochemistry (IHC), they have a score of 3 or more, wherein the expression level of PDGFRA and/or FGFR1 is scored using the addition of score for staining intensity and score for proportion of positive tumour cells, wherein for staining intensity scoring 0=absent, 1=weak, 2=moderate and 3=strong, and for proportion of positive tumour cells 0=absent, 1=1-10%, 2=11-50%, 3>50%.

In some embodiments, in the determining step, the protein expression levels of PDGFRA and FGFR1 are determined using immunohistochemistry (IHC).

The methods of selecting an individual with cancer for treatment with a TKI may comprise determining the mutation status of TP53 in a sample of, or a sample derived from, cancer cells from the individual, and selecting the individual for treatment if they have wildtype TP53. The mutation status may be determined using digital PCR, Sanger sequencing or next generation sequencing, for example.

The methods of selecting an individual with cancer for treatment with a TKI may comprise determining, within a sample of cancer cells from the individual, the expression levels of 5 or more of the genes selected from List 1, and selecting an individual for treatment with the TKI based on the expression levels of those genes. For example an individual may be selected for treatment if the expression levels resemble, for example closely resemble those of a subgroup with favourable TKI outcome.

In some embodiments, at least about 40 of the genes listed in List 1 are used in the PARSARC (Pazopanib Activity and Response in SARComa) classification model. In other embodiments, at least 41, at least 42, at least 43, at least 44, at least 45, at least 46, at least 47, at least 48, at least 49, at least 50, at least 60, at least 70, at least 80, at least 90, at least 100, at least 150, at least 200, or all 229 of the genes listed in List 1 are used in the model. As described in detail herein, the 229 genes listed in List 1 were detected at <10% FDR by SAM analysis. Without wishing to be bound by any particular theory, the present inventors believe that it is the combination of at least 115 of, or even substantially all of, the genes listed in List 1 that affords the most accurate classification of intrinsic subtype and prognostication of outcome or therapeutic response to treatment. Thus, in various preferred embodiments, the methods disclosed herein encompass obtaining the expression profile of a large number of the genes listed in List 1, for example, at least 47, at least 48, at least 49, at least 50, at least 60, at least 70, at least 80, at least 90, at least 100, at least 110, at least 115, at least 120, at least 150, at least 200, or all 229 of the genes listed in List 1. It will also be understood by one of skill in the art that one subset of the genes listed in List 1 can be used to train an algorithm to predict sarcoma subtype or outcome, and another subset of the genes used to characterize an individual subject. Preferably, all 229 genes are used to train the algorithm, and at least 5, 10, 15, 20, 25, 30, 35, 40, 45 or 50 of the genes are used to characterize a subject.

The methods may utilize a supervised algorithm to classify future subject samples according to sarcoma biological subtype. A particular exemplary algorithm, referred to herein as the PARSARC classification model, is based on the gene expression profile of a defined subset of genes that has been identified herein as superior for classifying sarcoma biological subtypes, and for predicting risk of relapse and/or response to therapy in a subject diagnosed with sarcoma. The subset of genes, is provided in List 1.

"Gene expression" used herein refers to the relative levels of expression and/or pattern of expression of a gene. The expression of a gene may be measured at the level of DNA, CDNA, RNA, mRNA, Or combinations thereof. "Gene expression profile" refers to the levels of expression of multiple different genes measured for the same sample. An expression profile can be derived from a biological sample collected from a subject at one or more time points prior to, during, or following diagnosis, treatment, or therapy for sarcoma (or any combination thereof), can be derived from a biological sample collected from a subject at one or more time points during which there is no treatment or therapy for sarcoma (e.g., to monitor progression of disease or to assess development of disease in a subject at risk for sarcoma), or can be collected from a healthy subject. Gene expression profiles may be measured in a sample, such as samples comprising a variety of cell types, different tissues, different organs, or fluids (e.g., blood, urine, spinal fluid, sweat, saliva or serum) by various methods including but not limited to next generation sequencing technologies, digital counting (such as nanostring), microarray technologies and quantitative and semi-quantitative RT-PCR techniques.

The expression levels of 10 or more, 15 or more, 20 or more, 30 or more, 40 or more, 50 or more, 60 or more, 70 or more, 80 or more, 90 or more, 100 or more, 120 or more, 140 or more, 160 or more, 180 or more 200 or more, or substantially all of, or all of the genes in List 1 may be determined, the expression levels of 10 or more, 15 or more, 20 or more, 30 or more, 40 or more, 50 or more, 60 or more, 70 or more, 80 or more, 90 or more, 100 or more, 110 or more, or substantially all of, or all of the genes in List 1 are determined.

An individual may be selected for treatment if the expression levels of genes in the sample are determined to be similar to, or to resemble, the expression levels of the same genes in a group of patients known to respond well to TKI treatment, wherein the group of patients has cancer (preferably, the same type of cancer as the individual). In other words the patients in the group all have cancer. An individual may be deselected from treatment with a TKI if the expression levels of genes in the sample are determined to be similar to, or to resemble, the expression levels of the same genes in a group of patients known to respond poorly to TKI treatment, wherein the group of patients has cancer (preferably the same type of cancer as the individual).

Accordingly, the methods may further comprise the step of comparing the expression levels of genes in the sample as determined, to the expression levels of the same genes in a group of patients known to respond well to TKI treatment, and to the expression levels of the same genes in a group of patients known to respond poorly to TKI treatment, wherein the group of patients has cancer (preferably, the same type of cancer as the individual), and selecting an individual for treatment with the TKI in step if the expression levels of the genes determined are more similar to the group of individuals which are known to respond well to TKI treatment. It is contemplated herein that the expression levels of said genes (in particular a centroid derived from the expression levels of said genes) may demonstrate predictive ability across cancer types. For example, the marker genes described herein and/or one or more centroids derived from the expression of the genes obtained from sarcoma samples may be amenable to matching a gene expression centroid of, e.g. a renal cancer sample and further more may be predictive of TKI treatment response of the renal cancer subject.

The TKI with which the groups of patients were treated may be any TKI which find use in the present invention. The TKI may be the same as that intended for treatment of the individual. In other words, the individual may be selected for treatment with the same TKI as that with which the groups of patients were treated. Alternatively, the TKI with which the groups of patients were treated may differ from that which is intended for treatment of the individual.

The expression levels determined may be nucleic acid expression levels. These may be determined using an RNA microarray, quantitative PCR or RNA-Seq, for example.

Methods of the invention may involve one, two or all three of the above approaches for selecting individuals for treatment.

Accordingly, a method of selecting an individual with cancer may comprise two or more of:
(a) determining the expression levels of PDGFRA and FGFR1 as 'high' (Hi) or 'low'(Lo) in a sample of cancer cells from the individual, and selecting an individual for treatment if they have expression levels of PDGFRA/FGFR1 that are not PDGFRA-Hi/FGFR1-Lo (e.g. PDGFRA-Hi/FGFR1-Hi, PDGFRA-Lo/FGFR1-Lo, or PDGFRA-Lo/FGFR1-Hi expression levels);
(b) determining the mutation status of TP53 in a sample of cancer cells from the individual and selecting an individual for treatment if they have wildtype TP53; and
(c) determining the expression levels of 5, 10, 20, 30, 40, 50, 60, 70, 80, 90, 100, 110, 115, 120 or more of the genes in List 1 in a sample of cancer cells from the individual, and selecting an individual for treatment with the TKI based on the expression levels of those genes.

The method may comprise step (a), and if an individual is selected in step (a), then step (b) may be carried out for the individual, and if the individual is selected in step (b) then step (c) may be carried out. An individual may be selected using all three of steps (a) to (c). In some cases, the method may comprise following the steps of the decision tree classifier depicted in FIG. 5.

A method of selecting an individual with cancer may comprise two or more of:
(a) determining the expression levels of PDGFRA and FGFR1 as 'high' (Hi) or 'low'(Lo) in a sample of cancer cells from the individual, and selecting an individual for treatment if they have PDGFRA-Lo and/or FGFR1-Hi expression levels;
(b) determining the mutation status of TP53 in a sample of cancer cells from the individual and selecting an individual for treatment if they have wildtype TP53; and
(c) determining the expression levels of 5, 10, 20, 30, 40, 50, 60, 70, 80, 90, 100, 110, 115, 120 or more of the genes in List 1 in a sample of cancer cells from the individual, and selecting an individual for treatment with the TKI based on the expression levels of those genes.

The method may comprise step (a), and if an individual is selected in step (a), then step (b) may be carried out for the individual, and if the individual is selected in step (b) then step (c) may be carried out. An individual may be selected using all three of steps (a) to (c). In some cases, the method may comprise following the steps of the decision tree classifier depicted in FIG. 5.

A method of selecting an individual with cancer may comprise two or more of:
(a) determining the expression levels of PDGFRA and FGFR1 as 'high' (Hi) or 'low'(Lo) in a sample of cancer cells from the individual, and selecting an individual for treatment if they have do not have PDGFRA-Hi and FGFR1-Lo expression levels;
(b) determining the mutation status of TP53 in a sample of cancer cells from the individual and selecting an individual for treatment if they have wildtype TP53; and
(c) determining the expression levels of 5, 10, 20, 30, 40, 50, 60, 70, 80, 90, 100, 110, 115, 120 or more of the genes in List 1 in a sample of cancer cells from the individual, and selecting an individual for treatment with the TKI based on the expression levels of those genes.

The method may comprise step (a), and if an individual is selected in step (a), then step (b) may be carried out for the individual, and if the individual is selected in step (b) then step (c) may be carried out. An individual may be selected using all three of steps (a) to (c). In some cases, the method may comprise following the steps of the decision tree classifier depicted in FIG. 5.

Any of the methods may comprise the step of obtaining a sample (e.g. a sample of cancer cells) from the individual. In other words the methods may involve the step of obtaining a sample of cancer cells from the individual before the determining step.

Methods of treatment and therapeutic uses are also contemplated.

In addition to aspects described above, the inventors have developed a gene signature for stratification of patients with differential responses to TKIs (e.g pazopanib). In place of determining the expression levels of PDGFRA and FGFR1 as 'high' (Hi) or 'low'(Lo) in a sample of cancer cells from the individual, in any of the aspects above, a 42 gene signature has been developed which characterises patients that have intrinsic resistance to a TKI as defined by the PDGFRA-high/FGFR1-low IHC status. In other words, instead of determining the expression levels of PDGFRA and FGFR1 as 'high' (Hi) or 'low' (Lo), the expression levels of 42 genes in table 5, may be used to classify/stratify the patients in all of the aspects described above.

Accordingly, in a second aspect of the invention, a patient may be selected for treatment with a TKI (e.g. pazopanib) based on the expression levels of these genes. For example an individual may be selected for treatment if the expression levels resemble, for example closely resemble those of a subgroup with favourable TKI outcome. In particular, an individual may be selected for treatment if the expression levels of the 42 genes, or a centroid derived from the expression of those genes more closely matches the 'other' centroid as shown in table 7. This centroid is representative of cancers having not having PDGFRA-Hi/FGFR1-Lo expression, for example, having PDGFRA-Lo and/or FGFR1-Hi expression, for example having PDGFRA-Hi/FGFR1-Hi, PDGFRA-Lo/FGFR1-Lo, or PDGFRA-Lo/FGFR1-Hi expression.

An individual may be "deselected" for treatment with TKIs (for example selected as more appropriately treated with an alternative therapy choice, such as in one example an anti-PDGFRA antibody (e.g. olaratumab), binding fragment thereof or a pharmaceutical composition comprising said antibody or said binding fragment), based on the expression levels of the 42 marker genes shown in table 5. In particular, an individual may be deselected for treatment (or selected for alternative treatment) if the expression levels of the 42 genes, or a centroid derived from the expression of those genes more closely matches the 'PDGFRA-Hi/FGFR1-Lo' centroid as shown in table 7. This centroid is representative of cancers having PDGFRA-Hi/FGFR1-Lo expression.

The comparison with a centroid may be carried out using nearest centroid single sample classification. This takes the gene expression profile of a new sample, and compares it to each of these class centroids and assigns a sample to a subtype based on the nearest centroid. Subgroup prediction is done by calculating the Spearman's rank correlation of each test case to the two centroids, and assigning a sample to a subtype based on closest Eucleadian distance (1-Spearman Correlation) the nearest centroid. Accordingly, Spearman's rank correlation may be used to calculate the distance to a centroid. Similar statistical tests to compare similarity are also known to the skilled person.

The expression levels may be determined in a sample of cancer cells from a patient. Accordingly, the methods of selecting an individual with cancer for treatment with a TKI may comprise determining, within a sample of cancer cells from the individual, the expression levels of 5 or more of the genes selected from table 5, and selecting an individual for treatment with the TKI based on the expression levels of those genes. Alternatively, an individual may be "deselected" from treatment with TKIs, or selected for treatment with an alternative therapy based on the expression levels of those genes. For example an individual be deselected from treatment with a TKI or selected for treatment with an alternative therapy if the expression levels resemble those of a subgroup with intrinsic resistance, or resemble those of a subgroup which have PDGFRA-hi/FGFR1-lo expression.

Accordingly, the invention provides a method of selecting an individual with cancer for treatment with a TKI, the method comprising:
(a) determining the expression levels in a sample of cancer cells from the individual of 20 or more of the genes selected from table 5, and
(b) selecting an individual for treatment with the TKI based on the expression levels of those genes.

The expression levels of said 20 or more of the genes determined in said step (a) may be compared with:
(i) at least a first reference centroid corresponding to the expression profile of said 20 or more genes determined in a first group of subjects known to have PDGFRA-Hi/FGFR1-Lo expression; and
(ii) at least a second reference centroid corresponding to the expression profile of said 20 or more genes determined in a second group of subjects known not to have PDGFRA-Hi/FGFR1-Lo expression (for example, having PDGFRA-Lo and/or FGFR1-Hi expression, for example having any of PDGFRA-Hi/FGFR1-Hi, PDGFRA-Lo/FGFR1-Lo, or PDGFRA-Lo/FGFR1-Hi expression),
wherein the individual is selected for treatment with the TKI in step (b) when the expression levels determined in said step (a) of the 20 or more genes are a closer match to said second reference centroid than said first reference centroid.

In some embodiments, at least about 20 of the genes listed in table 5 are used. In other embodiments, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or all 42 of the genes listed in table 5 are used. For example, at least 20, 25, 30, 35, 40 or all of the genes listed in table 5 are used.

Where fewer than all 42 genes are used, comparison to the centroid shown in table 7 is done using the centroid values shown for the genes used.

As described in detail herein, the 42 genes listed in table 5 were identified using the Classification of Nearest Centroid (CLANC) methodology. Without wishing to be bound by any particular theory, the present inventors believe that it is the combination of at least 35 of, 40 of, or even substantially all of, the genes listed in table 5 that affords the most accurate classification of patients to the PDGFRA-Hi/FGFR1-Lo or 'other' subtype, and thus prognostication of outcome or therapeutic response to treatment.

Accordingly, the invention provides a method of selecting an individual with cancer for treatment with a TKI, the method comprising:
(a) determining the expression levels in a sample of cancer cells from the individual of 20 or more of the genes selected from table 5, and
(b) selecting an individual for treatment with the TKI based if the expression levels determined in said step (a) of the 20 or more genes are a closer match to the 'other' centroid in table 7, than the PDGFRA-Hi/FGFR1-Lo centroid in table 7.

It will also be understood by one of skill in the art that one subset of the genes listed in table 5 can be used to train an algorithm to predict 'PDGFRA-Hi/FGFR1-Lo' or 'other' subtype or outcome, and another subset of the genes used to characterize an individual subject.

Preferably, all 42 genes are used to train the algorithm, and at least 20, 25, 30, 35, 40 or all 42 of the genes are used to characterize a subject.

The methods may utilize a supervised algorithm to classify future subject samples according to sarcoma biological subtype. A particular exemplary algorithm, referred to herein as the PARSARC classification model, is based on the gene expression profile of a defined subset of genes that has been identified herein as superior for classifying biological subtypes, and for predicting risk of relapse and/or response to therapy in a subject diagnosed with sarcoma. The subset of genes is provided in table 5.

Accordingly, the methods may further comprise the step of comparing the expression levels of genes in the sample as determined, to the expression levels of the same genes in a group of patients known to have PDGFRA-Hi/FGFR1-Hi, PDGFRA-Lo/FGFR1-Lo, or PDGFRA-Lo/FGFR1-Hi expression, and to the expression levels of the same genes in a group of patients known not to have PDGFRA-Hi/FGFR1-Lo expression (for example, having PDGFRA-Lo and/or FGFR1-Hi expression, for example having PDGFRA-Hi/FGFR1-Lo expression. The group of patients has cancer (preferably, the same type of cancer as the individual). In particular, centroids derived from the expression levels of the genes may be used for the comparison.

An individual may be selected for treatment with the TKI if the expression levels of the genes determined are more similar to the group of individuals which are known not to have PDGFRA-Hi/FGFR1-Lo expression (for example, having PDGFRA-Lo and/or FGFR1-Hi expression, for example having PDGFRA-Hi/FGFR1-Hi, PDGFRA-Lo/FGFR1-Lo, or PDGFRA-Lo/FGFR1-Hi expression.

The gene expression levels discussed above, can be used in place of determining PDGFRA and FGFR1 expression in any of the aspects described herein. For example, the methods of the invention may involve one, two or all three of:
(a) determining the expression levels of at least 20, 25, 30, 35, 40 or all 42 of the genes listed in table 5 in a sample of cancer cells from the individual, and selecting an individual for treatment based on the expression levels of those genes;
(b) determining the mutation status of TP53 in a sample of cancer cells from the individual and selecting an individual for treatment if they have wildtype TP53; and
(c) determining the expression levels of 5, 10, 20, 30, 40, 50, 60, 70, 80, 90, 100, 110, 115, 120 or more of the genes in List 1 in a sample of cancer cells from the individual, and selecting an individual for treatment with the TKI based on the expression levels of those genes.

The method may comprise step (a), and if an individual is selected in step (a), then step (b) may be carried out for the individual, and if the individual is selected in step (b) then step (c) may be carried out. An individual may be selected using all three of steps (a) to (c). In some cases, the method may comprise following the steps of the decision tree classifier depicted in FIG. 5.

Although the expression levels of the genes shown in table 5 may be used in the context of the decision tree, it may be preferable to use the expression levels of these genes (or a sub-group thereof) alone, in order to select individuals for treatment or provide a prognosis in accordance with the invention.

Any of the methods may comprise the step of obtaining a sample (e.g. a sample of cancer cells) from the individual. In other words the methods may involve the step of obtaining a sample of cancer cells from the individual before the determining step.

In addition to aspects described above, the inventors have developed a gene signature for stratification of patients into the distinct subtypes that were distinguished between using the decision tree, without the need to apply the decision tree workflow.

In particular, a gene signature using 225 genes shown in table 4 has been developed which distinguish between 5 groups which correspond to the outcomes of the decision tree as follows:
1) PDGFRA-high/FGFR1-low (shown in table 6 as IHC+)
2) TP53 mutated and not PDGFRA-Hi/FGFR1-Lo (e.g. having PDGFRA-Lo and/or FGFR1-Hi expression, for example having PDGFRA-Hi/FGFR1-Hi, PDGFRA-Lo/FGFR1-Lo, or PDGFRA-Lo/FGFR1-Hi) (shown in table 6 as TP53)
3) Subgroup A gene expression (using genes from List 1), TP53 wildtype and not PDGFRA-Hi/FGFR1-Lo (e.g. having PDGFRA-Lo and/or FGFR1-Hi expression, for example having PDGFRA-Hi/FGFR1-Hi, PDGFRA-Lo/FGFR1-Lo, or PDGFRA-Lo/FGFR1-Hi) (shown in table 6 as A)
4) Subgroup B gene expression (using genes from List 1), TP53 wildtype and PDGFRA-Hi/FGFR1-Hi, PDGFRA-Lo/FGFR1-Lo, or PDGFRA-Lo/FGFR1-Hi (shown in table 6 as B)
5) Subgroup C gene expression (using genes from List 1), TP53 wildtype and not PDGFRA-Hi/FGFR1-Lo (e.g. having PDGFRA-Lo and/or FGFR1-Hi expression, for example having PDGFRA-Hi/FGFR1-Hi, PDGFRA-Lo/FGFR1-Lo, or PDGFRA-Lo/FGFR1-Hi) (shown in table 6 as C)

In the above descriptions, 'Subgroup A gene expression' may refer to cancer with a gene expression levels having a closer match to the centroid of subgroup A shown in table 3 than subgroups B or C. 'Subgroup B gene expression' may refer to cancer with a gene expression levels having a closer match to the centroid of subgroup A shown in table 3 than subgroups A or C. 'Subgroup C gene expression' may refer to cancer with a gene expression levels having a closer match to the centroid of subgroup C shown in table 3 than subgroups A or B.

Accordingly, the 225 genes in table 4 (or a sub-group thereof) may be used to stratify patients into one of 5 groups, which correspond to the output of the decision tree. Similarly to the output of the decision tree, this stratification may be used to select an individual for treatment with a TKI (or for an alternative treatment), or to provide a prognosis.

Accordingly, in a third aspect the invention provides a method of selecting an individual for treatment with a TKI, the method comprising:
(a) determining the expression levels in a sample of cancer cells from the individual of 40 or more of the genes selected from table 4, and
(b) selecting an individual for treatment with the TKI based on the expression levels of those genes.

At least 40, at least 45, at least 50, at least 6, at least 70, at least 80, at least 90, at least 100, at least 110, at least 120, at least 130, at least 240, at least 150, at least 160, at least 170, at least 180, at least 190, at least 200, at least 210, at least 220 or all 225 of the genes in table 4 are used. For example substantially all of or all of the genes in table 4 are used.

Accordingly, the invention provides a method of selecting an individual for treatment with a TKI, the method comprising:
(a) determining the expression levels in a sample of cancer cells from the individual of 40 or more of the genes selected from table 4, and
(b) selecting an individual for treatment with the TKI based on the expression levels of those genes,
wherein the individual is selected for treatment with a TKI if the expression levels of the 40 or more of the genes determined in said step (a) are a closer match to the reference centroid 'A(3)' shown in table 6, than any other reference centroid (IHC+(1), TP53(2), B(4), C(5)) shown in table 6.

Similarly, an individual may be "deselected" for treatment with TKIs (for example selected as more appropriately treated with an alternative therapy choice, such as in one example an anti-PDGFRA antibody (e.g. olaratumab), binding fragment thereof or a pharmaceutical composition comprising said antibody or said binding fragment), based on the expression levels of the 225 marker genes shown in table 4, or a sub-group thereof. In particular, an individual may be deselected for treatment (or selected for alternative treatment) if the expression levels of the genes, or a centroid derived from the expression of those genes more closely matches any of the IHC+(1), TP53(2), B(4) or C(5) centroids as shown in table 6, than the A(3) centroid.

The comparison with a centroid may be carried out using nearest centroid single sample classification. This takes the gene expression profile of a new sample, and compares it to each of these class centroids and assigns a sample to a subtype based on the nearest centroid. Subgroup prediction is done by calculating the Spearman's rank correlation of each test case to the two centroids, and assigning a sample to a subtype based on closest Eucleadian distance (1-Spearman Correlation) the nearest centroid. Accordingly, Spearman's rank correlation may be used to calculate the distance to a centroid. Similar statistical tests to compare similarity are also known to the skilled person.

The expression levels may be determined in a sample of cancer cells from a patient. Accordingly, the methods of selecting an individual with cancer for treatment with a TKI may comprise determining, within a sample of cancer cells from the individual, the expression levels of 40 or more of the genes selected from table 4, and selecting an individual for treatment with the TKI based on the expression levels of those genes. Alternatively, an individual may be "deselected" from treatment with TKIs, or selected for treatment with an alternative therapy based on the expression levels of those genes. For example an individual be deselected from treatment with a TKI or selected for treatment with an alternative therapy if the expression levels resemble those of a subgroup with intrinsic resistance, or resemble those of a subgroup which have PDGFRA-hi/FGFR1-lo expression.

Where fewer than all 225 genes are used, comparison to the centroid shown in table 6 is done using the centroid values shown for the genes used.

As described in detail herein, the 225 genes listed in table 4 were identified using the Classification of Nearest Centroid (CLANC) methodology. Without wishing to be bound by any particular theory, the present inventors believe that it is the combination of at least 180 or 200 of, or even substantially all of, the genes listed in table 4 that affords the most accurate classification of patients, and thus prognostication of outcome or therapeutic response to treatment.

It will also be understood by one of skill in the art that one subset of the genes listed in table 4 can be used to train an algorithm to predict subtypes (1) to (5) or outcome, and another subset of the genes used to characterize an individual subject. Preferably, all 225 genes are used to train the algorithm, and at least 40 or more of the genes are used to characterize a subject.

The methods may utilize a supervised algorithm to classify future subject samples according to sarcoma biological subtype. A particular exemplary algorithm, referred to herein as the PARSARC classification model, is based on the gene expression profile of a defined subset of genes that has been identified herein as superior for classifying biological subtypes, and for predicting risk of relapse and/or response to therapy in a subject diagnosed with sarcoma. The subset of genes, is provided in table 4.

Accordingly, the methods may further comprise the step of comparing the expression levels of genes in the sample as determined, to the expression levels of the same genes in a group of patients known to correspond to groups (1)-(5) in the decision tree. The characteristics of these groups are set out above.

In other words, the expression levels of the 40 or more of the genes determined in said step may be compared with:
(i) a first reference centroid corresponding to the expression profile of said 40 or more genes determined in a first group of subjects known to have cancer with PDGFRA-Hi/FGFR1-Lo expression;
(ii) a second reference centroid corresponding to the expression profile of said 40 or more genes determined in a second group of subjects known to have cancer with mutated TP53 and not PDGFRA-Hi/FGFR1-Lo expression (e.g. having PDGFRA-Lo and/or FGFR1-Hi expression, e.g. PDGFRA-Hi/FGFR1-Hi, PDGFRA-Lo/FGFR1-Lo, or PDGFRA-Lo/FGFR1-Hi);
(iii) a third reference centroid corresponding to the expression profile of said 40 or more genes determined in a third group of subjects known to have cancer with (a) a gene expression profile having a closer match to the centroid of subgroup A shown in table 3 than subgroups B or C, and (b) TP53 wild-type, and (c) not PDGFRA-Hi/FGFR1-Lo expression (e.g. having PDGFRA-Lo and/or FGFR1-Hi expression, e.g. PDGFRA-Hi/FGFR1-Hi or PDGFRA-Lo/FGFR1-Lo or PDGFRA-Lo/FGFR1-Hi);
(iv) a fourth reference centroid corresponding to the expression profile of said 40 or more genes determined in a fourth group of subjects known to have cancer with (a) a gene expression profile having a closer match to the centroid of subgroup B shown in table 3 than subgroups A or C, and (b) TP53 wild-type, and (c) not PDGFRA-Hi/FGFR1-Lo expression (e.g. having PDGFRA-Lo and/or FGFR1-Hi expression, e.g. PDGFRA-Hi/FGFR1-Hi or PDGFRA-Lo/FGFR1-Lo or PDGFRA-Lo/FGFR1-Hi); and
(v) a fifth reference centroid corresponding to the expression profile of said 40 or more genes determined in a fifth group of subjects known to have cancer with (a) a gene expression profile having a closer match to the centroid of subgroup C shown in table 3 than subgroups B or C, and (b) TP53 wild-type, and (c) not PDGFRA-Hi/FGFR1-Lo expression (e.g. having PDGFRA-Lo and/or FGFR1-Hi expression, e.g. PDGFRA-Hi/FGFR1-Hi or PDGFRA-Lo/FGFR1-Lo or PDGFRA-Lo/FGFR1-Hi);

wherein the individual is selected for treatment with the TKI when the expression levels of the 40 or more genes determined are a closer match to said third reference centroid than said first, second, fourth or fifth reference centroids.

An individual may be selected for treatment with the TKI if the expression levels of the genes determined are most similar to the group of individuals which are known to be in subgroup (3), that is have (a) subgroup A gene expression, and (b) TP53 wildtype, and (c) not PDGFRA-Hi/FGFR1-Lo expression (e.g. having PDGFRA-Lo and/or FGFR1-Hi expression, e.g. PDGFRA-Hi/FGFR1-Hi or PDGFRA-Lo/FGFR1-Lo or PDGFRA-Lo/FGFR1-Hi).

An individual may be selected for treatment if the expression levels of at least 40 of the 225 genes in table 4 in the sample are determined to be similar to, or to resemble, or have the closest match to the expression levels of the same genes (for example as represented by a centroid) in a group of patients known to respond well to TKI treatment, wherein the group of patients has cancer (preferably, the same type of cancer as the individual). In other words the patients in the group all have cancer.

An individual may be deselected from treatment with a TKI if the expression levels of at least 40 of the 225 genes in table 4 in the sample are determined to be similar to, or to resemble, or have the closest match to the expression levels of the same genes (for example as represented by a centroid) in a group of patients known to respond poorly to TKI treatment, wherein the group of patients has cancer (preferably the same type of cancer as the individual).

The gene expression levels discussed above, can be used in place of the decision tree or in place of combinations of the tests for stratifying patients.

Any of the methods may comprise the step of obtaining a sample (e.g. a sample of cancer cells) from the individual. In other words the methods may involve the step of obtaining a sample of cancer cells from the individual before the determining step.

Any of these selection methods may be used to inform treatment choices, in the methods of treatment disclosed herein.

The methods described above may be described as methods of detecting inherent resistance to a TKI in a cancer in an individual. In these methods, the same determining and optionally comparing steps may be carried our as in the methods of selection. In place of step (b) selecting an individual for treatment, the methods of detecting inherent resistance to a TKI comprise step (b) identifying a cancer as having inherent resistance to a TKI.

A cancer is identified as having inherent resistance if it would not be selected for treatment according to the methods described herein.

For example: (1) if the cancer has one or more of:
(a) PDGFRA-Hi/FGFR1-Lo expression levels, or gene expression levels that match the PDGFRA-Hi/FGFR1-Lo centroid in table 6 or 7;
(b) mutated TP53
(c) the expression levels of 5 or more of the genes in List 1 are determined to be similar to the expression levels of the same genes in a group of patients known to respond poorly to TKI treatment, wherein the group of patients has cancer, preferably the same type of cancer as the individual;
or (2) the gene expression levels of 40 or more of the genes in table 4 are determined to more closely match the expression levels of the same genes in a group of patients known to respond poorly to TKI treatment, wherein the group of patients has cancer, preferably the same type of cancer as the individual. In particular inherent resistance is identified, when the gene expression levels of 40 or more of the genes in table 4 are determined to more closely match the centroids 1, 2, 4 or 5 shown in table 6 than the centroid 3 shown in table 6.

In a fourth aspect the invention provides a tyrosine kinase inhibitor for use in a method of treating cancer in an individual, wherein the individual has been selected for treatment according to the method of the first, second or third aspects of the invention.

In particular, the invention provides a tyrosine kinase inhibitor (TKI) for use in a method of treating cancer in an individual, said method comprising:
(i) performing the method of the first aspect of the invention on at least one sample obtained from the individual, wherein the individual is identified as having a cancer having one or more of:
(a) expression levels of PDGFRA/FGFR1 that are not PDGFRA-Hi/FGFR1-Lo (e.g. PDGFRA-Hi/FGFR1-Hi, PDGFRA-Lo/FGFR1-Lo, or PDGFRA-Lo/FGFR1-Hi expression levels);
(b) wildtype TP53; and
(c) expression levels of 5, 10, 20, 30, 40, 50, 60, 70, 80, 90, 100, 110, 115, 120 or more of the genes in List 1 similar to the expression levels of the same genes in a group of patients known to respond well to TKI treatment, wherein the group of patients has cancer, preferably the same type of cancer as the individual; and
(ii) administering the TKI to said individual.

In particular, the invention provides a tyrosine kinase inhibitor (TKI) for use in a method of treating cancer in an individual, said method comprising:
(i) performing the method of the second aspect of the invention on at least one sample obtained from the individual, wherein the individual is identified as having a cancer having expression levels of 20 or more of the genes in table 5 a closer match to a second reference centroid corresponding to the expression profile of said 20 or more genes determined in a second group of subjects known not to have PDGFRA-Hi/FGFR1-Lo expression than said first reference centroid corresponding the expression profile of said 20 or more genes determined in a first group of subjects known to have PDGFRA-Hi/FGFR1-Lo expression; and
(ii) administering the TKI to said individual.

In particular, the invention provides a tyrosine kinase inhibitor (TKI) for use in a method of treating cancer in an individual, said method comprising:
(i) performing the method of the third aspect of the invention on at least one sample obtained from the individual, wherein the individual is identified as having a cancer having the expression levels of the 40 or more genes in table 4 a closer match to a third reference centroid than said first, second, fourth or fifth reference centroids, wherein the reference centroids are:
(a) a first reference centroid corresponding to the expression profile of said 40 or more genes determined in a first group of subjects known to have cancer with PDGFRA-Hi/FGFR1-Lo expression;
(b) a second reference centroid corresponding to the expression profile of said 40 or more genes determined in a second group of subjects known to have cancer with mutated TP53 and not PDGFRA-Hi/FGFR1-Lo expression;

(c) a third reference centroid corresponding to the expression profile of said 40 or more genes determined in a third group of subjects known to have cancer with (a) a gene expression profile having a closer match to the centroid of subgroup A shown in table 3 than subgroups B or C, and (b) TP53 wild-type, and (c) not PDGFRA-Hi/FGFR1-Lo expression;

(d) a fourth reference centroid corresponding to the expression profile of said 40 or more genes determined in a fourth group of subjects known to have cancer with (a) a gene expression profile having a closer match to the centroid of subgroup B shown in table 3 than subgroups A or C, and (b) TP53 wild-type, and (c) not PDGFRA-Hi/FGFR1-Lo expression; and (e) a fifth reference centroid corresponding to the expression profile of said 40 or more genes determined in a fifth group of subjects known to have cancer with (a) a gene expression profile having a closer match to the centroid of subgroup C shown in table 3 than subgroups B or C, and (b) TP53 wild-type, and (c) not PDGFRA-Hi/FGFR1-Lo expression; and (ii) administering the TKI to said individual.

In a fifth aspect, the invention provides a method of treating cancer with a TKI in an individual in need thereof, wherein the individual has been selected for treatment according to the method of the first, second or third aspects of the invention.

In particular, the method may comprise:
(i) performing the method of the first aspect of the invention, wherein the individual is identified as having a cancer having one or more of:
(a) PDGFRA-Hi/FGFR1-Hi, PDGFRA-Lo/FGFR1-Lo, or PDGFRA-Lo/FGFR1-Hi expression levels;
(b) wildtype TP53; and
(c) expression levels of 5, 10, 20, 30, 40, 50, 60, 70, 80, 90, 100, 110, 115, 120 or more of the genes in List 1 similar to the expression levels of the same genes in a group of patients known to respond well to TKI treatment, wherein the group of patients has cancer, preferably the same type of cancer as the individual; and (ii) administering a therapeutically effective amount of a TKI to said individual.

In particular, the method may comprise:
(i) performing the method of the second aspect of the invention on at least one sample obtained from the individual, wherein the individual is identified as having a cancer having expression levels of 20 or more of the genes in table 5 a closer match to a second reference centroid corresponding to the expression profile of said 20 or more genes determined in a second group of subjects known not to have PDGFRA-Hi/FGFR1-Lo expression than said first reference centroid corresponding the expression profile of said 20 or more genes determined in a first group of subjects known to have PDGFRA-Hi/FGFR1-Lo expression; and (ii) administering a therapeutically effective amount of a TKI to said individual.

In particular, the method may comprise:
(i) performing the method of the third aspect of the invention on at least one sample obtained from the individual, wherein the individual is identified as having a cancer having the expression levels of the 40 or more genes in table 4 a closer match to a third reference centroid than said first, second, fourth or fifth reference centroids, wherein the reference centroids are:

(a) a first reference centroid corresponding to the expression profile of said 40 or more genes determined in a first group of subjects known to have cancer with PDGFRA-Hi/FGFR1-Lo expression;

(b) a second reference centroid corresponding to the expression profile of said 40 or more genes determined in a second group of subjects known to have cancer with mutated TP53 and not PDGFRA-Hi/FGFR1-Lo expression;

(c) a third reference centroid corresponding to the expression profile of said 40 or more genes determined in a third group of subjects known to have cancer with (a) a gene expression profile having a closer match to the centroid of subgroup A shown in table 3 than subgroups B or C, and (b) TP53 wild-type, and (c) not PDGFRA-Hi/FGFR1-Lo expression;

(d) a fourth reference centroid corresponding to the expression profile of said 40 or more genes determined in a fourth group of subjects known to have cancer with (a) a gene expression profile having a closer match to the centroid of subgroup B shown in table 3 than subgroups A or C, and (b) TP53 wild-type, and (c) not PDGFRA-Hi/FGFR1-Lo expression; and (e) a fifth reference centroid corresponding to the expression profile of said 40 or more genes determined in a fifth group of subjects known to have cancer with (a) a gene expression profile having a closer match to the centroid of subgroup C shown in table 3 than subgroups B or C, and (b) TP53 wild-type, and (c) not PDGFRA-Hi/FGFR1-Lo expression; and (ii) administering a therapeutically effective amount of a TKI to said individual.

In a sixth aspect, the present invention provides use of a TKI in the manufacture of a medicament for treating cancer in an individual, wherein the individual has been selected for treatment according to the method of the first, second or third aspects of the invention. In particular, the use may comprise use of a TKI in the manufacture of a medicament for use in a method of the fifth aspect of the invention.

According to any one of the aspects of the invention the cancer may be selected from: soft tissues sarcoma (STS), metastatic renal cell carcinomas (mRCC), gastrointestinal stromal tumour (GIST), hepatocellular carcinoma (HCC), neuroendocrine tumour (NET), medullary thyroid cancer (MTC), non-squamous non-small cell lung cancer (non-squamous NSCLC), and chronic myeloid leukaemia (CML). In particular the cancer may be STS. In particular the cancer may be advanced STS. The cancer in the individual and in the groups of patients for whom the TKI response is known may be selected from these cancer types.

As described in detail herein, particular biomarker signatures identified herein are predictive of treatment outcomes for pazopanib therapy. The present inventors believe that the methods and kits of the present invention are similarly predictive of treatment outcomes with other TKIs, and without wishing to be bound by any particular theory, the inventors believe that, in particular, TKIs having similar pharmacological action in terms of kinases targeted will be especially applicable to the present invention. Based on an analysis of overlapping molecular targets shared by pazopanib, regorafenib and sorafenib (see FIG. 6), TKIs (either presently known or to be discovered) that inhibit at least two targets from the following list do or will find use in accordance with the present invention:

BRAF
CSF1R
DDR1
DDR2
FGFR1
FGFR2
FGFR3
FLT1
FLT4
FRK
KDR
KIT
LCK
LYN
MAP2K6
NTRK1
PDGFRA
PDGFRB
RAF1
RET
TEK

In particular, according to any of the aspects of the invention the TKI may be selected from: Pazopanib, Regorafenib, Sorafenib, Sunitinib, Lenvatinib, Axitinib, Nintedanib, and Ponatinib, and pharmaceutically acceptable salts thereof. In particular, the TKI may be Pazopanib. While any pharmaceutically acceptable salt is contemplated herein, particular examples of salt forms of TKIs, which are contemplated in accordance with the present invention, include:

Pazopanib
  hydrochloride
  5-(4-chloropyrimidin-2ylamino)-2-methylbenzene-sulfonamide
  N,2,3-trimethyl-2H-indazol-6-amine
Regorafenib
  Isethionate
  Ethylsulfonate
  Hydrochloride
  Mesylate
  Phenylsulfonate
Sunitinib
  Hydrochloride
  Malate
  Fumurate
  D-tartrate
  L-tartrate
  Citrate
Lenvatinib
  Mesylate (main form)
  P-toluenesulfonate
Nindetanib
  Esiliate (main form)
Pontanib
  Hydrochloride In particular, the TKI is Pazopanib or a pharmaceutically acceptable salt thereof and the cancer is soft tissue sarcoma, for example advanced STS.

In a seventh aspect, the invention provides a kit for use in identifying a cancer suitable for treatment with a TKI. In line with the first aspects of the invention, the kit may have reagents, probes and/or instructions for detecting at least one of:
  (a) the expression levels of PDGFRA and FGFR1;
  (b) the mutation status of TP53; and
  (c) the expression levels of 5 or more of the genes in List 1.

For example, the kit may have probes for detecting the expression levels of 5 or more, 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1.

The kit may also have probes for detecting the expression levels of PDGFRA and FGFR1. The kit may also have probes for detecting the mutation status of TP53.

In some cases in accordance with the seventh aspect of the present invention, the kit takes the form of a companion diagnostic comprising:
  (i) said reagents, probes and/or instructions for detecting at least one of:
    (a) the expression levels of PDGFRA and FGFR1;
    (b) the mutation status of TP53; and
    (c) the expression levels of 5 or more of the genes in List 1; and
  (ii) a TKI or a pharmaceutical composition or dosage form comprising a TKI. The companion diagnostic may comprise (i) and (ii) in a single package or in separate or associated packages.

In line with the second aspect of the invention, the kit may have reagents, probes and/or instructions for detecting the expression levels of at least 20 of the genes in table 5, and optionally: (a) the mutation status of TP53; and (b) the expression levels of 5 or more of the genes in List 1.

For example, the kit may have probes for detecting the expression levels of at least about 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or all 42 of the genes listed in table 5.

The kit may also have probes for detecting the mutation status of TP53. The kit may have probes for detecting the expression levels of 5 or more, 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1.

In some cases in accordance with the seventh aspect of the present invention, the kit takes the form of a companion diagnostic comprising:
  (i) said reagents, probes and/or instructions for detecting the expression levels of at least 20 of the genes in table 5, and optionally: (a) the mutation status of TP53; and (b) the expression levels of 5 or more of the genes in List 1;
  (ii) a TKI or a pharmaceutical composition or dosage form comprising a TKI.

The companion diagnostic may comprise (i) and (ii) in a single package or in separate or associated packages.

In line with the third aspect of the invention, the kit may have reagents, probes and/or instructions for detecting the expression levels of at least 40 of the genes in table 4.

For example, the kit may have probes for detecting the expression levels of at least 40, at least 45, at least 50, at least 60, at least 70, at least 80, at least 90, at least 100, at least 110, at least 120, at least 130, at least 240, at least 150, at least 160, at least 170, at least 180, at least 190, at least 200, at least 210, at least 220 or all 225 of the genes in table 4.

In some cases in accordance with the seventh aspect of the present invention, the kit takes the form of a companion diagnostic comprising:
(i) said reagents, probes and/or instructions for detecting the expression levels of at least 40 of the genes in table 4; and
(ii) a TKI or a pharmaceutical composition or dosage form comprising a TKI.

The companion diagnostic may comprise (i) and (ii) in a single package or in separate or associated packages.

In an eighth aspect, the invention provides a method of determining a prognosis of TKI treatment response in an individual.

In line with the first aspect of the invention, the method may comprise one or more of:
(a) determining the expression levels of PDGFRA and FGFR1 as 'high' (Hi) or 'low'(Lo) in a sample of cancer cells from the individual;
(b) determining the mutation status of TP53 in a sample of cancer cells from the individual; and
(c) determining the expression levels of 5 or more 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1 in a sample of cancer cells from the individual.

An individual may be determined to have a good prognosis following TKI treatment if they have one or more of:
(a) expression levels of PDGFRA/FGFR1 that are not PDGFRA-Hi/FGFR1-Lo (e.g. PDGFRA-Hi/FGFR1-Hi, PDGFRA-Lo/FGFR1-Lo, or PDGFRA-Lo/FGFR1-Hi expression levels);
(b) wildtype TP53
(c) the expression levels of genes in the sample are determined to be similar to the expression levels of the same genes in a group of patients known to respond well to TKI treatment, wherein the group of patients has cancer, preferably the same type of cancer as the individual.

The individual may be determined to have a good prognosis if they meet all of the criteria or (a), (b) and (c) for which they were tested. In other words, an individual may not have a good prognosis if they do not meet any one of the criteria for which they are tested.

An individual may be determined to have a poor prognosis if they have one or more of:
(a) PDGFRA-Hi/FGFR1-Lo expression levels;
(b) mutated TP53
(c) the expression levels of 5 or more 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1 genes in the sample are determined to be similar to the expression levels of the same genes in a group of patients known to respond poorly to TKI treatment, wherein the group of patients has cancer, preferably the same type of cancer as the individual.

In line with the second aspect of the invention, the method may comprise determining the expression levels of 20 or more genes from table 5, and optionally:
(i) determining the mutation status of TP53 in a sample of cancer cells from the individual; and
(ii) determining the expression levels of 5 or more 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1 in a sample of cancer cells from the individual.

An individual may be determined to have a good prognosis following TKI treatment if they have a cancer having expression levels of 20 or more of the genes in table 5 a closer match to a second reference centroid corresponding to the expression profile of said 20 or more genes determined in a second group of subjects known not to have PDGFRA-Hi/FGFR1-Lo expression, than a first reference centroid corresponding to the expression profile of said 20 or more genes determined in a first group of subjects known to have PDGFRA-Hi/FGFR1-Lo expression, and optionally:
(i) wildtype TP53; and
(ii) the expression levels of genes in the sample are determined to be similar to the expression levels of the same genes in a group of patients known to respond well to TKI treatment, wherein the group of patients has cancer, preferably the same type of cancer as the individual.

An individual may be determined to have a poor prognosis if they have a cancer having expression levels of 20 or more of the genes in table 5 a closer match to a first reference centroid corresponding to the expression profile of said 20 or more genes determined in a first group of subjects known to have PDGFRA-Hi/FGFR1-Lo expression, than a second reference centroid corresponding to the expression profile of said 20 or more genes determined in a second group of subjects known not to have PDGFRA-Hi/FGFR1-Lo expression.

In line with the third aspect of the invention, the method may comprise determining the expression levels of 40 or more genes from table 4.

An individual may be determined to have a good prognosis following TKI treatment if they have a cancer having the expression levels of the 40 or more genes in table 4 a closer match to a third reference centroid than said first, second, fourth or fifth reference centroids, wherein the reference centroids are:
(a) a first reference centroid corresponding to the expression profile of said 40 or more genes determined in a first group of subjects known to have cancer with PDGFRA-Hi/FGFR1-Lo expression;
(b) a second reference centroid corresponding to the expression profile of said 40 or more genes determined in a second group of subjects known to have cancer with mutated TP53 and not PDGFRA-Hi/FGFR1-Lo expression;
(c) a third reference centroid corresponding to the expression profile of said 40 or more genes determined in a third group of subjects known to have cancer with (a) a gene expression profile having a closer match to the centroid of subgroup A shown in table 3 than subgroups B or C, and (b) TP53 wild-type, and (c) not PDGFRA-Hi/FGFR1-Lo expression;
(d) a fourth reference centroid corresponding to the expression profile of said 40 or more genes determined in a fourth group of subjects known to have cancer with (a) a gene expression profile having a closer match to the centroid of subgroup B shown in table 3 than subgroups A or C, and (b) TP53 wild-type, and (c) not PDGFRA-Hi/FGFR1-Lo expression; and (e) a fifth reference centroid corresponding to the expression profile of said 40 or more genes determined in a fifth group of subjects known to have cancer with (a) a gene expression profile having a closer match to the centroid of subgroup C shown in table 3 than subgroups B or C, and (b) TP53 wild-type, and (c) not PDGFRA-Hi/FGFR1-Lo expression.

An individual may be determined to have a poor prognosis if they have a cancer having the expression levels of the 40 or more genes in table 4 a closer match to a first, second, fourth or fifth reference centroid than a third reference centroids, wherein the reference centroids are:

(a) a first reference centroid corresponding to the expression profile of said 40 or more genes determined in a first group of subjects known to have cancer with PDGFRA-Hi/FGFR1-Lo expression;

(b) a second reference centroid corresponding to the expression profile of said 40 or more genes determined in a second group of subjects known to have cancer with mutated TP53 and not PDGFRA-Hi/FGFR1-Lo expression;

(c) a third reference centroid corresponding to the expression profile of said 40 or more genes determined in a third group of subjects known to have cancer with (a) a gene expression profile having a closer match to the centroid of subgroup A shown in table 3 than subgroups B or C, and (b) TP53 wild-type, and (c) not PDGFRA-Hi/FGFR1-Lo expression;

(d) a fourth reference centroid corresponding to the expression profile of said 40 or more genes determined in a fourth group of subjects known to have cancer with (a) a gene expression profile having a closer match to the centroid of subgroup B shown in table 3 than subgroups A or C, and (b) TP53 wild-type, and (c) not PDGFRA-Hi/FGFR1-Lo expression; and (e) a fifth reference centroid corresponding to the expression profile of said 40 or more genes determined in a fifth group of subjects known to have cancer with (a) a gene expression profile having a closer match to the centroid of subgroup C shown in table 3 than subgroups B or C, and (b) TP53 wild-type, and (c) not PDGFRA-Hi/FGFR1-Lo expression.

In a ninth aspect, the present invention provides an anti-PDGFRA antibody, binding fragment thereof or a pharmaceutical composition comprising said antibody or said binding fragment for use in a method of treating cancer in an individual who has not been selected for treatment with a TKI according to the first, second or third aspects of the invention.

In line with the first aspect of the invention, the individual may have been selected as having one or more of:
(a) PDGFRA-Hi/FGFR1-Lo expression levels;
(b) mutated TP53
(c) the expression levels of 5 or more 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1 genes in the sample are determined to be similar to the expression levels of the same genes in a group of patients known to respond poorly to a TKI, wherein the group of patients has cancer (for example, the same type of cancer as the individual). In particular, the anti-PDGFRA antibody, binding fragment thereof or a pharmaceutical composition may be for use in a method comprising:

(i) performing the method of the eighth aspect of the invention on at least one sample obtained from the individual, wherein the individual is identified as having a cancer having one or more of
(a) PDGFRA-Hi/FGFR1-Lo expression levels;
(b) mutated TP53
(c) the expression levels of 5 or more 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1 genes in the sample are determined to be similar to the expression levels of the same genes in a group of patients known to respond poorly to a TKI, wherein the group of patients has cancer (preferably the same type of cancer as the individual); and (ii) administering a therapeutically effective amount of said anti-PDGFRA antibody, said binding fragment thereof or said pharmaceutical composition.

In certain embodiments, the anti-PDGFRA antibody may comprise olaratumab.

In line with the second aspect of the invention, the individual may have been selected if they have a cancer having expression levels of 20 or more of the genes in table 5 a closer match to a first reference centroid corresponding to the expression profile of said 20 or more genes determined in a first group of subjects known to have PDGFRA-Hi/FGFR1-Lo expression, than a second reference centroid corresponding to the expression profile of said 20 or more genes determined in a second group of subjects known not to have PDGFRA-Hi/FGFR1-Lo expression.

In line with the third aspect of the invention, the individual may have been selected if they have a cancer having the expression levels of the 40 or more genes in table 4 a closer match to a first, second, fourth or fifth reference centroid than a third reference centroids, wherein the reference centroids are:

(a) a first reference centroid corresponding to the expression profile of said 40 or more genes determined in a first group of subjects known to have cancer with PDGFRA-Hi/FGFR1-Lo expression;

(b) a second reference centroid corresponding to the expression profile of said 40 or more genes determined in a second group of subjects known to have cancer with mutated TP53 and not PDGFRA-Hi/FGFR1-Lo expression;

(c) a third reference centroid corresponding to the expression profile of said 40 or more genes determined in a third group of subjects known to have cancer with (a) a gene expression profile having a closer match to the centroid of subgroup A shown in table 3 than subgroups B or C, and (b) TP53 wild-type, and (c) not PDGFRA-Hi/FGFR1-Lo expression;

(d) a fourth reference centroid corresponding to the expression profile of said 40 or more genes determined in a fourth group of subjects known to have cancer with (a) a gene expression profile having a closer match to the centroid of subgroup B shown in table 3 than subgroups A or C, and (b) TP53 wild-type, and (c) not PDGFRA-Hi/FGFR1-Lo expression; and (e) a fifth reference centroid corresponding to the expression profile of said 40 or more genes determined in a fifth group of subjects known to have cancer with (a) a gene expression profile having a closer match to the centroid of subgroup C shown in table 3 than subgroups B or C, and (b) TP53 wild-type, and (c) not PDGFRA-Hi/FGFR1-Lo expression.

In certain embodiments, the anti-PDGFRA antibody may comprise olaratumab.

The markers, methods of measuring them, cancers, tyrosine kinase inhibitors and other details of the invention are described below.

These details are applicable to all of the aspects of the invention.

Markers

In the context of the present invention the 'markers' or 'biomarkers' allow stratification of cancers based on their association with a patient outcome. The biomarkers may include expression level of particular genes, expression levels of particular proteins and mutational status of particular genes.

The markers may be detected by conventional means in a sample containing cancer cells or cancer cell material or components (e.g. nucleic acids and/or proteins), obtained from an individual. Accordingly, the methods and uses disclosed herein may involve the step of determining the presence or absence of, expression level of or mutation status of a biomarker. The methods and uses may base a prognostic or diagnostic decision on the presence or absence of, expression level of or mutation status of a biomarker as already determined. The methods and uses may involve the step of determining the presence or absence of, expression level of or mutation status of a biomarker in a sample of cancer cells obtained from an individual.

In some embodiments the methods may comprise the step of obtaining a sample of cancer cells or cancer cell material or components (e.g. nucleic acids and/or proteins) from an individual. The obtained sample may then be tested as described.

Expression Levels FGFR1 and PDGFRA

The present inventors have found that high levels of PDGFRalpha (herein "PRGFRA", also known as PDGFRa or PDGFRα) and low levels of FGFR1 expression in cancer cells are associated with a worse outcome when treated with a TKI, as compared to other PDGFRA/FGFR1 expression profiles. This expression profile may be described as an "FGFR1-Lo/PDGFRA-Hi", or "PDGFRA-Hi/FGFR1-Lo". In particular patient groups with a PDGFRA-Hi/FGFR1-Lo expression profile have lower overall survival (OS) and progression-free survival (PFS) than other patients.

Cancers with other expression profiles i.e. not PDGFRA-Hi/FGFR1-Lo (e.g. PDGFRA-Lo and/or FGFR1-Hi, e.g. PDGFRA-Hi/FGFR1-Hi, PDGFRA-Lo/FGFR1-Lo or PDGFRA-Lo/FGFR1-Hi) are therefore more suitable for treatment with a TKI as they have better patient outcomes. Accordingly, in some embodiments an individual may be selected for treatment with a TKI if they have a cancer that does not have not PDGFRA-Hi/FGFR1-Lo expression (e.g. having PDGFRA-Lo and/or FGFR1-Hi, e.g. PDGFRA-Hi/FGFR1-Hi, PDGFRA-Lo/FGFR1-Lo or PDGFRA-Lo/FGFR1-Hi expression).

Wherever cancers or individuals having PDGFRA-Hi/FGFR1-Hi or PDGFRA-Lo/FGFR1-Lo or PDGFRA-Lo/FGFR1-Hi are referred to herein, cancers or individuals not having PDGFRA-Hi/FGFR1-Lo expression can be used in the same way. Accordingly the embodiments disclosed herein in relation to PDGFRA-Hi/FGFR1-Hi or PDGFRA-Lo/FGFR1-Lo or PDGFRA-Lo/FGFR1-Hi can be equally applied to cancers or individuals not having PDGFRA-Hi/FGFR1-Lo (e.g. having PDGFRA-Lo and/or FGFR1-Hi).

Similarly, an individual may be deselected for TKI treatment, or considered for another therapy if they have a cancer which has PDGFRA-Hi/FGFR1-Lo expression.

In the present invention, references to PDGFRα denote the receptor tyrosine kinase (RTK) platelet-derived growth factor alpha. PDGFRα is a cell surface tyrosine kinase receptor.

The HUGO Gene Symbol report for PDGFRα can be found on the world wide web at genenames.org/cgi-bin/gene_symbol_report?hgnc_id=8803 which provides links to the human PDGFRA nucleic acid and amino acid sequences, as well as reference to the homologous murine and rat proteins. The human form has the HGNC ID: 8803, and the ensemble gene reference ENSG00000134853. The uniprot reference is P16234.

References to FGFR1 denote the fibroblast growth factor receptor 1. FGFR1 is a cell surface tyrosine kinase receptors.

The HUGO Gene Symbol report for FGFR1 can be found on the world wide web at genenames.org/cgi-bin/gene_symbol_report?hgnc_id=HGNC:3688 which provides links to the human FGFR1 nucleic acid and amino acid sequences, as well as reference to the homologous murine and rat proteins. The human form has the HGNC ID: 3688, and the ensemble gene reference ENSG00000077782. The uniprot reference is P11362.

The methods and uses disclosed herein may involve the step of determining the expression level of FGFR1 and PDGFRA or basing a prognostic or diagnostic decision on the expression level of FGFR1 and PDGFRA already determined. The methods and uses may involve the step of determining the expression level of FGFR1 and PDGFRA in a sample of cancer cells obtained from the individual.

In accordance with the invention the expression levels of FGFR1 and PDGFRA may be determined at the protein level or the nucleic acid level. In other words gene expression or protein expression levels of FGFR1 and PDGFRA may be determined.

Protein expression levels may be determined in a sample containing cancer cells obtained from an individual. Protein expression levels may be determined by any available means, including using immunological assays. For example, expression levels may be determined by immunohistochemistry (IHC), Western blotting, ELISA, immunoelectrophoresis, immunoprecipitation and immunostaining. Using any of these methods it is possible to determine the relative expression levels of PDGFRA and FGFR1 proteins.

Protein expression levels may be determined for example using specific binding agents capable of binding to FGFR1 or PDGFRA. A type of specific binding agent is an antibody, capable of specifically binding to FGFR1 or PDGFRA.

The antibody or other specific binding agent may be labelled to enable it to be detected or capable of detection following reaction with one or more further species, for example using a secondary antibody or binding agent that is labelled or capable of producing a detectable result, e.g. in an ELISA type assay. As an alternative a labelled binding agent may be employed in a Western blot to detect FGFR1 or PDGFRA protein.

In particular PDGFRA and FGFR1 expression levels may be determined in a sample of cancer cells, for example using immunohistochemical (IHC) analysis.

IHC analysis can be carried out using paraffin fixed samples or fresh frozen tissue samples, and generally involves staining the samples to highlight the presence, intensity and proportion of cells which express the target protein.

Using IHC, tumour/cancer specimens can be stained and scored for intensity and for proportion of positive tumour cells. For example, for intensity scoring 0=absent, 1=weak, 2=moderate, and 3=strong. For the proportion of positive tumour cells 0=absent, 1=1-10%, 2=11-50%, 3>50%. According to this system, sections with a score of >3 (intensity score+proportion score) may be counted as 'high' (Hi). Cumulative scores of <3 may be counted as 'low' (Lo). Accordingly, a cancer having PDGFRA-Hi/FGFR1-Hi, PDGFRA-Lo/FGFR1-Lo or PDGFRA-Lo/FGFR1-Hi or PDGFRA-Hi/FGFR1-Lo expression may be a cancer which meets the definition of Hi or Lo according to this IHC scoring system.

Expression levels may be measured using different techniques as described herein, but even if another measurement technique is used in the methods of the invention, expression may still be considered as Hi or Lo using the IHC scoring. In other words, the IHC score system above may be used to define the threshold between Hi and Lo expression, even if IHC itself is not used in the methods of the invention.

Representative examples of scored tumour tissue can be seen in supplementary FIG. 1. Using IHC scoring is a widely used approach for determining protein expression levels and there is good concordance between operators. Positive and negative controls can be used as reference points.

Alternatively or additionally, the determination of PDGFRA and FGFR1 expression levels may involve determining the presence or amount of PDGFRA and FGFR1 mRNA in a sample. Methods for doing this are well known to the skilled person. By way of example, they include using PCR involving one or more primers based on each of a PDGFRA and FGFR1 nucleic acid sequence to determine the level of PDGFRA and FGFR1 transcript is present in a sample.

Determining PDGFRA and FGFR1 mRNA levels may carried out by extracting RNA from a sample of cancer cells and measuring PDGFRA and FGFR1 expression specifically using quantitative real time RT-PCR. Alternatively or additionally, the expression of PDGFRA and FGFR1 could be assessed using RNA extracted from a sample of cancer cells for an individual using microarray analysis, which measures the levels of mRNA for a group of genes using a plurality of probes immobilised on a substrate to form the array.

Suitable kits for measuring the expression levels of these markers are described elsewhere herein. Expression levels (e.g. mRNA levels) may involve measuring expression (e.g. mRNA level) of PDGFRA and/or FGFR1 relative to the expression level (e.g. mRNA level) of one or more (e.g. 2, 3, 4, 5, 6, 7, 8, 9, 10, 11, 12, 13, 14, 15, 16, 17, 18, 18 or 20 or more) "housekeeping" genes. In this context, a housekeeping gene may be any gene for which the expression level is unaffected or largely unaffected by cancer subtype. In particular, suitable housekeeping genes may be selected from those referred to in Supplementary Methods 4 herein, i.e. ACAD9, AGK, AMMECR1L, C10orf76, CC2D1B, CNOT10, CNOT4, COG7, DDX50, DHX16, DNAJC14, EDC3, EIF2B4, ERCC3, FCF1, FTSJ2, GPATCH3, HDAC3, MRPS5, MTMR14, NOL7, NUBP1, PIAS1, PIK3R4 and PRPF38A.

As discussed elsewhere herein, the genes in table 5 (or a sub-set thereof) may be used in place of PDGFRA/FGFR1 expression to stratify patients, and identify those with inherent resistance to TKIs (e.g. pazopanib).

TP53 Status

Tumour protein p53 ('TP53' or 'p53') is a tumour suppressor protein encoded by the TP53 gene in humans. Mutation of TP53 was found to be associated with improved PFS in a retrospective study of 19 patients of mixed STS treated with an anti-angiogenic TKI (95% Pazopanib).[17]

In a phase 1 trial of Pazopanib combined with the histone deacetylase inhibitor vorinostat, hotspot TP53 mutations were discovered in 11 of 36 tested patients (3 of 11 sarcoma patients)[18]. TP53 mutation was significantly associated with improved rates of disease control and progression-free survival across all tested patients, and also with improved median overall survival in a subset of tested patients with either sarcoma or colorectal cancer. This study involved tiny numbers of TP53 mutant sarcomas, and the results are not conclusive, with the association between TP53 and TKIs requiring further investigation.

Using TP53 exon sequencing, the present inventors have found that the mutational status of TP53 was associated with patient outcomes for OS (overall survival) and PFS (progression-free survival). In particular, they found that wild-type TP53 was associated with longer OS and PFS, while TP53 mutations were associated with shorter OS and PFS.

Wildtype TP53 refers to TP53 which does not have non-synonymous mutations. In particular wildtype TP53 may have no non-synonymous mutations in the exons or splice sites.

TP53 mutant refers to TP53 having non-synonymous mutations. A TP53 mutation may be a described as a mutation in TP53 that is associated with cancer. A TP53 mutation may be in a protein coding region or in a splice site for example.

Mutations of TP53 include insertions, inversions, deletions, and/or point mutations.

Mutations in TP53 can be detected using sequencing technologies such as Sanger sequencing. The International Agency for Research on Cancer compile a database of TP53 mutations relating to cancer. These mutations may be detected using the protocol and probes they suggest.

Generally PCR can be used to amplify gene sequences from genomic DNA prepared from a sample of cancer cells. Primers for amplification of exons within TP53 are generally available. The amplified DNA can be sequenced, for example using Sanger sequencing, and mutations identified. Other sequencing techniques may be used, including next generation sequencing (NGS) methods. NGS offers the speed and accuracy required to detect mutations in cancer, either through whole-genome sequencing (WGS) or by focusing on specific regions or genes using whole-exome sequencing (WES) or targeted gene sequencing. Examples of NGS techniques include methods employing sequencing by synthesis, sequencing by hybridisation, sequencing by ligation, pyrosequencing, nanopore sequencing, or electrochemical sequencing.

Additional methods to detect the mutation include matrix-assisted laser desorption/ionization time-of-flight (MALDI-TOF) spectrometry, restriction fragment length polymorphism (RFLP), high-resolution melting (HRM) curve analysis, and denaturing high performance liquid Chromatography (DHPLC). Other PCR-based methods for detecting mutations include allele specific oligonucleotide polymerase chain reaction (ASO-PCR) and sequence-specific primer (SSP)-PCR. Mutations of may also be detected in mRNA transcripts through, for example, RNA sequence or reverse transcriptase PCR. Mutations may also be detected in the protein through, for example, peptide sequencing by mass spectrometry.

In certain embodiments, determining whether the individual has a mutated TP53 cancer is performed on genomic nucleic acid extracted from a sample of cells obtained from the cancer, from a sample of cancer cells circulating in blood and/or from circulating tumour DNA (ctDNA) in blood or plasma. Techniques for enriching a blood or plasma sample for circulating tumour DNA (e.g. based on fragment size) have been described. Moreover, sequencing techniques for identifying cancer-associated mutations in ctDNA have been described (e.g. based on digital PCR, targeted deep sequencing, nested real-time PCR, and the like). See, for example, PLoS Med. 2016 December; 13(12): e1002198.

Mutant allele specific probes may also be used to detect mutated TP53. These may be nucleic acid probes. For example, a series of allele-specific probes may be used to detect TP53 mutations. Such probes may be used in PCR. Mutation detection using Nanostring technology, e.g. as described on the world wide web at nanostring.com/application/files/9514/9636/4522/GLNS_PM0005_PB_nCounter_Vantage_3D_DNA_SNV_Solid Tumor_Panel.pdf, are specifically contemplated herein.

It is also possible to detect TP53 mutations using mismatch detection methods to detect mismatches in the DNA or mRNA using probes. It is possible to detect protein TP53 mutations using immunostaining, for example IHC, with antibodies specific to mutant alleles of p53 protein.

Suitable kits for determining the TP53 mutation status are described elsewhere herein.

The HUGO Gene Symbol report for TP53 can be found on the world wide web at genenames.org/cgi-bin/gene_symbol_report?hgnc_id=HGNC:11998 which provides links to the human TP53 nucleic acid and amino acid sequences, as well as reference to the homologous murine and rat proteins. The human form has the HGNC ID: 11998, and the ensemble gene reference ENSG00000141510. The uniprot reference is P04637.

Gene Expression Levels—List 1

There is growing evidence of shared aspects of molecular pathology that can stratify patients with mixed STS subtypes into groups of similar phenotype. The French Sarcoma Group reported an expression signature of 67 genes related to genomic instability and mitosis that was able to identify subgroups with distinct metastasis-free survival within 2 independent cohorts of mixed STS subtypes[15]. The so-called CINSARC (Complexity Index in SARComa) is now under prospective investigation as a possible predictive biomarker for neoadjuvant chemotherapy in unselected STS (NCT02789384). Meanwhile, molecular correlates with the long-observed variation in clinical behaviour within histological subtypes have been described in leiomyosarcoma through RNA-Seq gene expression profiling.

Given that pazopanib directly inhibits a number of growth-promoting RTKs, expression levels of these targets in tumour cells are attractive candidates for evaluation as predictive biomarkers. In a mRCC phase II trial of the combination of interferon-alpha with sorafenib, a multi-targeted kinase inhibitor with target selectivity that overlaps with that of pazopanib, Ho et al. demonstrated using in-situ hybridisation that higher FGFR1 transcript levels was associated with shorter PFS[40].

In contrast, it has recently been shown that malignant rhabdoid tumour cells that display high levels of PDGFRA and FGFR1 expression are sensitive to pazopanib treatment in vitro[19]. It appears likely that the effect of relative expression of these and other RTKs in modulating downstream signalling pathways and influencing drug sensitivity are complex and variably controlled at epigenetic, transcriptional and post-translational levels.

The inventors have investigated additional factors which allow further stratification of individuals with cancer. Clusters of patients with distinct gene expression signatures in the cancer cell samples were identified. These clusters were used to identify the genes which can be used to distinguish between groups of patients with differing prognosis following TKI treatment.

Identification of biological subtype samples and genes: An expanded cancer-pathway associated gene set, comprised primarily of genes found 13 cancer pathways, was initially used to identify biological subtypes. The 13 cancer pathways are: Notch
APC/Wnt
Hedgehog
Chromatin modification
Transcriptional regulation
DNA damage control
TGF-β
MAPK
STAT
PI3K
RAS
Cell cycle
Apoptosis Twenty two sarcomas with IHC-WT across 770 genes were analyzed by consensus clustering (CC). The CC algorithm statistically identifies significant/unique groups by testing the null hypothesis that a group of samples is from a single cluster, where a cluster is characterized as a multivariate normal distribution. CC was run to identify between 2 to 8 subgroups, with a permutation of 100 times and stopping when the test was no longer significant (p>0.001). Using a supervised approach, a minimized gene set was derived from these biological class labelled samples based on a non-parametric approach to identify the most significant differential genes across these three subgroups.

Using multivariable cox regression model, we confirmed the significant association of these 3 biological subgroups with progression free survival and overall survival respectively (p<0.001)

List 1: 229 genes identified at a false discovery rate (FDR)<10% in multiclass SAM analysis that identifies clinical outcome subgroups A, B and C in unbiased consensus clustering of 22 IHCneg (PDGFRA-Hi/FGFR1-Hi, PDGFRA-Lo/FGFR1-Hi, PDGFRA-Lo/FGFR1-Lo), P53 wt cases. Each gene is identified below by name with the Entrez number for each shown in brackets.

| | | |
|---|---|---|
| ACVR1B (91) | CCNA2 (890) | COMP (1311) |
| AMH (268) | CCNB1 (891) | CSF1R (1436) |
| APC (324) | CCND1 (595) | CXXC4 (80319) |
| ATM (472) | CCND2 (894) | DDB2 (1643) |
| B2M (567) | CCNE2 (9134) | DDIT3 (1649) |
| BAD (572) | CCR7 (1236) | DKK1 (22943) |
| BCL2A1 (597) | CDC25C (995) | DLL1 (28514) |
| BCL2L1 (598) | CDC7 (8317) | DNMT1 (1786) |
| BCOR (54880) | CDH1 (999) | DTX3 (196403) |
| BID (637) | CDKN2A (1029) | DTX4 (23220) |
| BIRC3 (330) | CDKN2B (1030) | DUSP10 (11221) |
| BRCA2 (675) | CDKN2C (1031) | DUSP4 (1846) |
| BRIP1 (83990) | CDKN2D (1032) | DUSP5 (1847) |
| CACNA1C (775) | CHAD (1101) | E2F1 (1869) |
| CACNA1G (8913) | CHEK1 (1111) | E2F5 (1875) |
| CACNA1H (8912) | CHUK (1147) | EFNA2 (1943) |
| CACNB2 (783) | CLCF1 (23529) | EFNA5 (1946) |
| CALML5 (51806) | COL1A1 (1277) | EIF4EBP1 (1978) |

-continued

| | | |
|---|---|---|
| CALML6 (163688) | COL27A1 (85301) | ERBB2 (2064) |
| CAPN2 (824) | COL3A1 (1281) | ETS2 (2114) |
| CARD11 (84433) | COL4A4 (1286) | ETV1 (2115) |
| CASP10 (843) | COL4A6 (1288) | EYA1 (2138) |
| CASP7 (840) | COL5A2 (1290) | FANCA (2175) |
| FANCE (2178) | IL22RA1 (58985) | MMP9 (4318) |
| FANCF (2188) | IL2RA (3559) | MPL (4352) |
| FBXW7 (55294) | IL2RB (3560) | MSH6 (2956) |
| FEN1 (2237) | IL3RA (3563) | MYC (4609) |
| FGF21 (26291) | IL6 (3569) | MYD88 (4615) |
| FGF5 (2250) | IL6R (3570) | NFATC1 (4772) |
| FGF7 (2252) | IL7R (3575) | NFKB1 (4790) |
| FGF9 (2254) | INHBA (3624) | NFKBIZ (64332) |
| FLNA (2316) | IRAK2 (3656) | NKD1 (85407) |
| FLNC (2318) | IRS1 (3667) | NOG (9241) |
| FN1 (2335) | ITGA3 (3675) | NOS3 (4846) |
| FOS (2353) | ITGA6 (3655) | NOTCH2 (4853) |
| FZD10 (11211) | ITGA7 (3679) | NOTCH3 (4854) |
| FZD9 (8326) | ITGA8 (8516) | NRAS (4893) |
| GADD45A (1647) | ITGB3 (3690) | NUPR1 (26471) |
| GADD45G (10912) | JAG1 (182) | PAX5 (5079) |
| GAS1 (2619) | JAK3 (3718) | PBX1 (5087) |
| GATA3 (2625) | KAT2B (8850) | PDGFC (56034) |
| GNA11 (2767) | LAMA3 (3909) | PDGFD (80310) |
| GNG12 (55970) | LAMA5 (3911) | PDGFRA (5156) |
| GRB2 (2885) | LAMB3 (3914) | PIK3CD (5293) |
| GRIN2A (2903) | LAMC2 (3918) | PIK3CG (5294) |
| GSK3B (2932) | LAMC3 (10319) | PIK3R5 (23533) |
| GZMB (3002) | LEFTY2 (7044) | PIM1 (5292) |
| HDAC10 (83933) | LFNG (3955) | PLA2G10 (8399) |
| HES1 (3280) | LIF (3976) | PLA2G4C (8605) |
| HGF (3082) | MAP2K1 (5604) | PLAT (5327) |
| HMGA2 (8091) | MAP2K2 (5605) | PLAU (5328) |
| HSPB1 (3315) | MAP2K6 (5608) | PLCB4 (5332) |
| ID2 (3398) | MAP3K8 (1326) | PLD1 (5337) |
| IDH1 (3417) | MAPK10 (5602) | POLD4 (57804) |
| IDH2 (3418) | MAPK8IP1 (9479) | POLE2 (5427) |
| IGF1 (3479) | MCM2 (4171) | PPARG (5468) |
| IL11RA (3590) | MCM4 (4173) | PPARGC1A (10891) |
| IL12RB2 (3595) | MCM5 (4174) | PPP3CC (5533) |
| IL15 (3600) | MET (4233) | PRKAA2 (5563) |
| IL19 (29949) | MFNG (4242) | PRKAR1B (5575) |
| PRKAR2A (5576) | SOCS2 (8835) | TNFSF10 (8743) |
| PRKCB (5579) | SOCS3 (9021) | TNR (7143) |
| PRKX (5613) | SPOP (8405) | TP53 (7157) |
| PTCH1 (5727) | SPRY1 (10252) | TSHR (7253) |
| PTEN (5728) | SPRY2 (10253) | TSPAN7 (7102) |
| PTPRR (5801) | SYK (6850) | TSPAN7 (7102) |
| PTTG2 (10744) | TGFB1 (7040) | TTK (7272) |
| RAC2 (5880) | TGFB3 (7043) | UBE2T (29089) |
| RASGRF2 (5924) | TGFBR2 (7048) | VEGFC (7424) |
| RASGRP2 (10235) | THBS1 (7057) | WHSC1 (7468) |
| RBX1 (9978) | TLR2 (7097) | WNT16 (51384) |
| RELA (5970) | TLR4 (7099) | WNT3 (7473) |
| RET (5979) | TLX1 (3195) | ZAK (51776) |
| RFC4 (5984) | TNC (3371) | ZBTB16 (7704) |
| RUNX1 (861) | TNFAIP3 (7128) | ZIC2 (7546) |
| SHC1 (6464) | TNFRSF10A (8797) | |
| SMAD3 (4088) | TNFRSF10D (8793) | |

As identified by multiclass Significance Analysis of Microarrays (SAM), these genes in List 1 are differentially expressed in subgroups of individuals which have different patient outcomes. In other words, the markers are differentially expressed between patients that are more or less susceptible to TKI treatment.

These markers can therefore be used to distinguish between subgroups of patients which have different PFS and OS outcomes after TKI treatment. The markers can be used to identify cancers as sensitive to TKI treatment or resistant to TKI treatment.

The markers are generally involved in key oncogenic pathways.

In the methods and uses of the invention, the expression levels of 5 or more, 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1 may be determined. For example, the expression levels of at least 41, at least 43, at least 44, at least 45, at least 46, at least 47, at least 48, at least 49, at least 50, at least 60, at least 70, at least 80, at least 90, at least 100, at least 150, at least 200, or all 229 the genes in List 1 may be determined.

In particular, the genes in List 1 are used to stratify cancers that are already known (a) not to have PDGFRA-Hi and FGFR1-Lo expression and (b) having TP53 wildtype, into subgroups.

Determining Expression Levels of Genes

The below techniques can be used for determination of expression levels of genes in List1, and also tables 4 and 5.

Reference to determining the expression level refers to determination of the expression level of an expression product of the gene. Expression level may be determined at the nucleic acid level or the protein level.

The gene expression levels determined may be considered to provide an expression profile. By "expression profile" is meant a set of data relating to the level of expression of one or more of the relevant genes in an individual, in a form which allows comparison with comparable expression profiles (e.g. from individuals for whom the prognosis is already known), in order to assist in the determination of prognosis and in the selection of an individual for treatment with a TKI.

The determination of gene expression levels may involve determining the presence or amount mRNA in a sample of cancer cells. Methods for doing this are well known to the skilled person. Gene expression levels may be determined in a sample of cancer cells using any conventional method, for example using nucleic acid microarrays or using nucleic acid synthesis (such as quantitative PCR). For example, gene expression levels may be determined using RNA microarrays. The nucleic acid quantification methods discussed elsewhere herein, for example in relation to FGFR1 and PDGFRA may also be applied to the genes in List 1 and tables 4 and 5.

Alternatively or additionally, the determination of gene expression levels may involve determining the protein levels expressed from the genes in a sample containing cancer cells obtained from an individual. Protein expression levels may be determined by any available means, including using immunological assays. For example, expression levels may be determined by immunohistochemistry (IHC), Western blotting, ELISA, immunoelectrophoresis, immunoprecipitation and immunostaining. Using any of these methods it is possible to determine the relative expression levels of the proteins expressed from the genes listed in List 1 and tables 4 and 5.

Methods of determining protein expression levels are discussed in relation to the determination of FGFR1 and PDGFRA expression levels and such methods may also be used here, for example using specific binding agents capable of binding each of the proteins expressed from the genes listed in List 1 and tables 4 and 5.

Suitable kits for measuring the expression levels of these markers are described elsewhere herein.

Comparing Gene Expression Levels to Control Groups

Gene expression levels (from List 1 or a subset thereof, or from table 4 or a subset thereof) may be compared with the expression levels of the same genes in cancers from a group of patients known to respond well (having a good prognosis, or good OS and PFS) to TKI treatment, or be sensitive to TKI treatment. Gene expression levels may be compared to the expression levels of the same genes in cancers from a group of patients known to respond poorly to TKI treatment (having a poor prognosis, or poor OS and PFS) or be resistant to TKI treatment.

The patients/individuals to which the comparison is made may be referred to as the 'control group'. Accordingly, the determined gene expression levels may be compared to the expression levels in a control group of individuals having cancer. The comparison may be made to expression levels determined in cancer cells of the control group. The comparison may be made to expression levels determined in samples of cancer cells from the control group. The cancer in the control group may be the same type of cancer as in the individual. For example, if the expression is being determined for an individual with soft tissue sarcoma (STS), the expression levels may be compared to the expression levels in the cancer cells of patients with soft tissue sarcoma.

Other factors may also be matched between the control group and the individual and cancer being tested. For example the stage of cancer may be the same. For example, if the individual being tested has advanced soft tissue sarcoma, the expression levels of the genes may be compared to the expression levels of the same genes in advanced soft tissue sarcomas in a group of patients known to have a good prognosis after treatment with a TKI and/or a group of patients known to have a poor prognosis after treatment with a TKI.

Additionally the control group may have been treated with the same TKI. For example, if the TKI is pazopanib, all of the patients in the control group(s) may have been treated with pazopanib.

Accordingly, an individual may be stratified or grouped according to their similarity of gene expression with the group with good or poor prognosis.

As used herein, a group of patients known to respond poorly to TKI treatment may be those known to have a poor outcome following TKI treatment as defined elsewhere herein. A group of patients known to respond well to TKI treatment may be those known to have a good outcome following TKI treatment as defined elsewhere herein, or a group having a superior outcome to those found to have a poor outcome following TKI treatment.

Methods for Classification Based on Gene Expression

As described in further detail in Example 1 herein, in order to create a test to identify biological subgroups, we used consensus clustering (CC) to objectively separate the 22 tumours into stable biological groups. The goal of the consensus clustering was to search for a partition of the 22 tumours into 2 or at most 8 groups using the expression of the 730 signature genes which had already been found to be associated with 13 canonical cancer pathway. We used hierarchical consensus clustering with 1-pearson correlation to identify robust unsupervised clusters by performing 200 iterations subsampling 80% of the samples each round. We identified 3 clearly separated biological groups, namely "A", "B" and "C". Using Multiclass Significant Analysis of Microarray (Tusher PNAS 2001, PMID:11309499), we identified a list of 229 genes with significant differential expressed among the three subgroups (see List 1). Using the Prediction Analysis of Microarray (PAM) algorithm, we built a standardised centroid for each of the biological subgroup (see Table 3 herein). The centroid was the average gene expression for each gene in each subtype (or "class", i.e. A or B or C) divided by the within-class standard deviation for that gene. Nearest centroid single sample classification takes the gene expression profile of a new sample, and compares it to each of these class centroids and assigns a sample to a subtype based on the nearest centroid. Subgroup prediction is done by calculating the Spearman's rank correlation of each test case to the three centroids, and assigning a sample to a subtype based on closest Eucleadian distance (1-Spearman Correlation) the nearest centroid.

The dominance of a particular biological subgroup for an individual tumour may be determined in an analogous fashion to that widely used for identifying intrinsic breast cancer subtypes using the PAM50 genes and Nanostring technology and a closest centroid approach (see, e.g., Parker et al. JCO, PMID: 19204204; Tibshirani 2002 PNAS PMID: 12011421).

In some embodiments, the present invention provides methods for classifying, prognosticating, or monitoring sarcoma in subjects. In particular, data obtained from analysis of gene expression may be evaluated using one or more pattern recognition algorithms. Such analysis methods may be used to form a predictive model, which can be used to classify test data.

For example, one convenient and particularly effective method of classification employs multivariate statistical analysis modelling, first to form a model (a "predictive mathematical model") using data ("modelling data") from samples of known subgroup (e.g., from subjects known to have a particular sarcoma biological subgroups: A, B and C as defined by the genes in List 1 and the centroids given in table 3; or from subjects known to have a particular sarcoma biological subgroups based on the genes listed in table 4 and the centroids given in table 6), and second to classify an unknown sample (e.g., "test sample") according to subgroup. Pattern recognition methods have been used widely to characterize many different types of problems ranging, for example, over linguistics, fingerprinting, chemistry and psychology. In the context of the methods described herein, pattern recognition is the use of multivariate statistics, both parametric and non-parametric, to analyse data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. However, this type of approach may not be suitable for developing a clinical assay that can be used to classify samples derived from subjects independent of the initial sample population used to train the prediction algorithm.

The other approach is termed "supervised" whereby a training set of samples with known class or outcome is used to produce a mathematical model which is then evaluated with independent validation data sets. Here, a "training set" of gene expression data is used to construct a statistical model that predicts correctly the "subgroup" of each sample. This training set is then tested with independent data (referred to as a test or validation set) to determine the robustness of the computer-based model. These models are sometimes termed "expert systems," but may be based on a range of different mathematical procedures such as support vector machine, decision trees, k-nearest neighbour and naïve Bayes. Supervised methods can use a data set with reduced dimensionality (for example, the first few principal components), but typically use unreduced data, with all dimensionality. In all cases the methods allow the quantitative description of the multivariate boundaries that characterize and separate each subtype in terms of its intrinsic gene expression profile. It is also possible to obtain confidence limits on any predictions, for example, a level of probability to be placed on the goodness of fit (see, for example, Kowalski et al., 1986). The robustness of the predictive models can also be checked using cross-validation, by leaving out selected samples from the analysis.

The PARSARC classification model described herein is based on the gene expression profile for a plurality of subject samples using the genes listed in List 1. The plurality of samples includes a sufficient number of samples derived from subjects belonging to each subgroup class. By "sufficient samples" or "representative number" in this context is intended a quantity of samples derived from each subtype that is sufficient for building a classification model that can reliably distinguish each subgroup from all others in the group. A supervised prediction algorithm is developed based on the profiles of objectively-selected IHCnegTP53 wt (non-PDGFRA-Hi/FGFR1-Lo; TP53 wt) prototype samples for "training" the algorithm. The samples are selected and subtyped using an expanded gene set, such as that of the genes of List 1.

A similar approach may be applied to the genes listed in table 4.

Alternatively, the samples can be subtyped according to any known assay for classifying sarcoma subgroups. After stratifying the training samples according to subtype, a centroid-based prediction algorithm is used to construct centroids based on the expression profile of the intrinsic gene set described in List 1. An exemplary centroid for each of three tumour subtypes A-C is shown in Table 3 herein.

Alternatively, after stratifying the training samples according to subtype, a centroid-based prediction algorithm is used to construct centroids based on the expression profile of the intrinsic gene set described in table 4. An exemplary centroid for each of five tumour subtypes is shown in Table 6 herein.

"Translation" of the descriptor coordinate axes can be useful. Examples of such translation include normalization and mean-centering. "Normalization" may be used to remove sample-to-sample variation. Some commonly used methods for calculating normalization factor include: (i) global normalization that uses all genes on the microarray or nanostring codeset; (ii) housekeeping genes normalization that uses constantly expressed housekeeping/invariant genes; and (iii) internal controls normalization that uses known amount of exogenous control genes added during hybridization (Quackenbush (2002) Nat. Genet. 32 (Suppl.), 496-501). In one embodiment, the genes listed in List 1 can be normalized to control housekeeping genes. Exemplary housekeeping genes include MRPL19, PSMC4, SF3A1, PUM1, ACTB, GAPD, GUSB, RPLPO, and TFRC. It will be understood by one of skill in the art that the methods disclosed herein are not bound by normalization to any particular housekeeping genes, and that any suitable housekeeping gene(s) known in the art can be used. Many normalization approaches are possible, and they can often be applied at any of several points in the analysis. In one embodiment, microarray data is normalized using the LOWESS method, which is a global locally weighted scatterplot smoothing normalization function. In another embodiment, qPCR data is normalized to the geometric mean of set of multiple housekeeping genes.

"Mean-centering" may also be used to simplify interpretation for data visualisation and computation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt(StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centered and unit variance scaled. This technique is a very useful because each descriptor is then weighted equally, and large and small values are treated with equal emphasis. This can be important for genes expressed at very low, but still detectable, levels.

In one embodiment, data is collected for one or more test samples and classified using the PARSARC classification model described herein. When comparing data from multiple analyses (e.g., comparing expression profiles for one or more test samples to the centroids constructed from samples collected and analyzed in an independent study), it will be necessary to normalize data across these data sets. In one embodiment, Distance Weighted Discrimination (DWD) is used to combine these data sets together (Benito et al. (2004) Bioinformatics 20(1): 105-114, incorporated by reference herein in its entirety). DWD is a multivariate analysis tool that is able to identify systematic biases present in separate data sets and then make a global adjustment to compensate for these biases; in essence, each separate data set is a multi-dimensional cloud of data points, and DWD takes two points clouds and shifts one such that it more optimally overlaps the other.

In some embodiments described herein, the prognostic performance of the PARSARC IHC, TP53 mutational status and biological and/or other clinical parameters is assessed utilizing a Cox Proportional Hazards Model Analysis, which is a regression method for survival data that provides an estimate of the hazard ratio and its confidence interval. The Cox model is a well-recognized statistical technique for exploring the relationship between the survival of a patient and particular variables. This statistical method permits estimation of the hazard (i.e., risk) of individuals given their prognostic variables (e.g., intrinsic gene expression profile with or without additional clinical factors, as described herein). The "hazard ratio" is the risk of death at any given time point for patients displaying particular prognostic variables.

Prognosis

An individual grouped with the good prognosis group, may be identified as having a cancer that is sensitive to TKI treatment, they may also be referred to as an individual that responds well to TKI treatment. An individual grouped with the poor prognosis group, may be identified as having a cancer that is resistant to TKI treatment, they may also be referred to as an individual that responds poorly to TKI treatment.

Where the individual is grouped with the good prognosis group, the individual may be selected for treatment with the TKI. Where the individual is grouped with the poor prognosis group, the individual may be deselected for treatment with the TKI.

Whether a prognosis is considered good or poor may vary between cancers and stage of disease. In general terms a good prognosis is one where the OS and/or PFS is longer than average for that stage and cancer type. A prognosis may be considered poor if PFS and/or OS is lower than average for that stage and type of cancer. The average may be the mean OS or PFS.

For example, a prognosis may be considered good if the PFS is >6 months and/or OS >18 months. Similarly PFS of <6 months or OS of <18 months may be considered poor. In particular PFS of >6 months and/or OS of >18 months may be considered good for advanced cancers.

In particular PFS of >6 months and/or OS of >18 months may be considered good for pazopanib treatment, for example of soft tissue sarcoma (STS), in particular advanced STS.

In general terms, a "good prognosis" is one where survival (OS and/or PFS) of an individual patient can be favourably compared to what is expected in a population of patients within a comparable disease setting. This might be defined as better than median survival (i.e. survival that exceeds that of 50% of patients in population).

In particular, PFS >4 months and/or OS >12 months may be considered good following pazopanib treatment for patients with advanced soft tissue sarcomas, based on median survival in the pazopanib arm in the PALLETTE trial. Very good survival in the same population might be considered PFS >6 months and/or OS >18 months.

"Predicting the likelihood of survival of a sarcoma patient" is intended to assess the risk that a patient will die as a result of the underlying sarcoma.

"Predicting the likelihood of progression-free survival" is intended to mean that the patient neither dies nor experiences radiological disease progression by RECIST criteria.

"Predicting the response of a sarcoma patient to a selected treatment" is intended to mean assessing the likelihood that a patient will experience a positive or negative outcome with a particular treatment.

As used herein, "indicative of a positive treatment outcome" refers to an increased likelihood that the patient will experience beneficial results from the selected treatment (e.g. reduction in tumour size, 'good' prognostic outcome, improvement in disease-related symptoms and/or quality of life).

"Indicative of a negative treatment outcome" is intended to mean an increased likelihood that the patient will not receive the aforementioned benefits of a positive treatment outcome.

Combinations of Tests

The present inventors have found that the FGFR1/PDGFRA expression, TP53 mutation status and gene expression signatures using the genes in List 1, or a sub-set thereof have more predictive power for response to TKI when used in combination. In one particular example, they may be combined in a decision tree classifier as depicted in FIG. 5.

Accordingly, in the methods of the invention, any of the three methods may be used individually or in combination.

For example, the TP53 mutational status and the expression levels of FGFR1 & PDGFRA may both be determined. These two tests were found to have an additive predictive ability for progression-free and overall survival.

For example, for an individual with a cancer determined to have the PDGFRA-Hi/FGFR1-Lo phenotype, an alternative therapy to the TKI may be considered. For cancers with other PDGFRA/FGFR1 expression profiles, further tests may be carried out. In other words in cancers determined not to have PDGFRA-Hi/FGFR1-Lo expression, e.g. to have PDGFRA-Hi/FGFR1-Hi, PDGFRA-Lo/FGFR1-Lo, PDGFRA-Lo/FGFR1-Hi further test may be carried out.

The mutation status of TP53 may be determined for a cancer determined not to have PDGFRA-Hi/FGFR1-Lo expression be PDGFRA-Hi/FGFR1-Hi, PDGFRA-Lo/FGFR1-Lo or PDGFRA-Lo/FGFR1-Hi.

Similarly, for cancers determined to be TP53 wildtype, further tests can be carried out. For example, PDGFRA/FGFR1 expression levels can be determined.

Accordingly, cancers which are determined not to have PDGFRA-Hi/FGFR1-Lo expression (e.g. as having PDGFRA-Hi/FGFR1-Hi, PDGFRA-Lo/FGFR1-Lo or PDGFRA-Lo/FGFR1-Hi) and TP53 wildtype may be identified as having a relatively good prognosis following TKI treatment and be selected for treatment with a TKI.

Cancers determined not to have PDGFRA-Hi/FGFR1-Lo expression (e.g. to be PDGFRA-Hi/FGFR1-Hi, PDGFRA-Lo/FGFR1-Lo or PDGFRA-Lo/FGFR1-Hi) and TP53 mutated may be deselected from TKI treatment. Cancers determined to be PDGFRA-Hi/FGFR1-Lo and TP53 wildtype may be deselected from TKI treatment. In other words if a cancer is determined to be TP53 mutated, and/or PDGFRA-Hi/FGFR1-Lo it may be determined to have a relatively poor prognosis following treatment with a TKI and deselected for treatment with a TKI.

The TP53 and FGFR1/PDGFRA statuses may also be combined with the levels of gene expression of the genes in List 1 to further select patients with cancers suitable for TKI (eg. Pazopanib) treatment. In particular, for a cancer which determined not to have PDGFRA-Hi/FGFR1-Lo expression (e.g. to have PDGFRA-Hi/FGFR1-Hi, PDGFRA-Lo/FGFR1-Lo or PDGFRA-Lo/FGFR1-Hi) and TP53 wildtype, the gene expression levels of genes selected from those in List 1 may be determined.

Any combination of the tests is possible. For example individuals may be selected or deselected for treatment with the TKI, stratified, or given a prognosis based on expression of PDGFRA and FGFR1 and the expression levels of genes selected from List 1. For example, individuals may be selected or deselected for treatment with the TKI, stratified, or given a prognosis based on expression of PDGFRA and FGFR1 and TP53 mutation status. For example individuals may be selected or deselected for treatment with the TKI, stratified, or given a prognosis based on TP53 mutation status and the expression levels of genes selected from List 1. For example individuals may be selected or deselected for treatment with the TKI, stratified, or given a prognosis based on expression of PDGFRA and FGFR1, TP53 mutation status, and the expression levels of genes selected from List 1.

In particular, an individual may be selected for treatment with a TKI or determined to have a good prognosis following TKI treatment if they meet one, two or all of the criteria:
(a) they do not to have PDGFRA-Hi/FGFR1-Lo expression (e.g. have PDGFRA-Hi/FGFR1-Hi, PDGFRA-Lo/FGFR1-Lo, or PDGFRA-Lo/FGFR1-Hi expression levels);
(b) they have wildtype TP53; and
(c) based on the expression levels of genes selected from List 1.

In particular, for part (c), an individual may be selected for treatment with a TKI or determined to have a good prognosis if they are identified as sensitive to TKI treatment based on the expression levels of genes selected from List 1. For example, an individual may be selected for treatment with a TKI if the expression profile of the genes of List 1 measured for the sample from the individual are a closest match to the centroid of subgroup A relative to the centroids of subgroup B and C. The centroids may be pre-determined centroids such as the exemplary centroids shown in Table 3 or otherwise pre-determined and, for example, retrieved from an electronic data record or the centroids may be established de novo by making use of a training set of gene expression profiles from a plurality of subjects known to have responded well to TKI therapy, and from a plurality of subjects known to have responded poorly to TKI therapy, for a cancer of interest.

In particular, an individual may be deselected from treatment with a TKI or determined to have a poor prognosis following TKI treatment if they meet one, two or all of the criteria:

(a) they have PDGFRA-Hi/FGFR1-Lo expression levels;
(b) they have mutated TP53; and
(c) based on the expression levels of genes selected from List 1.

In particular, for part (c), an individual may be deselected for treatment with a TKI or determined to have a poor prognosis if they are identified as resistant to TKI treatment based on the expression levels of genes selected from List 1. For example, an individual may be deselected for treatment with a TKI if the expression profile of the genes of List 1 measured for the sample from the individual are a closest match to the centroid of subgroup B or C relative to the centroid of subgroup A. The centroids may be pre-determined centroids such as the exemplary centroids shown in Table 3 or otherwise pre-determined and, for example, retrieved from an electronic data record or the centroids may be established de novo by making use of a training set of gene expression profiles from a plurality of subjects known to have responded well to TKI therapy, and from a plurality of subjects known to have responded poorly to TKI therapy, for a cancer of interest.

Details of the protocols are given elsewhere herein.

In some embodiments the determining steps are carried out in series. After a determining step an individual with cancer may be selected for a further determining step using the criteria above, or may be deselected. This makes a 'decision tree' allowing efficient selection of patients for treatment with a TKI. For example, the decision tree shown in FIG. 5 can be followed.

For example the PDGFRA and FGFR1 expression status may be determined in a sample of cancer cells from an individual. If the expression levels are PDGFRA-Hi/FGFR1-Lo, the individual is deselected or determined to have a poor prognosis.

If the expression levels are not PDGFRA-Hi/FGFR1-Lo (e.g. PDGFRA-Hi/FGFR1-Hi, PDGFRA-Lo/FGFR1-Lo or PDGFRA-Lo/FGFR1-Hi) then the individual is selected to determine the TP53 mutation status. If the TP53 is mutated, the individual may be deselected or determined to have a poor prognosis.

If TP53 is wildtype, then the individual is selected to determine the expression levels of 5 or more of the genes in List 1. The patient may be selected or deselected based on the expression profile. In particular, the gene expression profile measured for a sample from the individual may be assessed for closeness of fit to gene expression centroids of subgroups differing in respect of their TKI treatment outcome for the cancer of interest. For example, the gene expression profile measured for a sample from the individual may be assessed for closeness of fit to gene expression centroids shown in Table 3.

Similarly, the TP53 mutation status may be first determined. If the TP53 is mutated, the individual may be deselected or determined to have a poor prognosis. If TP53 is wildtype, then the individual is selected to determine PDGFRA and FGFR1 expression status. If the expression levels are PDGFRA-Hi/FGFR1-Lo, the individual is deselected or determined to have a poor prognosis. If the expression levels are not PDGFRA-Hi/FGFR1-Lo (e.g. PDGFRA-Hi/FGFR1-Hi, PDGFRA-Lo/FGFR1-Lo or PDGFRA-Lo/FGFR1-Hi) then the individual is selected to determine the expression levels of genes selected from List 1. The patient may be selected or deselected based on the expression profile of these genes.

In some embodiments the gene expression profile is only determined for an individual having a cancer which has been determined not to have PDGFRA-Hi/FGFR1-Lo expression (e.g. PDGFRA-Hi/FGFR1-Hi, PDGFRA-Lo/FGFR1-Lo or PDGFRA-Lo/FGFR1-Hi) and TP53 wildtype. Testing of PDGFRA & FGFR1 expression and TP53 mutation status may be sequential or in parallel.

In some embodiments the gene expression profile, PDGFRA & FGFR1 expression and TP53 mutation status are all determined in parallel.

Tyrosine Kinase Inhibitors

Tyrosine kinase inhibitors which can be used for the treatment of cancer find use in the present invention, in particular TKIs with a similar activity profile to Pazopanib.

These include the small molecule inhibitors Pazopanib (CAS number 444731-52-6), Regorafenib (CAS number 755037-03-7), Sorafenib (CAS number 284461-73-0), Sunitinib (CAS number 341031-54-7), Lenvatinib (CAS number 417716-92-8), Axitinib (CAS number 319460-85-0), Nintedanib (CAS number 656247-18-6), and Ponatinib (CAS number 943319-70-8), and pharmaceutically acceptable salts thereof.

Any one of these TKIs may be used in accordance with the present invention. In a preferred embodiment the TKI is Pazopanib.

Salts or derivatives of the exemplary inhibitors may be used for the treatment of cancer. As used herein "derivatives" of the therapeutic agents includes salts, coordination complexes, esters such as in vivo hydrolysable esters, free acids or bases, hydrates, prodrugs or lipids, coupling partners.

Salts of the compounds of the invention are preferably physiologically well tolerated and non-toxic. Many examples of salts are known to those skilled in the art. Compounds having acidic groups, such as phosphates or sulfates, can form salts with alkaline or alkaline earth metals such as Na, K, Mg and Ca, and with organic amines such as triethylamine and Tris (2-hydroxyethyl) amine. Salts can be formed between compounds with basic groups, e.g., amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques well known in the art.

Derivatives which as prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor. Coupling partners can be covalently linked to compounds of the invention via an appropriate functional group on the compound such as a hydroxyl group, a carboxyl group or an amino group. Other derivatives include formulating the compounds with liposomes.

Cancers

The cancers which are stratified and treated according to the present invention are any of the cancers treatable using the TKIs.

Accordingly, cancers to be treated or stratified according to the present invention include:

Soft tissues sarcomas (STS), for example advanced soft tissue sarcomas, metastatic renal cell carcinomas (mRCC), gastrointestinal stromal tumour (GIST), hepatocellular carcinoma (HCC), neuroendocrine tumour (NET), medullary thyroid cancer (MTC; also known as medullary thyroid carcinoma), non-squamous non-small cell lung cancer (NSCLC), and chronic myeloid leukaemia (CML).

In particular the cancer may be STS, for example advanced STS.

The treatment may be the first, second or third line treatment.

If the cancer is a soft tissues sarcoma (STS), the methods disclosed herein may be employed to determine suitability for treatment with Pazopanib or Regorafenib, in particular Pazopanib.

If the cancer is a metastatic renal cell carcinoma (mRCC), the methods disclosed herein may be employed to determine suitability for treatment with Pazopanib, Sorafenib, Sunitinib, Lenvatinib or Axitinib. In particular the methods may be used to determine suitability of Pazopanib for treatment of metastatic renal cell carcinoma.

If the cancer is a gastrointestinal stromal tumour (GIST), the methods disclosed herein may be employed to determine suitability for treatment with Regorafenib or Sunitinib. The methods may be used to determine suitability of Regorafenib as a third-line treatment for GIST.

If the cancer is a hepatocellular carcinoma (HCC), the methods disclosed herein may be employed to determine suitability for treatment with Sorafenib.

If the cancer is a neuroendocrine tumour (NET), the methods disclosed herein may be employed to determine suitability for treatment with Sunitinib.

If the cancer is a medullary thyroid cancer (MTC), the methods disclosed herein may be employed to determine suitability for treatment with Lenvatinib.

If the cancer is a non-squamous non-small cell lung cancer (non-squamous NSCLC), the methods disclosed herein may be employed to determine suitability for treatment with Nintedanib. The methods may be used to determine suitability of Nintedanib as a second-line treatment for non-squamous NSCLC.

If the cancer is a chronic myeloid leukaemia (CML), the methods disclosed herein may be employed to determine suitability for treatment with Ponatinib. The methods may be used to determine suitability of Ponatinib to treat solid tumour CML.

In particular the cancer may be a soft-tissue sarcoma and the TKI may be Pazopanib. For example the cancer may be an advanced soft tissue sarcoma.

Methods of stratification, identification and treatments disclosed herein particularly apply to soft-tissue sarcomas and treatment with pazopanib. In particular the soft-tissue sarcoma is advanced STS and the TKI is pazopanib.

The methods disclosed herein may be applied to advanced cancers. Generally 'advanced' cancers are not amenable to curative surgery, because they are locally advanced, locally recurrent or metastatic. For example, advanced STS is STS that is not amenable to curative surgery.

It is also contemplated that the methods disclosed herein would be useful in early stage disease, for example pre-operatively.

Individuals

The individuals to be treated, stratified or tested for selection in accordance with the present invention may, in some cases, not have previously been treated with the TKI, e.g. pazopanib. However, in certain cases, the individual may have been treated with, or may be undergoing treatment with, a TKI (e.g. pazopanib). In such cases, the methods of the present invention may find use in, for example, monitoring treatment and/or predicting the future course of continuing treatment with a TKI (e.g. pazopanib).

The individual to be treated is an animal, preferably a mammal, in particular a human.

Any individual that is not selected for treatment with a TKI, or who is given a poor prognosis with TKI treatment, may be 'deselected' from treatment with a TKI, or selected for an alternative treatment as discussed elsewhere herein.

The aspects of the invention relating to prognosis, treatment, selection of patients for treatment and devices suitable for use in these methods are discussed in more detail below. The details about particular TKIs, cancers and methods of carrying out tests on cancer cell samples as described above apply to all of these aspects.

Samples

A "test sample" as used herein may, in some cases, be a cell or tissue sample (e.g. a biopsy), a biological fluid, an extract (e.g. a protein or DNA extract obtained from the subject). In particular, the sample may be a tumour sample, a blood sample (including plasma or serum sample), a cerebrospinal fluid sample, or a non-tumour tissue sample. The sample may be one which has been freshly obtained from the subject or may be one which has been processed and/or stored prior to making a determination (e.g. frozen, fixed or subjected to one or more purification, enrichment or extractions steps). In some cases, the sample may be obtained directly from the tumour, obtained from circulating cancer cells and/or circulating tumour DNA.

Determining Prognosis, Selecting Individuals for Treatment and Stratification of Patients In one aspect, the invention relates to methods for determining a prognosis, and in particular to methods of identifying individuals with a poor prognosis or good prognosis following TKI treatment. Such a prognosis may help determine whether a TKI inhibitor should be administered.

The invention also relates to methods for stratification or grouping of individuals with cancer according to their prognoses following treatment with a TKI. The method may involve stratifying individuals into a sub-group having poor prognoses or good prognoses.

The invention also relates to methods of selecting individuals for treatment with a tyrosine kinase inhibitor. An individual determined to have a good prognosis following TKI treatment may be selected for treatment with a TKI. An individual determined to have a poor prognosis following TKI treatment may be deselected for treatment with a TKI.

These methods may be described as in vitro methods.

The methods may be useful for determining the likelihood of an individual responding to treatment with a TKI and for helping to determine appropriate treatments for individuals with cancer.

The methods may be useful for identifying individuals with cancer having inherent resistance to a TKI, e.g. pazopanib.

The markers identified by the present inventors are markers of patient outcomes. They can be used to predict prognosis following treatment with a tyrosine kinase inhibitor. In particular, the inventors have identified markers of progression-free survival (PFS) and overall survival (OS).

PFS is the time from first dose of TKI until radiological disease progression or death from any cause. OS is the time from first dose with a TKI until death from any cause. PFS and OS are generally expressed in months.

In this context the poor and good prognosis are relative. Whether a prognosis is considered good or poor may very between cancers and stage of disease. In general terms a good prognosis is one where the OS and/or PFS is longer than average for that stage and cancer type. A prognosis may be considered poor if PFS and/or OS is lower than average for that stage and type of cancer. The average may be the mean OS or PFS.

For example, a prognosis may be considered good if the PFS is >6 months and/or OS >18 months. Similarly PFS of <6 months or OS of <18 months may be considered poor. In particular PFS of >6 months and/or OS of >18 months may be considered good for advanced cancers.

In particular PFS of >6 months and/or OS of >18 months may be considered good for pazopanib treatment, for example of soft tissue sarcoma (STS), in particular advanced STS.

For example, a prognosis may be considered good if the PFS is >6 months and/or OS >18 months. Similarly PFS of <6 months or OS of <18 months may be considered poor. In particular PFS of >6 months and/or OS of >18 months may be considered good for advanced cancers.

In particular PFS of >6 months and/or OS of >18 months may be considered good for pazopanib treatment, for example of soft tissue sarcoma (STS), in particular advanced STS.

In general terms, a "good prognosis" is one where survival (OS and/or PFS) of an individual patient can be favourably compared to what is expected in a population of patients within a comparable disease setting. This might be defined as better than median survival (i.e. survival that exceeds that of 50% of patients in population).

In particular, PFS >4 months and/or OS >12 months may be considered good following pazopanib treatment for patients with advanced soft tissue sarcomas, based on median survival in the pazopanib arm in the PALLETTE trial. Very good survival in the same population might be considered PFS >6 months and/or OS >18 months.

Any of the methods may use one or more of: 1) expression of FGFR1 and PDGFRA, 2) TP53 mutational status, and 3) expression profiles for genes involved in key oncogenic pathways (those shown in list 1).

The methods may make use of the expression profiles of genes shown in table 5.

The methods may make use of the expression profiles of genes shown in table 4.

The same methods and markers may be applied to determine whether a cancer in an individual is likely to be sensitive to TKI treatment.

In other words, markers of a good prognosis following TKI treatment are also markers of a cancer that is sensitive to TKI treatment. Markers of a poor prognosis following TKI treatment are also markers of a cancer that is resistant to TKI treatment. Accordingly, the methods of determining a prognosis may also be considered methods of determining sensitivity of a cancer to TKI treatment.

The methods may comprise the step of determining the expression levels of PDGFRA and FGFR1 as 'high' (Hi) or 'low' (Lo) in a sample of cancer cells from an individual. The individual is selected for treatment or determined to have a good prognosis or stratified as having a good prognosis if they have:
  (i) PDGFRA-Hi/FGFR1-Hi
  (ii) PDGFRA-Lo/FGFR1-Lo, or
  (iii) PDGFRA-Lo/FGFR1-Hi
  expression levels.

The individual may be selected for treatment or determined to have a good prognosis or stratified as having a good prognosis if they have PDGFRA-Lo and/or FGFR1-Hi expression levels. Accordingly, the criteria of PDGFRA-Lo and/or FGFR1-Hi may be applied to any of the applications and methods disclosed herein in place of the PDGFRA-Hi/FGFR1-Hi or PDGFRA-Lo/FGFR1-Lo, or PDGFRA-Lo/FGFR1-Hi criterion.

The methods may also use the mutation status of TP53. Accordingly, the methods may comprise the step of determining the mutation status of TP53 in a sample of cancer cells from an individual. The individual is selected for treatment or determined to have a good prognosis or stratified as having a good prognosis if they have wildtype TP53.

The methods may also use gene expression profiles. Accordingly, the method may comprise the step of determining the expression levels in a sample of cancer cells from the individual of 5 or more of the genes selected from List 1. The individual is selected for treatment or determined to have a good prognosis or stratified as having a good prognosis based on the expression levels of those genes. In particular, the individual is selected for treatment or determined to have a good prognosis or stratified as having a good prognosis if the expression profile of the genes of List 1 measured in a sample obtained from the individual is a closest match for the centroid of subgroup A as defined herein (e.g. the exemplary centroids shown in Table 3). These gene expression profiles may be applied to cancers that are already determined (a) not to be PDGFRA-Hi/FGFR1-Lo, and (b) TP53 wildtype.

As mentioned elsewhere these methods may be combined for further selection and to give a better indication of patient outcome.

Accordingly the methods may comprise the steps of:
  (a) determining the expression levels of PDGFRA and FGFR1 as 'high' (Hi) or 'low'(Lo) in a sample of cancer cells from the individual, and selecting an individual for treatment or determining a good prognosis following treatment with a TKI if they have PDGFRA-Hi/FGFR1-Hi, PDGFRA-Lo/FGFR1-Lo, or PDGFRA-Lo/FGFR1-Hi expression levels,
  (b) determining the mutation status of TP53 in a sample of cancer cells from the individual and selecting an individual for treatment with a TKI or determining a good prognosis following treatment with a TKI if they have wildtype TP53, and (c) determining the expression levels of 5 or more of the genes in List 1 in a sample of cancer cells from the individual, and selecting an individual for treatment with the TKI or determining a good prognosis following treatment with a TKI based on the expression levels of those genes if the expression.

The methods may comprise the steps of:
(a) determining the expression levels of PDGFRA and FGFR1 as 'high' (Hi) or 'low'(Lo) in a sample of cancer cells from the individual, and selecting an individual for treatment or determining a good prognosis following treatment with a TKI if they have PDGFRA-Lo and/or FGFR1-Hi expression levels,
(b) determining the mutation status of TP53 in a sample of cancer cells from the individual and selecting an individual for treatment with a TKI or determining a good prognosis following treatment with a TKI if they have wildtype TP53, and
(c) determining the expression levels of 5 or more of the genes in List 1 in a sample of cancer cells from the individual, and selecting an individual for treatment with the TKI or determining a good prognosis following treatment with a TKI based on the expression levels of those genes if the expression.

The patient/individual may only selected for treatment with the TKI or determining a good prognosis following treatment with a TKI if the selection criteria are met for the determining steps carried out in the method.

A patient/individual may be selected for treatment with the TKI or determined to have a good prognosis following treatment with a TKI if they have PDGFRA-Hi/FGFR1-Hi, PDGFRA-Lo/FGFR1-Lo, or PDGFRA-Lo/FGFR1-Hi expression levels and they have wildtype TP53. A patient may be selected for treatment with the TKI or determined to have a good prognosis following treatment with a TKI if they have PDGFRA-Hi/FGFR1-Hi, PDGFRA-Lo/FGFR1-Lo, or PDGFRA-Lo/FGFR1-Hi expression levels and based on the expression levels of 5 or more of the genes in List 1. A patient may be selected for treatment with the TKI or determined to have a good prognosis following treatment with a TKI if they have wildtype TP53 and based on the expression levels of 5 or more of the genes in List 1.

A patient may be selected for treatment with the TKI or determined to have a good prognosis following treatment with a TKI if they have PDGFRA-Hi/FGFR1-Hi, PDGFRA-Lo/FGFR1-Lo, or PDGFRA-Lo/FGFR1-Hi expression levels, wildtype TP53, and based on the expression levels of 5 or more of the genes in List 1.

Patients who do not meet one more of the criteria may be deselected from treatment with the tyrosine kinase inhibitor.

In some embodiments the determining steps are carried out in series. After a determining step an individual with cancer may be selected for a further determining step using the criteria above, or may be deselected. This makes a 'decision tree' allowing efficient selection of patients for treatment with a TKI. For example, the decision tree shown in FIG. 5 can be followed.

Alternatively, the methods may make use of the expression profiles of genes shown in table 5. The method may comprise determining the expression levels of 20 or more genes from table 5, and optionally:
(i) determining the mutation status of TP53 in a sample of cancer cells from the individual; and
(ii) determining the expression levels of 5 or more 10 or more, 15 or more, 20 or more, 30 or more, 40 or more, 50 or more, 60 or more, 70 or more, 80 or more, 90 or more, 100 or more, 110 or more, 115 or more, 120 or more, 140 or more, 160 or more, 180 or more 200 or more, or substantially all of, or all of the genes in List 1 in a sample of cancer cells from the individual.

An individual may be determined to have a good prognosis following TKI treatment if they have a cancer having expression levels of 20 or more of the genes in table 5 a closer match to a second reference centroid corresponding to the expression profile of said 20 or more genes determined in a second group of subjects known not to have PDGFRA-Hi/FGFR1-Lo expression, than a first reference centroid corresponding to the expression profile of said 20 or more genes determined in a first group of subjects known to have PDGFRA-Hi/FGFR1-Lo expression, and optionally:
(i) wildtype TP53; and
(ii) the expression levels of genes in the sample are determined to be similar to the expression levels of the same genes in a group of patients known to respond well to TKI treatment, wherein the group of patients has cancer, preferably the same type of cancer as the individual.

An individual may be determined to have a poor prognosis if they have a cancer having expression levels of 20 or more of the genes in table 5 a closer match to a first reference centroid corresponding to the expression profile of said 20 or more genes determined in a first group of subjects known to have PDGFRA-Hi/FGFR1-Lo expression, than a second reference centroid corresponding to the expression profile of said 20 or more genes determined in a second group of subjects known not to have PDGFRA-Hi/FGFR1-Lo expression.

The methods may make use of the expression profiles of genes shown in table 4. The method may comprise determining the expression levels of 40 or more genes from table 4.

An individual may be determined to have a good prognosis following TKI treatment if they have a cancer having the expression levels of the 40 or more genes in table 4 a closer match to a third reference centroid than said first, second, fourth or fifth reference centroids, wherein the reference centroids are:
(a) a first reference centroid corresponding to the expression profile of said 40 or more genes determined in a first group of subjects known to have cancer with PDGFRA-Hi/FGFR1-Lo expression;
(b) a second reference centroid corresponding to the expression profile of said 40 or more genes determined in a second group of subjects known to have cancer with mutated TP53 and not PDGFRA-Hi/FGFR1-Lo expression;
(c) a third reference centroid corresponding to the expression profile of said 40 or more genes determined in a third group of subjects known to have cancer with (a) a gene expression profile having a closer match to the centroid of subgroup A shown in table 3 than subgroups B or C, and (b) TP53 wild-type, and (c) not PDGFRA-Hi/FGFR1-Lo expression;
(d) a fourth reference centroid corresponding to the expression profile of said 40 or more genes determined in a fourth group of subjects known to have cancer with (a) a gene expression profile having a closer match to the centroid of subgroup B shown in table 3 than subgroups A or C, and (b) TP53 wild-type, and (c) not PDGFRA-Hi/FGFR1-Lo expression; and
(e) a fifth reference centroid corresponding to the expression profile of said 40 or more genes determined in a fifth group of subjects known to have cancer with (a) a gene expression profile having a closer match to the centroid of subgroup C shown in table 3 than subgroups B or C, and (b) TP53 wild-type, and (c) not PDGFRA-Hi/FGFR1-Lo expression.

An individual may be determined to have a poor prognosis if they have a cancer having the expression levels of the 40 or more genes in table 4 a closer match to a first, second, fourth or fifth reference centroid than a third reference centroids, wherein the reference centroids are:
- (a) a first reference centroid corresponding to the expression profile of said 40 or more genes determined in a first group of subjects known to have cancer with PDGFRA-Hi/FGFR1-Lo expression;
- (b) a second reference centroid corresponding to the expression profile of said 40 or more genes determined in a second group of subjects known to have cancer with mutated TP53 and not PDGFRA-Hi/FGFR1-Lo expression;
- (c) a third reference centroid corresponding to the expression profile of said 40 or more genes determined in a third group of subjects known to have cancer with (a) a gene expression profile having a closer match to the centroid of subgroup A shown in table 3 than subgroups B or C, and (b) TP53 wild-type, and (c) not PDGFRA-Hi/FGFR1-Lo expression;
- (d) a fourth reference centroid corresponding to the expression profile of said 40 or more genes determined in a fourth group of subjects known to have cancer with (a) a gene expression profile having a closer match to the centroid of subgroup B shown in table 3 than subgroups A or C, and (b) TP53 wild-type, and (c) not PDGFRA-Hi/FGFR1-Lo expression; and
- (e) a fifth reference centroid corresponding to the expression profile of said 40 or more genes determined in a fifth group of subjects known to have cancer with (a) a gene expression profile having a closer match to the centroid of subgroup C shown in table 3 than subgroups B or C, and (b) TP53 wild-type, and (c) not PDGFRA-Hi/FGFR1-Lo expression.

More details of the determining steps and combinations thereof are given elsewhere herein.

In any of the methods described herein the determining steps may be historical, and the methods may make use of expression levels that have already been determined.

Treatment of Cancer with TKIs

In one aspect the present invention provides methods and medical uses for the treatment of cancers with TKIs. According to these methods and treatments the cancers are ones which are identified herein as being sensitive to treatment with TKI.

Accordingly, a tyrosine kinase inhibitor for use in a method of treating cancer in an individual is provided, wherein the cancer has PDGFRA-Hi/FGFR1-Hi, PDGFRA-Lo/FGFR1-Lo, or PDGFRA-Lo/FGFR1-Hi expression levels; and/or wildtype TP53; and/or has been identified as sensitive to TKI treatment based on the expression levels of 5 or more of the genes in List 1.

Also provided is the use of a TKI in the manufacture of a medicament for treating a cancer in an individual wherein the cancer has been identified as having PDGFRA-Hi/FGFR1-Hi, PDGFRA-Lo/FGFR1-Lo, or PDGFRA-Lo/FGFR1-Hi expression levels, and/or wildtype TP53, and/or has been identified as sensitive based on the expression levels of 5 or more of the genes in List 1.

Also provided is a method of treating a cancer in an individual comprising administration of a TKI, wherein the cancer has PDGFRA-Hi/FGFR1-Hi, PDGFRA-Lo/FGFR1-Lo, or PDGFRA-Lo/FGFR1-Hi expression levels, and/or wildtype TP53, and/or has been identified as sensitive based on the expression levels of 5 or more of the genes in List 1.

Also provided is a tyrosine kinase inhibitor for use in a method of treating cancer in an individual is provided, wherein the cancer has been identified as sensitive to TKI treatment based on the expression levels of 20 or more of the genes in table 5. Also provided is a tyrosine kinase inhibitor for use in a method of treating cancer in an individual is provided, wherein the cancer has been identified as sensitive to TKI treatment based on the expression levels of 40 or more of the genes in table 4.

Also provided is the use of a TKI in the manufacture of a medicament for treating a cancer in an individual wherein the cancer has been identified as sensitive to TKI treatment based on the expression levels of 20 or more of the genes in table 5. Also provided is the use of a TKI in the manufacture of a medicament for treating a cancer in an individual wherein the cancer has been identified as sensitive to TKI treatment based on the expression levels of 40 or more of the genes in table 4.

Also provided is a method of treating a cancer in an individual comprising administration of a TKI, wherein the cancer has been identified as sensitive to TKI treatment based on the expression levels of 20 or more of the genes in table 5. Also provided is a method of treating a cancer in an individual comprising administration of a TKI, wherein the cancer has been identified as sensitive to TKI treatment based on the expression levels of 40 or more of the genes in table 4.

The methods and treatments disclosed herein may involve the steps of determining whether a patient is suitable for treatment.

The methods and treatments may relate to treatment of an individual who has been pre-selected for treatment using the methods described herein. For example, a tyrosine kinase inhibitor is provided for use in a method of treating cancer in an individual, wherein the individual has been selected for treatment as described herein.

Also provided is the use of a tyrosine kinase inhibitor in the manufacture of a medicament for treating cancer in an individual, wherein the individual has been selected for treatment as described herein.

Also provided is a method of treating cancer in an individual in need thereof with a tyrosine kinase inhibitor, wherein the individual has been selected for treatment as described herein.

While the individuals or patients for treatment may have been pre-selected, the methods and uses may also comprise the active steps of selecting an individual for treatment.

The uses and methods may comprise the step of determining if the cancer is susceptible to TKI treatment using one or more of 1) baseline expression of FGFR1 and PDGFRA, for example using immunohistochemistry (IHC), 2) TP53 mutational status, and 3) mRNA transcript abundance for genes involved in key oncogenic pathways (shown in List 1).

The methods may involve the step of obtaining a sample of cancer cells from the individual, and selecting the individual for treatment based on the tests disclosed herein.

For example, the methods may involve the steps of:
a) obtaining a sample of cancer cells from an individual
b) determining one or more of: (i) the expression levels of PDGFRA and FGFR1 as 'high' (Hi) or 'low' (Lo) in the sample of cancer cells from the individual, (ii) the mutation status of TP53 in a sample of cancer cells from the individual, and (iii) the expression levels of 5 or more of the genes in List 1 in a sample of cancer cells from the individual; and c) selecting the patient for treatment if they meet the selection criteria for one or more of step (i) to (iii). For example a patient may be selected for treatment if they meet the selection criteria for all of the tests in part (i) to (iii) that are carried out.

For example, a patient may be selected for treatment if they have PDGFRA-Hi/FGFR1-Hi, PDGFRA-Lo/FGFR1-Lo, or PDGFRA-Lo/FGFR1-Hi expression levels, and/or wildtype TP53, and/or based on the expression levels of 5 or more of the genes in List 1.

The selection criteria are set out in more detail elsewhere herein, as are the methods and techniques for carrying out the determining steps.

The methods may involve the step:
(d) of treating the individual with a TKI.

The individual to be treated is preferably a mammal, in particular a human.

The treatments disclosed may be described including the step of administering the TKI to the individual, e.g. in a therapeutically effective amount. Treatment of an individual with cancer may also be described as treatment of a patient in need thereof.

Administration and Pharmaceutical Compositions

The TKIs disclosed herein for the treatment of cancer, may be administered alone, but it is generally preferable to provide them in pharmaceutical compositions that additionally comprise with one or more pharmaceutically acceptable carriers, adjuvants, excipients, diluents, fillers, buffers, stabilisers, preservatives, lubricants, or other materials well known to those skilled in the art and optionally other therapeutic or prophylactic agents. Examples of components of pharmaceutical compositions are provided in Remington's Pharmaceutical Sciences, 20th Edition, 2000, pub. Lippincott, Williams & Wilkins.

The term "pharmaceutically acceptable" as used herein includes compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The active agents disclosed herein for the treatment of cancer are preferably for administration to an individual in a "prophylactically effective amount" or a "therapeutically effective amount" (as the case may be, although prophylaxis may be considered therapy), this being sufficient to show benefit to the individual. For example, the agents (inhibitors) may be administered in amount sufficient to delay tumour progression, or prevent tumour growth and/or metastasis or to shrink tumours. For example, the agents may be administered in an amount sufficient to induce apoptosis of cancer cells.

The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

The agents disclosed herein for the treatment of deficient cancer may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising agents disclosed herein for the treatment of cancer may be used in the methods described herein in combination with standard chemotherapeutic regimes or in conjunction with radiotherapy. Examples of other chemotherapeutic agents include Amsacrine (Amsidine), Bleomycin, Busulfan, Capecitabine (Xeloda), Carboplatin, Carmustine (BCNU), Chlorambucil (Leukeran), Cisplatin, Cladribine (Leustat), Clofarabine (Evoltra), Crisantaspase (Erwinase), Cyclophosphamide, Cytarabine (ARA-C), Dacarbazine (DTIC), Dactinomycin (Actinomycin D), Daunorubicin, Docetaxel (Taxotere), Doxorubicin, Epirubicin, Etoposide (Vepesid, VP-16), Fludarabine (Fludara), Fluorouracil (5-FU), Gemcitabine (Gemzar), Hydroxyurea (Hydroxycarbamide, Hydrea), Idarubicin (Zavedos). Ifosfamide (Mitoxana), Irinotecan (CPT-11, Campto), Leucovorin (folinic acid), Liposomal doxorubicin (Caelyx, Myocet), Liposomal daunorubicin (DaunoXome®) Lomustine, Melphalan, Mercaptopurine, Mesna, Methotrexate, Mitomycin, Mitoxantrone, Oxaliplatin (Eloxatin), Paclitaxel (Taxol), Pemetrexed (Alimta), Pentostatin (Nipent), Procarbazine, Raltitrexed (Tomudex®), Streptozocin (Zanosar®), Tegafur-uracil (Uftoral), Temozolomide (Temodal), Teniposide (Vumon), Thiotepa, Tioguanine (6-TG) (Lanvis), Topotecan (Hycamtin), Treosulfan, Vinblastine (Velbe), Vincristine (Oncovin), Vindesine (Eldisine) and Vinorelbine (Navelbine).

Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound, and so the actual weight to be used is increased proportionately.

Kits

The invention also provides kits for use in the methods described herein. In other words, the invention provides a kit for stratifying individuals with cancer, for identifying a cancer suitable for treatment with a TKI, for determining a prognosis, and for determining if a cancer is likely to be sensitive to treatment with a TKI.

The kit may comprise specific binding agents for detecting the biomarkers. These specific binding agents may also be referred to as probes.

In particular, the kit may contain probes for detecting 5 or more, 10 or more, 15 or more, 20 or more, 30 or more, 40 or more, 50 or more, 60 or more, 70 or more, 80 or more, 90 or more, 100 or more, 120 or more, 140 or more, 160 or more, 180 or more 200 or more, or substantially all of, or all of the gene expression products of the genes in List 1. For example, the kit may contain nucleic acid probes which specifically bind to the mRNA expression products of the genes in List 1. The device (kit) can quantify the gene expression level of the genes in List 1.

The binding agents may be immobilised on one or more solid supports, for example on a microarray chip.

The kit may also have probes for expression analysis of PDGFRA and FGFR1. The kits may have probes for detection of PDGFRA and FGFR1 nucleic acids or proteins. For example, specific binding proteins such as antibodies may be used for the detection of PDGFRA and FGFR1 proteins, or specific nucleic acid probes may be used for the detection of PDGRA and FGFR1 gene or mRNA transcript.

The kit may also comprise probes for determining TP53 mutation status. For example, the kit may comprise probes specific for mutations in TP53.

Accordingly, the kit may comprise probes for determining TP53 mutation status, determining PDGFRA and FGFR1 expression and determining the expression of at least 5 genes selected from List 1.

The probes may all be used in a single device, for example on a single microarray. The kit may thus allow simultaneous determination of TP53 status, PDGFRA and FGFR1 expression and expression levels of 5 or more of the genes in List 1. In other words, the kit may allow determination of TP53 status, PDGFRA and FGFR1 expression and expression levels of 5 or more of the genes in List 1 in a single assay, or on a single microarray.

Suitable kits for mutation status, protein quantification and gene expression include nCounter® Vantage 3D™ Solid Tumor Assays (nanoString Technologies).

In addition, the kit may comprise one or more binding agents capable of binding specifically to an expression product of a control gene which is not differentially expressed between individuals affected and unaffected by the cancer of interest. The level of expression from this control gene may be measured in order to assist in quantification of the expression products of the genes of List 1, and/or for quality assurance of an assay performed using the kit. Preferably a control gene is chosen which is constitutively expressed in the cells of the biological sample (i.e. always expressed, at substantially the same level, under substantially all conditions). Such genes are often referred to as "housekeeping" genes. Exemplary housekeeping genes include any one or more of the housekeeping genes described in Supplementary methods 4 herein (ACAD9, AGK, AMMECR1L, C10orf76, CC2D1B, CNOT10, CNOT4, COG7, DDX50, DHX16, DNAJC14, EDC3, EIF2B4, ERCC3, FCF1, FTSJ2, GPATCH3, HDAC3, MRPS5, MTMR14, NOL7, NUBP1, PIAS1, PIK3R4 and PRPF38A).

The kit may comprise further binding agents capable of binding to expression products of other biomarker genes or control genes. However, in preferred embodiments, the kit comprises binding agents for expression products of less than 1000 different genes, e.g. less than 500 different genes, less than 400, less than 300, less than 250, less than 200, or less than 160 different genes. For example, the kit may comprise comprises binding agents for expression products of the genes listed in List 1 and/or PDGFRA & FGFR1, and/or TP53, and no more than 10, 20, 30, 40, 50, 60, 70, 80, 90, 100, 150, 200, 250, 300, 400, 500, 600, 700, 800 or 900 additional genes expression products.

Alternatively, the kit may have probes for detecting the expression levels of at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or all 42 of the genes listed in table 5. For example, the kit may contain nucleic acid probes which specifically bind to the mRNA expression products of the genes in table 5. The device (kit) can quantify the gene expression level of the genes in table 5.

Alternatively, the kit may have probes for detecting the expression levels of at least 40, at least 45, at least 50, at least 60, at least 70, at least 80, at least 90, at least 100, at least 110, at least 120, at least 130, at least 240, at least 150, at least 160, at least 170, at least 180, at least 190, at least 200, at least 210, at least 220 or all 225 of the genes in table 4. For example, the kit may contain nucleic acid probes which specifically bind to the mRNA expression products of the genes in table 4. The device (kit) can quantify the gene expression level of the genes in table 4.

These kits may contain binding agents/probes for control genes as described above.

The kit is suitable for use in the methods of the invention described in this specification, and may comprise instructions for performing one or more methods of the invention.

In certain embodiments, the kit of the invention takes the form of a companion diagnostic and includes (in addition to the components described above) with it, or is intended to be provided alongside, a TKI or pharmaceutical composition or dosage form comprising a TKI.

Embodiments of the present invention will now be described by way of example and not limitation with reference to the accompanying figures. However various further aspects and embodiments of the present invention will be apparent to those skilled in the art in view of the present disclosure.

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE FIGURES

FIG. 2A. Consensus clustering identified optimal separation of 22 IHCnegTP53 wt patients into 5 biological subgroups. Shown here is a heatmap of the 22 patients based on expression data of the list of 223 genes which were identified to be significantly differential among the 5 biological subgroups using multiclass SAM analysis set at <5% FDR. Kaplan Meier curves of the 5 biological subgroups for (FIG. 2B) PFS and (FIG. 2C) OS of 22 patients. FIG. 2D. Combination of biological subgroups 1 with 2, and 4 with 5, results in 3 clinical subgroups (A, B, C). Shown here is a heatmap of the 22 patients based on expression of list of 229 genes which were identified to be significantly differential among the 3 clinical subgroups using multiclass SAM analysis set at 10% FDR. Kaplan Meier curves of the 3 clinical subgroups for (FIG. 2E) PFS and (FIG. 2F) OS within the subset of 22 patients. SAM=Significance Analysis of Microarray. FDR=False Discovery Rate. PFS=Progression-free survival. OS=overall survival. HR=Hazard Ratio, 95% CI (95% Confidence Interval) and P value derive by log-rank testing.

FIG. 3C. Bar charts showing $LR\chi^2$ for PFS and OS for 5 proportional hazards regressions. All regression models included baseline clinico-pathological factors, with additional terms being either F-Lo/P-Hi IHC status alone; TP53 mutational status alone; IHC and TP53 mutational status as parallel terms; or decision tree-defined subgroups. Percentage increases in $LR\chi^2$ compared to regression model using clinico-pathological factors only are stated. PFS=progression-free survival. OS=overall survival. $LR\chi^2$=Likelihood ratio $\chi^2$ value. F-Lo/P-Hi=FGFR1-Low/PDGFRA-High. HR=Hazard Ratio, 95% CI (95% Confidence Interval) and P value derive by Cox proportional hazards testing.

FIG. 4A. Kaplan-Meier curves of F-Lo/P-Hi and all other patient subgroups for overall survival of 250 cases within TCGA-SARC dataset with available gene expression data. FIG. 4B. Kaplan-Meier curves of TP53 mutated and TP53 wildtype patient subgroups for overall survival of 232 cases within TCGA-SARC dataset with available TP53 sequence data. FIG. 4C. Kaplan-Meier curves of 3 clinical subgroups A-C for overall survival of 250 cases within TCGA-SARC dataset with available gene expression data. FIG. 4D. Kaplan-Meier Curves of 5 PAR-SARC classifier-defined subgroups for overall survival of 229 cases within TCGA-SARC dataset with available gene expression and TP53 sequence data. F-Lo/P-Hi=FGFR1-Low/PDGFRA-High. HR=hazard ratio, 95% CI (95% confidence interval) and P value derive by log-rank testing.

FIG. 8 shows exonic TP53 mutations detected by Sanger sequencing in pazopanib-treated STS cohort.

Lollipop plot showing position of detected mutations within coding exons on TP53. List of detected mutations of TP53. Each row represents one of 10 cases with detected TP53 mutation.

Figure 9:
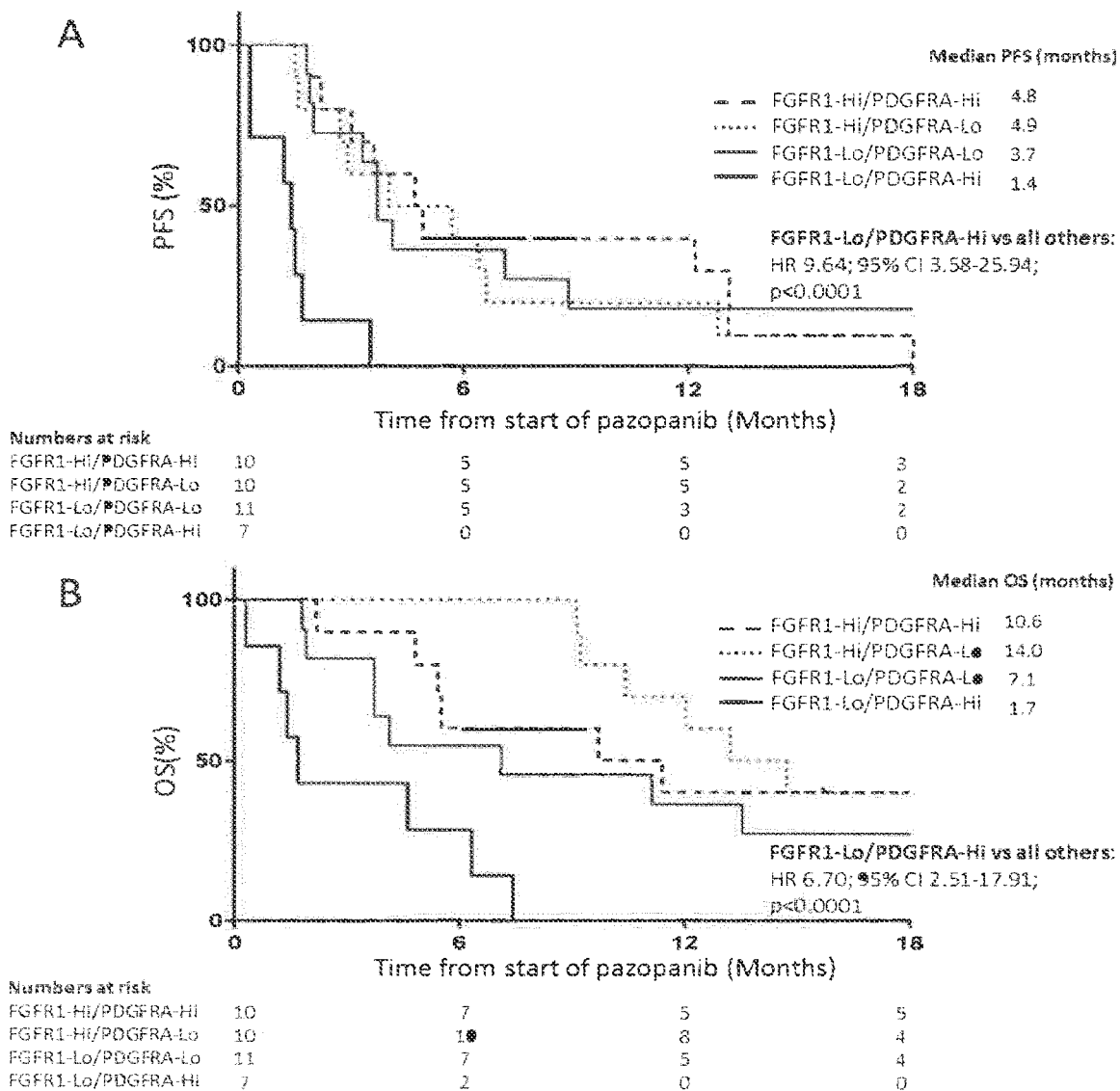

FIG. 9A-9C shows low FGFR1 expression and high PDGFRA expression identifies a subgroup with poor post-pazopanib outcome. FIG. 9A. Results of Cox Proportional Hazard modelling of PFS and OS association of FGFR1 and PDGFRA expression with and without inclusion of term for interaction between the two protein markers. Kaplan Meier curves of 4 subgroups defined by protein expression level of FGFR1 and PDGFRA as assessed by IHC for FIG. 9B) PFS and FIG. 9C) OS of 38 patients. PFS=progression-free survival. OS=overall survival. HR=Hazard ratio, 95% CI (95% Confidence Interval) and P value derive by log-rank testing, comparing FGFR1-Lo/PDGFRA-Hi subgroup to all other subgroups combined.

Figure 10:
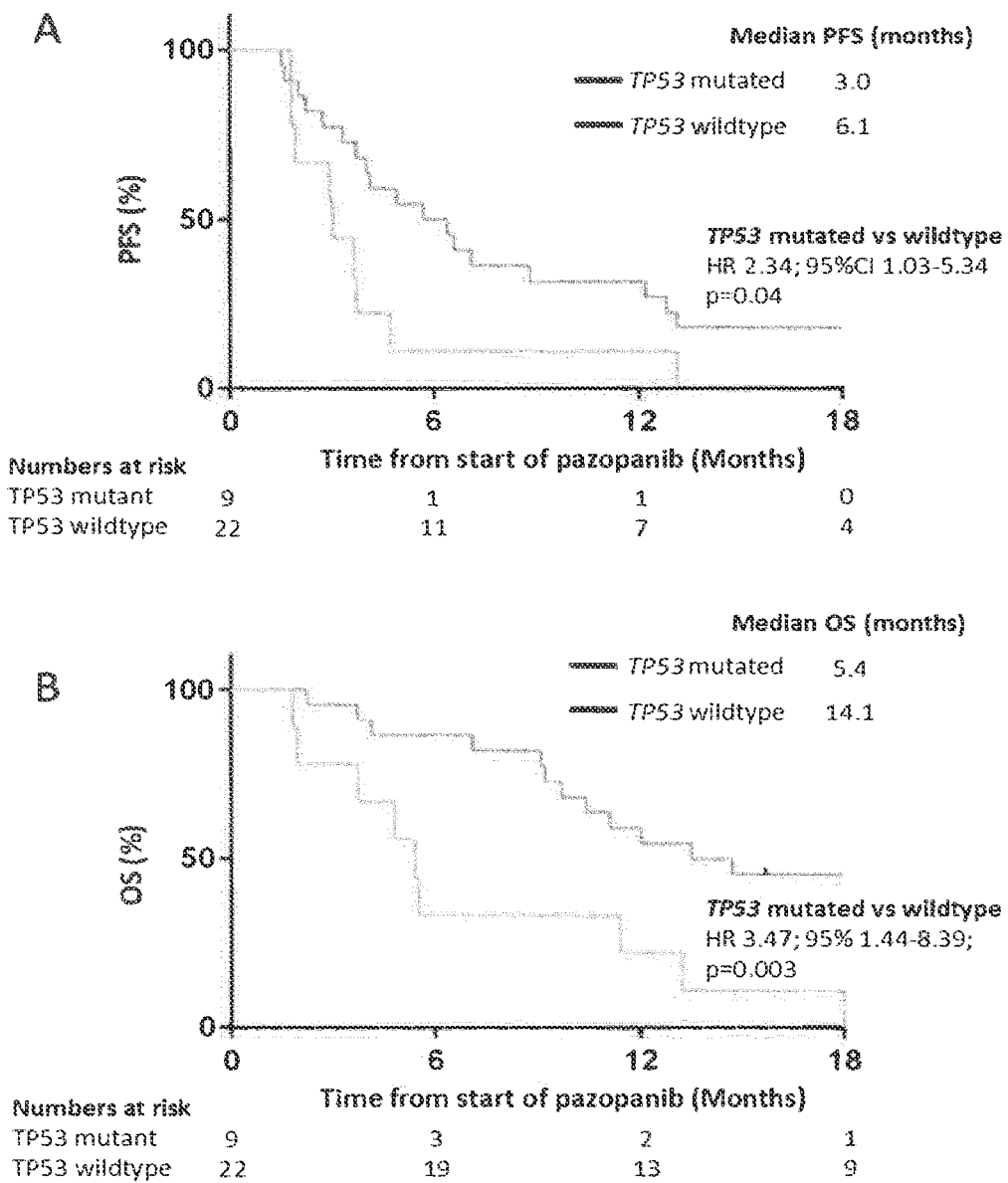

FIG. 10A-10B shows TP53 mutation is associated with worse post-pazopanib outcome in IHCneg patients. Kaplan Meier curves of 2 subgroup defined by presence or absence of detected TP53 mutation for (FIG. 10A) PFS and (FIG. 10B) OS of 31 IHCneg patients. PFS=progression-free survival. OS=overall survival. HR=Hazard ratio, 95% CI (95% Confidence Interval) and P value derive by log-rank testing.

Figure 11A:
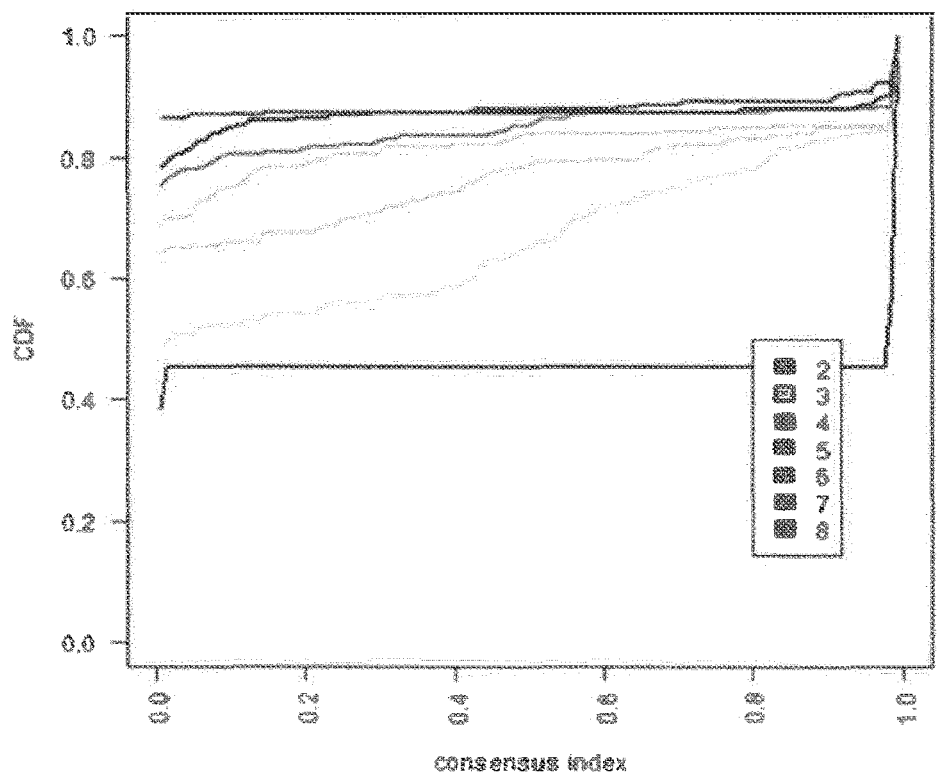
Figure 11:
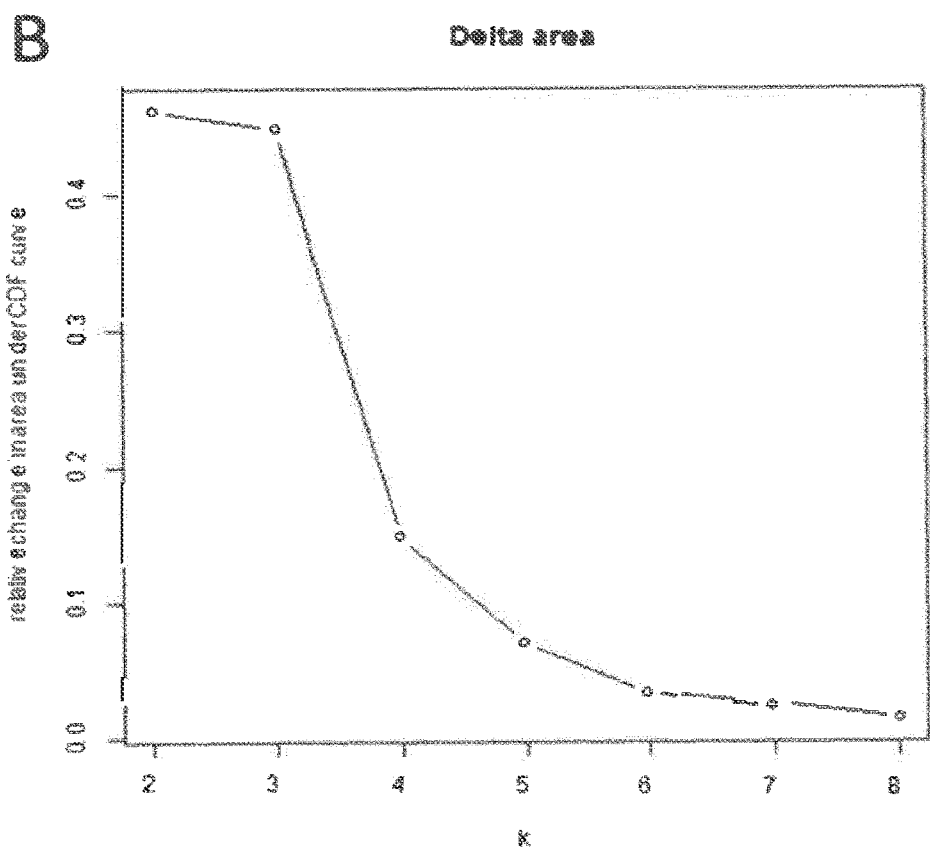
Figure 11C:
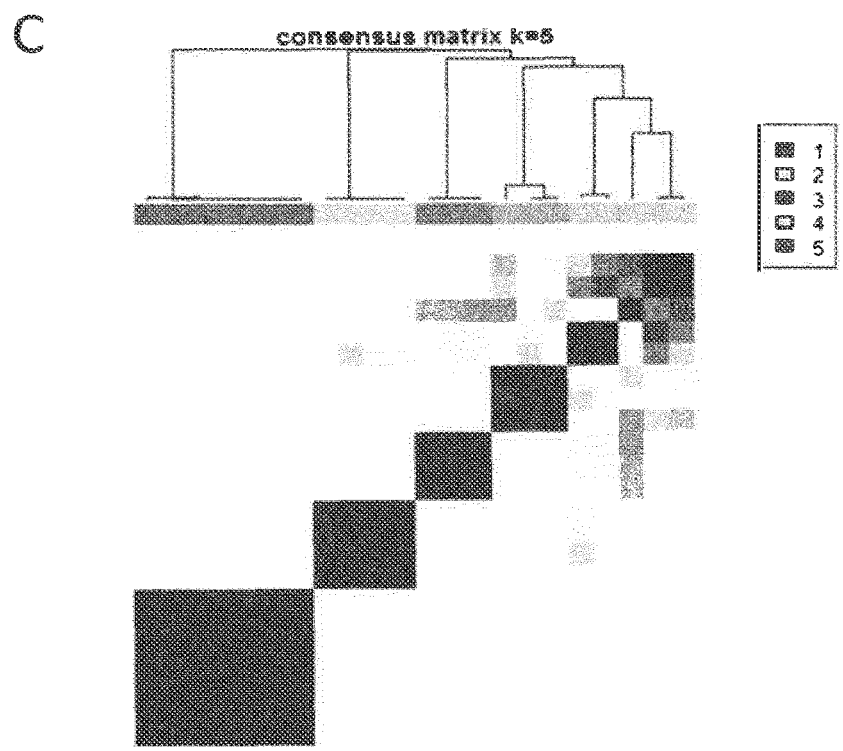

FIG. 11A-11C shows consensus clustering of IHCnegTP53 wt cases optimally identifies 5 clusters. FIG. 11A. Cumulative distribution plots for empirically imposed number of clusters. FIG. 11B. Relative increase in area under CDF curve with increasing number of imposed clusters. FIG. 11C. Consensus clustering matrix of gene expression of 22 IHCnegP53 wt patients using 5 subgroups (1-5).

Figure 12A:
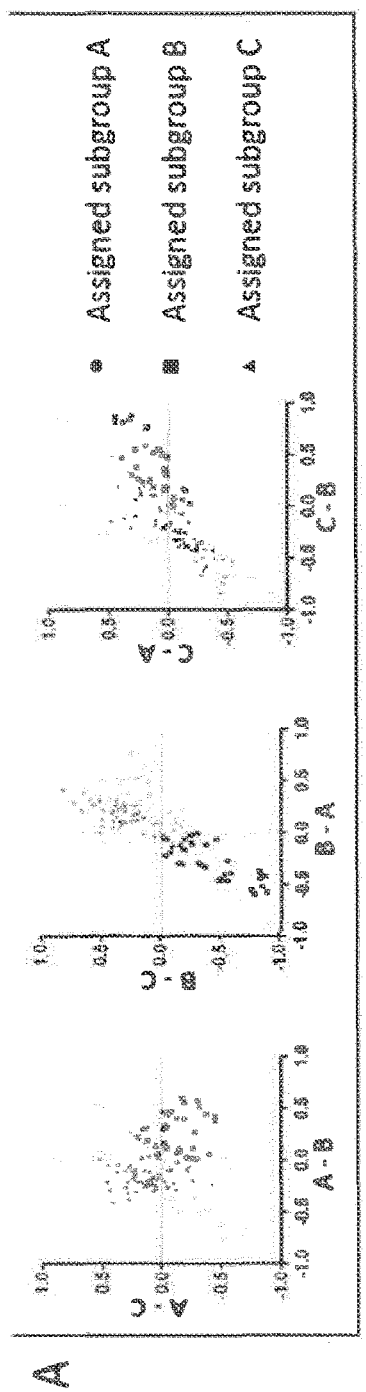
Figure 12D:
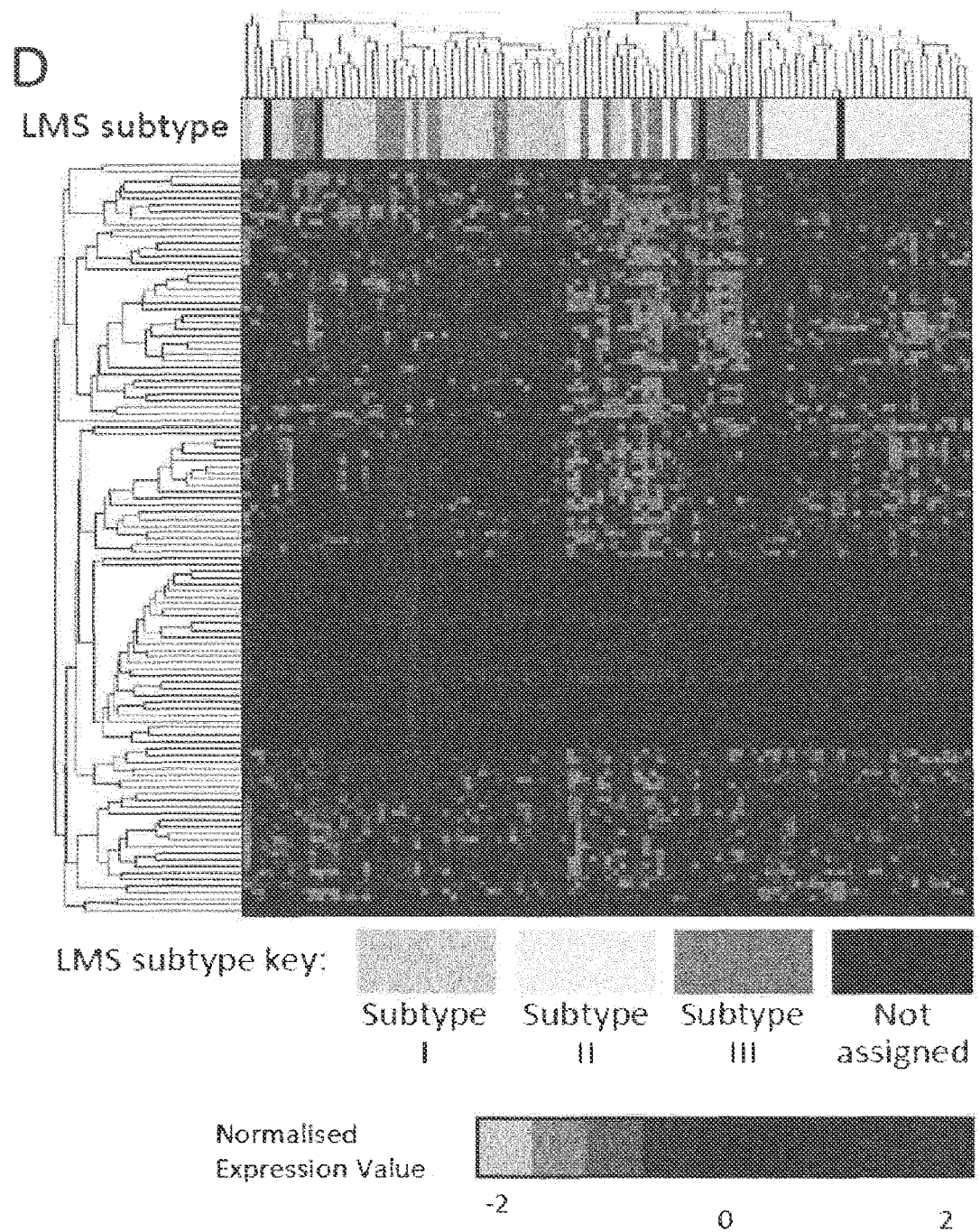

FIG. 12A-12D shows genes highly expressed in subgroup B cluster are also upregulated in smooth muscle-like leiomyosarcoma molecular subgroup in an independent LMS cohort. FIG. 12A. Scatter plots showing assignment of 99 LMS cases from independent Stanford-LMS dataset[16] to one of three subgroups A-C on basis of distance from centroid defined within our cohort. Axes values represent difference between distances of cases from pairs of centroids as indicated. Contingency tables showing enrichment of LMS subtype I compared to (FIG. 12B) LMS subtype II and (FIG. 12C) LMS subtype III in cases assigned to gene expression-defined subgroup B through assessment of centroid distance. P values derive from Fishers exact testing. FIG. 12D. Hierarchical clustering of Stanford-LMS cohort using 115 genes with significantly differential expression within RMH-SARC cohort. Shown here is a heat-map of 99 LMS cases with colour bar indicating LMS molecular subtype of each case as described by Guo et al[16]

Figure 13:
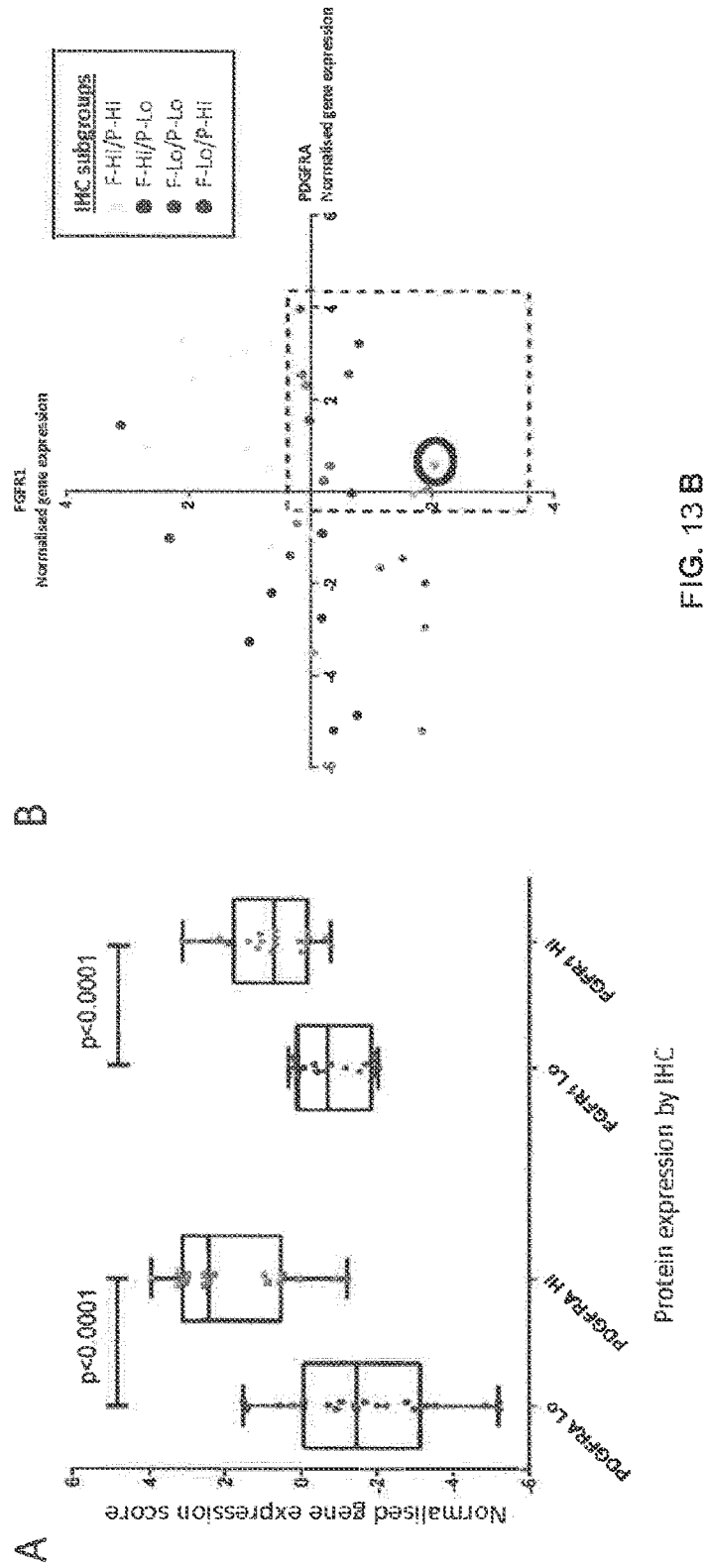
Figure 13:
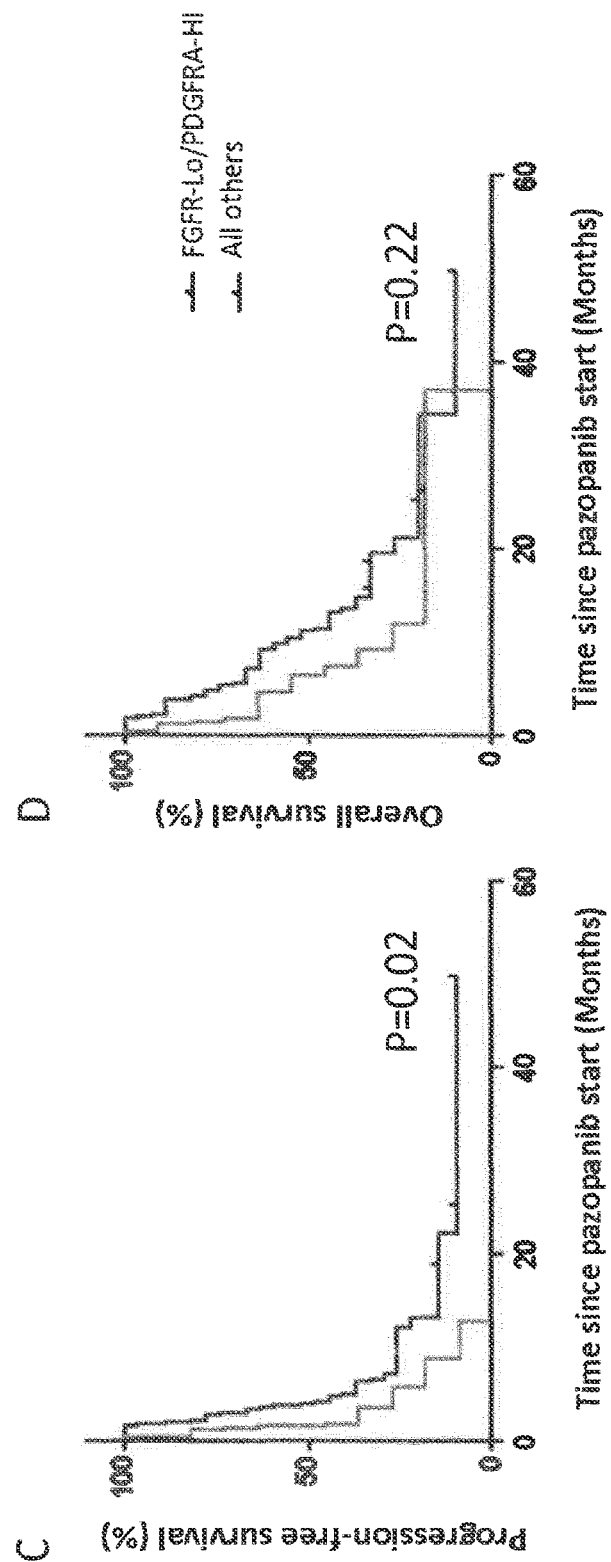

FIG. 13A-13D. Low FGFR1 and high PDGFRA high gene expression identify a patient subgroup with worse post-pazopanib PFS. FIG. 13A. Box and tail plot showing normalised gene expression levels for FGFR1 and PDGFRA when grouped by high or low protein expression as assessed by IHC. P values derive from unpaired T test. FIG. 13B. Scatter plot of normalised gene expression values for FGFR1 and PDGFRA, grouped by IHC assessment of protein expression. Dotted box denotes cases designated as FGFR1-Lo/PDGFRA-Hi by gene expression analysis. Circled case denotes single case of extraskeletal myxoid chondrosarcoma designated F-Lo/P-Lo by IHC but FGFR1-Lo/PDGFR-Hi by gene expression analysis. On IHC review, this case exhibited high PDGFRA expression in intratumor blood vessels but not in tumour cells themselves. As such, this case was re-designated as non-FGFR1-Lo/PDGFRA-Hi. Kaplan Meier curves of 2 subgroups defined by presence or absence or F-Lo/P-Hi status as determined by gene expression analysis for (FIG. 13C) PFS and (FIG. 13D) OS for 38 patients. F-Lo =FGFR1-Lo. F-Hi=FGFR1-Hi. P-Lo=PDGFRA-Lo. P-Hi=PDGFRA-Hi. PFS=progression-free survival. OS=overall survival. HR=Hazard ratio, 95% CI (95% Confidence Interval) and P value derive by log-rank testing, comparing FGFR1-Lo/PDGFRA-Hi subgroup to all other subgroups combined.

Figure 14:
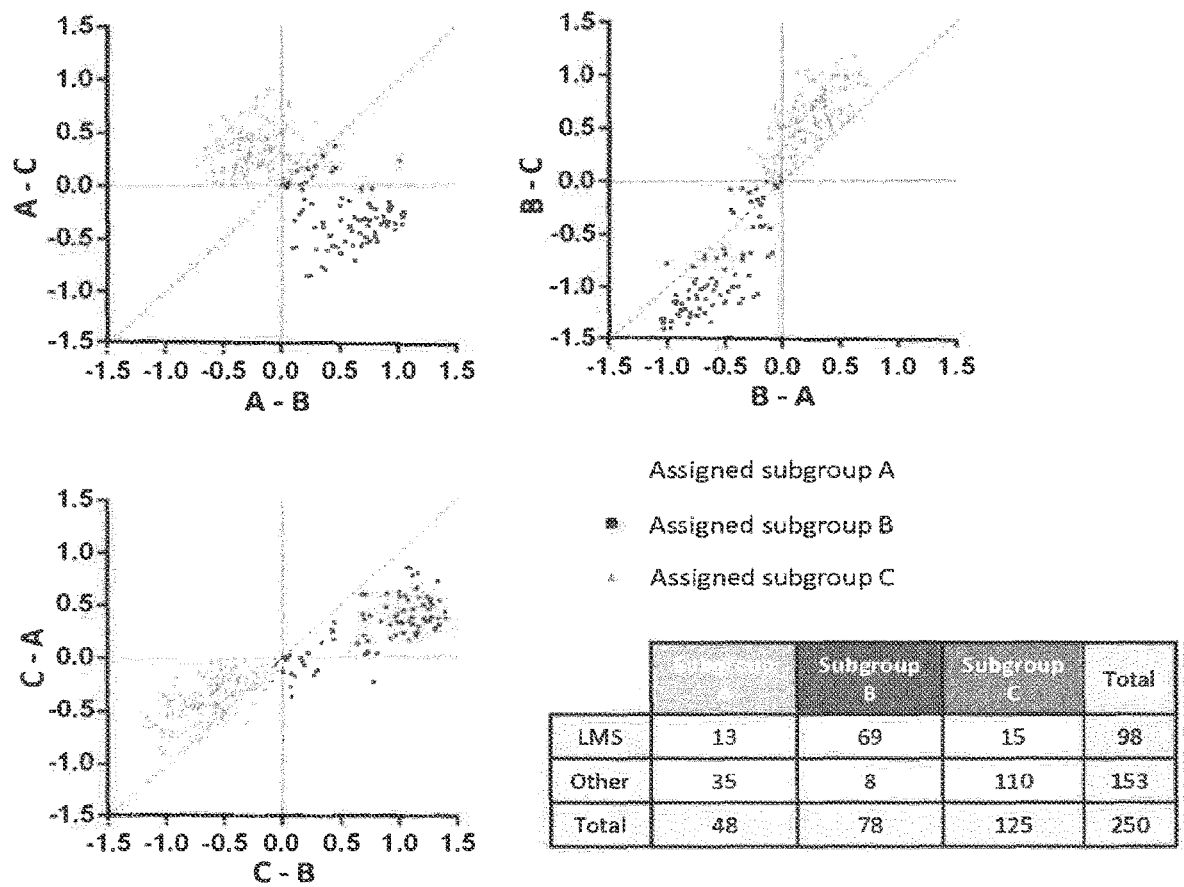

FIG. 14. Assignment of TCGA-SARC cases to subgroup A-C on basis of distance from centroids defined within RMH-SARC cohort. Scatter plots show distance of each of 251 eligible cases within TCGA-SARC dataset from centroids. Plot axes values represent difference between distances between pairs of centroid as indicated. Colours reflect assignment of each case to one of subgroups A-C. Table shows subgroup assignment of cases of LMS within TCGA-SARC cohort.

Figure 15A:
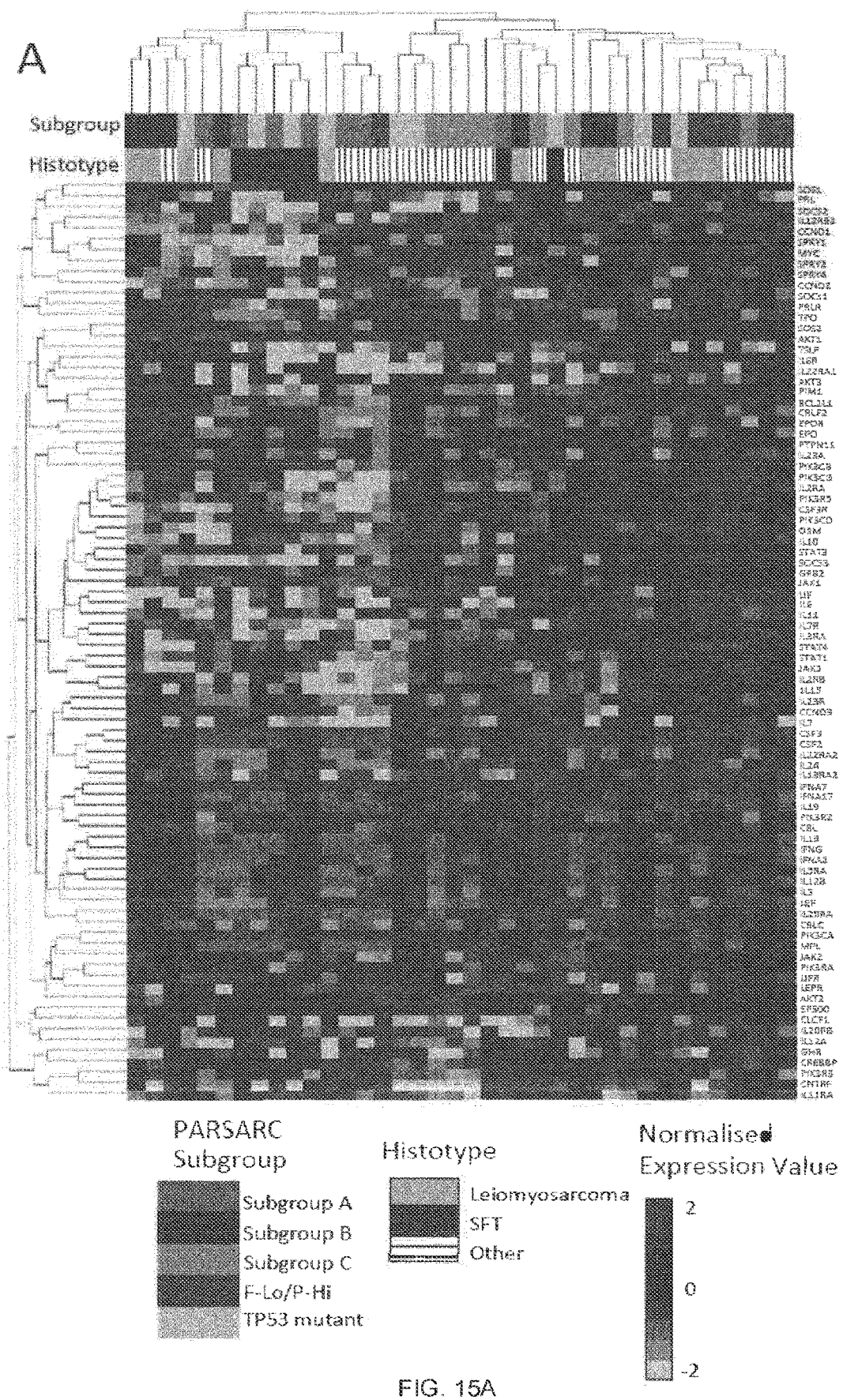
Figure 15B:
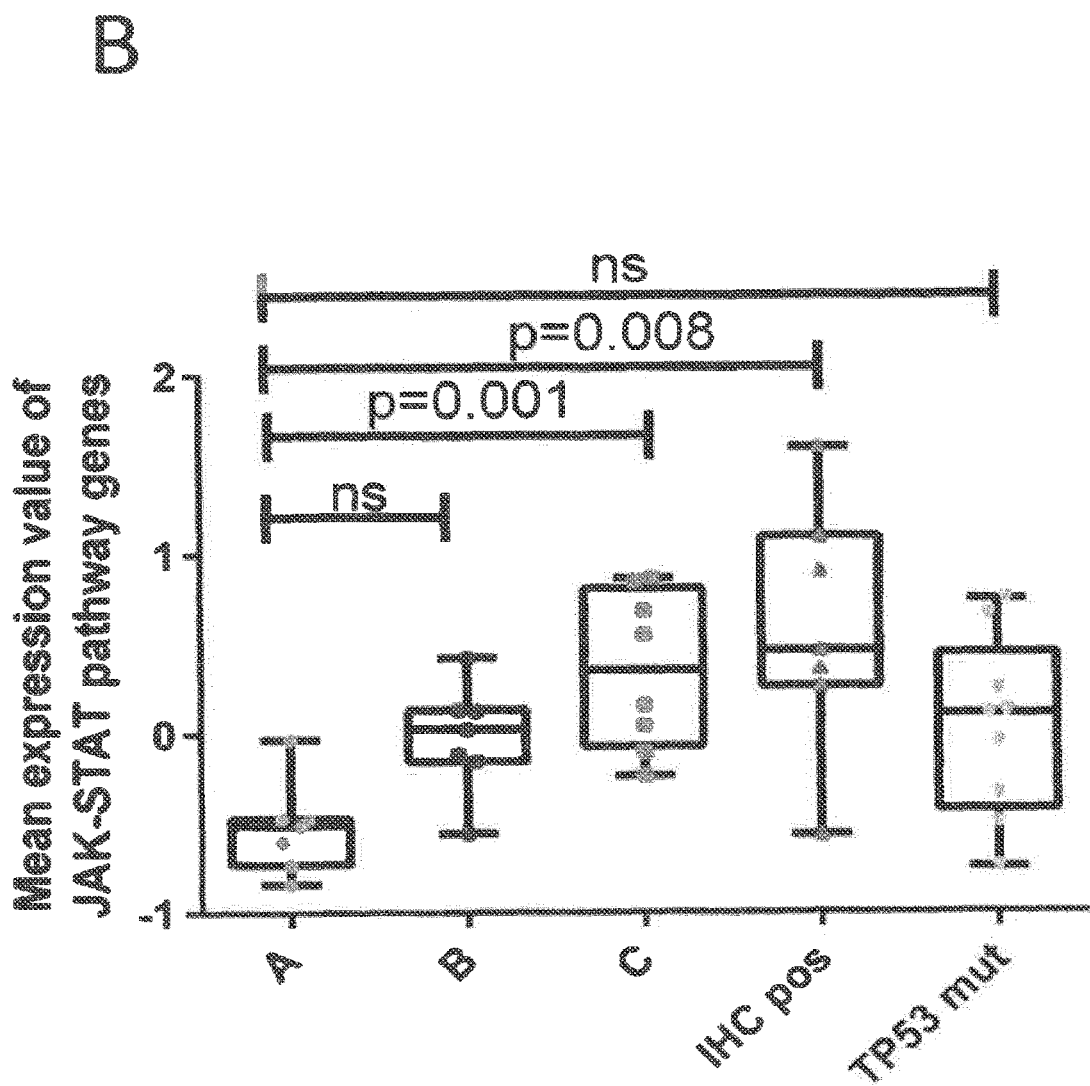

FIG. 15A-15B FGFR1-Lo/PDGFRA-Hi tumours are enriched for expression of JAK/STAT pathway-related genes. FIG. 15A. Hierarchical clustering and heatmap of 38 patients of RMH-SARC cohort based on expression data of 86 genes annotated as involved in JAK/STAT signalling pathway. FIG. 15B. Box and tail plots showing average expression level of JAK-STAT pathway-related genes in 5 PARSARC classifier subgroups within RMH-SARC cohort. P values derive from one way ANOVA and are corrected Average expression level of JAK-STAT pathway genes in 5 patient subgroups in decision tree risk classifier. P values derive from Tukey's multiple comparisons testing. NS=non-significant.

Figure 16A:
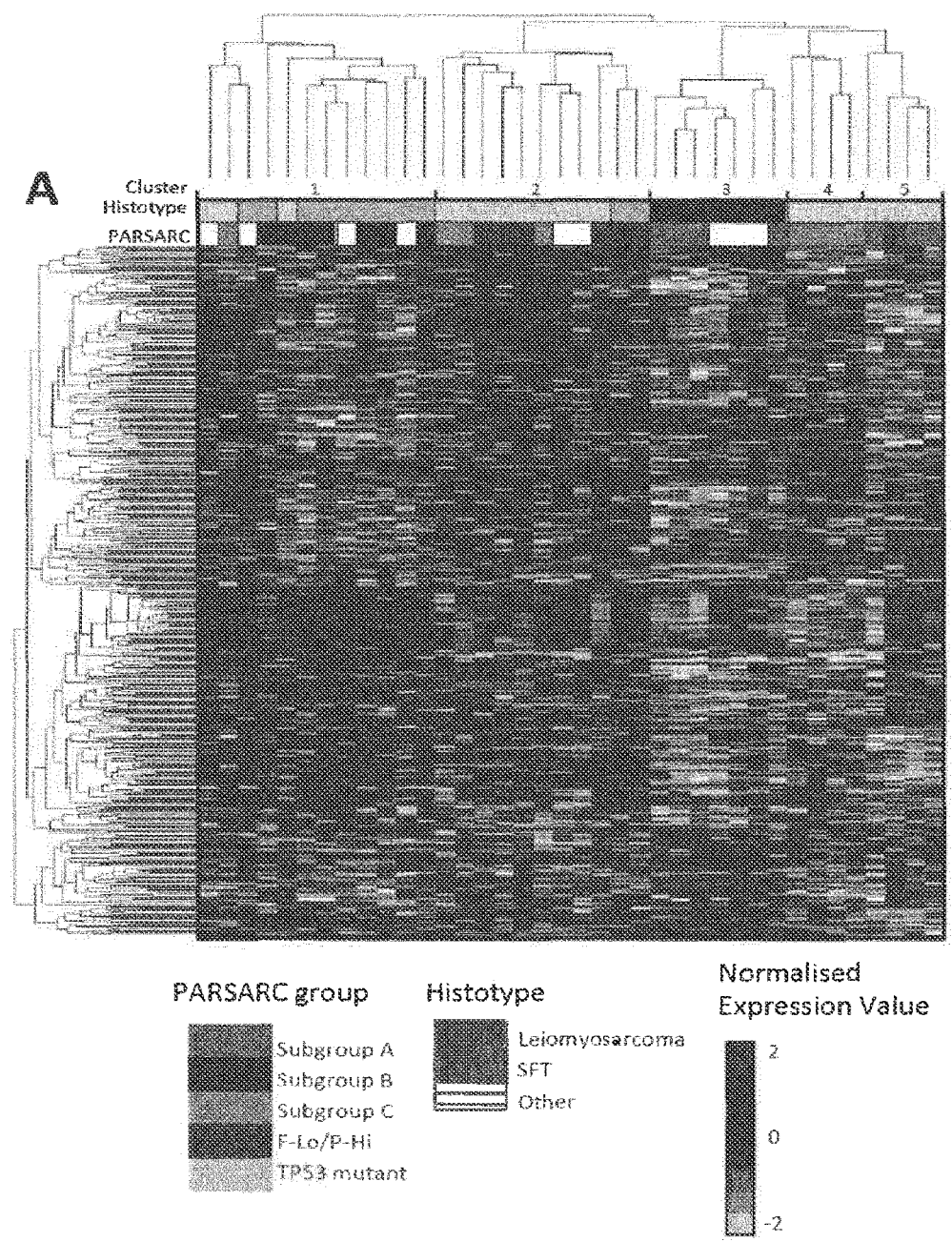
Figure 16B:
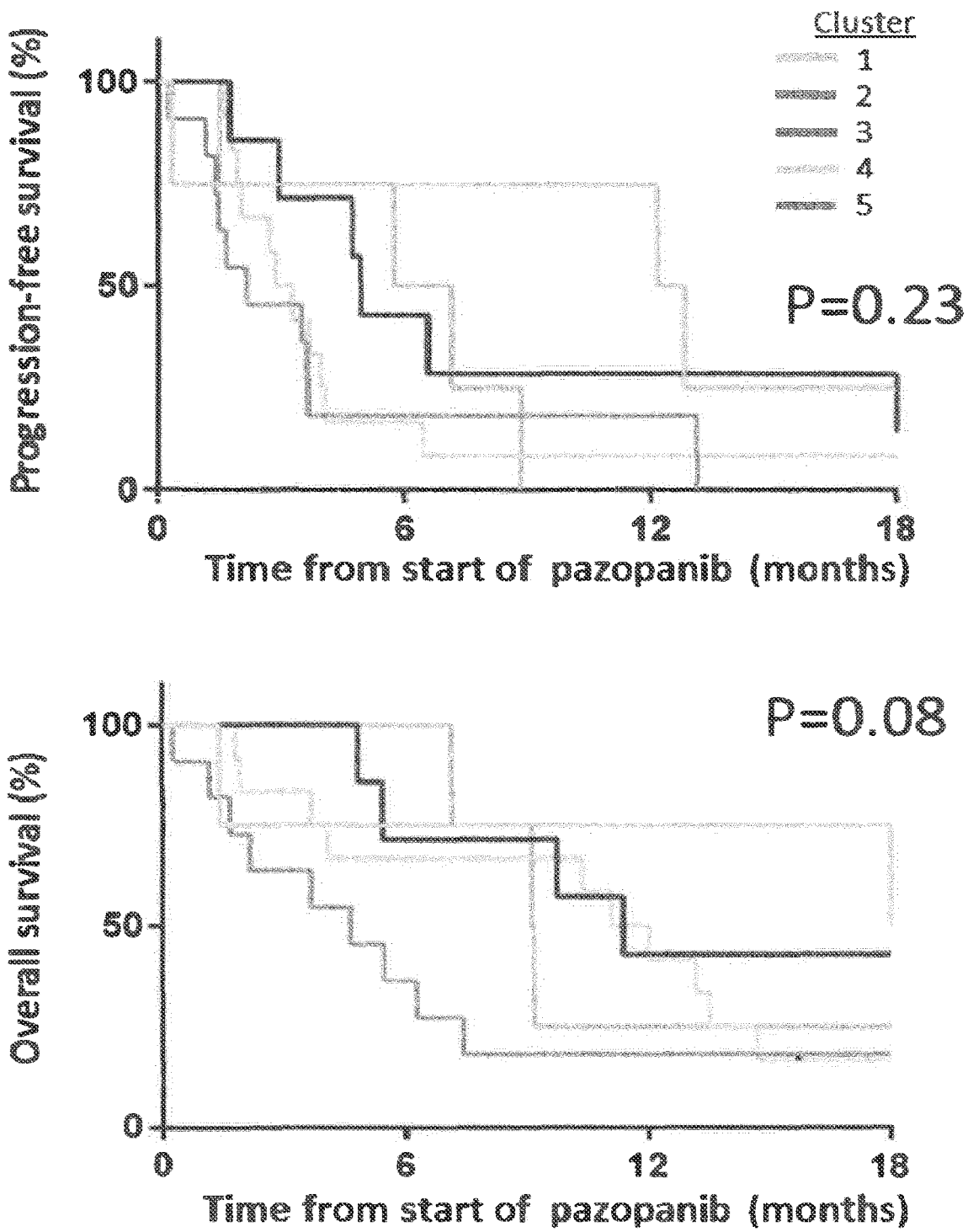

FIG. 16A-16B. Gene expression analysis of full 38 patient cohort fails to identify subgroups of distinct clinical outcome. FIG. 16A. Consensus clustering identified optimal separation of RMH-SARC cohort into 5 clusters. Shown here is a heatmap of the 38 patients based on expression data of 480 genes identified as significantly differential between the 5 clusters using multiclass SAM analysis set at <5% FDR. Kaplan Meier curves of patients in each of these 5 clusters for (FIG. 16B) PFS and (FIG. 16B) OS for 38 patients. PFS=progression-free survival. OS=overall survival. P values derive from log-rank testing.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The following is presented by way of example and is not to be construed as a limitation to the scope of the claims.

EXAMPLES

Example 1

Materials and Methods

Patient Selection and Treatment

Collection and analysis of anonymised archival FFPE tissue and associated clinical data was approved in as a sub-study protocol amendment to the Royal Marsden-sponsored Elucidation of a Molecular signature of Pazopanib Response in Advanced soft tissue Sarcoma including solitary fibrous tumours (EMPRASS) study. (RMH Committee for Clinical Research reference 4107, NHS Research Ethic Committee reference 14/WA/0164). This cohort is referred to as RMH-SARC in this manuscript.

Patients were retrospectively identified for inclusion by search of institutional database and electronic patient records compiled during routine clinical practice. Eligibility criteria for inclusion were: i) histopathological diagnosis of soft tissue tumour as confirmed by contemporaneous report by specialist sarcoma histopathologist; ii) received at least one dose of pazopanib for treatment of unresectable or advanced STS; iii) available FFPE tumour specimen, obtained from patient prior to first dose of pazopanib. Treatment and response monitoring was as per standard institutional practice, with pazopanib at 800 mg once daily until disease progression, intolerable toxicity or significant clinical deterioration. Dose interruption and/or reduction were instigated based on standard institutional guidelines and the discretion of the treating physician. Baseline clinicopathological characteristics and survival data were collected on retrospective review of contemporaneous electronic medical records. All related radiological imaging was retrospectively reviewed and disease response assessed according to RECIST 1.1. This manuscript is written according to the Reporting Recommendations for Tumor Marker Prognostic Studies (REMARK) guidelines15.

Tissue Selection and Processing

Available pre-pazopanib FFPE tumour specimens were identified and retrieved from an institutional diagnostic archive, with the specimen taken closest to pazopanib initiation processed in cases where several pre-treatment specimens were available. Newly sectioned haematoxylin and eosin (H&E) stained slides were reviewed to confirm viable tumour content. With reference to H&E, blocks containing tumour material of sufficient size were marked in three spatially discrete areas of representative viable tumour tissue. 1 mm diameter core biopsies were taken from each marked site and re-embedded lengthways into a new paraffin block to form a tissue microarray (TMA). Following coring, 4×10 µm sections were cut and, where necessary, macrodissected to enrich for >75% viable tumour content. Sections were then used for tumour DNA and total RNA extraction using All Prep DNA/RNA FFPE kit (Qiagen, Hilden, Germany) following vendor's standard protocol. DNA and RNA concentrations were measured using Qubit fluorometric quantitation (Thermo Fisher Scientific, Waltham, MA, USA). RNA Integrity Number and percentage of total RNA <300 bp in size was measured using 2100 Bioanalyzer system (Agilent, CA, USA). RNA and DNA samples were stored at −80° C. until use in downstream analyses.

Immunohistochemistry

Serial 4 µm sections were cut from TMA and from specimens not included in the TMA due to inadequate size. Tumour cell plasma membrane and cytoplasmic staining for PDGFRA (Cell Signalling, clone D1E1E) and FGFR1 (Epitomics, 2144-1) was assessed by immunohistochemistry by researchers blinded to associated outcome data (see Supplemental Methods for reagent and method details). IHC staining was scored in terms of intensity (0=absent, 1=weak, 2=moderate, 3=strong) and proportion of positive tumour cells (0=absent, 1=1-10%, 2: =11-50%, 3: >50%). The summation of the two scores give values ranging from 0 to 6 (Supplemental FIG. 1). Staining score ≥3 was classified as high expression and scores <3 as low expression. In cases of discrepancy between related TMA cores an average score was calculated and used to categorise the parent tumour as positive or negative.

TP53 Exon Sequencing

Extracted tumour DNA was used as a template for amplification and Sanger sequencing of exons 2-11 of TP53 as per International Agency for Research on Cancer (IARC) protocol16 (see Supplemental Methods for primer design and PCR experimental conditions). PCR products were Sanger sequenced (Eurofins Genomics, Ebersberg, Germany). Sequences were aligned to reference human TP53 sequence (GrCH38.p7) and analysed for variants using CLC Sequence Viewer v7.7 (Qiagen).

Gene Expression Analysis

Expression of 730 genes, representing 13 major cancer pathways including key driver genes was assessed using nCounter PanCancer Pathways panel (NanoString Technologies, Seattle, WA, USA). 150 ng total RNA was used as input for hybridisation and digital analysis as per manufacturer's instructions using nCounter Dx analysis system (NanoString Technologies). In cases with high RNA degradation, loading adjustments of up to 300 ng were made. Expression data was processed as follows: a) background correction was done by subtracting the geometric mean of the negative control probes, b) normalised by positive control normalization factor calculated as geometric mean of the positive controls followed by normalisation with the housekeeping genes. Expression values were then Log 2 transformed and subjected to gene-based centring.

In order to identify biological subgroups within a subset of 22 patients defined by the absence of identified IHC or TP53 sequencing-based markers, consensus clustering (CC) was used to objectively separate the tumours into stable biological subgroups17. The goal of CC was to search for a partition of the 22 tumours into at least 2 or, at most, 8 groups using expression of the 730 cancer pathway-associated genes. CC with 1-Pearson was used to identify robust unsupervised clusters by performing 200 iterations subsampling 80% of the samples each round. Having identified initially five clusters that were consolidated into three clearly separated subgroups, Multiclass Significance Analysis of Microarrays (SAM)18 was used to identify a subset of genes with significant differential expression (false discovery rate 5%) among the three subgroups. Functional enrichment analysis of these gene subsets was performed using the Database for Annotation, Visualization and Integrated Discovery (DAVID. Reference (training) gene expression profiles datasets for each of the three subgroups were built using gene subsets identified by SAM analysis. These gene subsets were also used to calculate a standardised centroid representing each of the three subgroups based on the Prediction Analysis of Microarray (PAM) algorithm. The nearest centroid single sample classification was used to assign individual tumour case to one of three subgroups from independent cohorts. The algorithm compared the individual cases' gene expression profile to each of three class centroids and was assigned to a subgroup based on the closest Euclidean distance to the centroid.

In order to assess whether gene expression data alone could be used to identify subgroups of distinct outcomes following pazopanib therapy, CC was also performed as above to partition all 38 patients into at least 2 or, at most, 8 groups using expression of the 730 cancer pathway-associated genes. Hierarchical clustering of the 38 patients using expression data for genes annotated as involved in each of 13 canonical cancer pathways was performed in order investigate for enrichment of biological processes in identified patient subgroups.

Independent Evaluation of identified biomarkers in TCGA-SARC dataset RNA sequencing (RNA-Seq) and accompanying clinical data for 261 cases of mixed STS were downloaded from The Cancer Genome Atlas (TCGA-SARC; accessed 27/02/2017). The abundance of transcripts was estimated using an Expectation-Maximization algorithm implemented in the software package RSEM8 v1.1.13. Quality control of RNA-Seq data was performed as described in TCGA, and RSEM data was upper quartile normalized and Log 2 transformed. When comparing data from multiple analyses (e.g. comparing expression profiles for one or more test samples to the centroids constructed from samples collected and analyzed in an independent study), it is necessary to normalize data across these data sets. Distance Weighted Discrimination (DWD) was used to combine TCGA-SARC and RMH-SARC data sets together to adjust for systematic biases between these two separate datasets23.

Each eligible case with available gene expression data was assigned to one of three subgroups on the basis of distance from centroids defined within the RMH-SARC cohort. High and low expression levels of FGFR1 and PDGFRA were defined using a cutoff at the first tertile of normalized gene expression values. Associated TP53 mutational status (defined as exonic non-synonymous single nucleotide variant or small indel) from DNA sequencing data for the cohort was downloaded from cBioPortal (accessed 22/04/2017).

Independent Evaluation of the Biological Subgroups on Stanford-LMS Dataset

Normalised gene expression profile data by 3'End RNA-sequencing (3SEQ) from a cohort of 99 cases of leiomyosarcoma (LMS) (GSE45510; accessed 09/03/2017) was obtained[16], referred to here as Stanford-LMS. DWD was used to combine Stanford-LMS and RMH-SARC datasets together to adjust for systematic biases between these two separate datasets. Each case was assigned to one of three subgroups on the basis of distance from centroids defined within our RMH-SARC cohort. Descriptive statistics was done to compare the frequency of our subgroups within each of the molecular LMS subgroups as described by Guo et all[16]. Hierarchical clustering of Stanford-LMS using our list of significant differential genes identified in RMH-SARC was used to illustrate the gene expression pattern.

Statistical Analysis

The stepwise primary objectives were to assess whether a surrogate of two immunohistochemical markers (FGFR1 and PDGFRA) and TP53 mutation status had statistical significant prognostic information for advanced STS. In this event, the two biomarkers panel were tested to determine if there is added statistically significant prognostic information to standard clinicopathological variables in multivariable comparisons. The secondary analyses included identification of biological subgroups based on gene expression profiles, and evaluation of the significance of these biological subgroups association with patient outcome. Progression free survival (PFS—defined as time in months from first dose of pazopanib to radiological disease progression or death from any cause) was the primary outcome endpoint, with overall survival (OS—defined as a time in months from first dose of pazopanib to death from any cause) as the secondary outcome endpoint. Data cut-off for survival follow-up was 30 Nov. 2016. Statistical analyses were performed by two senior statisticians. The Kaplan-Meier method was used to estimate PFS and OS, and the log-rank test to compare survival in different strata. Multivariable cox regression model was used to estimate the significance adjusted for the standard clinicopathological variables (including age, tumour grade, performance status and histological subtype). Proportional hazard assumption was tested using Schoenfeld residuals, and where deemed appropriate, Restricted Mean Survival was used. Interaction tests between FGFR1 and PDGFRA expression to predict for survival were evaluated for PFS and OS respectively. Likelihood ratio tests based on proportional hazards regression were used to test the prognostic information of all biomarkers. The quantification of the amount of prognostic information provided by one biomarker was assessed by the likelihood ratio $\chi^2$ value (LR$\chi^2$), and the additional information of one biomarker to biomarker score was measured by the increase of the likelihood ratio $\chi^2$ value ($\Delta$LR$\chi^2$) obtained from the proportional hazards model.

Ethics and Funding

Retrospective retrieval and analysis of anonymous archival FFPE tissue was approved in a protocol amendment to the Elucidation of a Molecular signature of Pazopanib Response in Advanced soft tissue Sarcoma including solitary fibrous tumours (EMPRASS) study, a Royal Marsden sponsored-single arm translational phase II study (CCR 4107, REC 14/WA/0164).

This is a summary of independent research supported by the National Institute for Health Research (NIHR) Biomedical Research Centre at The Royal Marsden NHS Foundation Trust and The Institute of Cancer Research, the Liddy Shriver Sarcoma Initiative and The Royal Marsden Charity. The views expressed are those of the author(s) and not necessarily those of the NHS, the NIHR or the Department of Health.

Supplementary Methods 1. IHC Antibody Details and Methods

DAKO link automated stainer was used for all IHC processing. Tissue sections were deparaffinised with xylene then rehydrated with graded ethanol (100%, 95% to 80%). Antigen retrieval was performed using DAKO FlexEnvision kit (K8002) with either microwave baking for 18 mins in citrate at pH6 (PDGFRa) or pressure cooking for 2 mins in citrate pH6 (FGFR1). Slides were incubated with primary antibodies (FRFR1—E pitomics 2144-1, 1:50 dilution; PDGFRA—Cell Signalling clone D1E1E, 1:250) for 60 minutes at room temperature and visualised using DAKO FlexEnvision (Rabbit/Mouse) kit (K8002), followed by application of DAB, resulting in visible brown colouration reaction at site of target antigen. Finally, nuclear counter-staining with haematoxylin was performed prior to cover-slipping. Positive controls were normal breast (PDGFRA) and appendix (FGFR1). Negative control was through omission of primary antibody.

Supplementary methods 2.
TP53 primer and PCR details (from IARC protocol)

| TP53 exon(s) | Forward primer[1] | Reverse Primer[1] | PCR program |
|---|---|---|---|
| 2-3 | Tctcatgctggatccccact(1) | Agtcagaggaccaggtcctc(2) | A |
| 4 | Tgaggacctggtcctctgac(3) | Agaggaatcccaaagttcca(4) | A |
| 5-6 | Tgttcacttgtgccctgact(5) | Ttaaccctcctcccagaga(6) | A |
| 7 | Aggcgcactggcctcatctt(7) | Tgtgcagggtggcaagtggc(8) | A |
| 8-9 | Ttgggagtagatggagcct(9) | Agtgttagactggaaacttt(10) | A |
| 10 | Caattgtaacttgaaccatc(11) | Ggatgagaatggaatcctat(12) | B |
| 11 | Agaccctctcactcatgtga(13) | Tgacgcacacctattgcaag(14) | A |

[1]SEQ ID Nos: are listed next to each sequence.
PCR program A:
94° C. for 2 min (94° C. for 30 sec, 63° C.* for 45 sec, 72° C. for 60 sec) x 20* = −0.5° C.
every 3 cycles (94° C. for 30 sec, 60° C. for 45 sec, 72° C. for 60 sec) x 30 72° C. for 10 min
PCR program B
94° C. for 2 min (94° C. for 30 sec, 58.5° C.* for 45 sec, 72° C. for 60 sec) x 20* = −0.5° C.
every 3 cycles (94° C. for 30 sec, 55° C. for 45 sec, 72° C. for 60 sec) x 30 72° C. for 10 min Supplementary methods 3. Endogenous 730 gene list for NanoString PanCancer Pathways Codeset

| | | | | |
|---|---|---|---|---|
| ABL1 | ATR | BMP7 | CACNG4 | CCND3 |
| ACVR1B | ATRX | BMP8A | CACNG6 | CCNE1 |
| ACVR1C | AXIN1 | BMPR1B | CALML3 | CCNE2 |
| ACVR2A | AXIN2 | BNIP3 | CALML5 | CCNO |
| AKT1 | B2M | BRAF | CALML6 | CCR7 |
| AKT2 | BAD | BRCA1 | CAMK2B | CD14 |
| AKT3 | BAIAP3 | BRCA2 | CAPN2 | CD19 |
| ALK | BAMBI | BRIP1 | CARD11 | CD40 |
| ALKBH2 | BAP1 | C19orf40 | CASP10 | CDC14A |
| ALKBH3 | BAX | CACNA1C | CASP12 | CDC14B |
| AMER1 | BCL2 | CACNA1D | CASP3 | CDC25A |
| AMH | BCL2A1 | CACNA1E | CASP7 | CDC25B |
| ANGPT1 | BCL2L1 | CACNA1G | CASP8 | CDC25C |
| APC | BCOR | CACNA1H | CASP9 | CDC6 |
| APH1B | BDNF | CACNA2D1 | CBL | CDC7 |
| AR | BID | CACNA2D2 | CBLC | CDH1 |
| ARID1A | BIRC3 | CACNA2D3 | CCNA1 | CDK2 |
| ARID1B | BIRC7 | CACNA2D4 | CCNA2 | CDK4 |
| ARID2 | BMP2 | CACNB1 | CCNB1 | CDK6 |
| ARNT2 | BMP4 | CACNB2 | CCNB3 | CDKN1A |
| ASXL1 | BMP5 | CACNB3 | CCND1 | CDKN1B |
| ATM | BMP6 | CACNG1 | CCND2 | CDKN1C |
| CDKN2A | CSF3 | EP300 | FGF22 | GATA2 |
| CDKN2B | CSF3R | EPHA2 | FGF23 | GATA3 |
| CDKN2C | CTNNB1 | EPO | FGF3 | GDF6 |
| CDKN2D | CUL1 | EPOR | FGF4 | GHR |
| CEBPA | CXXC4 | ERBB2 | FGF5 | GLI1 |
| CEBPE | CYLD | ERCC2 | FGF6 | GLI3 |
| CHAD | DAXX | ERCC6 | FGF7 | GNA11 |
| CHEK1 | DDB2 | ETS2 | FGF8 | GNAQ |
| CHEK2 | DDIT3 | ETV1 | FGF9 | GNAS |
| CHUK | DDIT4 | ETV4 | FGFR1 | GNG12 |
| CIC | DKK1 | ETV7 | FGFR2 | GNG4 |
| CLCF1 | DKK2 | EYA1 | FGFR3 | GNG7 |
| CNTFR | DKK4 | EZH2 | FGFR4 | GNGT1 |
| COL11A1 | DLL1 | FANCA | FIGF | GPC4 |
| COL11A2 | DLL3 | FANCB | FLNA | GRB2 |
| COL1A1 | DLL4 | FANCC | FLNC | GRIA3 |
| COL1A2 | DNMT1 | FANCE | FLT1 | GRIN1 |
| COL24A1 | DNMT3A | FANCF | FLT3 | GRIN2A |
| COL27A1 | DTX1 | FANCG | FN1 | GRIN2B |
| COL2A1 | DTX3 | FANCL | FOS | GSK3B |
| COL3A1 | DTX4 | FAS | FOSL1 | GTF2H3 |
| COL4A3 | DUSP10 | FASLG | FOXL2 | GZMB |
| COL4A4 | DUSP2 | FBXW7 | FOXO4 | H2AFX |
| COL4A5 | DUSP4 | FEN1 | FST | H3F3A |
| COL4A6 | DUSP5 | FGF1 | FUBP1 | H3F3C |
| COL5A1 | DUSP6 | FGF10 | FUT8 | HDAC1 |
| COL5A2 | DUSP8 | FGF11 | FZD10 | HDAC10 |
| COL6A6 | E2F1 | FGF12 | FZD2 | HDAC11 |
| COMP | E2F5 | FGF13 | FZD3 | HDAC2 |
| CREB3L1 | EFNA1 | FGF14 | FZD7 | HDAC4 |
| CREB3L3 | EFNA2 | FGF16 | FZD8 | HDAC5 |
| CREB3L4 | EFNA3 | FGF17 | FZD9 | HDAC6 |
| CREB5 | EFNA5 | FGF18 | GADD45A | HELLS |
| CREBBP | EGF | FGF19 | GADD45B | HES1 |
| CRLF2 | EGFR | FGF2 | GADD45G | HES5 |
| CSF1R | EIF4EBP1 | FGF20 | GAS1 | HGF |
| CSF2 | ENDOG | FGF21 | GATA1 | HHEX |
| HHIP | IL12RB2 | ITGA9 | LIG4 | MLH1 |
| HIST1H3B | IL13 | ITGB3 | LRP2 | MLLT3 |
| HIST1H3G | IL13RA2 | ITGB4 | LTBP1 | MLLT4 |
| HIST1H3H | IL15 | ITGB6 | MAD2L2 | MMP3 |
| HMGA1 | IL19 | ITGB7 | MAML2 | MMP7 |
| HMGA2 | IL1A | ITGB8 | MAP2K1 | MMP9 |
| HNF1A | IL1B | JAG1 | MAP2K2 | MNAT1 |
| HOXA10 | IL1R1 | JAG2 | MAP2K4 | MPL |
| HOXA11 | IL1R2 | JAK1 | MAP2K6 | MPO |
| HOXA9 | IL1RAP | JAK2 | MAP3K1 | MSH2 |
| HPGD | IL20RA | JAK3 | MAP3K12 | MSH6 |
| HRAS | IL20RB | JUN | MAP3K13 | MTOR |
| HSP90B1 | IL22RA1 | KAT2B | MAP3K14 | MUTYH |
| HSPA1A | IL22RA2 | KDM5C | MAP3K5 | MYB |
| HSPA2 | IL23A | KDM6A | MAP3K8 | MYC |
| HSPA6 | IL23R | KIT | MAPK1 | MYCN |
| HSPB1 | IL24 | KITLG | MAPK10 | MYD88 |
| IBSP | IL2RA | KLF4 | MAPK12 | NASP |
| ID1 | IL2RB | KMT2C | MAPK3 | NBN |
| ID2 | IL3 | KMT2D | MAPK8 | NCOR1 |
| ID4 | IL3RA | KRAS | MAPK8IP1 | NF1 |
| IDH1 | IL5RA | LAMA1 | MAPK8IP2 | NF2 |
| IDH2 | IL6 | LAMA3 | MAPK9 | NFATC1 |
| IFNA17 | IL6R | LAMA5 | MAPT | NFE2L2 |
| IFNA2 | IL7 | LAMB3 | MCM2 | NFKB1 |
| IFNA7 | IL7R | LAMB4 | MCM4 | NFKBIA |
| IFNG | IL8 | LAMC2 | MCM5 | NFKBIZ |
| IGF1 | INHBA | LAMC3 | MCM7 | NGF |
| IGF1R | INHBB | LAT | MDC1 | NGFR |
| IGFBP3 | IRAK2 | LEF1 | MDM2 | NKD1 |
| IKBKB | IRAK3 | LEFTY1 | MECOM | NODAL |
| IKBKG | IRS1 | LEFTY2 | MED12 | NOG |
| IL10 | ITGA2 | LEP | MEN1 | NOS3 |
| IL11 | ITGA3 | LEPR | MET | NOTCH1 |
| IL11RA | ITGA6 | LFNG | MFNG | NOTCH2 |
| IL12A | ITGA7 | LIF | MGMT | NOTCH3 |
| IL12B | ITGA8 | LIFR | MLF1 | NPM1 |
| NPM2 | PIK3R5 | PPP3R1 | RASGRF2 | SKP2 |
| NR4A1 | PIM1 | PPP3R2 | RASGRP1 | SMAD2 |
| NR4A3 | PITX2 | PRDM1 | RASGRP2 | SMAD3 |
| NRAS | PKMYT1 | PRKAA2 | RB1 | SMAD4 |
| NSD1 | PLA1A | PRKACA | RBX1 | SMAD9 |
| NTF3 | PLA2G10 | PRKACB | RELA | SMARCA4 |
| NTHL1 | PLA2G2A | PRKACG | RELN | SMARCB1 |
| NTRK1 | PLA2G3 | PRKAR1B | RET | SMC1A |
| NTRK2 | PLA2G4A | PRKAR2A | RFC3 | SMC1B |
| NUMBL | PLA2G4C | PRKAR2B | RFC4 | SMC3 |
| NUPR1 | PLA2G4E | PRKCA | RHOA | SMO |
| OSM | PLA2G4F | PRKCB | RIN1 | SOCS1 |
| PAK3 | PLA2G5 | PRKCG | RNF43 | SOCS2 |
| PAK7 | PLAT | PRKDC | RPA3 | SOCS3 |
| PAX3 | PLAU | PRKX | RPS27A | SOS1 |
| PAX5 | PLCB1 | PRL | RPS6KA5 | SOS2 |
| PAX8 | PLCB4 | PRLR | RPS6KA6 | SOST |
| PBRM1 | PLCE1 | PRMT8 | RRAS2 | SOX17 |
| PBX1 | PLCG2 | PROM1 | RUNX1 | SOX9 |
| PBX3 | PLD1 | PTCH1 | RUNX1T1 | SP1 |
| PCK1 | PML | PTCRA | RXRG | SPOP |
| PCNA | POLB | PTEN | SETBP1 | SPP1 |
| PDGFA | POLD1 | PTPN11 | SETD2 | SPRY1 |
| PDGFB | POLD4 | PTPN5 | SF3B1 | SPRY2 |
| PDGFC | POLE2 | PTPRR | SFN | SPRY4 |
| PDGFD | POLR2D | PTTG2 | SFRP1 | SRSF2 |
| PDGFRA | POLR2H | RAC1 | SFRP2 | SSX1 |
| PDGFRB | POLR2J | RAC2 | SFRP4 | STAG2 |
| PGF | PPARG | RAC3 | SGK2 | STAT1 |
| PHF6 | PPARGC1A | RAD21 | SHC1 | STAT3 |
| PIK3CA | PPP2CB | RAD50 | SHC2 | STAT4 |
| PIK3CB | PPP2R1A | RAD51 | SHC3 | STK11 |
| PIK3CD | PPP2R2B | RAD52 | SHC4 | STMN1 |
| PIK3CG | PPP2R2C | RAF1 | SIN3A | SUV39H2 |
| PIK3R1 | PPP3CA | RASA4 | SIRT4 | SYK |
| PIK3R2 | PPP3CB | RASAL1 | SIX1 | TBL1XR1 |
| PIK3R3 | PPP3CC | RASGRF1 | SKP1 | TCF3 |
| TCF7L1 | UTY | | | |
| TCL1B | VEGFA | | | |
| TET2 | VEGFC | | | |
| TFDP1 | VHL | | | |
| TGFB1 | WEE1 | | | |
| TGFB2 | WHSC1 | | | |
| TGFB3 | WHSC1L1 | | | |
| TGFBR2 | WIF1 | | | |
| THBS1 | WNT10A | | | |
| THBS4 | WNT10B | | | |
| THEM4 | WNT11 | | | |
| TIAM1 | WNT16 | | | |
| TLR2 | WNT2 | | | |
| TLR4 | WNT2B | | | |
| TLX1 | WNT3 | | | |
| TMPRSS2 | WNT4 | | | |
| TNC | WNT5A | | | |
| TNF | WNT5B | | | |
| TNFAIP3 | WNT6 | | | |
| TNFRSF10A | WNT7A | | | |
| TNFRSF10B | WNT7B | | | |

Supplementary methods 3. Endogenous 730 gene list
for NanoString PanCancer Pathways Codeset

| | |
|---|---|
| TNFRSF10C | WT1 |
| TNFRSF10D | XPA |
| TNFSF10 | XRCC4 |
| TNN | ZAK |
| TNR | ZBTB16 |
| TP53 | ZBTB32 |
| TPO | ZIC2 |
| TRAF7 | |
| TSC1 | |
| TSHR | |
| TSLP | |
| TSPAN7 | |
| TTK | |
| U2AF1 | |
| UBB | |
| UBE2T | |

Figure 1:
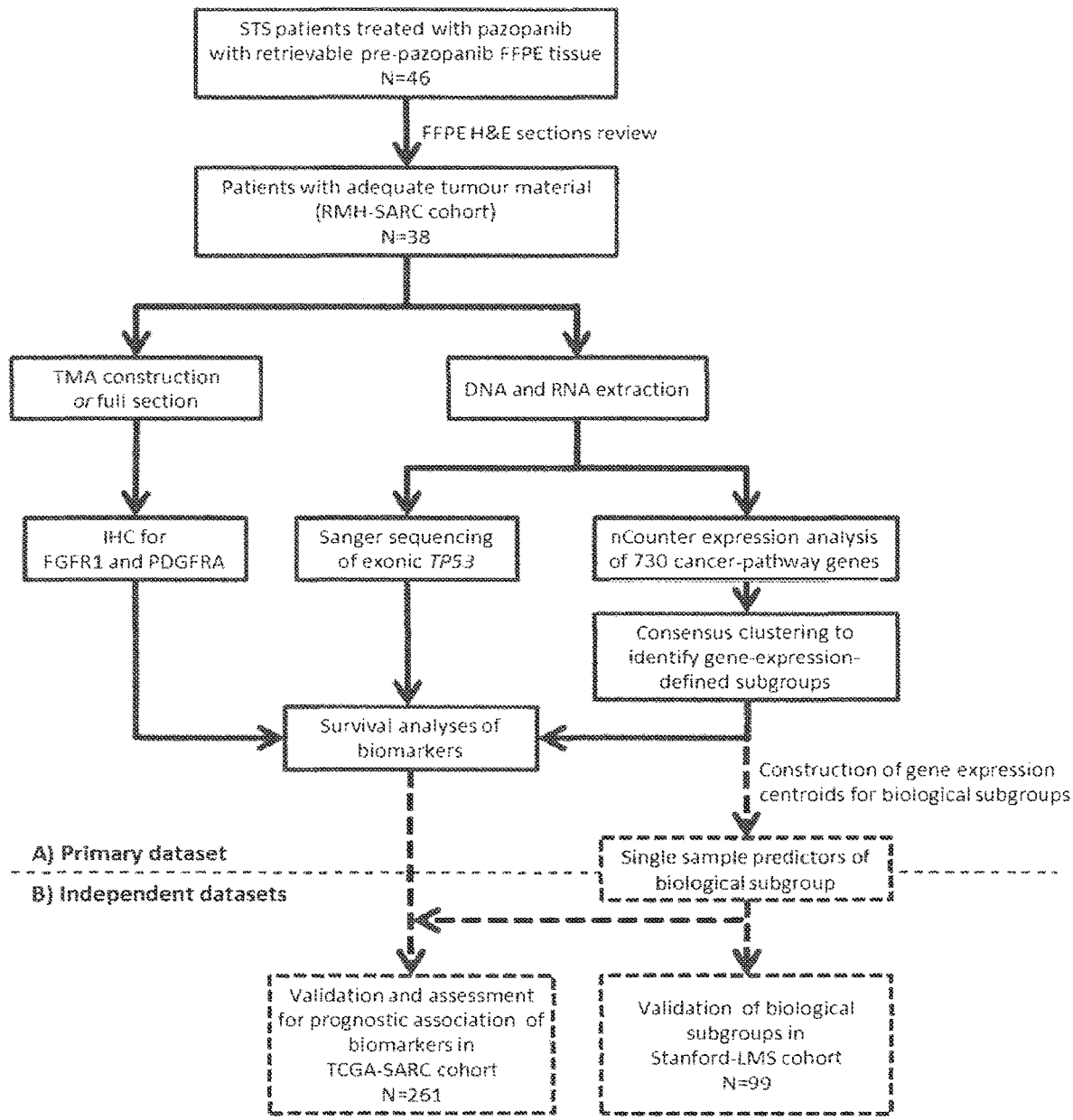
FIG. 1 shows a flow diagram of identification of the study cohort and experimental plan.

Supplementary methods 4. Housekeeping genes used in analysis
of NanoString PanCancer Pwathways gene expression data ACAD9
AGK
AMMECR1L
C10orf76
CC2D1B
CNOT10
CNOT4
COG7
DDX50
DHX16
DNAJC14
EDC3
EIF2B4
ERCC3
FCF1
FTSJ2
GPATCH3
HDAC3
MRPS5
MTMR14
NOL7
NUBP1
PIAS1
PIK3R4
PRPF38A Results Patients Between October 2009 and September 2016, 99 patients with advanced soft tissue sarcoma were treated with pazopanib at the Royal Marsden Hospital. Of these, 46 patients had retrievable FFPE tumour material that had been sampled prior to initiation of pazopanib. On examination of these materials, tissue that was adequate for downstream analysis was available for 38 patients (FIG. 1). Baseline clinic-pathological characteristics are summarised in Table 1.

TABLE 1

Baseline clinico-pathological factors

| | N = 38 (%) |
|---|---|
| Age: | |
| <45 years | 10 (26) |
| 45-65 years | 18 (48) |
| >65 years | 10 (26) |
| Gender: | |
| Female | 25 (66) |
| Male | 13 (34) |
| Performance status | |
| 0 | 7 (18) |
| 1 | 17 (44) |
| 2 | 7 (18) |
| NA | 7 (18) |
| Prior lines of systemic therapy | |
| 0 | 10 (26) |
| 1-2 | 19 (50) |
| 3+ | 9 (24) |
| Disease stage | |
| Unresectable localised | 1 (3) |
| Metastatic | 37 (97) |
| Organs involved | |
| 1 | 11 (29) |
| 2 | 12 (32) |
| 3 | 5 (13) |
| 4+ | 10 (26) |
| Grade | |
| 1 | 2 (5) |
| 2 | 18 (47) |
| 3 | 18 (47) |
| Histopathological subtype | |
| Leiomyosarcoma | 11 (29) |
| Solitary fibrous tumour | 7 (18) |
| Spindle cell sarcoma | 3 (8) |
| Myxofibrosarcoma | 3 (8) |
| Undifferentiated pleomorphic sarcoma | 2 (5) |
| Myxoid liposarcoma | 2 (5) |
| Other * | 10 (26) |

* 'Other' subtype groups consisted of single cases of mesenchymal chondrosarcoma, extraskeletal myxoid chondrosarcoma, fibrosarcoma, malignant peripheral nerve sheath tumour, malignant PEComa, granular cell tumour, clear cell sarcoma, alveolar soft part sarcoma, malignant epithelioid haemangioendothelioma, angiosarcoma Average age was 54.4 years (range 19.8-81.2). Median number of prior lines of therapy was 1.5 (interquartile range (IQR) 0-2). All patients with documented performance status were ECOG 0-2. All but one patient had metastatic disease, with a median of 2 organ sites involved by disease (IQR1.75-3.25). Sixteen distinct STS subtypes were represented within our cohort, with leiomyosarcoma the most common subtype (11 cases). Solitary fibrous tumour (SFT) was the second most represented subtype (7 cases)—the over-representation of this rare subtype resulted from the stated focus of the EMPRASS study on SFT and subsequent pursuit of tissue blocks from referring centres. All but two of 38 cases were intermediate or high histological grade—of the two cases with low histological grade by FNLCC criteria, one was unresectable solitary fibrous tumour of the retroperitoneum whilst the other was a metastatic case of extraskeletal myxoid chondrosarcoma, an STS subtype not typically allocated grade on the basis of low grade morphological appearances that are incongruent with a more aggressive clinical phenotype. In this case, grade 1 was allocated on basis of FNLCC differentiation score of 2, <10 mitoses/high power field and no necrosis present.

At data cut-off on 30 Nov. 2016 (median follow-up 26.2 months), 35 of 38 patients (92%) had experienced a progression-free survival event and 31 (82%) had died. Median PFS for the cohort was 3.7 months (IQR 1.8-6.9), median OS was 9.5 months (IQR 3.9-19.6). Following retrospective review of imaging series by RECIST 1.1 criteria, 1/38 (2.6%) patient experienced objective radiological response, 20/38 (52.6%) had stable disease and 17/38 (44.7%) progression as best response. For patients with partial response or stable disease, median PFS was 6.4 months (IQR 3.7-12.9).

We analysed pre-pazopanib tumour material to categorise cases as having either high or low tumour expression of FGFR1 and PDGFRA by IHC, and as either TP53 mutated or wildtype tumours through Sanger sequencing of TP53 coding exons. 20/38 cases had high FGFR1 expression, 17/38 had high PDGFRA expression, and 10/38 tumours harboured non-synonymous mutations of TP53. These mutations were primarily missense single nucleotide variants (SNV) within the DNA binding domain of the gene, although single examples of small frameshift deletion, SNV at splice donor site and a 272 bp intragenic inversion were found (Supplemental FIG. 2).

FGFR1 expression level was not significantly associated with post-pazopanib PFS or OS. High PDGFRA was associated with worse OS (HR 2.08; 95% CI 1.01-4.35; p=0.04) but no difference in PFS. The interaction test between FGFR1 and PDGFRA expression status for PFS was statistically significant (p=0.001), suggesting that the effect of PDGFRA expression on progression depends on FGFR1 and vice versa. To examine the clinical value of combining the FGFR1 and PDGFRA expression status, patients were stratified into 4 subgroups as follows: FGFR1-Hi/PDGFRA-Hi, FGFR1-Hi/PDGFRA-Lo, FGFR1-Lo/PDGFRA-Lo and FGFR1-Lo/PDGFRA-Hi. In univariate analysis, patients with FGFR1-Lo/PDGFRA-Hi tumours (henceforth designated F-Lo/P-Hi) had significantly associated with worse PFS (HR 9.64; 95% CI 3.58-25.94; p<0.0001) and OS (HR 6.70; 95% CI 2.51-17.91; p<0.0001) when compared to patients with tumours exhibiting one of the other three FGFR1/PDGFRA combinations (hereafter designated IHCneg) (Table 2; Supplemental FIG. 3A-B). These data indicate that assessment of pre-treatment protein expression of these two RTKs that are targeted by pazopanib can be a surrogate panel to identify a subgroup of STS patients with poor treatment outcome.

Figure 4A:
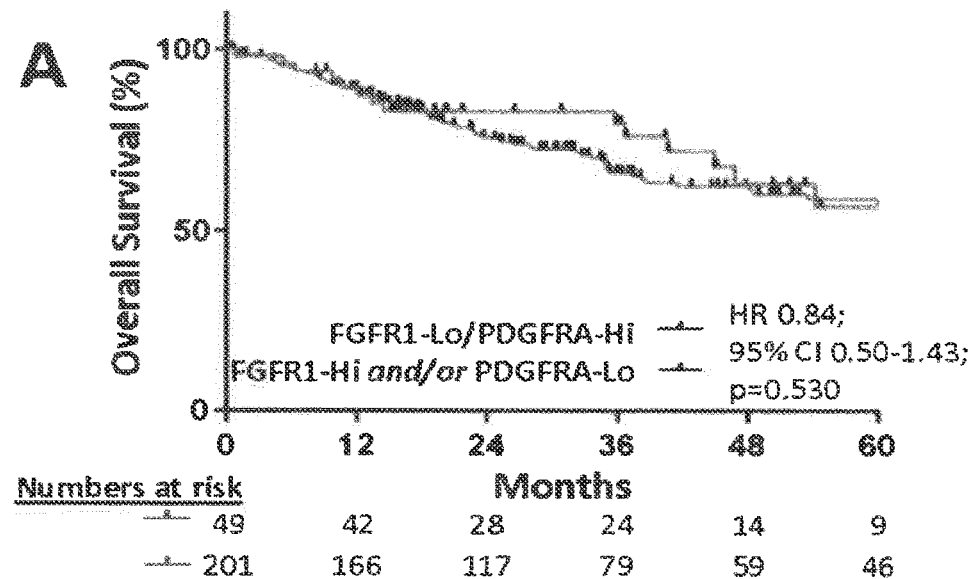
FIGS. 4A-4D shows that there is no prognostic association between PARSARC risk classifier and overall survival in TCGA SARC dataset.

Only one of the seven F-Lo/P-Hi cases harboured a TP53 mutation. In the remaining 31 IHCneg cases, TP53 mutation was associated with significantly worse PFS (HR 2.34; 95% CI 1.03-5.34; p=0.04) and OS (HR 3.47; 95% CI 1.44-8.39; p=0.003) when compared to those with wildtype TP53 (TP53 wt) (Supplemental FIG. 4A-B). This indicates that TP53 mutational status identified a further subgroup of patients with poor post-pazopanib outcome that had little overlap with the F-Lo/P-Hi subgroup.

The independent association of F-Lo/P-Hi status and TP53 mutation status with poor outcome was evaluated in multivariable Cox proportional hazard models adjusted for clinico-pathological factors (age, tumour grade, performance status, tumour histological subtype) (Table 2). F-Lo/P-Hi status (IHCneg vs F-Lo/P-Hi: PFS HR 12.54; 95% CI 3.86-40.72; p<0.001) and TP53 mutation (TP53 wt vs mutation: PFS HR 3.97; 95% CI 1.45-10.86; p=0.007) were independently associated with significantly higher risk of progression. F-Lo/P-Hi status (OS HR 22.11; 95% CI 5.90-82.81; p<0.001) and TP53 mutation (OS HR 7.90; 95% CI 2.56-24.41; p<0.001) also demonstrated independent association with OS. Higher histological grade (HR 3.51; 95% CI 1.40-8.79; p=0.007) and performance status (HR 8.23; 95% CI 2.54-26.69; p<0.001) were also independently associated with worse OS but not with PFS. Histological subtype did not demonstrate independent association with either PFS or OS[6,7]. Taken together, these data show that both F-Lo/P-Hi IHC status and TP53 mutational status separately identify subgroups of patients with poor outcome following pazopanib, and that this prognostic information is independent of STS histological subtype or other clinico-pathological factors.

TABLE 2

Univariate and multivariate analysis of PFS and OS by clinical and tumour factors

| | | PFS event | | Univariate analysis | | | Multivariable analysis | | | OS event | | Univariate analysis | | | Multivariable analysis | | |
|---|---|---|---|---|---|---|---|---|---|---|---|---|---|---|---|---|---|
| | N | N | % | HR | 95% CI | P | HR | 95% CI | P | N | % | HR | 95% CI | P | HR | 95% CI | P |
| Age (continous) | 38 | 35 | 92.1 | 0.99 | 0.97-1.02 | 0.62 | 0.99 | 0.96-1.02 | 0.36 | 31 | 81.6 | 1.01 | 0.98-1.03 | 0.65 | 0.99 | 0.96-1.03 | 0.73 |
| Grade | | | | | | | | | | | | | | | | | | |
| 1/2 | 20 | 18 | 90.0 | 1 | — | — | 1 | — | — | 14 | 70.0 | 1 | — | — | 1 | — | — |
| 3 | 18 | 17 | 94.4 | 1.54 | 1.79-3.00 | 0.21 | 1.18 | 0.51-2.71 | 0.70 | 17 | 94.0 | 2.01 | 0.99-4.09 | 0.06 | 3.51 | 1.40-8.79 | 0.007 |
| Performance Status | | | | | | | | | | | | | | | | | | |
| 0/1 | 24 | 23 | 95.8 | 1 | — | — | 1 | — | — | 20 | 83.3 | 1 | — | — | 1 | — | — |
| 2 | 7 | 7 | 100.0 | 1.00 | 0.42-2.37 | 0.99 | 1.17 | 0.45-3.03 | 0.75 | 7 | 100.0 | 2.41 | 0.96-6.09 | 0.06 | 8.23 | 2.54-26.69 | <0.001 |
| NA | 7 | 5 | 71.4 | 0.39 | 0.14-1.06 | 0.06 | 0.28 | 0.08-0.95 | 0.04 | 4 | 57.1 | 0.49 | 0.16-1.43 | 0.19 | 0.17 | 0.04-0.73 | 0.02 |
| Histological subtype | | | | | | | | | | | | | | | | | | |
| Leiomyosarcoma | 11 | 10 | 90.1 | 1 | — | — | 1 | — | — | 9 | 81.8 | 1 | — | — | 1 | — | — |
| Solitary Fibrous Tissue | 7 | 6 | 85.7 | 0.48 | 0.17-1.36 | 0.17 | 0.77 | 0.23-2.62 | 0.68 | 5 | 71.4 | 0.68 | 0.22-2.06 | 0.50 | 20.6 | 0.53-7.98 | 0.56 |

TABLE 2-continued

Univariate and multivariate analysis of PFS and OS by clinical and tumour factors

| | N | PFS event N | % | Univariate analysis HR | 95% Cl | P | Multivariable analysis HR | 95% Cl | P | OS event N | % | Univariate analysis HR | 95% Cl | P | Multivariable analysis HR | 95% Cl | P |
|---|---|---|---|---|---|---|---|---|---|---|---|---|---|---|---|---|---|
| Other | 20 | 19 | 95.0 | 0.76 | 0.35-1.66 | 0.49 | 1.25 | 0.47-3.37 | 0.66 | 17 | 85.0 | 1.06 | 0.46-2.45 | 0.89 | 2.57 | 0.86-7.67 | 0.09 |
| IHC Signature | | | | | | | | | | | | | | | | | |
| FGFR1-Hi and/or PDGFRA-Lo | 31 | 28 | 90.3 | 1 | — | — | 1 | — | — | 24 | 77.4 | 1 | — | — | 1 | — | — |
| FGFR1-Lo and PDGFRA-Hi | 7 | 7 | 100.0 | 9.64 | 3.58-25.94 | <0.001 | 12.54 | 3.86-40.72 | <0.001 | 7 | 100.0 | 6.70 | 2.51-17.91 | <0.001 | 22.11 | 5.90-82.81 | <0.001 |
| TP53 status | | | | | | | | | | | | | | | | | | |
| Wildtype | 28 | 25 | 89.3 | 1 | — | — | 1 | — | — | 21 | 75.0 | 1 | — | — | 1 | — | — |
| Mutated | 10 | 10 | 100.0 | 1.77 | 0.83-3.76 | 0.14 | 3.97 | 1.45-10.86 | 0.007 | 10 | 100.0 | 2.51 | 1.15-5.51 | 0.02 | 7.90 | 2.56-24.41 | <0.001 |

Figure 2:
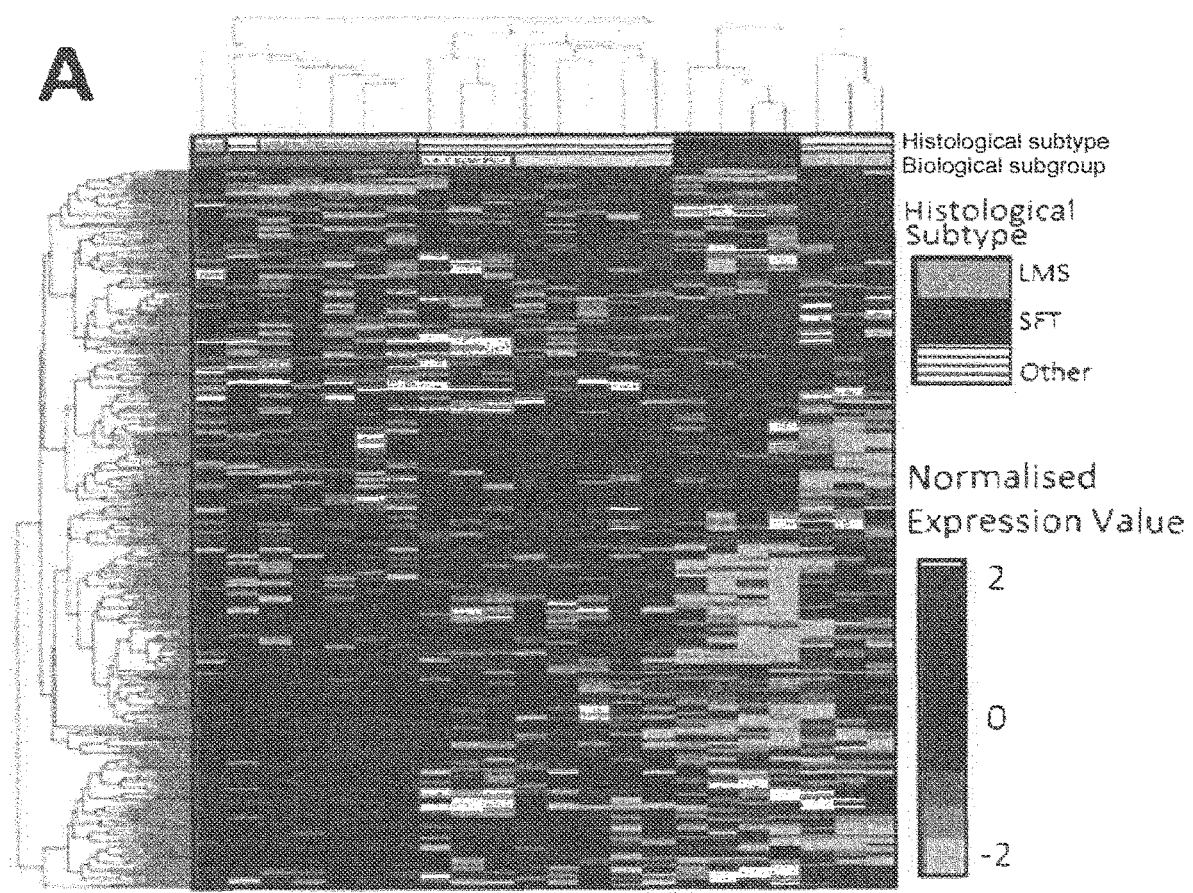
FIGS. 2A-2F shows identification of 3 clinical subgroups in IHCnegP53 wt patients based on analysis of gene expression data for 730 cancer pathway-related genes.
Figure 2B:
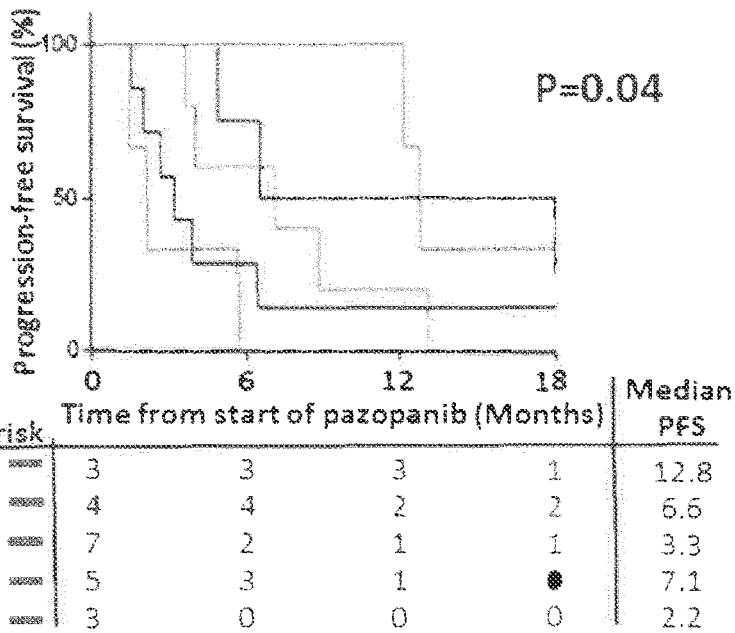
Figure 2C:
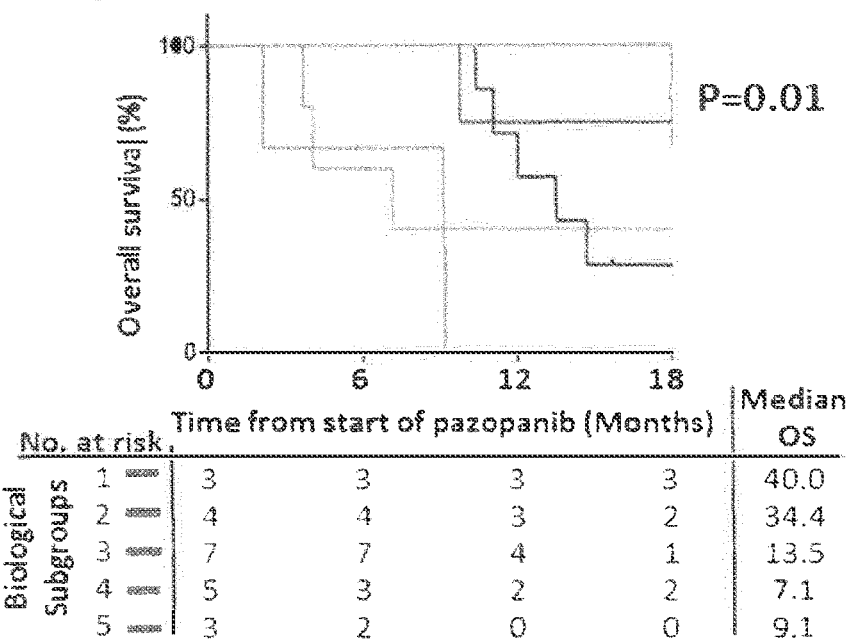
Figure 2D:
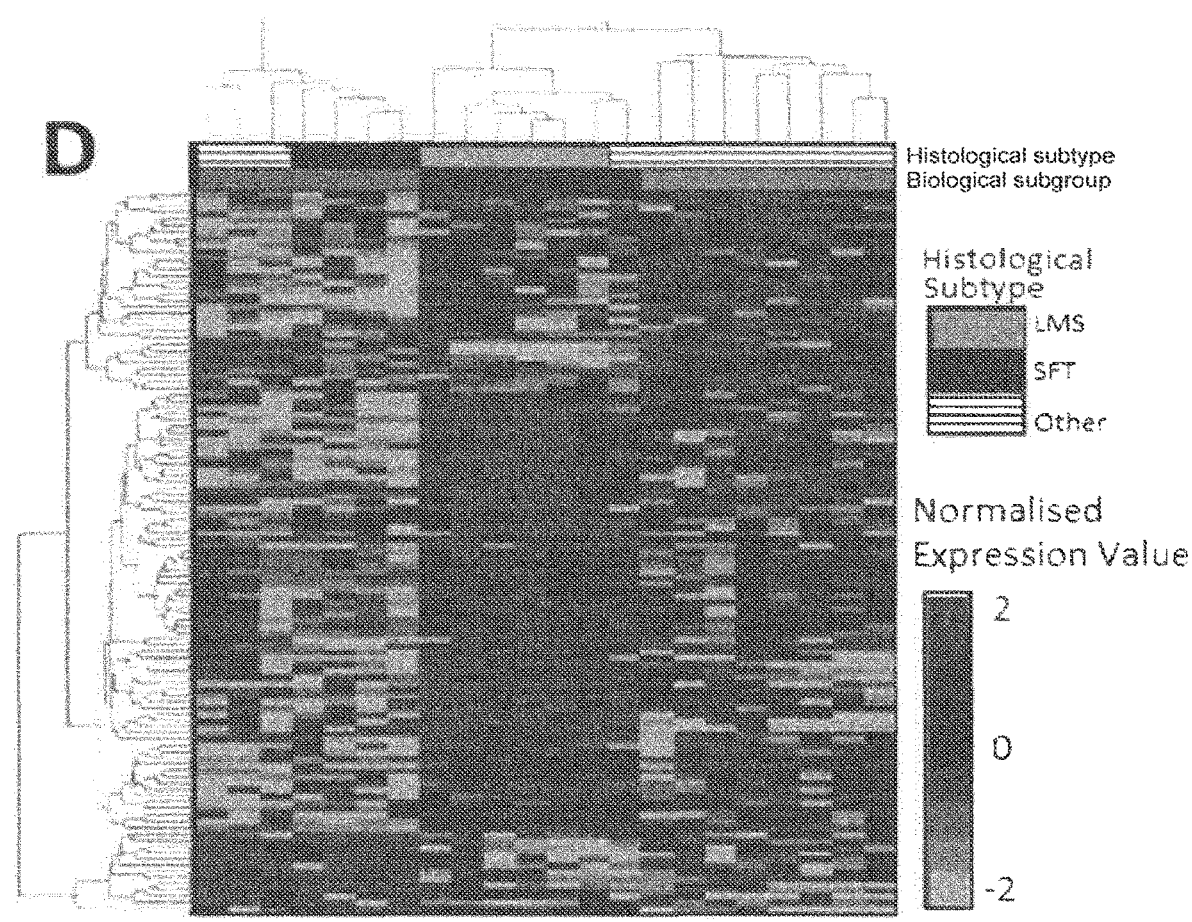
Figure 2E:
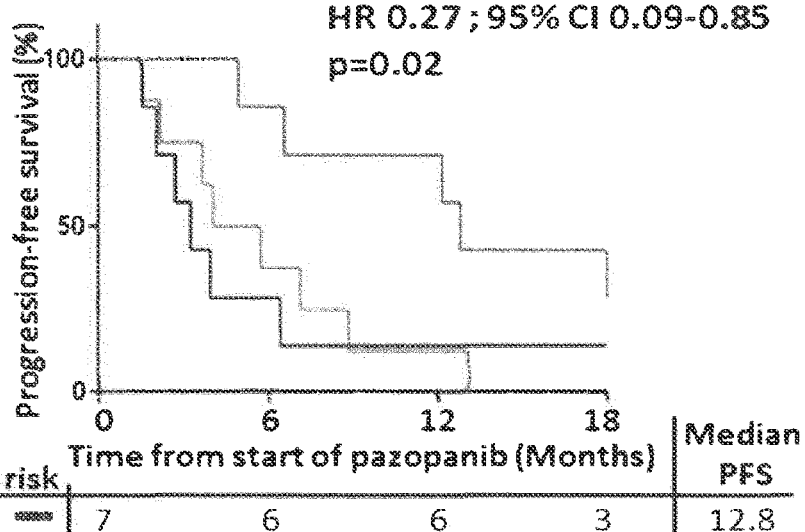
Figure 2F:
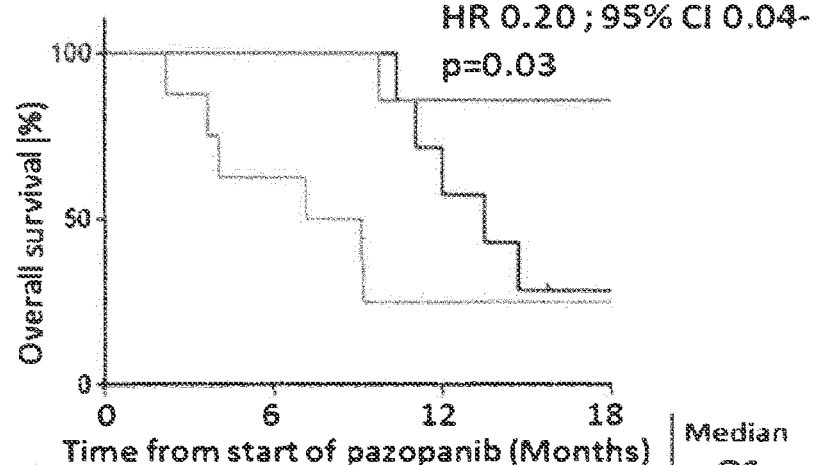

Analysis of Cancer Pathway-Related Gene Expression Reveals Subgroups with Distinct Pazopanib Outcomes To gain a better understanding of the underlying biology driving improved pazopanib outcome in the remaining 22 IHCnegTP53 wt patients within our cohort, we performed expression analysis of cancer pathway-related genes in these cases. Consensus clustering demonstrated optimal separation of the cases into five biologically-defined clusters, labelled as biological subgroups 1-5 (FIG. 2A and Supplemental FIG. 5A-C). Log rank tests revealed statistically significant differences in both PFS and OS between these subgroups (FIG. 2B-C). Notably, we found that the five biologically-defined subgroups could be consolidated into three subgroups with comparable outcome and shared dendrogram clades—patients in subgroup 1 and 2 having comparable good outcomes, subgroups 4 and 5 comparable poor outcomes, and subgroup 3 intermediate/poor outcomes. Hence, we consolidated these 5 groups into 3 based on their similarities in survival estimates, designated as Clinical subgroup A (combining subgroups 1 and 2), subgroup B (subgroup 3) and subgroup C (combining subgroups 4 and 5) for further analysis. Comparing survival outcomes between subgroups by log rank test and Cox proportional hazards models, we found that patients in subgroup A had significantly improved PFS (HR 0.27; 95% CI 0.09-0.85; p=0.02) and OS (HR 0.20; 95% CI 0.04-0.96; p=0.03) compared to patients in subgroup B or C (FIG. 2E-F). Subgroup B and C exhibited similar PFS; Subgroup B appeared to have an intermediate OS that was not statistically significantly different to subgroup C. SAM analysis identified 229 genes (FDR <=10%) showing significant differential expression across these 3 subgroups (FIG. 2D and List 1); we built a standardised centroid for each of the clinical subgroup using gene expression data of these 229 genes.

Figure 6:
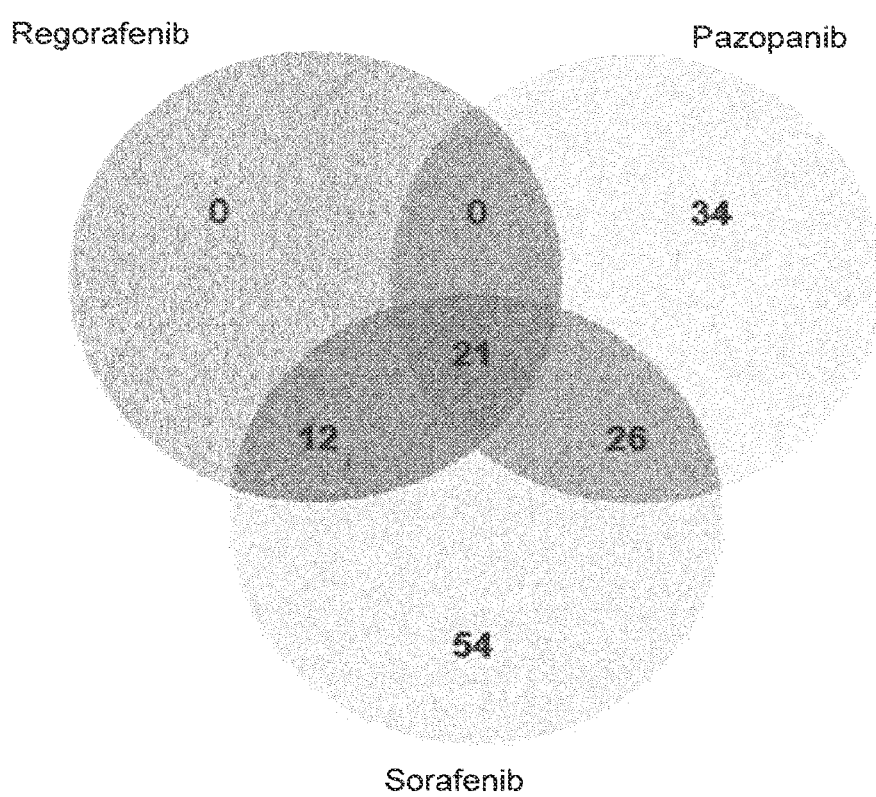
FIG. 6 shows a Venn diagram depicting the number of targets for Regorfenib (upper left); Pazopanib (upper right); and Sorfenib (lower circle).

Noting that all six cases of LMS within the 22 patients clustered together in subgroup B (FIG. 2D), we sought to compare the gene expression profile of our subgroup with the three LMS molecular subtypes previously reported by Guo et al on the Stanford-LMS dataset[12]. We assigned each of the 99 case from the same Stanford-LMS dataset into one of our three Clinical subgroups based on the nearest distance to subgroup centroids (Supplemental FIG. 6A). We found that cases assigned to Clinical subgroup B were significantly enriched for LMS molecular subtype I (Supplemental FIG. 6B-C). This subgroup, as described by Guo et al, was enriched for genes related to smooth muscle and associated with better survival outcomes when compared to the other LMS molecular subtypes. Hierarchical clustering of the 99 LMS cases using the list of 229 genes differentially expressed between Clinical subgroups A-C demonstrated that both LMS subtype I and subgroup B shared an overlapping set of upregulated genes (Supplemental FIG. 6D). This analysis provides independent validation that that we have identified an intermediate outcome, LMS-enriched subgroup and suggests that LMS subtype I may represent a disease entity with distinct pazopanib sensitivity. Meanwhile, gene ontology enrichment and interrogation of manually curated databases showed that Clinical subgroup A was enriched for genes involved with developmental and proliferation pathways including Notch and MAP kinase/growth factor RTK signalling respectively, while Clinical subgroup C displayed upregulation of genes involved in key inflammatory pathways including NFkB.

Integration of Molecular Risk Classifiers into a Clinical Decision Tree Model

Figure 3A:
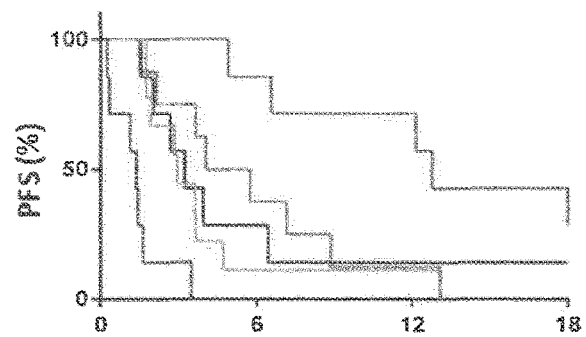
FIGS. 3A-3C shows that combination of FGFR1 and PDGFRA IHC, TP53 mutation status and gene expression analysis provides optimal risk classification. Kaplan Meier curves of the 5 decision tree-defined subgroups for (FIG. 3A) PFS and (FIG. 3B) OS of 38 patients.
Figure 3B:
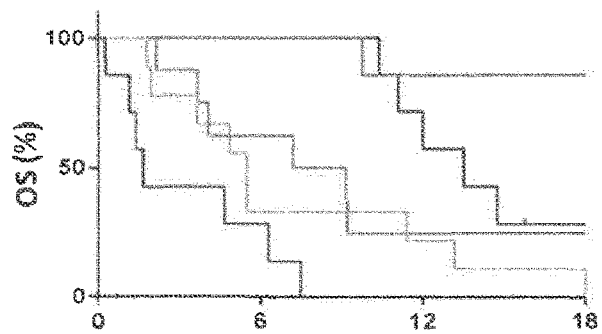
Figure 3C:
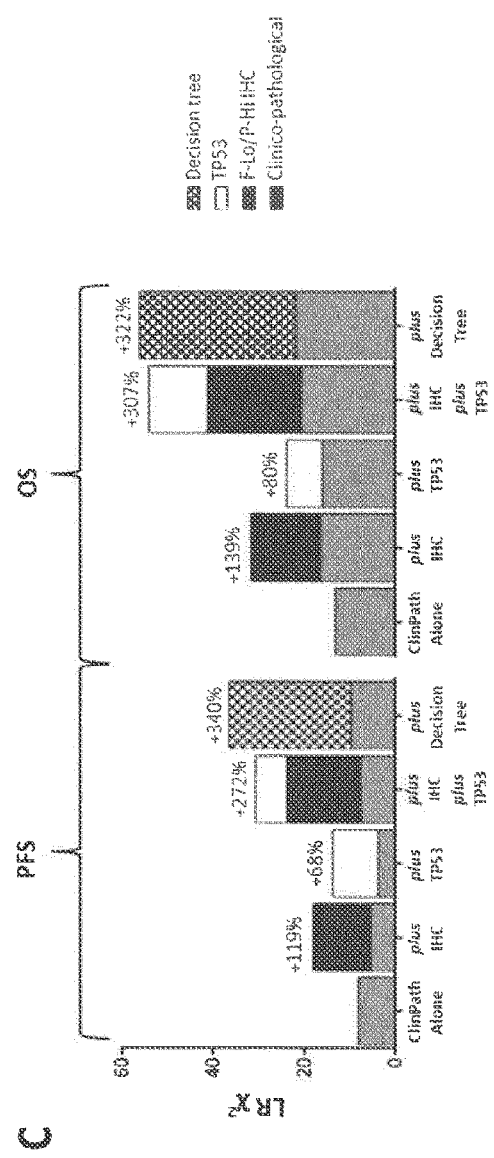

Based on the observation that our cohort could be stratified into subgroups of contrasting post-pazopanib outcome through the sequential assessment of FGFR1/PDGFRA IHC, TP53 mutational status and then gene expression analysis, we conceived a clinical decision tree based on this approach for molecular risk classification (FIG. 3A). We allocated the 38 cases according to this decision tree classifier, namely into one of five molecularly-defined subgroups (F-Lo/P-Hi, TP53 mutated or gene expression-defined subgroups A-C). As expected, there was significant differential PFS and OS among the five subgroups (FIG. 3B-C). The F-Lo/P-HI subgroup had the worst PFS and OS overall (median PFS 1.4 months, median OS 1.7 months), whilst gene expression subgroup A had significantly superior PFS and OS (median PFS 12.8 months, median OS 34.4 months) compared to F-Lo/P-Hi, TP53 mutated and clinical subgroup C.

Figure 7:
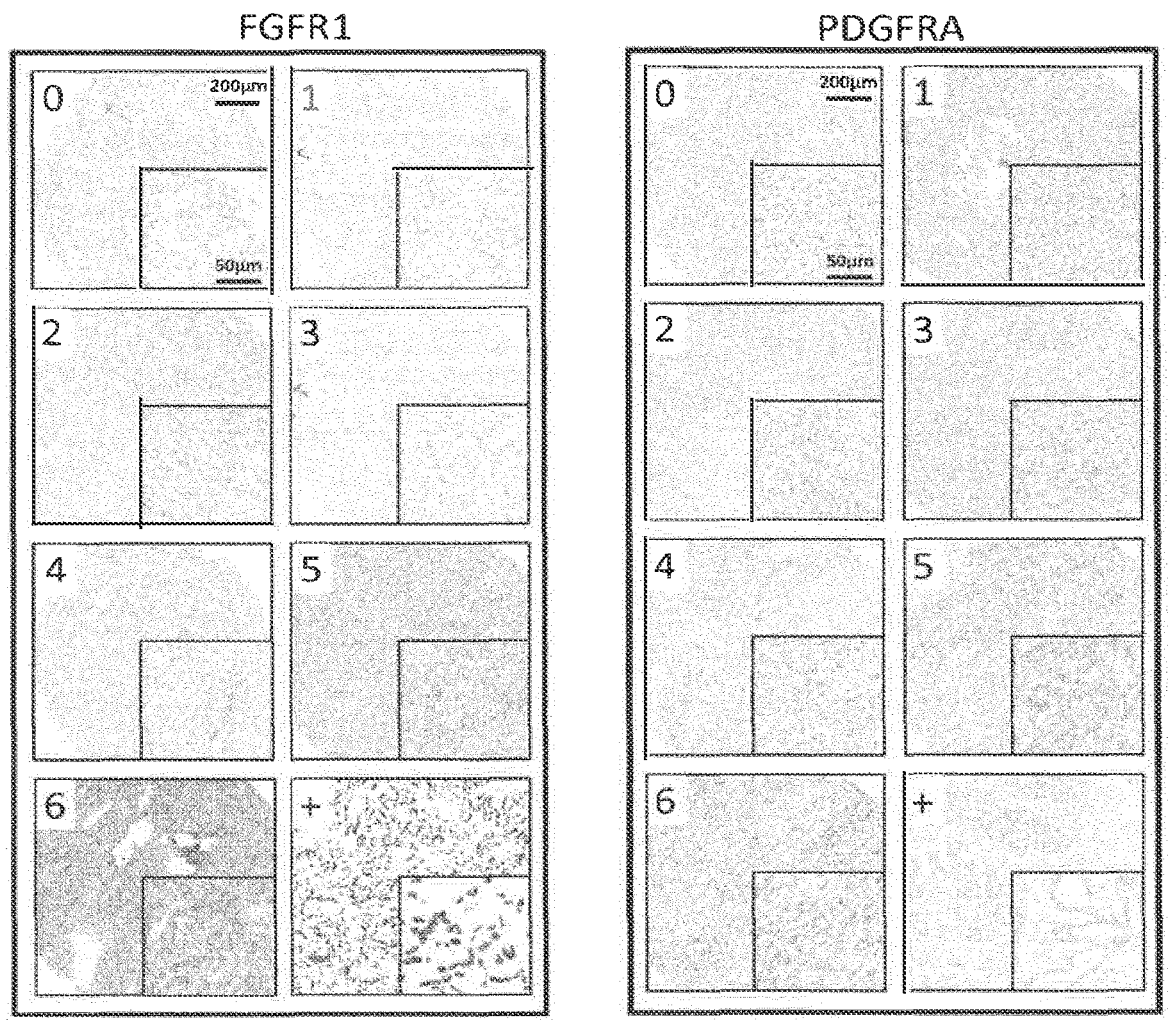
FIG. 7 shows representative IHC images of FGFR1 and PDGFRA expression levels in pre-pazopanib STS tumour specimen. FFPE tumour tissue from each case was stained for FGFR1 and PDGFRA. Representative images (×100 magnification, insert at ×400) demonstrate examples of staining scores 0-6, derived from the sum of scores for percentage of tumour cells with plasma membrane and/or cytoplasmic staining (0—absent, 1—1-10%, 2—11-50%, 3—>50%) and staining intensity (0—absent, 1—weak, 2—moderate, 3—strong). For each stain, tumours with a score ≥3 were classed as 'high' expression; tumours with a score <3 were classed as 'low expression' Positive controls T740 cells (FGFR1) and myoepithelial cells within breast tissue (PDGFRA). Digital microscopy images captured with Hamamatsu Nanozoomer at ×40 resolution.

Multivariable comparison is shown in FIG. 3D. Both IHC status and TP53 mutational status provided statistical significant prognostic value for PFS (change in $\Delta LR\chi^2$+22.5 [272%]) and OS (change in $\Delta LR\chi^2$+40.83 [307%]) when added to a model comprising of baseline clinicopathological variables. The decision tree classifier, because of its additional risk stratification, provided the largest additional amount of prognostic information, with a 340% and 322% increase in predictive information for PFS and OS respectively relative to the use of clinicopathological factors only, compared to 272% and 307% when using FGFR1/PDGFRA IHC and TP53 mutational status as parallel terms in the model. These findings demonstrate that while the use of both the F-Lo/P-Hi IHC signature and TP53 mutational status considerably improves risk classification for both PFS and OS after pazopanib therapy compared to clinic-pathological variable alone, a decision tree classifier that sequentially integrates F-Lo/P-Hi IHC status, TP53 mutational status and gene expression subgroup analysis performed best for risk classification of PFS and OS. We have named this decision tree the Pazopanib Activity and Response in SARComas (PARSARC) classifier Evaluation of Prognostic Value of the PARSARC Classifier in an Independent, Pazopanib-Naive STS Population Recognising that the PARSARC classifier could potentially reflect general prognostic associations in STS rather than a pazopanib-specific effect, we sought to assess whether the classifier was indeed associated with differential OS in an independent cohort of patients with STS who had not received pazopanib. While no such cohort with annotated FGFR1 and PDGFRA protein expression is publicly available, a 261 case STS cohort annotated with genomic and mRNA transcript data is publically available from TCGA, referred here as TCGA-SARC. Due to lack of IHC data, we first sought to assess whether quantitation of FGFR1 and PDGFRA mRNA transcripts can be used as a surrogate marker to recapitulate the group defined by F-Lo/P-Hi IHC in our RMH-SARC cohort. We also assessed the degree to which FGFR1 and PDGFRA mRNA transcript abundance reflected IHC scoring of these proteins in our cohort. Cases with high FGFR1 or PDGFRA protein expression on IHC had significantly higher gene transcript levels than those with low protein expression (Supplementary FIG. 7A). When gene expression levels for FGFR1 and PDGFRA were plotted by the 4 IHC-defined subgroups, (F-Hi/P-Hi, F-Lo/P-Lo, F-Lo/P-Hi, F-Hi P-Lo), we found all 7 F-Lo/P-Hi cases had corresponding low FGFR1 and high PDGFRA gene expression (Supplementary FIG. 7B), as did several other cases without F-Lo/P-Hi assignment by IHC. However, on IHC review, one case scored FGFR1-Lo/PDGFRA-Lo on IHC but FGFR1-Lo/PDGFRA-Hi by gene expression was found to have high levels of PDGFRA expression in tumour-associated vasculature but not tumour cells themselves. When this case was reallocated to the FGFR1-Lo/PDGFRA-Lo gene expression subgroup, significantly worse PFS was seen in the FGFR1-Lo/PDGFRA-Hi subgroup, in line with the IHC findings (supplementary FIGS. 7C and 7D). This analysis indicates that the poor outcome associated with the F-Lo/P-Hi IHC status is also reflected at the transcript level in our cohort, while also highlighting the greater resolution of IHC over gene expression analysis to detect tumour cell-specific expression. We therefore continued to evaluate the TCGA dataset, including the use of FGFR1 and PDGFRA transcript level as a surrogate for protein expression.

Figure 4B:
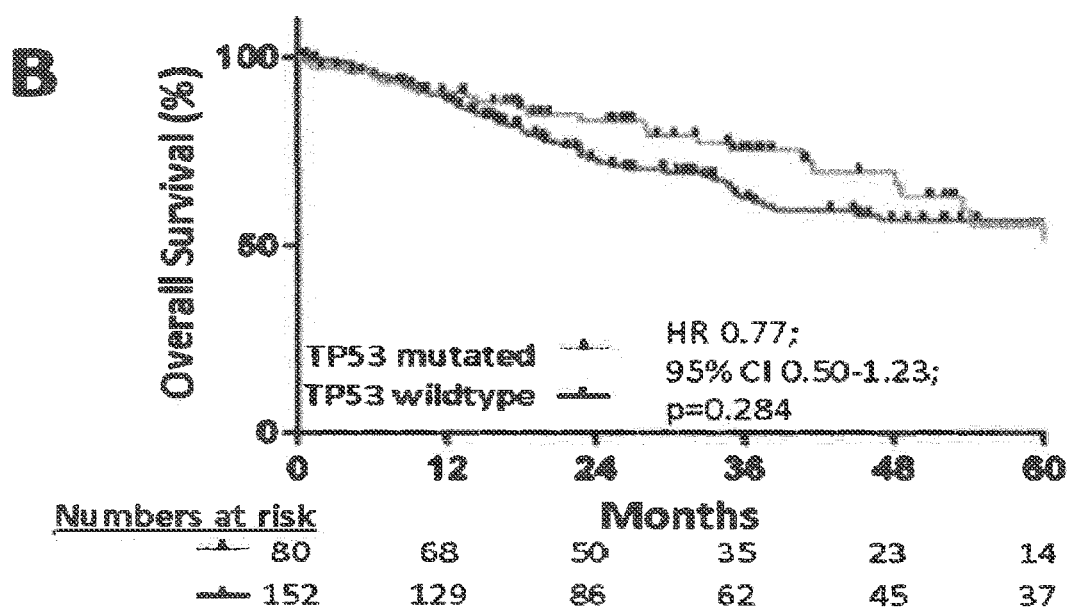
Figure 4C:
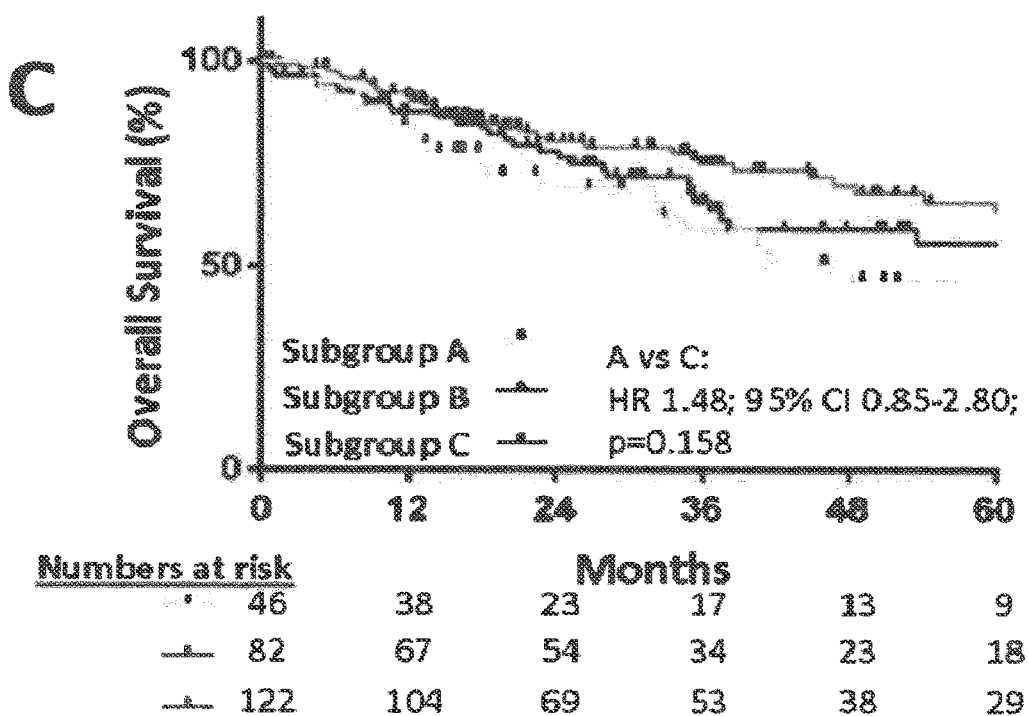
Figure 4D:
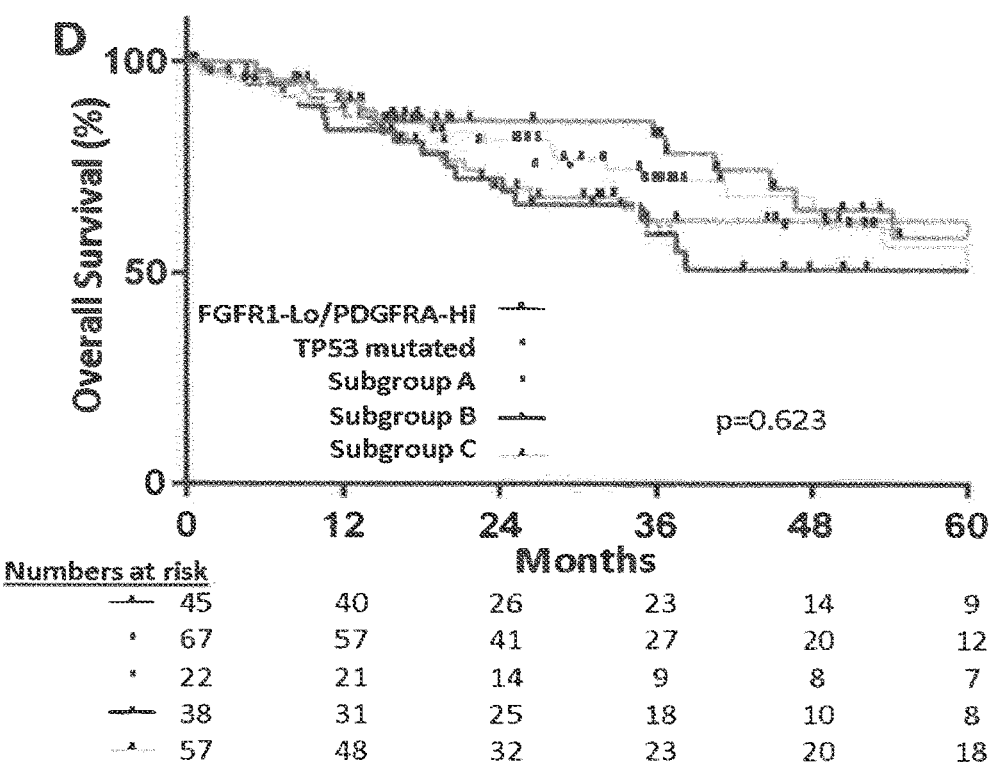

We assessed whether F-Lo/P-Hi gene expression, TP53 mutation and/or gene expression-defined subgroups A-C had prognostic associations in a STS cohort which had not received pazopanib therapy using the TCGA-SARC dataset. After exclusion of 7 cases who had received pazopanib, gene expression data and TP53 sequencing data were available for 250 and 232 patients respectively. Having defined a high/low expression cut-off at the $1^{st}$ tertile of normalised expression scores for FGFR1 and PDGFRA, 49/250 (19.6%) of TCGA patients exhibited low FGFR1 and high PDGFRA expression. No significant difference in overall survival was seen between these patients and those without the F-Lo/P-Hi signature (FIG. 4A). 80/232 (34%) patients had tumours with detected single nucleotide variants or small indels of TP53. Again, no significant difference in overall survival was seen between these TP53 mutated cases and those without TP53 mutation (FIG. 4B). From the 250 cases with gene expression data, 46, 82 and 122 cases were respectively assigned to Clinical subgroup A, B and C based on the nearest distance to each of the three subgroups centroids (Supplemental FIG. 8). There was no overall survival difference observed across the 3 subgroups (FIG. 4C). Finally, we allocated the 229/254 pazopanib-naïve patients for whom both DNA and RNA sequencing data was available to one of the five subgroups defined the PARSARC risk classifier (F-Lo/P-Hi 45; TP53 mutated—67; Clinical subgroup A—22 cases; subgroup B—38; subgroup C—57) (FIG. 4D). We again found no significant difference in overall survival between any of the five subgroups.

Collectively, this analysis finds that while the molecular risk classifiers can be used to categorize subgroups demonstrating significantly different prognosis in our pazopanib-treated cohort, we did not observe significant different prognosis of these subgroups when applied in an independent mixed STS cohort of patients who had not received pazopanib therapy.

Discussion

In this retrospective study of a heterogeneous cohort of STS patients treated with pazopanib, we performed targeted molecular analysis including assessing expression levels of pazopanib targets FGFR1 and PDGFRA, TP53 mutational analysis and cancer pathway-related gene expression profiling. To our knowledge, this is the largest molecular study of pazopanib-treated STS to date and the first to provide an in-depth examination of multiple aspects of molecular pathology within the same cohort.

Figure 5:
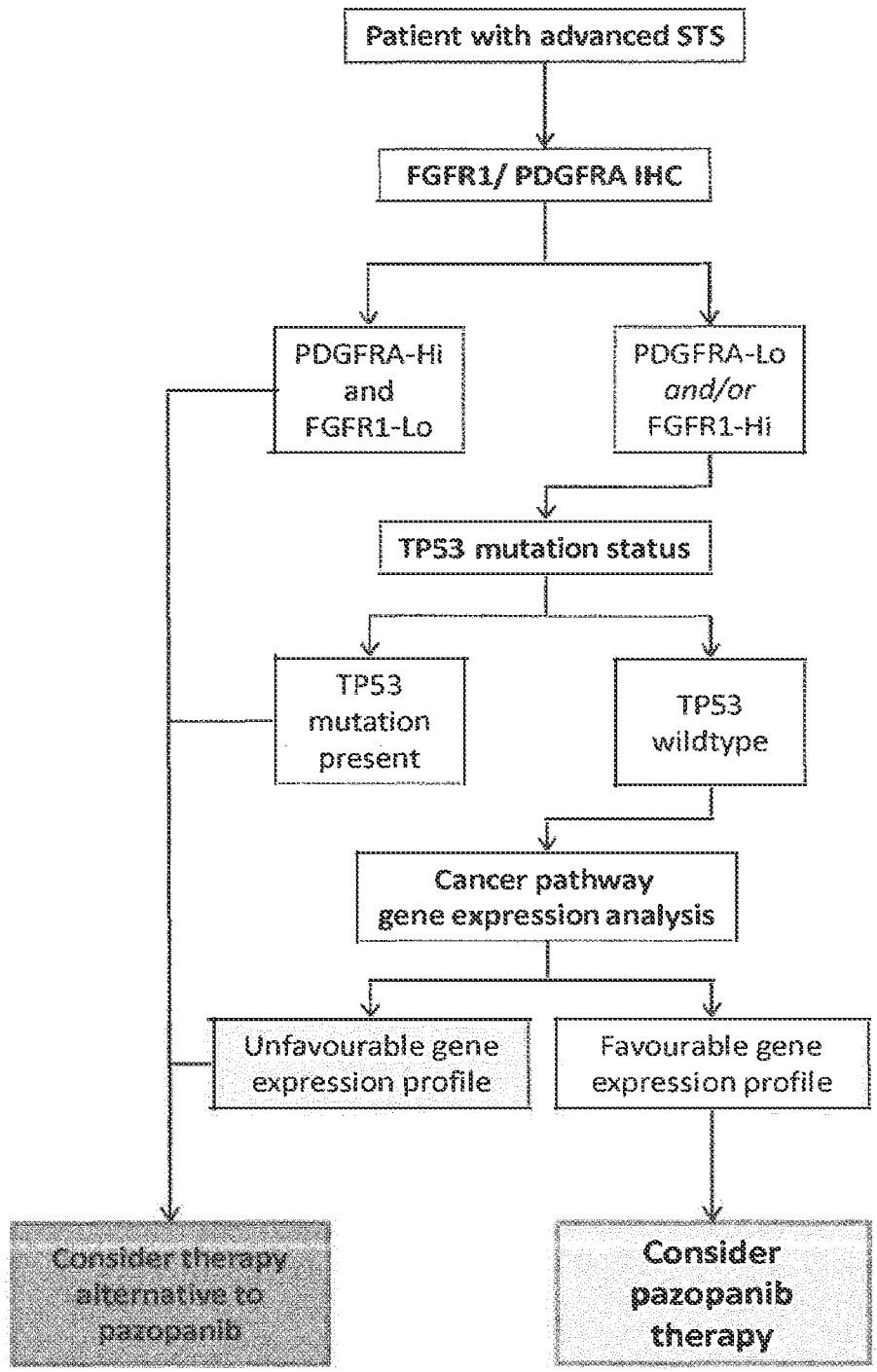
FIG. 5 shows a decision tree for patients with advanced STS under consideration for pazopanib therapy.

When assessing tumour specimens sampled prior to initiation of pazopanib therapy, the combination of low FGFR1 and high PDGFRA protein expression on IHC was associated with very poor PFS and OS following pazopanib therapy. Furthermore, the presence or absence of TP53 mutation in the IHC negative tumours was able to identify two subgroups of contrasting outcomes, with cases harbouring TP53 mutations experiencing worse PFS and OS compared to TP53 wildtype cases. Finally, consensus clustering of gene expression data was able to further stratify the remaining patients with IHCnegTP53 wt tumours resulting in three clinical subgroups with patients in subgroup A associated with the best outcomes. Inclusion of F-Lo/P-Hi IHC status, TP53 mutational status and gene expression subgroup allocation into multivariable analysis produced the best performing predictive model. Taken together, we propose that these data form the basis for a clinical decision making tree that could potentially assist in identifying suitable candidates for pazopanib therapy from an unselected advanced STS population (FIG. 5).

Pazopanib shows selectivity for both FGFR1 and PDGFRA which are RTKs with documented capacity to activate multiple canonical oncogenic pathways[24-26]. We recently reported that malignant rhabdoid tumour cells with high expression of both FGFR1 and PDGFRα are sensitive to pazopanib, and that downregulation of PDGFRA expression was associated with the development of an acquired pazopanib resistance that could be overcome through the addition of a selective FGFR1 inhibitor[27]. In our cohort, there was significant interaction between protein expression levels of FGFR1 and PDGFRA in predicting PFS, suggesting that the poor prognosis F-Lo/P-Hi IHC subgroup may reflect a currently undefined oncogenic pathway biology that confers primary pazopanib resistance. Pathway enrichment analysis of gene expression data from the full 38 patient cohort finds an upregulation of genes involved in the JAK-STAT signalling pathway in 6 of 7 IHC-positive cases, reflecting a potential role of this pathway in pazopanib resistance (supplementary FIG. 9). Further investigation of our cohort to determine the underlying biology reflected in the F-Lo/P-Hi IHC subgroup is planned.

The presence of TP53 mutation provided independent prognostic information in multivariable analysis for PFS and OS in our 38 patient cohort. Additionally, in patients without the poor prognosis F-Lo/P-Hi signature, presence of TP53 mutation identified a further poor prognosis subgroup that had significantly worse PFS and OS compared to IHCnegTP53 wt patients. This finding is in contrast to the reported findings of a study by Koehler et al where the presence of TP53 mutation as detected with targeted next-generation gene sequencing was associated with favourable PFS following pazopanib therapy compared to patients with TP53 wildtype tumours (HR0.38; 95CI 0.09-0.83; p=0.036)[17]. The reason for the inconsistency of the associations of TP53 mutation with pazopanib-related between the two studies is unclear. Both studies included patients from a broad range of STS subtypes, with few patients representing each subtype, and so random error in patient selection may have introduced biological differences between the two study cohorts. Whilst LMS was the most represented subtype in both studies, SFT accounted for 0 of 19 patients in Koehler's study as opposed to 7 of 38 patients in our study, with TP53 mutation found in 3 of 7 SFT cases. The functional impact of the TP53 mutations in our cohort has not been established. Koehler et al did not state the specific mutations detected in their cohort, although note that all were predicted to be loss of function. As it is recognised that specific point mutations of TP53 can result in loss or gain of function[28] it is possible that variation in the functional impact of TP53 mutation between studies resulted in opposite clinical phenotypes in relation to pazopanib. Differences in TP53 sequencing methods used in the two studies could also have contributed to the discrepancy—the higher rate of TP53 mutation seen in Koehler's study (10 of 19 patients vs. 10 of 38 patients) may indicate the greater sensitivity of their next-generation sequencing over our Sanger sequencing in terms of ability to detect low level TP53-mutant clones. The role of TP53 mutation as a marker for both pazopanib therapy and overall prognosis in advanced STS requires further investigation—of note, in our cohort the presence of TP53 mutation was almost mutually exclusive to the F-Lo/P-Hi IHC subgroup, with TP53 mutation detected in only 1 of 7 cases with the poor-outcome-related IHC signature.

Gene expression analysis has been widely used in translational cancer research as a means of identifying tumour subgroups of distinct clinical behaviour and underlying biology. A number of reported studies have demonstrated that different STS histological subtypes have distinct, subtype-specific gene expression profiles[29-31]. On analysing gene expression data from our heterogeneous 38 patient cohort, cases of the same STS subtype clustered together in a manner consistent with these previously reported findings and thus providing validation to our data (supplementary FIG. 10). Consensus clustering of the 38 patient cohort did not, however, identify subgroups with significantly distinct post-pazopanib outcomes, indicating that gene expression analysis alone was insufficient to stratify our cohort (supplemental FIG. 10B+C). Only when F-Lo/P-Hi and TP53 mutated cases were excluded from the cohort did gene expression analysis provide additional prognostic information in identifying 3 gene expression signature-defined subgroups (FIGS. 2 and 3). A relative strength of IHC over mRNA transcript abundance-based gene expression analysis was highlighted by a single case of extraskeletal myxoid chondrosarcoma. IHC provided the compartmental spatial resolution to distinguish between vessel and tumour cell PDGFRA expression, allowing for allocation to the better prognosis F-Lo/P-Lo subgroup, whereas the high levels of PDGFRA detected by NanoString analysis within this sample resulted into misallocation to a poor prognosis F-Lo/P-Hi subgroup. Whilst pathway enrichment analysis of gene expression data offers preliminary clues, our cohort is underpowered to provide reliable information on the biology that underlies the range of outcomes seen. Overall, PFS and OS in our cohort is broadly in keeping with other reported pazopanib-treated STS cohorts[32-35]. As was the case in the pazopanib phase II and III trials, a minority of patients in our cohort experienced PFS greater than 6 months and overall survival greater than 18 months. It is important that further research explores the biology underlying such exceptional responders to enable further biomarker development and an understanding of the mechanisms of sensitivity and primary and acquired resistance to pazopanib.

There are several limitations to our study. Our single institution cohort, although the largest tissue-based study of a pazopanib-treated cohort to date, is small and has been assessed retrospectively, producing vulnerability to systematic and random biases. Clinical annotation was based on retrospective review of contemporaneous medical documentation, where the absence of a prospective protocol will have contributed to variations in management such as decisions regarding dose reductions/interruptions, timing of radiological assessment and cessation of therapy. The included patients represented a broad range of STS subtypes, representing heterogeneous biology and reflecting daily clinical practice. Further heterogeneity was introduced by the study of archival tumour tissue which variably represented primary, recurrence or metastatic lesions that were taken only days prior to pazopanib commencement in some cases, whilst in other cases the archival sample originated several years earlier with several lines of intervening systemic therapy delivered. Some patients died during or shortly after completion of pazopanib therapy, whilst others went on to receive varied post-pazopanib therapies. Despite these limitations, we have been able to identify molecular signatures that identify patient subgroups with a significantly distinct post-pazopanib outcome. The heterogeneity of disease and specimen studied is representative of a typical scenario faced by oncologists considering prescribing pazopanib for patients with advanced STS, and supports the potential usefulness of our candidate decision tree. Whilst we found no such associations in the TCGA STS cohort not defined by pazopanib exposure, it cannot be established in our retrospective cohort whether the association between the identified molecular readouts and outcome is specific to pazopanib treatment, rather than a more general prognostic association unrelated to drug exposure. Our findings should be considered as hypothesis generating, with analysis of carefully selected pazopanib-naïve control cohorts and/or prospective assessment of the identified molecular signature required to provide greater insight into any predictive relationship with pazopanib.

Advanced STS remains associated with poor prognosis and limited lines of effective treatment[36]. The recruitment of heterogeneous 'all-comer' cohorts to phase III drug trials in STS continues to contribute to the frequent failure to translate early efficacy signals into definitive evidence of survival benefit[37]. Whilst pazopanib received regulatory approval on the basis of PFS advantage over placebo in a mixed STS cohort, the drug's clinical effectiveness is limited by the lack of predictive biomarkers for benefit. In a retrospective, heterogeneous advanced STS cohort, we have identified a method of molecular classification of tumours that identifies patient subgroups with distinct PFS and OS following pazopanib therapy. If successfully validated, our proposed clinical decision tree would assist in the prospective identification a group less likely to benefit from pazopanib for whom alternative drugs or best supportive care should be considered. Notably, the PDGFRa-targeting monoclonal antibody olaratumab recently received accelerated FDA approval for the 1st line treatment of advanced STS in combination with doxorubicin on the basis of marked OS benefit in a randomised phase II study—this drug would represent an avenue of interest in the F-Lo/P-Hi PDGFRA-overexpressing, poor prognosis patient group that we have identified[38]. Furthermore, recently published results of a randomised phase II trial of regorafenib, a TKI with target selectivity overlap with pazopanib, indicates efficacy in several STS subtypes but not adipocytic tumours[39]. The similarity of these clinical data with those of pazopanib raises the question of whether the molecular signature we have identified can also provide risk classification for treatment with regorafenib and other related TKIs. Our study presents a basis for development of biomarkers that may employ simple IHC or genotyping approaches or more sophisticated companion diagnostic assays that can identify STS patients most likely to benefit from pazopanib and other related TKIs.

TABLE 3

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| FGF9 NM_002010.2 | TGTTGCCAAACTTTGT CGCATGCATAATGTAT GATGGAGGCTTTGATG GGAATATGCTGATTTT GTTCTGCACTTAAAGG CTTCTCCTCCTGGAGG GCTG (SEQ ID NO: 15) | NM_002010 | −0.787299586 | 0.684375081 | 0.071127474 |
| NFATC1 NM_172389.1 | CGAATTCTCTGTGGT TGAGATCCCGCCATTT CGGAATCAGAGGATAA CCAGCCCCGTTCACGT CAGTTTCTACGTCTGC AACGGGAGAGAAAGC GAAG (SEQ ID NO:16) | NM_172389; NM_001278675; NM_172390; NM_001278672; NM_001278670; NM_172387; NM_006162; NM_001278669; NM_172388; NM_001278673 | −0.371691666 | 0.704052833 | 0.023044704 |
| FZD10 NM_007197.2 | CCGTGCCGGCCACCTG TGTGATCGCCTGCTAC TTTTACGAACGGCCTCA ACATGGATTACTGGAA GATCCTGGCGGCGCAG CACAAGTGCAAAATGA ACAA (SEQ ID NO: 17) | NM_007197 | −0.440193224 | 0.660391129 | 0.172537497 |
| HMGA2 NM_003484.1 | GAGGAGGAATTCTTTC CCCGCCTAACATTTCA AGGGACACAATTCACT CCAAGTCTCTTCCCTT TCCAAGCCGCTTCCGA AGTGCTCCCGGTGCCC GCAA (SEQ ID NO: 18) | NM_003484; NM_003483 | −1.323612428 | 0.295732763 | 0.90817728 |
| FZD9 NM_003508.2 | CCTGCCCGCGCTCAAG ACCATCGTCATCCTGA CCCTGCGCAAGGTGGC GGGTGATGAGCTGACT GGGCTTTGCTACGTGG CAGCACGGATGCAGC AGCG (SEQ ID NO: 19) | NM_003508 | −1.075145616 | 0.616942772 | 0.410943305 |

TABLE 3-continued

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| PRKX NM_005044.1 | CAGTGAAGCTGGTGC GGTGGTGCACTCCTGT AACCCTGGGACTTTGG GAAGCTGAGGCAGGAA GATTGAGACCTAGGAGT TCGAGACTGACCTGGG CAGC (SEQ ID NO: 20) | NM_005044 | -1.153743629 | 0.02023958 | 1.480748471 |
| CCND1 NM_053056.2 | TTGAACACTTCCTCTC CAAAATGCCAGAGGCG GAGGAGAACAAACAGA TCATCCGCAAACACGC GCAGACCTTCGTTGCC CTCTGTGCCACAGATG TGAA (SEQ ID NO: 21) | NM_053056 | -0.847605437 | -0.047679935 | 0.844326227 |
| MAP2K6 NM_002758.3 | AGCCAGGAACAGAAAC GGCTACTGATGGATTT GGATATTTCCATGAGG ACGGTGGACTGTCCAT TCACTGTCACCTTTTA TGGCGCACTGTTTCGG GAGG (SEQ ID NO: 22) | NM_002758 | -1.186458783 | 0.341738061 | 1.094717343 |
| TP53 NM_000546.2 | GGGGAGGCAGGGCTCAC TCCAGCCACCTGAAGT CCAAAAAGGGTCAGTC TACCTCCCGCCATAAA AAACTCATGTTCAAGA CAGAAGGGCCTGACTC AGAC (SEQ ID NO: 23) | NM_000546; NM_001126117; NM_001126118; NM_001126113; NM_001276760; NM_001276699; NM_001276697; NM_001276695; NM_001126115; NM_001276761; NM_001126116; NM_001126112; NM_001276696; NM_001276698; NM_001126114 | -1.053931167 | 0.276137891 | -0.07221507 |
| FANCF NM_022725.2 | CTGTCTATCTGGGTCT GCTAACAGACTGGGGT CAACGTTTGCACTATG ACCTTCAGAAAGGCAT TTGGGTTGGAACTGAG TCCCAAGATGTGCCCT GGGA (SEQ ID NO: 24) | NM_022725 | -2.562689656 | 0.02114079 | 0.285248682 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| HDAC10 | NM_032019.5 | CCAGCGTCCTTTACTT CTCCTGCACCGCTAT GAGCATGGGCGCTTCT GGCCTTTCCTGCGAGA GTCAGATGCAGACGCA GTGGGGCGGGGACAGG GCCT (SEQ ID NO: 25) | NM_032019; NM_001159286 | -0.864986527 | -0.466408988 | 1.358279782 |
| CARD11 | NM_032415.2 | TTGAAAATCGGCCCAA GAAGGAGCAGGTTCTG GAACTGGAGCGGGAGA ATGAAATGCTGAAGAC CAAAAACCAGGAGCTG CAGTCCATCATCCAGG CCGG (SEQ ID NO: 26) | NM_032415 | -1.225657695 | 0.031589204 | 1.277944476 |
| FGF5 | NM_004464.3 | AAGAGTTACCTCCTCC ATCTTACTCTGCCCTA TTTGAAAGTCTTCAGGG GAGAAAAGGGAACAAG ATGCTGATCCAACCTG AGTGGAGTCAGGTGAG GCAT (SEQ ID NO: 27) | NM_004464; NM_033143 | -1.030325063 | 0.388725522 | 0.844361302 |
| DUSP4 | NM_057158.2 | GCACCGTAGCATGCAG ATGTCAAGGCAGTTAG GAAGTAAATGGTGTCT TGTAGATATGTGCAAG GTAGCATGATGAGCAA CTTGAGTTTGTTGCCA CTGA (SEQ ID NO: 28) | NM_057158; NM_001394 | -0.851980221 | -0.18231116 | 0.820109581 |
| IL12RB2 | NM_001559.2 | CCTCCGTGGGACATTA GAATCAAATTTCAAAA GGCTTCTGTGAGCAGA TGTACCCTTTATTGGA GAGATGAGGGACTGGT ACTGCTTAATCGACTC AGAT (SEQ ID NO: 29) | NM_001559; NR_047584; NR_047583; NM_001258216; NM_001258215; NM_001258214 | -0.380856163 | -0.42852557 | 0.791789922 |
| E2F5 | NM_001951.3 | AATTGAAGATCTAGAA CTGAAGGAAAGAGAAC TTGATCAGCAGAAGTT | NM_001951; NM_001083589; NM_001083588 | -1.194613628 | -0.049929218 | 0.829615055 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| CCR7 | NM_001838.2 | GTGGCTACAGCAAAGC ATCAAAAATGTGATGG ACGATTCCATTAATAA TAGA (SEQ ID NO: 30) | NM_001838 | -0.084056229 | -0.0392025 | 0.836628323 |
| PAX5 | NM_016734.1 | TTCCGAAAACCAGGCC TTATCTCCAAGACCAG AGATAGTGGGAGACT TCTTGGCTTGGTGAGG AAAAGCGGACATCAGC TGGTCAAACAAACTCT CTGA (SEQ ID NO: 31) | NM_016734; NR_104000; NR_103999; NM_001280556; NM_001280555; NM_001280554; NM_001280553; NM_001280549; NM_001280548; NM_001280547; NM_001280552; NM_001280551; NM_001280550 | -0.643065022 | 0.250705882 | 0.802373206 |
| NOG | NM_005450.4 | CTCCAAGAGGAGCACA CTTTGGGAGATGTCC TGGTTTCCTGCCTCCA TTTCTCTGGGACCGAT GCAGTATCAGCAGCTC TTTTCCAGATCAAAGA ACTC (SEQ ID NO: 32) | NM_005450 | -0.995613082 | 0.777936727 | -0.257207914 |
| PTCH1 | NM_000264.3 | ACAGAGAAAAGAGAGA CTTATTCTGGTTGTTG CTAATAATGTTAACCT GCTATTTATATTCCAG TGCCCTTCGCATGGCG AAGCAGGGGGAAAAG TTAT (SEQ ID NO: 33) | NM_000264; NM_001083607; NM_001083606; NM_001083605; NM_001083604; NM_001083603; NM_001083602 | -0.633931616 | 2.131940241 | -0.891766233 |
|  |  | AATCTCCTTCTTCTCGG ATCATTGTGATGGATG CTGGAACCTCAGGGTA TGGAGCTCACATCAGT TCATCATGGTGGGTGT TAGAGAATTCCGTGAC ATGC (SEQ ID NO: 34) |  |  |  |  |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| ZIC2 | NM_007129.2 | AAAAATAAAAACCCAC AAAAATGTTGAACCAA ACCTCCCTGCTAATCT CCATGCCCACGTTCTT TCCCACCCTGTTCCCA GTCTTCTGACAAACTG TGTA (SEQ ID NO: 35) | NM_007129 | 0.148829172 | 0.771918368 | -0.805607102 |
| CACNA1G | NM_198397.1 | TTTGACACACATTGGCT ATGCCTGATCGCCAT CTTCCAGGTCATCACG CTGGAGGGCTGGGTCG ACATCATGTACTTTGT GATGGATGCTCATTCC TTCT (SEQ ID NO: 36) | NM_198397; NM_001256359; NM_198382; XM_006722161; NM_001256327; NM_198396; NM_198384; NM_001256333; NM_001256325; NM_198379; NM_001256328; NM_001256360; XM_006722160; NR_046054; NM_198376; NM_198383; NM_001256334; NM_198377; NM_198386; NM_001256324; NM_001256330; NM_018896; NR_046055; NM_001256326; NM_001256361; NM_198385; NM_001256331; NR_046057; NM_198388; NR_046058; NM_198378; NM_001256329; NM_198387; NR_046056; NM_001256332; NM_198380 | -0.66346841 | 0.911704604 | -0.1016264 |
| SMAD3 | NM_005902.3 | TTAAAGGACAGTTGAA AAGGGCAAGAGGAAAC CAGGGCAGTTCTAGAG GAGTGCTGGTGACTGG ATAGCAGTTTTAAGTG GCGTTCACCTAGTCAA CACG (SEQ ID NO: 37) | NM_005902; NM_001145104; NM_001145102; NM_001145103 | -0.393760319 | 1.018703135 | -0.451762506 |
| CHAD | NM_001267.2 | ACACCAACCTGGAGAA GTTCTCAGATGGTGCC TTCCTGGGTGTAACCA CGCTGAAACACGTCCA TTTGGAGAACAACCGC TTGAACCAGCTACCCT CCAA (SEQ ID NO: 38) | NM_001267 | 0.029259868 | 0.92288135 | 0.235476291 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| TLX1 | NM_005521.3 | ACCACACATCCCAGCCCAATCCAGGTAGCACAGACAGTTTTCACATAAATGCAGCCCATTCTCCAGAACCCATTTGAGGGGTGGGGGTGTTAATT (SEQ ID NO: 39) | NM_005521; NM_001195517 | 0.06809746 | 0.867855103 | -0.263254402 |
| BCOR | NM_001123383.1 | CACCTCCTCTGTTGGAGAAGCAGACCGTTACCAAAGACGTCACAGATAAGCCACTAGACTTGTCTTCTAAAGTGGTGGATGTAGATGCTTCCAAAGCTGA (SEQ ID NO: 40) | NM_001123383; NM_001123384; NM_001123385; NM_017745 | 0.102427544 | 1.716828147 | -1.525569877 |
| EFNA2 | NM_001405.3 | TCCCTCTCCGAGGCCGAGAAGACCTTCTGTTCCTGTAAATACAGCCAGCAAGTGCAAACTGTGATTTTATTTTCCACGTATTCCTGAGGACGGACTGGAC (SEQ ID NO: 41) | NM_001405 | 0.452825555 | 0.641136053 | -0.36647518 |
| LEFTY2 | NM_003240.2 | AGTGCTCCTGTGTGACCTTCGCCCTGTGTCCTTCCATTTCCTGTCTTTCCCGTCCATCACCATCCTAAGCACTTACGTGAGTAAATAATGCAGCTCAGA (SEQ ID NO: 42) | NM_003240; NM_001172425 | 0.779378173 | 0.416545389 | -0.967518679 |
| NOTCH2 | NM_024408.3 | AAGAGTCACCAAATTTTGAGAGTTATACTTGCTTGTGTGCTCCTGGCTGGCAAGTCAGCGGTGTACCATTGACATTGACGAGTGTATCTCCAAGCCCTG (SEQ ID NO: 43) | NM_024408; NM_001200001 | 0.252055478 | 0.336041946 | -0.976488588 |
| ATM | NM_138292.3 | CTTTATGGCAGGGGTGGAAGGAGGTACATTTAATTCCCACTGCCTGCC | NM_138292; NM_000051 | -1.079149788 | -0.154750465 | 0.653606333 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| TNFRSF10D | NM_003840.3 | TTTGGCAAGCCCTGGG TTCTTTGCTCCCCATA TAGATGTCTAAGCTAA AAGC (SEQ ID NO: 44) | | | | |
| | | GTATCTTTGGGAAGCC ATGTGTCTGGTTTGTC GTGCTGGGACAGTCAT GGGACTGCATCTTCCG ACTTGTCCACAGCAGA TGAGGACAGTGAGAAT TAAG (SEQ ID NO: 45) | NM_003840 | -1.120751017 | -0.023301806 | 0.695417144 |
| TGFB1 | NM_000660.3 | TATATGTTCTTCAACA CATCAGAGCTCCGAGA AGCGGTACCTGAACCC GTGTTGCTCTCCCGGG CAGAGCTGCGTCTGCT GAGGCTCAAGTTAAAA GTGG (SEQ ID NO: 46) | NM_000660 | -0.899502256 | 0.365260494 | 0.465688467 |
| DKK1 | NM_012242.2 | CGGCACGGTTTCGTGG GGACCCAGGCTTGCAA AGTGAGGGTCATTTTC TCTTTCTTTCTCCCTC TTGAGTCCTTCTGAGA TGATGGCTCTGGGCGC AGCG (SEQ ID NO: 47) | NM_012242 | -0.51629809 | 0.494457312 | 0.681706191 |
| IDH1 | NM_005896.2 | GTGGCGCCCCAACTCT TCGCCAGCATATCATC CCGGCAGGCGATAAAC TACATTCAGTTGAGTC TGCAAGACTGGGAGGA ACTGGGGTGATAAGAA ATCT (SEQ ID NO: 48) | NM_005896 | -0.456773483 | 0.280037814 | 1.328340834 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| COMP | NM_000095.2 | TGGCTGTGGGTTACAC TGCCTTCAATGGCGTG GACTTCGAGGGCACGT TCCATGTGAACACGGT CACGGATGACGACTAT GCGGGCTTCATCTTTG GCTA (SEQ ID NO: 49) | NM_000095 | -0.493285797 | 0.819951452 | 0.559484802 |
| PTEN | NM_000314.3 | TGTGGTCTGCCAGCTA AAGGTGAAGATATATT CCTCCAATTCAGGACC CACACGACGGGAAGAC AAGTTCATGTACTTTG AGTTCCCTCAGCCGTT ACCT (SEQ ID NO: 50) | NM_000314 | -0.764885608 | 0.128186717 | 0.825774951 |
| CALML6 | NM_138705.2 | ATGGCCAAGGATGTGG ACAGACAACAAAGG GTTCTTCAACTGCGAT GGTTTCCTGGCACTAA TGGGAGTTACCATGA GAAGGCCCAGAACCAG GAGA (SEQ ID NO: 51) | NM_138705 | -1.273555604 | 0.849952584 | 0.267196887 |
| ERBB2 | NM_004448.2 | CTGAAAGAGACCGAGC TGAGGAAGGTGAAGGT GCTTGGATCTGGCGCT TTTGGCACAGTCTACA AGGGCATCTGGATCCC TGATGGGGAGAATGTG AAAA (SEQ ID NO: 52) | NM_004448; NM_001005862 | -0.657891493 | 0.868247895 | -0.336671826 |
| IL11RA | ND4_1147162.1 | TCCAGCCGCCCTGTT GTCTCCTGCCAAGCAG CCGACTATGAGAACTT CTCTTGCACTTGGAGT CCCAGCCAGATCAGCG GTTTACCACCCGCTA CCTC (SEQ ID NO: 53) | ND4_1147162; NR_052010; NM_001142784 | -0.574798229 | 0.757662318 | -0.163619158 |
| PDGFD | NM_025208.4 | CATACCATGACCGGAA GTCAAAAGTTGACCTG GATAGGCTCAATGATG | NM_025208; NM_033135 | -1.453013751 | 0.553101435 | 0.342655917 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| PRKAR1B | NM_001164759.1 | ATGCCAAGCGTTACAG TTGCACTCCCAGGAAT TACTCGGTCAATATAA GAGA (SEQ ID NO: 54) CGTGTGCTGGGCCCT GCTCTGAGATCCTCAA GAGGAACATTCAGCGT TACAACAGCTTCATCT CCCTCACCGTCTGAGC ACAGCTCCCGCCCTGC AGCC (SEQ ID NO: 55) | NM_001164759; NM_001164761; NM_001164762; NM_001164760; NM_002735 | -0.861735578 | 0.972622807 | -0.165967303 |
| DDB2 | NM_000107.1 | GGGGAACGTGATCCTG CTGAACATGGACGGCA AAGAGCTTTGGAATCT CAGAATGCACAAAAAG AAAGTGACGCATGTGG CCCTGAACCATGCTG TGAT (SEQ ID NO: 56) | NM_000107 | -1.048250131 | 1.204621227 | 0.153767602 |
| TSPAN7 | NM_004615.3 | GGCGTTTGGAATCGCA TTCTCCCAGTTAATTG GCATGCTGCTGGCCTG CTGTCTGTCCCGGTTC ATCACGGCCAATCAGT ATGAGATGGTGTAAGG AGAA (SEQ ID NO: 57) | NM_004615 | -0.586966677 | 1.295666073 | -0.034132673 |
| FBXW7 | NM_018315.4 | TGGGTCATGTTGCAGC AGTCCGCTGTGTTCAA TATGATGGCAGGAGGG TTGTTAGTGGAGCATA TGATTTTATGGTAAAG GTGTGGGATCCAGAGA CTGA (SEQ ID NO: 58) | NM_018315; NM_001013415; NM_033632 | -0.551931516 | 0.743952534 | -0.032066214 |
| DLL1 | NM_005618.3 | ACCAGTCGGTGTACGT CATATCCGAGGAGAAG GATGAGTGCGTCATAG CAACTGAGGTGTAAAA | NM_005618 | -0.787054447 | 1.297166278 | -0.028735448 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| HES1 | NM_005524.2 | TGGAAGTGAGATGGCA AGACTCCCGTTTCTCT TAAA (SEQ ID NO: 59) | NM_005524 | -1.350029079 | 1.708702854 | -0.435881651 |
| COL27A1 | NM_032888.2 | GCTGGAGGCGGCTA AGTGTTTGGAGGCTT CCAGTGGTACCGGCT CCCGATGGCCAGTTTG CTTTCCTCATTCCCAA CGGGGCCTTCGCGCAC AGCG (SEQ ID NO: 60) | NM_032888 | -0.678678331 | 0.932985532 | -0.06990641 |
| PDGFRA | NM_006206.3 | GGATCCAAACTTGGC TGCTCCTCTGACACCA TCGAGGTCTCCTGCAA CTTCACTCATGGTGGA CAGACGTGTCTCAAGC CCATCACGGCCTCCAA GGTC (SEQ ID NO: 61) | NM_006206 | -0.631137099 | 0.771453391 | 0.002225072 |
| CCND2 | NM_001759.2 | TAGTGCTTGGTCGGGT CTTGGGGTCTGGAGCG TTTGGAAGGTGGTTG AAGGAACAGCCTATGG ATTAAGCCGGTCCCAA CCTGTCATGAAAGTTG CAGT (SEQ ID NO: 62) | NM_001759 | -0.962072017 | 0.560935922 | 0.380438596 |
| CXXC4 | NM_025212.1 | AGCCTCGCATCCCTTCG CCTGCAGCCTACTTTG GGGAAATAAAGTGCCT TACTGACTGTAGCCAT TACAGTATCCAATGTC TTTTGACAGGTGCCTG TCCT (SEQ ID NO: 63) | | | | |
| | | AGCCTCAGCAGCCGTC ACAGACAGTGCGTTTC AAATTGCCAATCTGGC AGATGCCCGCAGAAT CATTCCTCCTCCTCCT CGTCCTCCTCAGGGGG AGCT (SEQ ID NO: 64) | NM_025212 | -1.135455693 | 0.927997254 | 0.168080612 |

TABLE 3-continued

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| ACVR1B NM_004302.3 | CGGGAGAGACTCGCTC ACTCCCATGTTGGGTT TGAGACAGACACCTTT TCTATTTACCTCCTAA TGGCATGGAGACTCTG AGAGCGAATTGTGTGG AGAA (SEQ ID NO: 65) | NM_004302; NM_020328; NM_020327 | -0.715425503 | 1.035669748 | -0.09835060 |
| DTX4 NM_015177.1 | GCATCTACTACCTTGA CACAGAGTGTTTTCCC ACTAGAAGCTCTGCTC TGCTCTCCTGGCCCAA GTAGGGGATTCATGC CTTCCCTTTCATGGTC TTAG (SEQ ID NO: 66) | NM_015177 | -0.980772905 | 1.188830049 | 0.344156922 |
| TGFB3 NM_003239.2 | CCCTCGATCATATTTC CCCTTGGACACTTGGT TAGACGCCTTCCAGGT CAGGATGCACATTTCT GGATTGTGGTTCCATG CAGCCTTGGGGCATTA TGGG (SEQ ID NO: 67) | NM_003239 | 0.779010809 | 0.453512809 | -1.151684947 |
| ZBTB16 NM_006006.4 | TCCTGGATAGTTTGCG GCTGAGAATGCACTTA CTGGCTCATTCAGCGG GTGCCAAAGCCTTTGT CTGTGATCAGTGCGGT GCACAGTTTTCGAAGG AGGA (SEQ ID NO: 68) | NM_006006; NM_001018011 | 0.744144038 | 0.300340307 | -1.501842069 |
| MAPK10 NM_002753.2 | GTATTCATACAGCACT ACTTACTTAGAGATGC TACTGTCAGTGTCCTC AGGGCTCTACCAAGAC ATAATGCACTGGGGTA CCACATGGTCCATTTC ATGT (SEQ ID NO: 69) | NM_002753; NM_138982; NM_138981; NM_138980 | 0.746376668 | -0.429814494 | -0.788117541 |
| SPOP NM_001007226.1 | GCCTTGTCTCTTGGGT CTGAGTCCCTTGCTTA AGGGATTTTGAAGTCC | NM_001007226; NM_001007230; NM_001007229; NM_001007228; NM_003563; NM_001007227 | 1.211367282 | -0.57725145 | -0.550759513 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | TAGTTTTCAGCTTGCA GAGATTATGTCTGAAA TGCCTAATGAGTCGCA GGGA (SEQ ID NO: 70) | | | | |
| CASP7 | NM_001227.3 | ATCAATGACACAGATG CTAATCCTGATACAA GATCCCAGTGGAAGCT GACTTCCTCTTTCGCCT ATTCCACGGTTCCAGG CTATTACTCGTGGAGG AGCC (SEQ ID NO: 71) | NM_001227; NM_001267058; NM_001267057; NM_001267056; NM_033340; NM_033339; NM_033338 | 0.943717067 | -1.042835031 | 0.467273755 |
| FGF21 | NM_019113.2 | GATCACCTGAGGACCC GAGCCATTGATGGACT CGGACGAGACCGGGTT CGAGCACTCAGGACTG TGGGTTTCTGTGCTGG CTGGTCTTCTGTCTGGG AGCC (SEQ ID NO: 72) | NM_019113 | 0.616732498 | -1.397117511 | -0.041120318 |
| BAD | NM_004322.3 | CAGCACAGCGCTATGG CCGCGAGCTCCGGAGG ATGAGTGACGAGTTTG TGGACTCCTTTAAGAA GGGACTTCCTCGCCCG AAGAGCGCGGGCACAG CAAC (SEQ ID NO: 73) | NM_004322; NM_032989 | 0.606883027 | -1.201194407 | 0.232550134 |
| GSK3B | NM_002093.2 | ACTGATTATACCTCTA GTATAGATGTATGGTC TGCTGGCTGTGTGTTG GCTGAGCTGTTACTAG GACAACCAATATTTCC AGGGGATAGTGGTGTG GATC (SEQ ID NO: 74) | NM_002093; NM_001146156 | 0.885705342 | -1.39075106 | 0.610667114 |
| RBX1 | NM_014248.2 | ATTATGGATCTTTGCA TAGAATGTCAAGCTAA CCAGGCGCTCCGCTACT TCAGAAGAGTGTACTG | NM_014248 | 0.166483538 | -1.055858889 | 0.71029212 |

TABLE 3-continued

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| RELA NM_021975.2 | TCGCATGGGGAGTCTG TAACCATGCTTTCAC TTCC (SEQ ID NO: 75) | NM_021975; NM_001243985; NM_001243984; NM_001145138 | 0.611208315 | −0.869112536 | 0.201460338 |
| NUPR1 NM_001042483.1 | GATGGCTTCTATGAGG CTGAGCTCTGCCCGGA CCGCTGCATCCACAGT TTCCAGAACCTGGGAA TCCAGTGTGTGAAGAA GCGGGACCTGGAGCAG GCTA (SEQ ID NO: 76) | | | | |
| | GAAACTGGGGCTCCTC CAGGGTGCAGCAACA ATAAATAGACACGCAC GGCAGCCACAGCTTGG GTGTGTTCATCCTT GTTAAAAAAAAAAAA AAAA (SEQ ID NO: 77) | NM_001042483; NM_012385 | 0.939785066 | −0.614213269 | −0.451309641 |
| DDIT3 NM_004083.4 | TTAAAGATGAGCGGGT GGCAGGCGACAGAGCCA AAATCAGAGCTGGAAC CTGAGGAGAGCTGTT CAAGAAGGAAGTGTAT CTTCATACATCACCAC ACCT (SEQ ID NO: 78) | NM_004083; NM_001195057; NM_001195056; NM_001195053; NM_001195054; NM_001195055 | 1.18240637 | −1.318487563 | 0.223796918 |
| LAMB3 NM_000228.2 | AAATGGGGGAAGGTC CAACTTAACCTTATGG ATTTAGTGTCTGGGAT TCCAGCAACTCAAAGT CAAAAAATTCAAGAGG TGGGGAGATCACAAA CTTG (SEQ ID NO: 79) | NM_000228; NM_001017402; NM_001127641 | 1.552616212 | −0.901993606 | 0.038750971 |
| TSHR NM_001018036.2 | GGATATGCTTTCAATG GGACAAAGCTGATGC TGTTTACCTAAACAAG AATAAATACCTGACAG TTATTGACAAAGATGC ATTTGGAGGAGTATAC AGTG (SEQ ID NO: 80) | NM_001018036; NM_001142626; NM_000369 | 0.452978334 | −1.281483556 | 0.321335827 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| BCL2L1 | NM_138578.1 | CTAAGAGCCATTTAGG GGCCACTTTGACTAG GGATTCAGGCTGCTTG GGATAAAGATGCAAGG ACCAGGACTCCCTCCT CACCTCTGGACTGGCT AGAG (SEQ ID NO: 81) | NM_138578; NM_001191 | 0.490231758 | -0.792877145 | 0.85930403 |
| PIM1 | NM_002648.2 | CTTCATCATGAGTTCT GCTGAATGCCGCGATG GGTCAGTAGGGGGGA AACAGGTTGGGATGGG ATAGGACTAGCACCAT TTTAAGTCCCTGTCAC CTCT (SEQ ID NO: 82) | NM_002648; NM_001243186 | 1.163851083 | -0.58387838 | 0.43760126 |
| PRKCB | NM_212535.1 | GCATTTGGAGTCCTGC TGTATGAAATGTTGGC TGGGCAGGCACCCTTT GAAGGGAGGATGAAG ATGAACTCTTCCAATC CATCATGGAACACAAC GTAG (SEQ ID NO: 83) | NM_212535; NM_002738 | -0.220213795 | -0.44819218 | 0.693162357 |
| PLD1 | NM_002662.3 | AGTCCAGAAATCTTCC TGAAACGCCCAGTGGT TGAGGAAATCGTTGG AGGTTGACTGCATTC TTAAACGAAAAGCACA ACAAGGAGTGAGGATC TTCA (SEQ ID NO: 84) | NM_002662; NM_001130081 | 0.078761527 | -0.747955173 | 0.330941788 |
| WNT3 | NM_030753.3 | CCAACTCGCCTGTGA CGGGAGGCTCTCCCT CTCTCTCATCTTACAT TTCTCACCCTACTCTG GATGGTGTGTGTTTT TAAAGAAGGGGCTTT CTTT (SEQ ID NO: 85) | NM_030753 | 0.443885608 | -0.810662403 | 0.009175691 |
| EIF4EBP1 | NM_004095.3 | CTGCGCAATAGCCCAG AAGATAAGCGGCGGG CGGTGAAGAGTCAG | NM_004095 | -0.070945866 | -0.897973905 | 0.010952684 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| IRAK2 | NM_001570.3 | TTTGAGATGGACATTT AAAGCACCAGCCATCG TGTGGAGCACTACCAA GGGG (SEQ ID NO: 86) | | | | |
| | | GTGTTGCCGAGGTCC TCACGGGCATCCCTGC AATGGATAACAACCGA AGCCCGTTTACCTGA AGGACTTACTCCTCAG TGATATTCCAAGCAGC ACCG (SEQ ID NO: 87) | NM_001570 | 1.48428277 | -1.194483728 | -0.40789912 |
| PRKAA2 | NM_006252.2 | ATAGTGTGACCCTCA AGACCAGCTTGCAGTG GCTTATCATCTTATCA TTGACAATCGGAGAAT AATGAACCAAGCCAGT GAGTTCTACCTCGCCT CTAG (SEQ ID NO: 88) | NM_006252 | 1.381125373 | -0.775485013 | -0.577567956 |
| DUSP5 | NM_004419.3 | GTGGATGTAAAACCCA TTTCACAAGAGAAGAT TGAGAGTGAGAGAGCC CTCATCAGCCAGTGTG GAAAACCAGTGGTAAA TGTCAGCTACAGGCCA GCTT (SEQ ID NO: 89) | NM_004419 | 0.327417325 | -1.005227809 | 0.322905127 |
| IL8 | #N/A | #N/A | #N/A | 0.47273382 | -1.183932351 | 0.413001976 |
| MAP2K1 | NM_002755.2 | ACGGAATGGACAGCCG ACCTCCCATGGCAATT TTTGAGTTGTTGGATT ACATAGTCAACGAGCC TCCTCCAAAACTGCCC AGTGGAGTGTTCAGTC TGGA (SEQ ID NO: 90) | NM_002755 | 0.630232347 | -1.253785345 | -0.076450981 |
| BIRC3 | NM_182962.1 | GTGAGACTCGCGCCCT CCGGCACGGAAAAGGC CAGGCGACAGGTGTCG CTTGAAAAGACTGGGC TTGTCCTTGCTGGTGC | NM_182962; NM_001165 | 0.718062464 | -1.255101549 | 0.237248246 |

TABLE 3-continued

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| | ATGCGTCGTCGGCCTC TGGG (SEQ ID NO: 91) | | | | |
| PLA2G4C NM_003706.2 | CCAATGTCCAGATGGC CAGAATGAATGTGATA GTTCAGACCAATGCCT TCCACTGCTCCTTTAT GACTGCACTTCTAGCC AGTAGCTCTGCACAAG TTAG (SEQ ID NO: 92) | NM_003706; NM_001159323; NM_001159322 | 1.496594473 | -1.346242957 | -0.15784499 |
| PPP3CC NM_005605.3 | AGCAGAAGGAAGCACT ACAGTTCGTAAGGAGA TCATCAGGAATAAGAT CAGAGCCATTGGGAAG ATGGCACGGGTCTTTT CAATTCTTCGGCAAGA AAGT (SEQ ID NO: 93) | NM_005605; NM_001243975; NM_001243974 | 0.664650863 | -1.36423635 | 0.256830574 |
| CAPN2 NM_001748.4 | CCATGAATTCCTATGA AATGCGGAAGGCATTA GAAGAAGCAGTTTCA AGATGCCCTGTCAACT CCACCAAGTCATCGTT GCTCGGTTTGCAGATG ACCA (SEQ ID NO: 94) | NM_001748; NM_001146068 | 0.643376276 | -1.155868131 | 0.247414615 |
| GZMB NM_004131.3 | ACACTACAAGAGGTGA AGATGACAGTGCAGGA AGATCGAAAGTGCGAA TCTGACTTACGCCATT ATTACGACAGTACCAT TGAGTTGTGCGTGGGG GACC (SEQ ID NO: 95) | NM_004131 | 0.675014406 | -1.142799947 | 0.722529353 |
| CLCF1 NM_013246.2 | GATGGGTGTTGCTCCC TTATCCCAAATCACT CTATACATCCAATTCA GGAAACAAACATGGTG GCAATTCTACACAAAA AGAGATGAGATTAACA GTGC (SEQ ID NO: 96) | NM_013246; NM_001166212 | 0.716776379 | -0.847605107 | 0.342471593 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| HGF | NM_000601.4 | TCATTGTAAGGACG CAGCTACAAGGAACA GTATCTATCACTAAGA GTGGCATCAAATGTCA GCCCTGGAGTTCATG ATACCACGAACACA GCTT (SEQ ID NO: 97) | NM_000601; NM_001010934; NM_001010931; NM_001010932; NM_001010933 | 0.290481662 | −0.610592648 | 0.50255412 |
| ITGA3 | NM_005501.2 | CATGATTCAGCGCAAG GAGTGGGACTTATCTG AGTATAGTTACAAGGA CCCAGAGGACCAAGGA AACCTCTATATTGGGT ACACGATGCAGTAGG CAGC (SEQ ID NO: 98) | NM_005501; NM_002204 | 0.656718626 | −2.639015229 | 0.467661891 |
| IL6R | NM_000565.2 | CTTTCTACATAGTGTC CATGTGCGTCGCCAGT AGTGTCGGGAGCAAGT TCAGCAAAACTCAAAC CTTTCAGGGTTGTGAA ATCTTGCAGCCTGATC CGCC (SEQ ID NO: 99) | NM_000565; NM_001206866; NM_181359 | 1.25332586 | −1.599829447 | −0.032175941 |
| POLD4 | NM_021173.2 | AGGCACCACGTAAGAC CTCCTGCCCTTAGCTC TCTTGCTCACCACCCA AGAACCTCAGGACAGA AGCGAGCCCATTGC TCCTGCTCAGCTCAGC CCGG (SEQ ID NO: 100) | NM_021173; NR_046412; NR_046411; NM_001256870; NR_046413 | 0.672053389 | −1.147721365 | 0.210396896 |
| AMH | NM_000479.3 | GACCTCCGCGCCGAGC GCTCCGTACTCATCCC CGAGACCTACCAGGCC AACAATTGCCAGGGCG TGTGCCGCTGGCCTCA GTCCGACCGCAACCCG CGCT (SEQ ID NO: 101) | NM_000479 | 0.288540555 | 0.250910932 | −0.994093078 |
| CACNA1C | NM_199460.2 | TGAAACACCCTGTGGT AGCAGCTTTGCTGTCT TCTACTTCATCAGCTT CTACATGCTCTGTGCC | NM_199460; NM_001129840; NM_001129835; NM_001129834; NM_001129830; NM_001129837; NM_001129832; NM_001129838; | 1.676167163 | −0.351229666 | −0.670030512 |

TABLE 3-continued

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| | TTCCTGATCATCAACC TCTTTGTAGCTGTCAT CATG (SEQ ID NO: 102) | NM_000719; NM_001167625; NM_001129843; NM_001129846; NM_001129839; NM_001129827; NM_001129829; NM_001129831; NM_001167624; NM_001129833; NM_001129841; NM_001129836; NM_001167623; NM_001129842; NM_001129844 | | | |
| CACNA1H NM_021098.2 | GACACGGACGAGGACA AGACGTCGGTCCACTT CGAGGAGGACTTCCAC AAGCTCAGAGAACTCC AGACCACAGAGCTGAA GATGTGTCCCTGGCC GTGA (SEQ ID NO: 103) | NM_021098; NM_001005407 | 0.850490171 | 0.252197083 | -0.853900562 |
| GNA11 NM_002067.1 | TTCGAGCATCAGTACG TCAGTGCCATCAAGAC CCTGTGGGAGGACCCG GGCATCCAGGAATGCT ACGACCGCAGGCGCGA GTACCAGCTCTCCGAC TCTG (SEQ ID NO: 104) | NM_002067 | 1.124323404 | -0.745622387 | -0.153580798 |
| ITGA7 NM_002206.1 | TGATAGTGGGTGCCCC CTACTTCTTTGAGCGC CAAGAAGAGCTGGGGG GTGCTGTGTATGTGTA CTTGAACCAGGGGGGT CACTGGGCTGGGATCT CCCC (SEQ ID NO: 105) | NM_002206; NM_001144997; NM_001144996 | 1.042754581 | -0.659327019 | -0.17332686 |
| JAG1 NM_000214.2 | TTGCTTGTGGAGGCGT GGGATTCCAGTAATGA CACCGTTCAACCTGAC AGTATTATTGAAAAGG CTTCTCACTCGGGCAT GATCAACCCCAGCCGG CAGT (SEQ ID NO: 106) | NM_000214 | 0.728317828 | -0.512594469 | -0.375946652 |
| LAMA5 NM_005560.3 | GCCATGAATTTCTCCT ACTCGCCGCTGCTACG TGAGTTCACCAAGGCC ACCAAGGTCCGCCTGC | NM_005560 | 1.622724844 | -1.060012408 | 0.072913031 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | GCTTCCTGCGTACCAA CACGCTGCTGGGCCAT CTCA (SEQ ID NO: 107) | | | | |
| IDH2 | NM_002168.2 | CACCGGCTCATTGATG ACATGGGCTCAGGT CCTCAAGTCTTCGGGT GGCTTTGTGTGGGCCT GCAAGAACTATGACGG AGATGTGCAGTCAGAC ATCC (SEQ ID NO: 108) | NM_002168 | 1.478046247 | -0.923619017 | 0.358613769 |
| PLA2G10 | NM_003561.1 | CAGAGCGTCCTGTGCG GACCGGCAGAGAACAA ATGCCAAGAACTGTTG TGCAAGTGTGACCAGG AGATTGCTAACTGCTT AGCCCAAACTGAGTAC AACT (SEQ ID NO: 109) | NM_003561 | 0.931837184 | -0.102139226 | 0.154420614 |
| HSPB1 | NM_001540.3 | AGCCGCGCGCTCAGCC GGCAACTCAGCAGCGG GGTCTCGGAGATCCGG CACACTGCGGACCGCT GGCGCGTGTCCCTGGA TGTCAACCACTTCGCC CCGG (SEQ ID NO: 110) | NM_001540 | 1.258279601 | -1.731442887 | 0.471013239 |
| LAMC2 | NM_005562.2 | CAAGCGGAAATTGAAG CAGATAGGTCTTATCA GCACAGTCTCCGCCTC CTGGATTCAGTGTCTC GGCTTCAGGGAGTCAG TGATCAGTCCTTTCAG GTGG (SEQ ID NO: 111) | NM_005562; NM_018891 | 1.16859924 | -1.360857477 | 0.005444094 |
| FLNC | NM_001127487.1 | GGGCCTGTCCATTGCT GTGGAGGGTCCTAGCA AAGCGGAGATTGCATT TGAGGATCGCAAAGAT GGCTCCTGCGGCGTCT CCTATGTCGTCCAGGA ACCA (SEQ ID NO: 112) | NM_001127487; NM_001458 | 1.839552557 | -1.255013658 | 0.013631778 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| NFKBIZ | NM_001005474.1 | ATTTGGTTCCGATGG CCCTGTGGAGAACAG ATCCGACGTATCCTGA AGGGAAAGTCCATTCA GCAGAGAGCTCCACCG TATTAGCTCCATTAGC TTGG (SEQ ID NO: 113) | NM_001005474; NM_031419 | 2.315727502 | -1.292126131 | 0.19745825 |
| FN1 | NM_212482.1 | GGGAATGGACATGCAT TGCCTACTCGCAGCTT CGAGATCAGTGCATTG TTGATGACATCACTTA CAATGTGAACGACACA TTCCACAAGCGTCATG AAGA (SEQ ID NO: 114) | NM_212482; NM_212476; NM_054034; NM_002026; NM_212478; NM_212474 | 0.660402717 | -1.171486781 | 0.234728184 |
| GNG12 | NM_018841.3 | ATAAAGGTTTCGAAGG CATCAGCGGACCTCAT GTCCTACTGTGAGGAA CATGCCAGGAGTGACC CTTTGCTGATAGGAAT ACCAACTTCAGAAAAC CCTT (SEQ ID NO: 115) | NM_018841 | 0.867571726 | -0.981276666 | 0.471261377 |
| PDGFC | NM_016205.1 | CCGCATCTATTGGCAG CTTTGTTATTGATCAG AAACTGCTCGCGCCG ACTTGGCTTCCAGTCT GGCTGCCGGGCAACCCT TGAGTTTTCGCCTCTG TCCT (SEQ ID NO: 116) | NM_016205; NR_036641 | 1.196009475 | -1.133981891 | 0.004647767 |
| GAS1 | NM_002048.2 | CTGTGGCTTGGGACAG ATAGAAGGGATGGTTG GGGATACTTCCCAAAA CTTTTTCAAGTCAAC TTGGTGTAGCCGGTTC CCCGGCCACGACTCTG GGCA (SEQ ID NO: 117) | NM_002048 | 0.779622888 | -0.752350475 | 0.219109788 |
| CDKN2D | NM_001800.3 | CTTTCTCTTCTTTGTTT CTCCTGCCACTGCTG CAGTAGGGAGGAGCA | NM_001800; NM_079421 | 1.442455149 | -2.288021107 | 0.432605996 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | CAGTTTGTGGCTTATA GGTGTTGGTTTTGGGG GTGTGAGTGTTTGGGG GACG (SEQ ID NO: 118) | | | | |
| TNC | NM_002160.3 | CGCCAACTGAAAAAGT GGGAAAGGATGTCTGG AGGCGAGGCGTCCCAT TACAGAGGAAGGAGCT CGCTATATAAGCCAGC CAAAGTTGGCTGCACC GGCC (SEQ ID NO: 119) | NM_002160 | 2.489192272 | -1.589168535 | -0.18592867 |
| CDKN2A | NM_000077.3 | AAGCGCACATTCATGT GGGCATTTCTTGCGAG CCTCGCAGCCTCCGGA AGCTGTCGACTTCATG ACAAGCATTTTGTGAA CTAGGAAGCTCAGGG GGGT (SEQ ID NO: 120) | NM_000077; NM_058197; NM_058195; NM_001195132 | 1.509085425 | -0.73385756 | -0.063471162 |
| CDKN2B | NM_004936.3 | CACTTGGGTGACGGCA GTCGATGCGTTCACTC CAATGTCTGCTGAGGA GTTATGTGAACCCAC AACTTAGGCCCTAGCG GCAAGAAGGAAAACCT GAAG (SEQ ID NO: 121) | NM_004936; NM_078487 | 1.969916123 | -1.427909465 | 0.040850212 |
| INHBA | NM_002192.2 | GCGCTTCTGAACGCGA TCAGAAAGCTTCATGT GGGCAAAGTCGGGGAG AACGGGTATGTGGAGA TAGAGGATGACATTGG AAGGAGGGCAGAAATG AATG (SEQ ID NO: 122) | NM_002192 | 1.701129382 | -1.951616488 | 0.011540028 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| PTPRR | NM_001207015.1 | AAACCAGTGAGCAGTA TGAATTGTGCACCAT GCTCTGTGCCTGTATG AGAGCAGACTTTCAGC AGAGACTGTCCAGTGA GTCATTGAAGACTGT CAGA (SEQ ID NO: 123) | NM_001207015; NM_001207016; NM_002849; NM_130846; NR_073474 | 1.451595841 | -1.532015885 | 0.509429781 |
| NOTCH3 | NM_000435.2 | CTTTGGAGTCTGCCGT GATGGCATCAACCGCT ACGACTGTGTCTGCCA ACCTGGCTTCACAGGG CCCCTTTGTAACGTGG AGATCAATGAGTGTGC TTCC (SEQ ID NO: 124) | NM_000435 | 0.896323229 | -0.97089252 | 0.204819781 |
| FLNA | NM_001456.3 | CCCTCAGGAGCCCTGG AGGAGTGCTATGTCAC AGAAATTGACCAAGAT AAGTATGCTGTGCGCT TCATCCCTCGGAGAA TGGCGTTTACCTGATT GACG (SEQ ID NO: 125) | NM_001456; NM_001110556 | 3.352606408 | -1.630559407 | 0.110599618 |
| ITGB3 | NM_000212.2 | GAATAAGCCTTGGAAT TAGATATGGGCAATG ACTGAGCCCTGTCTCA CCCATGATTACTCCT TACTGTAGGGAATGGC AGTATGGTAGAGGGAT AAAT (SEQ ID NO: 126) | NM_000212 | 2.029627821 | -1.363726479 | 0.172308131 |
| CDH1 | NM_004360.2 | CGATAATCCTCCGATC TTCAATCCCACCACGT ACAAGGGTCAGTGCC TGAGAACGAGGCTAAC GTCGTAATCACCACAC GTGAAAGTGACTGATGC TGAT (SEQ ID NO: 127) | NM_004360 | 1.417579351 | -0.563519168 | -0.012000775 |
| IL22RA1 | NM_021258.2 | GACGGGTACAATAACA CACTGTACTGATGTCA CAACTTTGCAAGCTCT | NM_021258 | 0.677423648 | -0.861368018 | -0.084338277 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| PRKAR2A | NM_004157.2 | GCCTTGGGTTCAGCCC ATCTGGGCTCAAATTC CAGCCTCACCACTCAC AAGC (SEQ ID NO: 128) | NM_004157 | 0.954173113 | -1.411559699 | -0.110220662 |
| DTX3 | NM_178502.2 | ATTTAGAAACTTGAA AGTCAGCACTAAAGGA TGGGCAGAGGTTCAAC CCACACCTCCACTTG CTTCTGAAGGCCCATT CATTAGACCACTTGTA AAGA (SEQ ID NO: 129) | NM_178502; NM_001286246; NM_001286245 | 0.836185822 | -0.362975758 | -0.481378145 |
| GRIN2A | NM_000833.3 | CTCCCCGTGTACATAT ACTCCCGGTTTCCCTG CCCCTCCATTGCCCTT GGCTTTTTCTGGTATG TGCTGTGCTCCACGAC CAAGCCGAGAAAGGAC CTAG (SEQ ID NO: 130) | NM_000833; NM_001134407; NM_001134408 | 1.367454914 | -0.535776184 | -0.271174006 |
| POLE2 | NM_002692.2 | GAATGACAGCTATCTT CGGTCGTCCTTGAGGT CAACGGCATCGTACTG TTCCAGGACAGTCGG GGCCACAATGATGTGT ATATTTCGGAGCATGT TATG (SEQ ID NO: 131) | NM_002692; NM_001197330 | 0.797767805 | -0.686659307 | -0.015103545 |
| CDKN2C | NM_001262.2 | GAGAGTGTATCCTGTG CCCGATCTACTTGTCA TTGCAGACAAATATGA TCCTTTCACTACGACA AATACCGAATGCCTCT GCATAAACCCTGGCTC TTTT (SEQ ID NO: 132) | NM_001262; NM_078626 | 1.659187221 | -0.368692467 | -0.280435804 |
|  |  | ATAATGTAAACGTCAA TGCACAAAATGGATTT GGAAGGACTGCGCTGC AGGTTATGAAACTTGG |  |  |  |  |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | AAATCCCGAGATTGCC AGGAGACTGCTACTTA GAGG (SEQ ID NO: 133) | | | | |
| CCNE2 | NM_057735.1 | CGCCAGCTGAGCCGAG CGGTAGCTGGTCTGGC GAGGTTTATACACCT GAAAGAAGAGAATGTC AAGACGAAGTAGCCGT TTACAAGCTAAGCAGC AGCC (SEQ ID NO: 134) | NM_057735; NM_057749 | 2.322615612 | −0.285274237 | −0.620886998 |
| FANCE | NM_021922.2 | CCAGAAGCCTCTCTTCT TGGACGGATCCTCTCC TTGACTTCCTCAGCCT CCCGCCTGCTTACAAC TGCCCTGACCTCCTTC TGTGCCAAATATACAT ACCC (SEQ ID NO: 135) | NM_021922 | 1.739950882 | −0.174523797 | −1.115444165 |
| CDC25C | NM_001790.2 | CTCTCTGTGTGACATT ACTATCACTCAGATGC TGGAGGAAGATTCTAA CCAGGGGCAACCTGATT GGTGATTTTCCAAGG TATGTGCGCTGCCAAC CGTG (SEQ ID NO: 136) | NM_001790; NM_001287582; NM_022809; NM_001287583 | 0.885753996 | −0.614233996 | −0.633132809 |
| FANCA | NM_000135.2 | GCAAAGTGATTGACTG TGACAGTTCTGAGGCC TATGCTAATCATTCTA GTTCATTATAGGCTC TGCTTTGCAGGATCAA GCCTCAAGGCTGGGGG TTCC (SEQ ID NO: 137) | NM_000135; NM_001286167; NM_001018112 | 0.843349767 | −0.327032636 | −0.853923908 |
| CCNA2 | NM_001237.2 | CGGGACAAAGTGGCC TGAATCATTAATACGA AAGACTGGATATACCC TGGAAAGTCTTAAGCC TTGTCTCATGGACCTT CACCAGACCTACCTCA AAGC (SEQ ID NO: 138) | NM_001237 | 1.709739605 | −0.762854153 | −0.151256005 |

TABLE 3-continued

Sarcoma Centroids

| Gene Symbol | Accession | Isoform Coverage Hit List | Target Sequence | Subgroup B centroid | Subgroup A centroid | Subgroup C centroid |
|---|---|---|---|---|---|---|
| DNMT1 | NM_001379.2 | NM_001379; NM_001130823 | CAAAACCAATCTATGATGATGACCCATCTCTTGAAGGTGTTAATGGCAAAAATCTTGGCCCCATAAATGAATGGTGGATCACTGGCTTTGATGGAGG (SEQ ID NO: 139) | 1.087975952 | -0.772201927 | -0.139753541 |
| WHSC1 | NM_007331.1 | NM_007331; NM_133334; NM_133335; NM_133330; NM_001042424 | AAAAGAGTGCACGCCAGTATCACGTACAGTTCTTTGGTGACGCCCCAGAAAGAGCTTGGATATTTGAGAAGAGCCTCGTAGCTTTTGAAGGAGAAGGACA (SEQ ID NO: 140) | 1.011227482 | -0.710351274 | 0.184213773 |
| E2F1 | NM_005225.1 | NM_005225 | CCAGCTCCAAGCCGTGGACTCTTCGGAGAACTTTCAGATCTCCCTTAAGAGCAAACAAGGCCCGATCGATGTTTTCCTGTGCCCTGAAGGAGACCGTAGGT (SEQ ID NO: 141) | 1.066547328 | -0.894977636 | -0.186057173 |
| PTTG2 | NM_006607.2 | NM_006607 | TACTCTGATCTACGTTGATAAGGAAATTGGAGAACCAGGCACCCGTGTGGCTGCCAAGGATGTGCTGAAGCTGGAGTCTAGACCTTCAATCAAAGCATTA (SEQ ID NO: 142) | 0.995372679 | -1.454954386 | 0.043486443 |
| RFC4 | NM_181573.2 | NM_181573; NM_002916 | ACAGGTGGAAAGGAGATCACAGAGAAAGTGATTACAGACATTGCCGGGGTAATACCAGCTGAGAAAATTGATGGAGTATTTGCTGCCTGTCAGAGTGGCT (SEQ ID NO: 143) | 1.730057786 | -0.638599876 | -0.508480338 |
| MCM2 | NM_004526.2 | NM_004526; NR_073375 | TTTGTGCTTCTCACCTTTGGGTGGGATGCCTTGCCAGTGTGTCTTACT | 1.529183146 | -0.36493793 | -0.479749297 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| MCM4 | NM_182746.1 | TGGTTGCTGAACATCT TGCCACCTCCGAGTGC TTTGTCTCCACTCAGT ACCT (SEQ ID NO: 144) CAGTTATCCTGTTTGC TCACAATGATCTCGTT GACAAGGTCCAGCCTG GGGACAGAGTGAATGT TACAGGCCATCTATCGA GCTGTGCCTATTCGAG TCAA (SEQ ID NO: 145) | NM_182746; NM_005914 | 1.070557299 | -0.628650321 | 0.140545393 |
| BRCA2 | NM_000059.3 | GGGGACAGATTTGTGA CCGGCGCGGTTTTTGT CAGCTTACTCCGGCCA AAAAGAACTGCACCT CTGGAGCGGACTTATT TACCAAGCATTGGAGG AATA (SEQ ID NO: 146) | NM_000059 | 1.292667438 | -0.897838271 | 0.100241908 |
| TTK | NM_003318.3 | AACCAGAGGTTCCAGA GAGTAACCAGAAACAG TGGCAATCTAAGAGAA AGTCAGAGTGTATTAA CCAGAATCCTGCTGCA TCTTCAAATCACTGGC AGAT (SEQ ID NO: 147) | NM_003318; NM_001166691 | 2.388139352 | -0.618834387 | -0.128012393 |
| CCNB1 | NM_031966.2 | AACTTGAGGAAGAGCA AGCAGTCAGACCAAAA TACCTACTGGGTCGGG AAGTCACTGGAAACAT GAGAGCCATCCTAATT GACTGGCTAGTACAGG TTCA (SEQ ID NO: 148) | NM_031966 | 1.451881304 | -0.619865956 | -0.079524277 |
| MSH6 | NM_000179.1 | GCTGGCTTATTAGCTG TAATGCCCAGATGGG TTGTTACGTCCCTGCT GAAGTGCAGGCTCA | NM_000179; NM_001281494; NM_001281493; NM_001281492 | 1.499274067 | -0.5013127 | -0.336590614 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | CACCAATTGATAGAGT GTTTACTAGACTTGGT GCCT (SEQ ID NO: 149) | | | | |
| MOMS | NM_006739.3 | ATGAGACGAAGGGGGA GGACAACATTGACTTC ATGCCCACCATCTTGT CGCGCTTCGACATGAT CTTCATCGTCAAGGAT GAGCACATGAGGAGA GGGA (SEQ ID NO: 150) | NM_006739 | 1.98081102 | −0.697209461 | −0.578660576 |
| UBE2T | NM_014176.3 | AAACAAAAGGCTGATG AGGAAGAGATGCTTGA TAATCTACCAGAGGCT GGTGACTTCCAGAGTAC ACAACTCAACACAGAA AAGGAAGGCCAGTCAG CTAG (SEQ ID NO: 151) | NM_014176 | 1.85853348 | −0.105697652 | −0.665881982 |
| FEN1 | NM_004111.4 | CCGGAGAATGACATC AAGAGCTACTTTGGCC GTAAGGTGGCCATTGA TGCCTCTATGAGCATT TATCAGTTCCTGATTG CTGTTCGCCAGGGTGG GGAT (SEQ ID NO: 152) | NM_004111 | 1.86125434 | −0.646411517 | −0.576062555 |
| CHEK1 | NM_001114121.1 | AGGGTGATGAGATTGGA GTTCAAGAGACACTTC CTGAAGATTAAAGGGA AGCTGATTGATATTGT GAGCAGCCAGAAGATT TGGCTTCCTGCCACAT GATC (SEQ ID NO: 153) | NM_001114121; NR_045205; NR_045204; NM_001244846; NM_001274; NM_001114122 | 1.448005524 | −0.836815017 | −0.357022212 |
| BRIP1 | NM_032043.1 | GATGTGCAAAGCCTGG GATATAGAAGAACTTG TCAGCCTGGGAAGAA ACTAAAGGCCTGTCCA TATTACACAGCCCGAG AACTAATACAAGATGC TGAC (SEQ ID NO: 154) | NM_032043 | 1.969177489 | −0.504861708 | −0.218232737 |

TABLE 3-continued

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| CDC7 NM_003503.2 | ATCCCACATAATCACAGGAAACAAGATTCCACTGAGTGGCCCAGTACCTAAGGAGCTGGATCAGCAGTCCACCACAAAAGCTTCTGTTAAAGACCCTAC (SEQ ID NO: 155) | NM_003503; NM_001134420; NM_001134419 | 1.699141198 | -0.915926744 | -0.522885786 |
| ITGA8 NM_003638.1 | ATCGGAGTGCCTTTTGCAGGCAAGGATCAAAGAGGCAAAGTGCTCATTTATAATGGGAACAAAGATGGCTTAAACACCAAGCCTTCCCAAGTTCTGCAAG (SEQ ID NO: 156) | NM_003638 | 1.543535453 | -0.238387103 | -1.639134229 |
| ETS2 NM_005239.4 | CAACCATGTCTTTCAAGGATTACATCCAAGAGAGGAGTGACCCAGTGGAGCAAGGCAAACCAGTTATACCTGCAGCTGTGCTGGCCGGCTTCACAGGAAG (SEQ ID NO: 157) | NM_005239; NM_001256295 | 0.779810809 | 0.198093282 | -0.575997412 |
| COL4A6 NM_001847.2 | TGGGATTTCCTGGGCTTAATGATTCCAAGGAATTGAGGGTCAAAAGGGTGACATTGGCCTGCCAGGCCCAGATGTTTTCATCGATATAGATGGTGCTGT (SEQ ID NO: 158) | NM_001847; NM_001287760; NM_001287759; NM_001287758; NM_033641 | 1.658235267 | -0.282608549 | -1.56570051 |
| LAMA3 NM_000227.3 | CAGAGGACTGGTGTTTCACACGGGCACTAAGAACTCCTTTATGGCTCTTTATCTTTCAAAAGGACGTCTGGTCTTTTGCACTGGGGACAGATGGGAAAAAA (SEQ ID NO: 159) | NM_000227; NM_011127717; NM_198129; NM_011127718 | 2.083772989 | -0.709274494 | -0.584584899 |
| GADD45G NM_006705.3 | CAAAGTCTTGAACGTGGACCCCGACAATGTGACCTTCTGTGTGCTGGC | NM_006705 | 1.022032515 | -0.43766438 | -0.202119219 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | TGCGGGTGAGGAGGAC GAGGGCGACATCGCGC TGCAGATCCATTTAC GCTG (SEQ ID NO: 160) | | | | |
| ID2 | NM_002166.4 | CGGATATCAGCATCCT GTCCTTGCAGGCTTCT GAATTCCTTCTGAGT TAATGTCAAATGACAG CAAAGCACTGTGTGGC TGAATAAGCGGTGTTC ATGA (SEQ ID NO: 161) | NM_002166 | 0.62903887 | -0.510034449 | 0.119602389 |
| CACNB2 | NM_000724.3 | TCTTTTGTAAGTGCTA CATAAATTGGCCTGGT ATGGCTGCAGTCCTCC GGTTGCATACTGGACT CTTCAAAAACTGTTT GGGTAGCTGCCACTTG AACA (SEQ ID NO: 162) | NM_000724; NM_201572; NM_201571; NM_001167945; NM_201570; NM_201593; NM_201597; NM_201590; NM_201596 | 0.981132087 | -0.865116096 | 0.038963893 |
| NKD1 | NM_033119.3 | ACAGTGATACACACAC GTATTAAGGACTATC CCTGAGACCATCCCTC TCATTTTGGAAACTGC TAGGGAGGGAACCAAC CACTTAAACAAGCGTG GTTT (SEQ ID NO: 163) | NM_033119 | 2.691019394 | -0.322986548 | -0.744692386 |
| SOCS2 | NM_003877.3 | GGAACGGCACTGTTCA CCTTTATCTGACCAAA CCGCTCTACACGTCAG CACCATCTCTGCAGCA TCTCTGTAGGCTCACC ATTAACAAATGTACCG GTGC (SEQ ID NO: 164) | NM_003877; NM_001270469; NM_001270468; NM_001270467; NM_001270470; NM_001270471 | 0.834990812 | -0.655453649 | -0.071526563 |
| PLCB4 | NM_000933.3 | TATTCGTCGGGAGCC ATACCAAAGGATCCCA AAATCTTGGCTGCTCT TGAAGCTGTTGGAAAA | NM_000933; NM_182797; NM_001172646 | 0.508382694 | -1.029629816 | -0.727123493 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| RASGRP2 | NM_001098670.1 | CAGACGTGGAGGATG GGGTGTTTGACATCCA CTTGTAATAGATGCTG TGGTTGATCAAGGAC TCATTCCTGCCTTGA GAAAATACTTCAACCA GAGC (SEQ ID NO: 166) | NM_001098670; NM_001098671; NM_153819 | 1.415707148 | −0.84422873 | −0.216800183 |
| IRS1 | NM_005544.2 | TTGATGTGGCATCAA ACTACCGATTTAAAAC TGGAAGTTGCTGGTAC TCAAACCAAAAGTTCA TACTCTGGCGACACGA AGGGTTTCCTTTGAGC AACG (SEQ ID NO: 167) | NM_005544 | 1.47181196 | −0.40396467 | 0.227234957 |
| TNR | NM_003285.2 | CAAAAGACATCACAAT TAGCAATGTGACCAAG GACTCAGTGATGGTCT CCTGGAGCCCTCCTGT TGCATCTTTCGATTAC TACCGAGTATCATATC GACC (SEQ ID NO: 168) | NM_003285 | 1.180868996 | −0.840068366 | −0.092317008 |
| GADD45A | NM_001924.2 | GTTACTCCCTACACTG ATGCAAGGATTACAGA AACTGATGCCAAGGGG CTGAGTGAGTTCAACT ACATGTTCTGGGGGCC CGGAGATAGATGACTT TGCA (SEQ ID NO: 169) | NM_001924; NM_001199741; NM_001199742 | 1.287113277 | −1.517075592 | 0.011215464 |
| ZAK | NM_016653.2 | GACACGAGCCTTCCTG ACAAGTGTAACTCATT CCTACACAACAAGGCG GAGTGGAGGTGCGAAA TTGAGGCAACTCTTGA GAGGCTAAAGAAACTA GAGC (SEQ ID NO: 170) | NM_016653; NM_133646 | 1.643122992 | −0.497654428 | −0.637329531 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| FGF7 | NM_002009.3 | GAAAGGTCAAGTTGC ACCAGGCAGACAACAG ACATGGAATTCTTATA TATCCAGCTGTTAGCA ACAAAACAAAAGTCAA ATAGCAAACAGCGTCA CAGC (SEQ ID NO: 171) | NM_002009 | 1.698227137 | -1.240536774 | -0.522181449 |
| PBX1 | NM_002585.2 | CGGGAGAAGCAGGAC ATTGGAGACATTTTAC AGCAAATTATGACCAT CACAGACCAGAGTTTG GATGAGGCGCAGGCCA GAAAACATGCTTTAAA CTGC (SEQ ID NO: 172) | NM_002585; NM_001204963; NM_001204961 | 1.467757304 | -0.234263903 | -0.375071496 |
| PPARG | NM_015869.3 | GAGCAAAGAGGTGGCC ATCCGCATCTTTCAGG GCTGCCAGTTTCGCTC CGTGGAGGCTGTGCAG GAGATCACAGAGTATG CCAAAAGCATTCCTGG TTTT (SEQ ID NO: 173) | NM_015869; NM_138712; NM_138711; NM_005037 | 0.138766121 | -0.932222796 | 0.483262572 |
| THBS1 | NM_003246.2 | ACCCTCGTCACATAGG CTGGAAAGATTTCACC GCCTACAGATGGCGTC TCAGCCACAGGCCAAA GACGGGTTTCATTAGA GTGGTGATGTATGAAG GGAA (SEQ ID NO: 174) | NM_003246 | 0.254930123 | -0.997056609 | 0.173708474 |
| TNFAIP3 | NM_006290.2 | CAAAGCCCTCATCGAC AGAAACATCCAGGCCA CCCTGGAAAGCCAGAA GAAACTCAACTGGTGT CGAGAAGTCCGAAGC TTGTGCGCTGAAAAC GAAC (SEQ ID NO: 175) | NM_006290; NM_001270508; NM_001270507 | 0.145328112 | -1.051965129 | 0.524290309 |
| EYA1 | NM_172059.2 | CACAGCAGAGTACAGC ACAATCCACAGCCCAT CAACACCCATTAAAGA | NM_172059; XM_006716435; XM_005251182; NM_000503; NM_172058; NM_001288574; | 0.2928126 | -1.028756263 | 0.071321766 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | TTCAGATTCTGATCGA TTGCGTCGAGGTTCAG ATGGGAAATCACGTGG ACGG (SEQ ID NO: 176) | XM_005251184; NM_001288575; XM_006716437; XM_006716436; NM_172060 | | | |
| EFNA5 | NM_001962.2 | AGTCAAAATCCGCTCT CCATGCTTACTCTTGA CACCCCATTGAAGCCA CTCATTGTGTGTGCGT CTGGGTGTGAAGTCCA GCTCCGTGTGGTCCTG TGCT (SEQ ID NO: 177) | NM_001962 | 0.001526286 | -1.149909284 | 0.044343314 |
| MYC | NM_002467.3 | TCGGACACCGAGGAGA ATGTCAAGAGGCGAAC ACACAACGTCTTGGAG CGCCAGAGGAGGAACG AGCTAAAACGGAGCTT TTTTGCCCTGCGTGAC CAGA (SEQ ID NO: 178) | NM_002467 | 0.001204978 | -1.246321996 | 0.792535029 |
| NFKB1 | NM_003998.2 | AGGGTATAGCTTCCCA CACTATGGATTTCCTA CTTATGGTGGGATTAC TTTCCATCCTGGAACT ACTAAATCTAATGCTG GGATGAAGCATGGAAC CATG (SEQ ID NO: 179) | NM_003998; NM_001165412 | -0.04492968 | -1.203821974 | 0.563903708 |
| RUNX1 | NM_001754.4 | CAGCCATGAAGAACCA GGTTGCAAGATTTAAT GACCTCAAGGTTTGTCG GTCGAAGTGGAAGAGG GAAAAGCTTCACTCTG ACCATCACTGTCTTCA CAAA (SEQ ID NO: 180) | NM_001754; NM_001001890 | -0.29660105 | -0.587183221 | 0.975896848 |
| COL3A1 | NM_000090.3 | TTGGCACAACAGGAAG CTGTTGAAGGAGGATG TTCCCATCTTGTCAG TCCTATGCGGATAGAG | NM_000090 | -0.05310455 | -0.938619869 | 0.330406692 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| COL5A2 | NM_000393.3 | ATGTCTGGAAGCCAGA ACCATGCCAAATATGT GTCT (SEQ ID NO: 181) | NM_000393 | 0.066324157 | -1.298836749 | 0.702791004 |
| SPRY1 | NM_005841.1 | GGTTCATGCTACCCTG AAGTCACTCAGTAGTC AGATTGAAACCATGCG CAGCCCGATGGCTCG AAAAAGCACCCAGCC GCACGTGTGATGACCT AAAG (SEQ ID NO: 182) | NM_005841; NM_199327; NM_001258038; NM_001258039 | -0.261396451 | -0.572573824 | 0.808702985 |
| VEGFC | NM_005429.2 | GGATGACTTGAAGGGT TCCTTGAAAGAGGACC TGACACAGCACAAGTT CATTTGTGAAACAGTGT GGGAAGTGCAAGTGTG GAGAATGCACTGCTCC CAGG (SEQ ID NO: 183) | NM_005429 | 0.277920507 | -0.584003317 | 0.583459169 |
| COL4A4 | NM_000092.4 | GGCGAGGCCACGGCTT ATGCAAGCAAAGATCT GGAGGAGCAGTTACGG TCTGTGTCCAGTGTAG ATGAACTCATGACTGT ACTCTACCCAGAATAT TGGA (SEQ ID NO: 184) | NM_000092 | -0.215428822 | -0.865628696 | 0.850231366 |
| SOCS3 | NM_003955.3 | CGTGCTGGAAATCTGG GATGCTTCCTTCTGGG TTCTGATTCTCAGTGA GTGGAGCCCATTCATC CAGGCAGGTTTCCATG CTATGAGTGGCCCTTT CGTT (SEQ ID NO: 185) | NM_003955 | 0.190162345 | -0.966843307 | 1.157732644 |
| | | GGAGGATGGAGGAGAC GGGACATCTTTCACCT CAGGCTCCTGGTAGAG AAGACAGGGGATTCTA CTCTGTGCCTCCTGAC TATGTCTGGCTAAGAG ATTC (SEQ ID NO: 186) | | | | |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| ETV1 | NM_004956.4 | CACATACCAACGGCGAGGATCACTTCAGCTCTGGCAGTTTTGGTAGCTCTTCTGATGACCCTTCAAATTCTCATTTTATTGCCTGGACTGGTCGAGGC (SEQ ID NO: 187) | NM_004956; NM_001163150; NM_001163152; NM_001163151; NM_001163148; NM_001163149; NM_001163147 | -0.483944692 | -0.472162475 | 0.667492018 |
| NRAS | NM_002524.3 | ACCCTGTCCTGACTTCCCTGGAGGAGAAGTATTCCTGTTGCTGTCTTCAGTCTCACAGAGAAGCTCCTGCTACTTCCCCAGCTCTCCAGTAGTTTAGTAC (SEQ ID NO: 188) | NM_002524 | -0.40205324 | -0.741671466 | 0.61842163 |
| LIF | NM_002309.3 | GGGATGGAAGGCTGTCTTCTTTTGAGGATGATCAGAGAACTTGGCATAGGAACAATCTGGCAGAAGTTTCCAGAAGGAGGTCACTTGGCATTCAGGCTC (SEQ ID NO: 189) | NM_002309; NM_001257135 | -0.427733236 | -0.89005586 | 0.6585878 |
| APC | NM_000038.3 | AAACAGCCACCACTTCTCCTAGAGGAGCCAAGCCATCTGTGAAATCAGAATTAAGCCCTGTTGCCAGGCAGACATCCCAAATAGGTGGGTCAAGTAAAGC (SEQ ID NO: 190) | NM_000038; NM_001127511; NM_001127510 | -0.41323835 | -1.145962291 | 0.569063763 |
| PLAT | NM_000931.2 | CAAGGTTACCAACTACCTAGACTGGATTCGTGACAACATGGACCGTGACCAGGAACACCCGACTCCTCAAAAGCAAATGAGATCCCGCCTCTTCTTCTT (SEQ ID NO: 191) | NM_000931; NM_000930; NM_033011 | 0.255086414 | -0.897781696 | 0.652706703 |
| KAT2B | NM_003884.3 | CATCTGAGGCACCATCTCAAGAAGACTGCCGATCTCCCAATGATGAT | NM_003884 | 0.169588215 | -0.715561144 | 0.808610693 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| MET | NM_000245.2 | ATTTCTGGATACAAAG AGAACTACACAAGGTG GCTGTGTTACTGCAAC GTGC (SEQ ID NO: 192) | NM_000245; NM_001127500 | | | |
| | | AAATGAGGAAGACCTT CAGAAGGTTGCTGAGT ACAAGACTGGGCCTGT GCTGGAACACCCAGAT TGTTTCCCATGTCAGG ACTGCAGCAGCAAAGC CAAT (SEQ ID NO: 193) | | -0.487219685 | -0.569517119 | 0.528969462 |
| DUSP10 | NM_144728.2 | AGTTCGAGGAAGACCT AAACAACGGTGTGACA CCGAGAATCCTTACAC CAAAGCTGATGGGCGT GGAGACGGTTGTGTGA CAATGGTCTGGATGGA AAGG (SEQ ID NO: 194) | NM_144728; NM_007207 | 1.162440885 | -1.43248128 | 0.453731599 |
| PPARGC1A | NM_013261.3 | GAACAAGCACTTCGGT CATCCCAGTCAAGCTG TTTTTGACGACGAAGC AGACAAGACCGTGAA CTGAGGGACAGTGATT TCAGTAATGAACAATT CTCC (SEQ ID NO: 195) | NM_013261 | 1.101127687 | -0.885265217 | 0.209763192 |
| WNT16 | NM_057168.1 | GAAGATAATCTGTTTC CTAAGCAAGAAATAAC AGGAAAGATCCCTTAT GCCAGGAGGCCTGCCA TACTCAGGATAAGATC CTTGAATATGGAACTT AGTT (SEQ ID NO: 196) | NM_057168; NM_016087 | 0.569244222 | -1.353938971 | 0.786026088 |
| CALML5 | NM_017422.4 | CCGGTGAGCTGACTCC TGAGGAGGAGCCCAG TACAAAAAGGCTTTCT | NM_017422 | -0.254803322 | -1.202570257 | 0.868342334 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | CCGCGGTTGACACGGA TGGAAACGGCACCATC AATGCCCAGGAGCTGG GCGC (SEQ ID NO: 197) | | | | |
| GATA3 | NM_001002295.1 | AAGAGTCCGGCGGCAT CTGTCTTGTCCCTATT CCTGCAGCCTGTGCTG AGGGTAGCAGTGTATG AGCTACCAGCGTGCAT GTCAGCGGACCCTGGCC CGAC (SEQ ID NO: 198) | NM_001002295; NM_002051 | -0.095593162 | -1.173998403 | 0.559141534 |
| IL15 | NM_172174.1 | AGGGTGATAGTCAAAT TATGTATTGGTGGGGC TGGGTACCAATGCTGC AGGTCAACAGCTATGC TGGTAGCTCCTGCCA GTGTGGAACCACTGAC TACT (SEQ ID NO: 199) | NM_172174; NM_172175; NM_000585; NR_037840 | 0.185965654 | -0.529551785 | 0.811668987 |
| IL2RB | NM_000878.2 | GTCCTGCTGCCCGAGC CAGGAACTGTGTGTGT TGCAGGGGGCAGTAA CTCCCCAACTCCCTCG TTAATCACAGGATCCC ACGAATTTAGGCTCAG AAGC (SEQ ID NO: 200) | NM_000878 | 0.867636615 | -0.725722192 | 0.404721588 |
| IL7R | NM_002185.2 | TTGCTTTGACCACTCT TCCTGAGTTCAGTGGC ACTCAACATGAGTCAA GAGCATCCTGCTTCTA CCATGTGGATTTGGTC ACAAGGTTTAAGGTGA CCCA (SEQ ID NO: 201) | NM_002185 | 0.500044032 | -1.04018038 | 0.461856038 |
| IL3RA | NM_002183.2 | GACGTCCAGTACGACC TGTACTTGAACGTTGC CAACAGGCGTCAACAG TACGAGTGTCTTCACT ACAAAACGGATGCTCA GGGAAACACGTATCGGG TGTC (SEQ ID NO: 202) | NM_002183; NM_001267713 | 0.322997508 | -0.744100389 | 0.710771403 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| NOS3 | NM_000603.4 | CCGGACCACCTCGTCC CTGTGGAAAGACAAGG CAGCAGTGGAAATCAA CGTGGCCGTGCTGCAC AGTTACCAGCTAGCCA AAGTCACCATGTGGA CCAC (SEQ ID NO: 203) | NM_000603; NM_001160111; NM_001160110; NM_001160109 | 0.031965527 | -0.55997275 | 1.008066472 |
| IL6 | NM_000600.1 | TGACAAACAAATTCGG TACATCCTCGACGGCA TCTCAGCCCTGAGAAA GGAGACATGTAACAAG AGTAACATGTGTGAAA GCAGCAAAGAGGCACT GGCA (SEQ ID NO: 204) | NM_000600 | 0.25202091 | -1.057818045 | 0.521808798 |
| MAP3K8 | NM_005204.2 | CTGGCTACTTCAATCT TGTTCGGGACCACCA ACGCTTGAATATGGCT GAAGGATGCCATGTTT GCTCTAAATTAAGACA GCATTGATCTCCTGGA GGCT (SEQ ID NO: 205) | NM_005204; NM_001244134 | 0.525534565 | -0.629689865 | 0.558661012 |
| BCL2A1 | NM_004049.2 | TCATGTGTCATAACTC AGTCAAGCTCAGTGAG CATTCTCAGCACATTG CCTCAACAGCTTCAAG GTGAGCCAGCTTCAAGA CTTTGCTCTCCACCAG GCAG (SEQ ID NO: 206) | NM_004049; NM_001114735 | -0.118492282 | -1.248060312 | 0.535233973 |
| SHC1 | NM_183001.4 | TGGCCTTGTGATAAG GGAGAGTTGACCGTTT TCATCCTGGCCTCCTT TTGCTGTTTGGATGTT TCCACGGGTCTCACTT ATACCAAAGGGAAAAC TCTT (SEQ ID NO: 207) | NM_183001; NM_001130041; NM_001202859; NM_001130040; NM_003029 | 0.432448249 | -1.095032147 | 0.793300777 |
| TNFRSF10A | NM_003844.2 | CACAACGAGATTCTGA GCAACCGAGACTCGCT GTCCACTTCGTCTCT | NM_003844 | -0.469698881 | -0.657359638 | 0.525516546 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | GAGCAGCAAATGGAAA GCCAGGAGCCGGCAGA TTTGACAGGTGTCACT GTAC (SEQ ID NO: 208) | | | | |
| CASP10 | NM_032977.3 | GAAAGCTGAAGCACT TTGTGGCTTCCACGGG TTCGTTTCTAGGAAGC TTTTGCTTTACCTGGG GAAACCCCAAGCTCTA CAGTGAGAAAGTTGTA AATT (SEQ ID NO: 209) | NM_032977; NM_001206524; NM_001230; NM_032974; NM_001206542; NM_032976 | -0.489827618 | -0.346416482 | 1.154981817 |
| TLR4 | NM_138554.2 | ACTCAGAAAAGCCCTG CTGGATGGTAAATCAT GGAATCCAGAAGGAAC AGTGGGTACAGGATGC AATTGGCAGGAAGCAA CATCTATCTGAAGAGG AAAA (SEQ ID NO: 210) | NM_138554; NM_138557; NM_003266 | -0.502549677 | -0.321086708 | 0.889080653 |
| GRB2 | NM_002086.4 | TCAAAAGGGGGACAT CCTCAAGGTTTTGAAC GAAGAATGTGATCAGA ACTGGTACAAGCAGA GCTTAATGGAAAAGAC GGCTTCATTCCCAAGA ACTA (SEQ ID NO: 211) | NM_002086; NM_203506 | -0.437187727 | -0.814409187 | 2.119019854 |
| RAC2 | NM_002872.3 | GCTGCCACAACTTGTG TACCTTCAGGGATGGG GCTCTTACTCCCTCCT GAGGCCAGCTGCTCTA ATATCGATGGTCCTGC TTGCCAGAGAGTTCCT CTAC (SEQ ID NO: 212) | NM_002872 | -0.813796838 | -0.558222741 | 0.746175214 |
| CSF1R | NM_005211.2 | CATACTGGTACTGCTG TAATGAGCCAAGTGGC AGCTAAAAGTTGGGGG | NM_005211; NR_109969; NM_001288705 | -0.763822741 | -0.332235482 | 1.156562363 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| PIK3R5 | NM_001142633.1 | TGTTCTGCCCAGTCCC GTCATTCTGGCTAGA AGGCAGGGACCTTGG CATG (SEQ ID NO: 213) | | | | |
| | | TTTCTCTCAAGTTTCC TGAGTCTCCAGAAAAA CAGCACTAACGCTGGA CCTGTCTACTCTCAGA ACCCGGCACAGATTCT CTCTTGATCTCCTTTT GGAA (SEQ ID NO: 214) | NM_001142633; NM_001251855; NM_001251852; NM_001251851; NM_014308; NM_001251853 | −0.422120799 | −0.424025806 | 1.087625971 |
| TLR2 | NM_003264.3 | CTGCTTTCAACTGGTA GTTGTGGGTTGAAGCA CTGGACAATGCCACAT ACTTTGTGGATGGTGT GGGTCTTGGGGGTCAT CATCAGCCTCTCCAAG GAAG (SEQ ID NO: 215) | NM_003264 | −0.457895575 | −0.566882875 | 1.200496741 |
| PIK3CG | NM_002649.2 | AAAACATACCAATTGT TGGCCAGAAGGGAAGT CTGGGATCAAAGTGCT TTGGATGTTGGGTTAA CAATGCAGCTCCTGGA CTGCAACTTCTCAGAT GAAA (SEQ ID NO: 216) | NM_002649; NM_001282427; NM_001282426 | −0.498928755 | −0.404086965 | 1.099985115 |
| SYK | NM_003177.3 | CGGACTCTCCAAAGCA CTGCGTGCTGATGAAA ACTACTACAAGGCCCA GACCCATGGAAAGTGG CCTGTCAAGTGGTACG CTCCGGAATGCATCAA CTAC (SEQ ID NO: 217) | NM_003177; NM_001174168; NM_001174167; NM_001135052 | −0.471120916 | −0.497930912 | 1.929710234 |
| IL2RA | NM_000417.1 | CTTGGTAAGAAGCCGG GAACAGACAACAGAAG TCATGAAGCCCAAGTG AAATCAAAGGTGCTAA | NM_000417 | −0.030524763 | −0.840889014 | 0.663049508 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| | | ATGGTCGCCCAGGAGA CATCCGTTGTGCTTGC CTGC (SEQ ID NO: 218) | | | | |
| MFNG | NM_002405.2 | CGAACAGGACCAGATT TTGTTTGGAGCCTCAG CATGCCGGGCCCAGA TGATGGAGCATAACGG GTCCCAGCCAATTGTG ATGATCCTTTTTGCTC ATTT (SEQ ID NO: 219) | NM_002405; NR_029413; NM_001166343 | -0.384916371 | -0.481471138 | 1.033405111 |
| BID | NM_197966.1 | GCTTAGCTTTAGAAAC AGTGCAACACTGGTCT GCTGTTCCAGTGGTAA GCTATGTCCCAGGAAT CAGTTTAAAAGCACGA CAGTGGATGCTGGGTC CATA (SEQ ID NO: 220) | NM_197966; NM_001244569; NM_197967; NM_001244567; NM_001244572; NM_001244570; NM_001196 | 0.088886574 | -0.575331123 | 0.818429222 |
| PIK3CD | NM_005026.3 | TGACACTCATTGATTC TAAAGCATCTTTAATC TGCCAGGCGAGGGGG CTTTGCTGGTCTTTCT TGGACTATTCCAGAGA GGACAACTGTCATCTG GGAA (SEQ ID NO: 221) | NM_005026 | -0.17143245 | 0.010877708 | 1.174375031 |
| RASGRF2 | NM_006909.1 | GAGTCCACCAGGCTTT AACAACACCGAGAGAA CATGTGATAAAGAGTT TATTATACGGAGAACG GCTACCAATCGAGTTC TGAACGTCCTCCGTCA CTGG (SEQ ID NO: 222) | NM_006909 | -0.455902975 | -0.189934532 | 0.843247694 |
| TNFSF10 | NM_003810.2 | GGGGGGACCAGCCTG TGACAGACCTGCGTGC TGATCGTGATCTTCAC AGTGCTCCTGCAGTCT CTCTGTGTGGCTGTAA CTTACGTGTACTTTAC CAAC (SEQ ID NO: 223) | NM_003810; NR_033994; NM_001190943; NM_001190942 | -0.475279967 | -0.931256638 | 1.231408832 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| ITGA6 | NM_000210.1 | CTCATGCGAGCCTTCA TTGATGTGACTGCTGC TGCCGAAAATATCAGG CTGCCAAATGCAGGCA CTCAGGTTCGAGTGAC TGTGTTTCCCTCAAAG ACTG (SEQ ID NO: 224) | NM_000210; NM_001079818 | -0.832468699 | -0.251085473 | 0.693305201 |
| MMP9 | NM_004994.2 | CACTACTGTGCCTTTG AGTCCGGTGGACGATG CCTGCAACGTGAACAT CTTCGACGCCATCGCG GAGATTGGGAACCAGC TGTATTTGTTCAAGGA TGGG (SEQ ID NO: 225) | NM_004994 | -0.182247094 | -0.647025881 | 1.303500224 |
| IGF1 | NM_000618.3 | CGTGGATGAGTGCTGC TTCCGAGCTGTGATC TAAGGAGGCTGAGAT GTATTGCGCACCCTC AAGCCTGCCAAGTCAG CTCGCTCTGTCCGTGC CCAG (SEQ ID NO: 226) | NM_000618; NM_001111285; NM_001111284; NM_001111283 | -1.319084701 | 0.348703024 | 0.801157409 |
| JAK3 | NM_000215.2 | GTGCTGCTGAAGGTCA TGGATGCCAAGCACAA GAACTGCATGGAGTCA TTCCTGGAAGCAGGA GCTTGATGAGCCAAGT GTCGTACCGGCATCTC GTGC (SEQ ID NO: 227) | NM_000215 | -1.313284985 | 0.162243618 | 0.887569963 |
| TGFBR2 | NM_001024847.1 | ATTTGGAGAATGTTGA GTCCTTCAAGCAGACC GATGTCTACTCCATGG CTCTGGTGCTCTGGAA AATGACATCTCGCTGT AATGCAGTGGGAGAAG TAAA (SEQ ID NO: 228) | NM_001024847; NM_003242 | -0.576704709 | -0.33857086 | 0.682451581 |
| SPRY2 | NM_005842.2 | AAAGAGGAAATACTCC GCGTGCGCTTGTAGAA GGGGAGTCGTCTCCAG CTCCGAACCCCGGAGT | NM_005842 | -0.648697274 | -0.11309924 | 0.649505825 |

TABLE 3-continued

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| | GTTCATCAGCGGGAA TCTGGCTCCGAATTCT CTTT (SEQ ID NO: 229) | | | | |
| LFNG NM_001040168.1 | TCCAGGCCATGGAGCG GGTCAGCGAGAACAAG GTGCGTCCTGTCCACT TCTGGTTTGCCACGGG CGGCGCTGGCTTCTGC ATCAGCCGTGGGCTGG CTCT (SEQ ID NO: 230) | NM_001040168; NM_001040167; NM_001166355; NM_002304 | -0.644681481 | -0.098858024 | 0.709630093 |
| MPL NM_005373.2 | CAGTGGCACTTGGACT GCAATGCTTTACCTTG GACCTGAAGAATGTTA CCTGTCAATGGCAGCA ACAGGACCATGCTAGC TCCCAAGGCTTCTTCT ACCA (SEQ ID NO: 231) | NM_005373 | -0.067370728 | -0.6571279 | 0.612307561 |
| LAMC3 NM_006059.3 | CCGCCAGCCTCCTGGG TGGAGATTTGTTCATG TCCCACTGGCTACACG GGCCAGTTCTGTGAAT CCTGTGCTCCGGATA CAAGAGGGAGATGCCA CAGG (SEQ ID NO: 232) | NM_006059 | -0.133458348 | -0.185543739 | 1.057434835 |
| RET NM_020630.4 | AGGAGCCAGGGTCGGA TTCCAGTTAAATGGAT GGCAATTGAATCCCTT TTTGATCATATCTACA CCACGCAAAGTGATGT ATGGTCTTTTGTGTC CTGC (SEQ ID NO: 233) | NM_020630; NM_020975 | -0.205916792 | -0.027391926 | 0.770810755 |
| FOS NM_005252.2 | ACTCAAGTCCTTACCT CTTCCGGAGATGTAGC AAAACGCCATGGAGTGT GTATTGTTCCCAGTGA CACTTCAGAGAGCTGG TAGTTAGTAGCATGTT GAGC (SEQ ID NO: 234) | NM_005252 | -0.49262419 | -0.199625214 | 0.643536599 |

TABLE 3-continued

Sarcoma Centroids

| Gene Symbol | Accession | Target Sequence | Isoform Coverage Hit List | Subgroup B centroid | Subgroup A centroid | Subgroup C centroid |
|---|---|---|---|---|---|---|
| MAPK8IP1 | NM_005456.2 | TCCCAATTTCAGGCTC ACCCATGACATCAGCC TGGAGGAGTTTGAGGA TGAAGACCTCTCGAG ATCACTGATGAGTGTG GCATCAGCTTACAGTG CAAA (SEQ ID NO: 235) | NM_005456 | -0.239136578 | -0.505341384 | 0.517286908 |
| B2M | NM_004048.2 | CGGGCATTCCTGAAGC TGACAGCATTCGGGCC GAGATGTCTCGCTCCG TGGCCTTAGCTGTGCT CGCGCTACTCTCTCTT TCTGGCCTGGAGGCTA TCCA (SEQ ID NO: 236) | NM_004048 | 0.234106651 | -0.551781156 | 1.21151026 |
| MYD88 | NM_002468.3 | ACGTTTTTCTAGTAC AGCTCCCAGGAACAGC TAGGTGGGAAAGTCCC ATCACTGAGGAGCCT AACCATGTCCCTGAAC AAAAATTGGGCACTCA TCTA (SEQ ID NO: 237) | NM_002468; NM_001172569; NM_001172568; NM_001172567; NM_001172566 | -1.01250718 | -0.955275251 | 1.683288678 |
| CHUK | NM_001278.3 | TAGAACCCATGGAAAA CTGGCTACAGTTGATG TTGAATTGGGACCCTC AGCAGAGAGGAGGACC TGTTGACCTTACTTTG AAGCAGCCAAGATGTT TTGT (SEQ ID NO: 238) | NM_001278 | 0.031111998 | -0.563848617 | 1.112479518 |
| MAP2K2 | NM_030662.2 | GCGGACCTGAAGATGC TCACAAACCACACCTT CATCAAGCGGTCCGAG GTGGAAGAAGTGGATT TTGCCGGCTGGTTGTG TAAAACCCTGCGGCTG AACC (SEQ ID NO: 239) | NM_030662 | 0.297626549 | -1.301076449 | 0.810353045 |
| IL19 | NM_013371.3 | CCACAGACATGCACCA TATAGAAGAGAGTTTC CAAGAATCAAAGAG | NM_013371; NM_153758 | 0.114049756 | -1.237506873 | 0.753586963 |

TABLE 3-continued

Sarcoma Centroids

| Gene Symbol Accession | Target Sequence | Isoform Coverage Hit List | Subgroup B centroid | Subgroup A centroid | Subgroup C centroid |
|---|---|---|---|---|---|
| | CCATCCAAGCTAAGGA CACCTTCCCAAATGTC ACTATCCTGTCCACAT TGGA (SEQ ID NO: 240) | | | | |
| COL1A1 NM_000088.3 | CAGAAACATCCGATTT GGGGAACGCGTGTCAA TCCCTTGTGCCGCAGG GCTGGGCGGGAGAGAC TGTTCTGTTCCTTGTG TAACTGTGTTGCTGAA AGAC (SEQ ID NO: 241) | NM_000088 | -0.295920059 | -0.715165274 | 0.638320928 |
| PLAU NM_002658.2 | TTCATTGATTACCCAA AGAAGGAGGACTACAT CGTCTACCTGGGTCGC TCAAGGCTTAACTCCA ACACGCAAGGGGAGAT GAAGTTTGAGTGGAA AACC (SEQ ID NO: 242) | NM_002658; NM_001145031 | 0.011625842 | -0.971909393 | 0.821172402 |

Example 2

Materials and Methods

Patient Selection and Treatment

Patients were identified by retrospective search of prospectively compiled institutional database and electronic patient records. Eligibility criteria for inclusion were: i) histopathological diagnosis of soft tissue tumour as confirmed by contemporaneous report by specialist sarcoma histopathologist; ii) received at least one dose of Pazopanib for treatment of unresectable or advanced STS; iii) available FFPE tumour specimen, obtained from patient prior to first dose of Pazopanib. Treatment and response monitoring was as per local practice, with Pazopanib at 800 mg once daily until disease progression, intolerable toxicity or significant clinical deterioration. Dose interruption and/or reduction were used as per treating physician's judgement. Baseline clinico-pathological characteristics and survival data was collected on retrospective review of contemporaneous electronic medical records. All related radiological imaging was retrospectively reviewed and disease response assessed according to RECIST 1.1.

Tissue Selection and Processing

Available pre-Pazopanib FFPE tumour specimens were identified and retrieved from our institutional diagnostic archive. Where more than one pre-treatment specimen was identified, the one taken closest to Pazopanib start date was processed. Newly sectioned H&E slides were reviewed to confirm viable tumour content. With reference to H&E, blocks containing tumour material of sufficient size were marked in three spatially discrete areas of representative viable tumour tissue. Sections were then used for total RNA extraction using All Prep DNA/RNA FFPE kit (Qiagen, Hilden, Germany) following vendor's standard protocol. RNA concentrations were measured using Qubit fluorometric quantitation (Thermo Fisher Scientific, Waltham, MA, USA). RNA Integrity Number and percentage of tRNA <300 bp in size was measured using 2100 Bioanalyzer system (Agilent, CA, USA). RNA were stored at −80c until use in downstream analyses.

Gene Expression Analysis

Expression of 730 genes, representing 13 major cancer pathways including key driver genes was assessed using nCounter PanCancer Pathways panel (NanoString Technologies, Seattle, WA, USA). 150 ng total RNA was used as input for hybridisation and digital analysis as per manufacturer's instructions using nCounter Dx analysis system (NanoString Technologies). In cases with high RNA degradation, loading adjustments of up to 300 ng were made. Expression data was processed as follows: a) background correction was done by subtracting the geometric mean of the negative control probes, b) normalised by positive control normalization factor calculated as geometric mean of the positive controls followed by normalisation with the housekeeping genes. Expression values were then Log λ transformed and subjected to gene-based centring.

Gene-Expression Based Algorithm for the PARSARC Tree-Based Classifier

A 225-gene subtype predictor was developed using cancer pathway-related gene expression profiles from Nanostring using 38 prototype samples obtained at Royal Marsden Hospital (RMH-SARC). The Classification of Nearest Centroid (CLANC) and cross-validation (random 10% left out in each of 10 cycles) were used to assess the robustness of the minimized gene set for reproducibility of classification[19]. The 225 genes selected genes contributing to distinguishing the different subtypes are provided in Table 6. The final algorithm consists of centroids constructed as described for the PAM algorithm[20] and distances calculated using Spearman's rank correlation (or similar statistical tests to compare similarity). The centroids of the training set using the 225-gene classifier and their contributions are provided in Table 6.

Gene-Expression Based Algorithm to Identify PDGFRA-High/FGFR1-Low IHC Patients which are Intrinsically Resistant to Pazopanib.

A 42-gene predictor for pazopanib resistance was developed based on the 225-gene algorithm. The list of 42 genes provided in Table 7 was selected based on their relative importance contributing to identify the tumours resistant to pazopanib therapy (as defined by PDGFRA-high/FGFR1-low IHC) from others. The final algorithm consists of the two centroids constructed for pazopanib resistant cases and others (Table 7), and the distance respectively calculated using Spearman's rank correlation (or similar statistical tests to compare similarity). A test sample will be assigned to resistant type based on the following formula $$A = [\text{Correlation coefficient to Resistant} - \text{Correlation coefficient to others}]$$

With $A \geq 0.5$

Results

Building on earlier reports, we assembled a clinically annotated tumour cohort from patients with STS treated with pazopanib at the Royal Marsden Hospital (RMH-SARC). Eligible patients were identified through retrospective search of hospital medical and histopathology records. Eligibility for inclusion was defined as: i) histopathological diagnosis of soft tissue tumour as confirmed by contemporaneous report by specialist sarcoma histopathologist; ii) received at least one dose of pazopanib for treatment of unresectable or advanced STS; and iii) available adequate FFPE tumour specimen, obtained from patient prior to first dose of pazopanib. In total, 38 cases that met eligibility criteria were identified, with collected tumour specimen and associated clinical data included in the analyses described below (clinic-pathological characteristics summarised in Table 1 in example 1, above). Average age was 54.4 years (range 19.8-81.2). Median number of prior lines of therapy was 1.5 (interquartile range (IQR) 0-2). All patients with documented performance status were ECOG 0-2. All but one patient had metastatic disease, with a median of 2 organ sites involved by disease (IQR 1.75-3.25). 16 distinct STS subtypes were represented within our cohort, with leiomyosarcoma and solitary fibrous tumour the most represented subtypes (11 and 7 cases respectively). All but two tumours were intermediate or high grade on archival pre-treatment specimen—of the two cases with low histological grade, one was extraskeletal myxoid chondrosarcoma with metastatic disease, and the other was unresectable solitary fibrous tumour of the retroperitoneum.

Progression free survival (PFS), defined as time in months from first dose of pazopanib to radiological disease progression or death from any cause, was the primary clinical outcome endpoint. Overall survival (OS), defined as a time in months from first dose of pazopanib to death from any cause, was the secondary clinical outcome endpoint. The Kaplan-Meier method was used to estimate PFS and OS, and the log-rank test to compare survival in different strata. Multivariable cox regression model was used to estimate the significance adjusted for the standard clinic-pathological variables (including age, tumour grade and performance status). Interaction tests for biomarkers, FGFR and PDGFR, for survival effect were performed for association with PFS and OS. Proportional hazard assumption was tested using Schoenfeld residuals. Restricted mean progression free and overall all survival estimates were also calculated by the biomarkers strata.

At the time of data collection (median follow-up 26.2 months), 35 of 38 patients (92%) had experienced a progression-free survival event and 31 (82%) had experienced an overall survival event. Median PFS for the cohort was 3.7 months (IQR 1.8-6.9), median OS was 9.5 months (IQR 3.9-19.6m). Following radiology review of imaging series, 1/38 (2.6%) patient experienced objective radiological response, 20/38 (52.6%) had stable disease and 17/38 (44.7%) progression as best response. For patients with partial response or stable disease, median PFS was 6.4m (IQR 3.7-12.9).

Our overarching goal in this study was to identify a gene signature that allows for the stratification of patients into the five distinct subgroups without the need to apply the previously reported decision tree workflow. In addition, we sought to identify a set of genes that is capable of identifying PDGFR-high/FGFR1-low IHC intrinsic resistant poor responder cases from other subgroups. Using the Classification of Nearest Centroid (CLANC) methodology described in the methods section, we identified a set of 225 genes that is capable of classifying patients into one of the 5 previously described subgroups (Table 4).

TABLE 4

225 gene risk classifier identified by CLANC analysis as optimally describing 5 PARSARC-defined subgroups

| Gene name | ENTREZ ID |
|---|---|
| ACVR1B | 91 |
| AKT2 | 208 |
| ALKBH3 | 221120 |
| AMH | 268 |
| ARID2 | 196528 |
| AMER1 | 139285 |
| ATM | 472 |
| ATR | 545 |
| B2M | 567 |
| BAD | 572 |
| BCL2 | 596 |
| BCOR | 54880 |
| BID | 637 |
| BIRC3 | 330 |
| BMP4 | 652 |
| BNIP3 | 664 |
| BRAF | 673 |
| CACNA1C | 775 |
| CACNA1E | 777 |
| CACNA1G | 8913 |
| CALML6 | 163688 |
| CARD11 | 84433 |
| CASP10 | 843 |
| CCNB1 | 891 |
| CCND1 | 595 |
| CCNE1 | 898 |
| CCNE2 | 9134 |
| CCNO | 10309 |
| CDC25C | 995 |
| CDC6 | 990 |
| CDC7 | 8317 |
| CDH1 | 999 |
| CDK4 | 1019 |
| CDK6 | 1021 |
| CDKN2A | 1029 |
| CDKN2B | 1030 |
| CDKN2C | 1031 |
| CDKN2D | 1032 |
| CHEK1 | 1111 |
| CHUK | 1147 |

TABLE 4-continued 225 gene risk classifier identified by CLANC analysis as optimally describing 5 PARSARC-defined subgroups

| Gene name | ENTREZ ID |
|---|---|
| COL27A1 | 85301 |
| COL3A1 | 1281 |
| COL4A4 | 1286 |
| COL4A6 | 1288 |
| COL5A1 | 1289 |
| COL5A2 | 1290 |
| CREB3L4 | 148327 |
| CREBBP | 1387 |
| CSF2 | 1437 |
| CXXC4 | 80319 |
| DAXX | 1616 |
| DDB2 | 1643 |
| DLL1 | 28514 |
| DLL3 | 10683 |
| DNMT1 | 1786 |
| DTX3 | 196403 |
| DTX4 | 23220 |
| DUSP4 | 1846 |
| DUSP6 | 1848 |
| E2F1 | 1869 |
| E2F5 | 1875 |
| EFNA1 | 1942 |
| EFNA5 | 1946 |
| ERBB2 | 2064 |
| ERCC6 | 2074 |
| ETV4 | 2118 |
| EZH2 | 2146 |
| FANCA | 2175 |
| FANCB | 2187 |
| FANCE | 2178 |
| FANCL | 55120 |
| FAS | 355 |
| FBXW7 | 55294 |
| FEN1 | 2237 |
| FGF12 | 2257 |
| FGF5 | 2250 |
| FGF7 | 394217 |
| FGF7 | 2252 |
| FGF7 | 100132771 |
| FLNA | 2316 |
| FLNC | 2318 |
| FN1 | 2335 |
| FOSL1 | 8061 |
| FUBP1 | 8880 |
| GADD45A | 1647 |
| GLI3 | 2737 |
| GNA11 | 2767 |
| GNG12 | 55970 |
| GRIN2A | 2903 |
| GSK3B | 2932 |
| GTF2H3 | 2967 |
| HDAC10 | 83933 |
| HDAC11 | 79885 |
| HDAC4 | 9759 |
| HDAC5 | 10014 |
| HELLS | 3070 |
| HES1 | 3280 |
| HIST1H3B | 8358 |
| HOXA9 | 3205 |
| HSPB1 | 3315 |
| IBSP | 3381 |
| IDH1 | 3417 |
| IDH2 | 3418 |
| IL11 | 3589 |
| IL11RA | 3590 |
| IL12RB2 | 3595 |
| IL6 | 3569 |
| IL8 | 3576 |
| INHBA | 3624 |
| IRS1 | 3667 |
| ITGA6 | 3655 |
| ITGA7 | 3679 |
| ITGA8 | 8516 |
| ITGB3 | 3690 |
| JAG1 | 182 |

TABLE 4-continued 225 gene risk classifier identified by CLANC analysis as optimally describing 5 PARSARC-defined subgroups

| Gene name | ENTREZ ID |
| --- | --- |
| JAK3 | 3718 |
| KAT2B | 8850 |
| KITLG | 4254 |
| KMT2C | 58508 |
| LAMA3 | 3909 |
| LAMA5 | 3911 |
| LAMB3 | 3914 |
| LAMC3 | 10319 |
| LEFTY2 | 7044 |
| LFNG | 3955 |
| LIF | 3976 |
| LIG4 | 3981 |
| MAD2L2 | 10459 |
| MAP2K4 | 6416 |
| MAP2K6 | 5608 |
| MAPK10 | 5602 |
| MAPK8IP1 | 9479 |
| MCM2 | 4171 |
| MCM4 | 4173 |
| MCM5 | 4174 |
| MDC1 | 9656 |
| MDM2 | 4193 |
| MEN1 | 4221 |
| MET | 4233 |
| MFNG | 4242 |
| MLF1 | 4291 |
| MLH1 | 4292 |
| MLLT3 | 4300 |
| MLLT4 | 4301 |
| MMP7 | 4316 |
| MMP9 | 4318 |
| MSH2 | 4436 |
| MSH6 | 2956 |
| MTOR | 2475 |
| MUTYH | 4595 |
| MYC | 4609 |
| MYD88 | 4615 |
| NASP | 4678 |
| NFKB1 | 4790 |
| NFKBIZ | 64332 |
| NOS3 | 4846 |
| NOTCH2 | 4853 |
| NPM1 | 4869 |
| NTHL1 | 4913 |
| NUMBL | 9253 |
| PAX5 | 5079 |
| PBX1 | 5087 |
| PCNA | 5111 |
| PDGFC | 56034 |
| PDGFRA | 5156 |
| PLCB4 | 5332 |
| PPP2CB | 5516 |
| PPP2R2C | 5522 |
| PPP3R1 | 5534 |
| PRKACA | 5566 |
| PRKAR1B | 5575 |
| PRKAR2A | 5576 |
| PRKCB | 5579 |
| PRKX | 5613 |
| PRLR | 5618 |
| PTCH1 | 5727 |
| PTEN | 5728 |
| PTTG2 | 10744 |
| RAD21 | 5885 |
| RAD52 | 5893 |
| RB1 | 5925 |
| RBX1 | 9978 |
| RET | 5979 |
| RFC4 | 5984 |
| SF3B1 | 23451 |
| SHC2 | 25759 |
| SHC4 | 399694 |
| SIN3A | 25942 |
| SKP1 | 6500 |
| SKP2 | 6502 |
| SMAD3 | 4088 |
| SMAD4 | 4089 |
| SOCS2 | 8835 |
| SOCS3 | 9021 |
| SP1 | 6667 |
| SPOP | 8405 |
| SPRY1 | 10252 |
| SPRY2 | 10253 |
| SSX1 | 6756 |
| STAT4 | 6775 |
| MYC | 4609 |
| MYD88 | 4615 |
| NASP | 4678 |
| NFKB1 | 4790 |
| NFKBIZ | 64332 |
| NOS3 | 4846 |
| NOTCH2 | 4853 |
| NPM1 | 4869 |
| NTHL1 | 4913 |
| NUMBL | 9253 |
| PAX5 | 5079 |
| PBX1 | 5087 |
| PCNA | 5111 |
| PDGFC | 56034 |
| PDGFRA | 5156 |
| PLCB4 | 5332 |
| PPP2CB | 5516 |
| PPP2R2C | 5522 |
| PPP3R1 | 5534 |
| PRKACA | 5566 |
| PRKAR1B | 5575 |
| PRKAR2A | 5576 |
| PRKCB | 5579 |
| PRKX | 5613 |
| PRLR | 5618 |
| PTCH1 | 5727 |
| PTEN | 5728 |
| PTTG2 | 10744 |
| RAD21 | 5885 |
| RAD52 | 5893 |
| RB1 | 5925 |
| RBX1 | 9978 |
| RET | 5979 |
| RFC4 | 5984 |
| SF3B1 | 23451 |
| SHC2 | 25759 |
| SHC4 | 399694 |
| SIN3A | 25942 |
| SKP1 | 6500 |
| SKP2 | 6502 |
| SMAD3 | 4088 |
| SMAD4 | 4089 |
| SOCS2 | 8835 |
| SOCS3 | 9021 |
| SP1 | 6667 |
| SPOP | 8405 |
| SPRY1 | 10252 |
| SPRY2 | 10253 |
| SSX1 | 6756 |
| STAT4 | 6775 |
| STK11 | 6794 |
| SYK | 6850 |
| TFDP1 | 7027 |
| TGFB3 | 7043 |
| TGFBR2 | 7048 |
| THBS1 | 7057 |
| TLR4 | 7099 |
| TLX1 | 3195 |
| TNC | 3371 |
| TNFRSF10B | 8795 |
| TNFRSF10D | 8793 |
| TNFSF10 | 8743 |
| TNR | 7143 |
| TP53 | 7157 |
| TSPAN7 | 7102 |

TABLE 4-continued 225 gene risk classifier identified by CLANC analysis as optimally describing 5 PARSARC-defined subgroups

| Gene name | ENTREZ ID |
|---|---|
| TTK | 7272 |
| U2AF1 | 7307 |
| UBE2T | 29089 |
| VEGFA | 7422 |
| WEE1 | 7465 |
| WHSC1L1 | 54904 |
| WNT10B | 7480 |
| WNT6 | 7475 |
| WT1 | 7490 |
| ZAK | 51776 |
| ZBTB16 | 7704 |
| ZIC2 | 7546 |

We also identified a 42 gene predictor to classify patients that have intrinsic resistance to pazopanib as defined by the PDGFRA-high/FGFR1-low IHC status (Table 5).

TABLE 5

42 genes identified by CLANC analysis as identifying F-Lo/P-Hi subgroup vs all other patients

| Gene name | ENTREZ IDs |
|---|---|
| ART2 | 208 |
| ALKBH3 | 221120 |
| AMER1 | 139285 |
| ATR | 545 |
| BMP4 | 652 |
| CCNO | 10309 |
| COL5A1 | 1289 |
| CSF2 | 1437 |
| DAXX | 1616 |
| DUSP6 | 1848 |
| ETV4 | 2118 |
| FANCL | 55120 |
| FOSL1 | 8061 |
| GSK3B | 2932 |
| HDAC11 | 79885 |
| HDAC5 | 10014 |
| IL11 | 3589 |
| IL6 | 3569 |
| IL8 | 3576 |
| LIF | 3976 |
| LIG4 | 3981 |
| MDC1 | 9656 |
| MLF1 | 4291 |
| MSH2 | 4436 |
| MUTYH | 4595 |
| NPM1 | 4869 |
| NTHL1 | 4913 |
| PCNA | 5111 |
| PPP2CB | 5516 |
| PPP2R2C | 5522 |
| PRKACA | 5566 |
| RAD21 | 5885 |
| RBX1 | 9978 |
| SMAD4 | 4089 |
| SOCS3 | 9021 |
| SPRY1 | 10252 |
| SSX1 | 6756 |
| STAT 4 | 6775 |
| STK11 | 6794 |
| THBS1 | 7057 |
| WEE1 | 7465 |
| WNT10B | 7480 |

TABLE 6 centroids for 225 gene risk classifier

| | IHC+ (1) | TP53 (2) | Subgroup A centroid (3) | Subgroup B centroid (4) | Subgroup C centroid (5) |
|---|---|---|---|---|---|
| ACVR1B | −0.15832131 | −0.15832131 | 0.54151057 | −0.15832131 | −0.15832131 |
| AKT2 | −0.30994329 | −0.01919342 | −0.01919342 | −0.01919342 | −0.01919342 |
| ALKBH3 | −0.51139577 | −0.06705258 | −0.06705258 | −0.06705258 | −0.06705258 |
| AMER1 | −0.53544069 | −0.00240749 | −0.00240749 | −0.00240749 | −0.00240749 |
| AMH | −0.15178973 | −0.15178973 | −0.15178973 | −0.15178973 | −1.44283676 |
| ARID2 | −0.01621451 | −0.21931165 | −0.01621451 | −0.01621451 | −0.01621451 |
| ATM | −0.14140818 | −0.14140818 | −0.14140818 | −0.59982807 | −0.14140818 |
| ATR | −0.41755241 | −0.0616667 | −0.0616667 | −0.0616667 | −0.0616667 |
| B2M | 0.03806218 | 0.03806218 | 0.03806218 | 0.03806218 | 0.47297616 |
| BAD | 0.0248534 | 0.27474345 | 0.0248534 | 0.0248534 | 0.0248534 |
| BCL2 | 0.06351095 | 0.06351095 | 0.88344382 | 0.06351095 | 0.06351095 |
| BCOR | 0.05103077 | 0.05103077 | 1.27280929 | 0.05103077 | 0.05103077 |
| BID | 0.58151032 | 0.0455798 | 0.0455798 | 0.0455798 | 0.0455798 |
| BIRC3 | −0.02761286 | −0.02761286 | −1.18099641 | −0.02761286 | −0.02761286 |
| BMP4 | 1.30239681 | 0.21301304 | 0.21301304 | 0.21301304 | 0.21301304 |
| BNIP3 | −0.19708889 | −0.90886955 | −0.19708889 | −0.19708889 | −0.19708889 |
| BRAF | −0.05422312 | −0.05422312 | 0.2484416 | −0.05422312 | −0.05422312 |
| CACNA1C | −0.13582518 | −0.13582518 | −0.13582518 | 0.96758744 | −0.13582518 |
| CACNA1E | 0.17105202 | −0.67762073 | 0.17105202 | 0.17105202 | 0.17105202 |
| CACNA1G | 0.01978593 | 0.99078335 | 0.01978593 | 0.01978593 | 0.01978593 |
| CALML6 | 0.01910958 | 0.01910958 | 0.93075557 | 0.01910958 | 0.01910958 |
| CARD11 | 0.3510245 | 0.3510245 | 0.3510245 | 0.3510245 | 1.54991905 |
| CASP10 | −0.18050625 | −0.18050625 | −0.18050625 | −0.18050625 | 0.39904926 |
| CCNB1 | −0.08780076 | 0.35186891 | −0.08780076 | −0.08780076 | −0.08780076 |
| CCND1 | 0.06716593 | 0.06716593 | 0.06716593 | 0.06716593 | 0.89918266 |
| CCNE1 | 0.03028376 | 0.4673283 | 0.03028376 | 0.03028376 | 0.03028376 |
| CCNE2 | −0.02855095 | −0.02855095 | −0.02855095 | 0.96943946 | −0.02855095 |
| CCNO | −0.74650411 | 0.05814408 | 0.05814408 | 0.05814408 | 0.05814408 |
| CDC25C | −0.20812329 | 0.4321119 | −0.20812329 | −0.20812329 | −0.20812329 |

TABLE 6-continued centroids for 225 gene risk classifier

|  | IHC+ (1) | TP53 (2) | Subgroup A centroid (3) | Subgroup B centroid (4) | Subgroup C centroid (5) |
|---|---|---|---|---|---|
| CDC6 | −0.13977911 | 0.25507254 | −0.13977911 | −0.13977911 | −0.13977911 |
| CDC7 | −0.0401465 | −0.0401465 | −0.0401465 | −0.0401465 | −0.48566159 |
| CDH1 | 0.5933622 | 0.5933622 | 0.5933622 | 2.70632966 | 0.5933622 |
| CDK4 | 0.02878578 | 0.02878578 | 0.02878578 | 0.02878578 | 0.43127765 |
| CDK6 | −0.09882276 | −0.80702231 | −0.09882276 | −0.09882276 | −0.09882276 |
| CDKN2A | −0.43348608 | 0.40775211 | −0.43348608 | −0.43348608 | −0.43348608 |
| CDKN2B | −0.30199667 | −0.30199667 | −1.13360288 | −0.30199667 | −0.30199667 |
| CDKN2C | −0.0741678 | 0.71842723 | −0.0741678 | −0.0741678 | −0.0741678 |
| CDKN2D | −0.07445202 | −0.07445202 | −0.88415539 | −0.07445202 | −0.07445202 |
| CHEK1 | −0.03670758 | 0.36086714 | −0.03670758 | −0.03670758 | −0.03670758 |
| CHUK | 0.01020521 | 0.01020521 | 0.01020521 | 0.01020521 | 0.3304295 |
| COL27A1 | −0.058947 | −0.058947 | −0.058947 | −1.02899246 | −0.058947 |
| COL3A1 | −0.04583553 | −0.04583553 | −1.12616257 | −0.04583553 | −0.04583553 |
| COL4A4 | −0.19065625 | −0.19065625 | −0.19065625 | −0.19065625 | 0.4691999 |
| COL4A6 | −0.07291156 | −0.07291156 | −0.07291156 | 2.30094864 | −0.07291156 |
| COL5A1 | 0.82895474 | 0.02869965 | 0.02869965 | 0.02869965 | 0.02869965 |
| COL5A2 | −0.10633063 | −0.10633063 | −1.20961533 | −0.10633063 | −0.10633063 |
| CREB3L4 | −0.11547721 | −0.11547721 | −0.11547721 | −0.11547721 | −0.52285762 |
| CREBBP | −0.06115984 | −0.06115984 | 0.41412808 | −0.06115984 | −0.06115984 |
| CSF2 | 1.21387949 | 0.22876539 | 0.22876539 | 0.22876539 | 0.22876539 |
| CXXC4 | 0.1857577 | 0.1857577 | 1.56739048 | 0.1857577 | 0.1857577 |
| DAXX | −0.51598315 | −0.03754511 | −0.03754511 | −0.03754511 | −0.03754511 |
| DDB2 | −0.02877707 | −0.02877707 | 0.73742541 | −0.02877707 | −0.02877707 |
| DLL1 | −0.02445967 | −0.02445967 | 1.38299745 | −0.02445967 | −0.02445967 |
| DLL3 | 0.11550972 | 0.11550972 | 0.11550972 | 0.11550972 | 0.99134018 |
| DNMT1 | −0.06492494 | 0.22828132 | −0.06492494 | −0.06492494 | −0.06492494 |
| DTX3 | −0.00091037 | −0.00091037 | −0.00091037 | 0.57881747 | −0.00091037 |
| DTX4 | −0.13468574 | −0.13468574 | −0.13468574 | −1.34786396 | −0.13468574 |
| DUSP4 | −0.06613786 | −0.06613786 | −0.06613786 | −0.06613786 | 0.79464751 |
| DUSP6 | 0.64607125 | −0.13511565 | −0.13511565 | −0.13511565 | −0.13511565 |
| E2F1 | −0.15690288 | 0.58630128 | −0.15690288 | −0.15690288 | −0.15690288 |
| E2F5 | −0.15133642 | −0.15133642 | −0.15133642 | −0.15133642 | 0.49181536 |
| EFNA1 | −0.11668426 | −0.11668426 | −0.11668426 | −0.11668426 | 0.53773733 |
| EFNA5 | −0.36099156 | −0.36099156 | −2.00486828 | −0.36099156 | −0.36099156 |
| ERBB2 | −0.17090683 | −0.17090683 | 0.56247468 | −0.17090683 | −0.17090683 |
| ERCC6 | −0.03591121 | −0.03591121 | 0.35637641 | −0.03591121 | −0.03591121 |
| ETV4 | 1.42923832 | 0.17676653 | 0.17676653 | 0.17676653 | 0.17676653 |
| EZH2 | −0.13282806 | −0.13282806 | −0.13282806 | −0.13282806 | −0.54806145 |
| FANCA | −0.09874728 | −0.09874728 | −0.09874728 | −0.09874728 | −0.73163501 |
| FANCB | −0.07545182 | 0.28149725 | −0.07545182 | −0.07545182 | −0.07545182 |
| FANCE | 0.03359085 | 0.03359085 | 0.03359085 | 0.82988961 | 0.03359085 |
| FANCL | −0.56516661 | −0.01293858 | −0.01293858 | −0.01293858 | −0.01293858 |
| FAS | −0.11858783 | 0.47425096 | −0.11858783 | −0.11858783 | −0.11858783 |
| FBXW7 | −0.03157043 | −0.03157043 | 0.54732624 | −0.03157043 | −0.03157043 |
| FEN1 | 0.05373816 | 0.05373816 | 0.05373816 | 0.82272386 | 0.05373816 |
| FGF12 | −0.14368413 | −0.91516385 | −0.14368413 | −0.14368413 | −0.14368413 |
| FGF5 | 0.48339559 | 0.48339559 | 0.48339559 | 0.48339559 | 1.59245056 |
| FGF7 | −0.45472135 | −0.45472135 | −0.45472135 | 1.11593826 | −0.45472135 |
| FLNA | 0.13671796 | 0.13671796 | 0.13671796 | 1.69109283 | 0.13671796 |
| FLNC | −0.467287 | −0.467287 | −0.467287 | 0.96770635 | −0.467287 |
| FN1 | −0.04593874 | −0.04593874 | −1.18366565 | −0.04593874 | −0.04593874 |
| FOSL1 | 0.85033616 | 0.03958811 | 0.03958811 | 0.03958811 | 0.03958811 |
| FUBP1 | −0.06703661 | −0.06703661 | 0.36412825 | −0.06703661 | −0.06703661 |
| GADD45A | 0.06766933 | 0.06766933 | 0.06766933 | 0.84508039 | 0.06766933 |
| GLI3 | −0.17664829 | −0.17664829 | −0.17664829 | −0.17664829 | −0.77449891 |
| GNA11 | 0.02755931 | 0.02755931 | 0.02755931 | 0.64967723 | 0.02755931 |
| GNG12 | −0.16995566 | −0.16995566 | −0.85810693 | −0.16995566 | −0.16995566 |
| GRIN2A | 0.36120599 | 1.33705393 | 0.36120599 | 0.36120599 | 0.36120599 |
| GSK3B | −0.3289616 | −0.04260185 | −0.04260185 | −0.04260185 | −0.04260185 |
| GTF2H3 | −0.09051522 | −0.09051522 | 0.33573726 | −0.09051522 | −0.09051522 |
| HDAC10 | −0.12352944 | −0.12352944 | −0.12352944 | −0.12352944 | 0.1647408 |
| HDAC11 | −0.66902718 | −0.09322847 | −0.09322847 | −0.09322847 | −0.09322847 |
| HDAC4 | −0.02614516 | −0.02614516 | 0.6056055 | −0.02614516 | −0.02614516 |
| HDAC5 | −0.44311772 | −0.02343759 | −0.02343759 | −0.02343759 | −0.02343759 |
| HELLS | −0.08627003 | 0.26759075 | −0.08627003 | −0.08627003 | −0.08627003 |
| HES1 | −0.14475643 | −0.14475643 | 1.09720336 | −0.14475643 | −0.14475643 |
| HIST1H3B | −0.02480871 | 0.56445002 | −0.02480871 | −0.02480871 | −0.02480871 |
| HOXA9 | −0.12800919 | 0.60420276 | −0.12800919 | −0.12800919 | −0.12800919 |
| HSPB1 | −0.10464244 | −0.10464244 | −0.10464244 | 0.60254908 | −0.10464244 |
| IBSP | 0.25316339 | 1.48773858 | 0.25316339 | 0.25316339 | 0.25316339 |
| IDH1 | −0.0139642 | −0.0139642 | −0.0139642 | −0.0139642 | 0.35797145 |
| IDH2 | 0.14237266 | 0.14237266 | 0.14237266 | 0.97071118 | 0.14237266 |
| IL11 | 1.73407021 | 0.23740715 | 0.23740715 | 0.23740715 | 0.23740715 |
| IL11RA | −0.01835972 | −0.01835972 | 0.89759852 | −0.01835972 | −0.01835972 |

TABLE 6-continued

| | centroids for 225 gene risk classifier | | | | |
|---|---|---|---|---|---|
| | IHC+ (1) | TP53 (2) | Subgroup A centroid (3) | Subgroup B centroid (4) | Subgroup C centroid (5) |
| IL12RB2 | 0.12363856 | 0.12363856 | 0.12363856 | 0.12363856 | 1.18873886 |
| IL6 | 1.68316336 | 0.1815675 | 0.1815675 | 0.1815675 | 0.1815675 |
| IL8 | 2.10056954 | 0.1309187 | 0.1309187 | 0.1309187 | 0.1309187 |
| INHBA | −0.44395722 | −0.44395722 | −1.93039159 | −0.44395722 | −0.44395722 |
| IRS1 | 0.06052758 | 0.06052758 | 0.06052758 | 1.18660836 | 0.06052758 |
| ITGA6 | 0.0423311 | 0.0423311 | 0.0423311 | 0.0423311 | 0.62988286 |
| ITGA7 | 0.0163744 | 0.0163744 | 0.0163744 | 1.40919398 | 0.0163744 |
| ITGA8 | −0.60196552 | −0.60196552 | −0.60196552 | 1.2401644 | −0.60196552 |
| ITGB3 | −0.03320016 | −0.03320016 | −1.24850492 | −0.03320016 | −0.03320016 |
| JAG1 | 0.16492599 | 0.71120586 | 0.16492599 | 0.16492599 | 0.16492599 |
| JAK3 | −0.20341296 | −0.20341296 | −0.20341296 | −1.06969998 | −0.20341296 |
| KAT2B | −0.04101357 | −0.04101357 | −0.04101357 | −0.04101357 | 0.32993194 |
| KITLG | −0.11534823 | 0.37839946 | −0.11534823 | −0.11534823 | −0.11534823 |
| KMT2C | −0.06007021 | −0.06007021 | 0.27599606 | −0.06007021 | −0.06007021 |
| LAMA3 | −0.02993329 | −0.02993329 | −0.02993329 | 1.33919007 | −0.02993329 |
| LAMA5 | 0.22274146 | 0.22274146 | 0.22274146 | 1.55832429 | 0.22274146 |
| LAMB3 | −0.12041485 | −0.12041485 | −0.12041485 | 1.14007598 | −0.12041485 |
| LAMC3 | 0.04945966 | 0.04945966 | 0.04945966 | 0.04945966 | 1.10866665 |
| LEFTY2 | 0.51860941 | 0.51860941 | 0.51860941 | 0.51860941 | −0.56354027 |
| LFNG | 0.10700215 | 0.10700215 | 0.10700215 | −0.67796456 | 0.10700215 |
| LIF | 1.39370879 | −0.06116073 | −0.06116073 | −0.06116073 | −0.06116073 |
| LIG4 | −0.50530259 | −0.04785678 | −0.04785678 | −0.04785678 | −0.04785678 |
| MAD2L2 | 0.03722618 | 0.6081764 | 0.03722618 | 0.03722618 | 0.03722618 |
| MAP2K4 | 0.08248544 | 0.08248544 | 0.08248544 | 0.64727212 | 0.08248544 |
| MAP2K6 | −0.13138211 | −0.13138211 | −0.13138211 | −1.47415459 | −0.13138211 |
| MAPK10 | −0.07793461 | −0.07793461 | −0.07793461 | 1.43393339 | −0.07793461 |
| MAPK8IP1 | −0.00825569 | −0.00825569 | −0.00825569 | −0.00825569 | 0.92651997 |
| MCM2 | −0.07381755 | 0.42160047 | −0.07381755 | −0.07381755 | −0.07381755 |
| MCM4 | −0.04139259 | 0.37963662 | −0.04139259 | −0.04139259 | −0.04139259 |
| MCM5 | −0.13706634 | −0.13706634 | −0.13706634 | 0.29064389 | −0.13706634 |
| MDC1 | −0.37977203 | −0.06129361 | −0.06129361 | −0.06129361 | −0.06129361 |
| MDM2 | 0.0314102 | −0.47856785 | 0.0314102 | 0.0314102 | 0.0314102 |
| MEN1 | −0.10998162 | −0.10998162 | 0.25826164 | −0.10998162 | −0.10998162 |
| MET | 0.03488567 | −0.86253667 | 0.03488567 | 0.03488567 | 0.03488567 |
| MFNG | 0.08194644 | 0.08194644 | 0.08194644 | 0.08194644 | 0.69798176 |
| MLF1 | −0.7380756 | −0.07707883 | −0.07707883 | −0.07707883 | −0.07707883 |
| MLH1 | −0.10111681 | −0.10111681 | 0.31198563 | −0.10111681 | −0.10111681 |
| MLLT3 | −0.15727151 | −0.58592957 | −0.15727151 | −0.15727151 | −0.15727151 |
| MLLT4 | −0.21907125 | −0.68832348 | −0.21907125 | −0.21907125 | −0.21907125 |
| MMP7 | 0.39833697 | 1.54606409 | 0.39833697 | 0.39833697 | 0.39833697 |
| MMP9 | −0.10394205 | 1.60133616 | −0.10394205 | −0.10394205 | −0.10394205 |
| MSH2 | −0.55489979 | −0.03095062 | −0.03095062 | −0.03095062 | −0.03095062 |
| MSH6 | −0.05432838 | −0.05432838 | −0.05432838 | 0.27491694 | −0.05432838 |
| MTOR | −0.06272839 | 0.18781661 | −0.06272839 | −0.06272839 | −0.06272839 |
| MUTYH | −0.50532612 | −0.06272888 | −0.06272888 | −0.06272888 | −0.06272888 |
| MYC | −0.18641001 | −0.18641001 | −0.18641001 | −0.18641001 | 0.74902785 |
| MYD88 | −0.08502077 | −0.08502077 | −0.08502077 | −0.58812129 | −0.08502077 |
| NASP | −0.02523895 | −0.02523895 | −0.02523895 | −0.02523895 | −0.55068349 |
| NFKB1 | −0.1830597 | −0.51522965 | −0.1830597 | −0.1830597 | −0.1830597 |
| NFKBIZ | −0.02574918 | −0.02574918 | −1.18521256 | −0.02574918 | −0.02574918 |
| NOS3 | −0.0004462 | −0.0004462 | −0.0004462 | −0.0004462 | 0.5365944 |
| NOTCH2 | −0.14817229 | −0.14817229 | −0.14817229 | −0.14817229 | −0.72029657 |
| NPM1 | −0.57600022 | 0.00332197 | 0.00332197 | 0.00332197 | 0.00332197 |
| NTHL1 | −0.50778533 | −0.07866785 | −0.07866785 | −0.07866785 | −0.07866785 |
| NUMBL | −0.00052321 | −0.00052321 | 0.59451543 | −0.00052321 | −0.00052321 |
| PAX5 | 0.25809009 | 0.25809009 | 0.25809009 | 0.25809009 | 1.00231025 |
| PBX1 | 0.08501597 | 0.08501597 | 0.08501597 | 0.92159476 | 0.08501597 |
| PCNA | −0.62485093 | −0.01603919 | −0.01603919 | −0.01603919 | −0.01603919 |
| PDGFC | −0.11165439 | −0.11165439 | −0.83987243 | −0.11165439 | −0.11165439 |
| PDGFRA | −0.16915031 | −0.16915031 | −0.16915031 | −1.68249338 | −0.16915031 |
| PLCB4 | −0.35341736 | −0.35341736 | −0.35341736 | 0.81476038 | −0.35341736 |
| PPP2CB | −0.48697106 | 0.0230338 | 0.0230338 | 0.0230338 | 0.0230338 |
| PPP2R2C | −0.68521206 | 0.56494494 | 0.56494494 | 0.56494494 | 0.56494494 |
| PPP3R1 | −0.29772681 | −0.04706913 | −0.04706913 | −0.04706913 | −0.04706913 |
| PRKACA | −0.42317444 | −0.03705625 | −0.03705625 | −0.03705625 | −0.03705625 |
| PRKAR1B | −0.28935676 | −0.28935676 | 0.84966941 | −0.28935676 | −0.28935676 |
| PRKAR2A | −0.00446406 | −0.00446406 | −0.00446406 | 0.37327539 | −0.00446406 |
| PRKCB | −0.04967629 | −0.04967629 | −0.04967629 | −0.04967629 | 0.78745301 |
| PRKX | −0.05123099 | −0.05123099 | −0.05123099 | −0.70281335 | −0.05123099 |
| PRLR | 0.26338038 | −0.55930099 | 0.26338038 | 0.26338038 | 0.26338038 |
| PTCH1 | −0.07195229 | −0.07195229 | 2.15165073 | −0.07195229 | −0.07195229 |
| PTEN | −0.10472757 | −0.10472757 | −0.10472757 | −0.86880722 | −0.10472757 |
| PTTG2 | −0.01924501 | −0.01924501 | −0.59690658 | −0.01924501 | −0.01924501 |
| RAD21 | −0.3994352 | −0.0135588 | −0.0135588 | −0.0135588 | −0.0135588 |

TABLE 6-continued centroids for 225 gene risk classifier

| | IHC+ (1) | TP53 (2) | Subgroup A centroid (3) | Subgroup B centroid (4) | Subgroup C centroid (5) |
|---|---|---|---|---|---|
| RAD52 | −0.04587358 | −0.04587358 | 0.38455164 | −0.04587358 | −0.04587358 |
| RB1 | −0.03910675 | −0.6771363 | −0.03910675 | −0.03910675 | −0.03910675 |
| RBX1 | −0.39080421 | −0.04389815 | −0.04389815 | −0.04389815 | −0.04389815 |
| RET | 0.18149733 | 0.18149733 | 0.18149733 | 0.18149733 | 1.43631232 |
| RFC4 | −0.05754212 | −0.05754212 | −0.05754212 | 0.54843713 | −0.05754212 |
| SF3B1 | −0.11220033 | −0.11220033 | 0.23297253 | −0.11220033 | −0.11220033 |
| SHC2 | 0.15686283 | −0.51491502 | 0.15686283 | 0.15686283 | 0.15686283 |
| SHC4 | 0.13709987 | 0.13709987 | 0.13709987 | 0.13709987 | 1.1213424 |
| SIN3A | −0.03351662 | −0.03351662 | −0.03351662 | −0.03351662 | −0.26555161 |
| SKP1 | −0.03003935 | −0.03003935 | 0.30725406 | −0.03003935 | −0.03003935 |
| SKP2 | −0.04245311 | 0.24218446 | −0.04245311 | −0.04245311 | −0.04245311 |
| SMAD3 | −0.02574518 | −0.02574518 | −0.02574518 | −0.02574518 | −0.51213148 |
| SMAD4 | −0.33056479 | 0.00374378 | 0.00374378 | 0.00374378 | 0.00374378 |
| SOCS2 | 0.0433981 | 0.0433981 | 0.0433981 | 1.45120858 | 0.0433981 |
| SOCS3 | 0.71728949 | −0.23035904 | −0.23035904 | −0.23035904 | −0.23035904 |
| SP1 | −0.0610679 | 0.152345 | −0.0610679 | −0.0610679 | −0.0610679 |
| SPOP | −0.01412036 | −0.01412036 | −0.01412036 | 0.49523109 | −0.01412036 |
| SPRY1 | 0.84793748 | −0.07997049 | −0.07997049 | −0.07997049 | −0.07997049 |
| SPRY2 | −0.04705577 | −0.04705577 | −0.04705577 | −0.04705577 | 0.47891039 |
| SSX1 | 2.35670991 | 0.66335378 | 0.66335378 | 0.66335378 | 0.66335378 |
| STAT4 | 0.73250358 | 0.06969255 | 0.06969255 | 0.06969255 | 0.06969255 |
| STK11 | −0.33740066 | −0.0326569 | −0.0326569 | −0.0326569 | −0.0326569 |
| SYK | −0.03690692 | −0.03690692 | −0.03690692 | −0.03690692 | 0.40943317 |
| TFDP1 | 0.0962478 | 0.54940854 | 0.0962478 | 0.0962478 | 0.0962478 |
| TGFB3 | 0.07718645 | 0.07718645 | 0.07718645 | 0.07718645 | −0.67517129 |
| TGFBR2 | 0.48530313 | 0.00452876 | 0.00452876 | 0.00452876 | 0.00452876 |
| THBS1 | 0.66888057 | −0.21515608 | −0.21515608 | −0.21515608 | −0.21515608 |
| TLR4 | 0.04571647 | 0.04571647 | 0.04571647 | 0.04571647 | 0.67564346 |
| TLX1 | 0.48484768 | 0.48484768 | 2.37838279 | 0.48484768 | 0.48484768 |
| TNC | −0.02780559 | −0.02780559 | −1.65410027 | −0.02780559 | −0.02780559 |
| TNFRSF10B | −0.01012048 | −0.01012048 | 0.53370864 | −0.01012048 | −0.01012048 |
| TNFRSF10D | −0.02057269 | −0.02057269 | −0.02057269 | −1.20440978 | −0.02057269 |
| TNFSF10 | −0.09580323 | −0.09580323 | −0.09580323 | −0.09580323 | 0.56529496 |
| TNR | 0.11575176 | 0.11575176 | 0.11575176 | 1.38183963 | 0.11575176 |
| TP53 | −0.26722651 | −0.26722651 | −0.26722651 | −1.37187095 | −0.26722651 |
| TSPAN7 | 0.07016174 | 0.07016174 | 1.15874199 | 0.07016174 | 0.07016174 |
| TTK | −0.09832583 | −0.09832583 | −0.09832583 | 0.56938185 | −0.09832583 |
| U2AF1 | −0.00812952 | 0.24625843 | −0.00812952 | −0.00812952 | −0.00812952 |
| UBE2T | −0.02355507 | −0.02355507 | −0.02355507 | −0.02355507 | −0.58524998 |
| VEGFA | −0.03429483 | −0.03429483 | −0.03429483 | −0.03429483 | −0.69022185 |
| WEE1 | −0.6704469 | −0.09453667 | −0.09453667 | −0.09453667 | −0.09453667 |
| WHSC1L1 | 0.00932376 | 0.00932376 | 0.52040958 | 0.00932376 | 0.00932376 |
| WNT10B | 1.04430335 | 0.1033825 | 0.1033825 | 0.1033825 | 0.1033825 |
| WNT6 | −0.03094321 | 0.46879856 | −0.03094321 | −0.03094321 | −0.03094321 |
| WT1 | 0.46923473 | −0.36957191 | 0.46923473 | 0.46923473 | 0.46923473 |
| ZAK | 0.11046378 | 0.11046378 | 0.11046378 | 0.94265393 | 0.11046378 |
| ZBTB16 | −0.16972395 | −0.16972395 | −0.16972395 | −0.16972395 | −1.98760677 |
| ZIC2 | 0.10008527 | 0.10008527 | 1.69354244 | 0.10008527 | 0.10008527 |

TABLE 7 centroids for 42 genes for identifying F-Lo/P-Hi subgroup

| gene | PDGFRA-HI/FGFR1-Lo | Other (PDGFRA-Hi/FGFR1-Hi, PDGFRA-Lo/FGFR1-Lo, or PDGFRA-Lo/FGFR1-Hi) |
|---|---|---|
| CCNO | −0.7465041 | 0.05814408 |
| MLF1 | −0.7380756 | −0.07707883 |
| PPP2R2C | −0.6852121 | 0.56494494 |
| WEE1 | −0.6704469 | −0.09453667 |
| HDAC11 | −0.6690272 | −0.09322847 |
| PCNA | −0.6248509 | −0.01603919 |
| NPM1 | −0.5760002 | 0.00332197 |
| FANCL | −0.5651666 | −0.01293858 |
| MSH2 | −0.5548998 | −0.03095062 |
| AMER1 | −0.5354407 | −0.00240749 |
| DAXX | −0.5159832 | −0.03754511 |
| ALKBH3 | −0.5113958 | −0.06705258 |
| NTHL1 | −0.5077853 | −0.07866785 |
| MUTYH | −0.5053261 | −0.06272888 |
| LIG4 | −0.5053026 | −0.04785678 |
| PPP2CB | −0.4869711 | 0.0230338 |
| HDAC5 | −0.4431177 | −0.02343759 |
| PRKACA | −0.4231744 | −0.03705625 |
| ATR | −0.4175524 | −0.0616667 |
| RAD21 | −0.3994352 | −0.0135588 |
| RBX1 | −0.3908042 | −0.04389815 |
| MDC1 | −0.379772 | −0.06129361 |
| STK11 | −0.3374007 | −0.0326569 |
| SMAD4 | −0.3305648 | 0.00374378 |
| GSK3B | −0.3289616 | −0.04260185 |
| AKT2 | −0.3099433 | −0.01919342 |

TABLE 7-continued centroids for 42 genes for identifying F-Lo/P-Hi subgroup

| gene | PDGFRA-HI/FGFR1-Lo | Other (PDGFRA-Hi/FGFR1-Hi, PDGFRA-Lo/FGFR1-Lo, or PDGFRA-Lo/FGFR1-Hi) |
|---|---|---|
| DUSP6 | 0.64607125 | −0.13511565 |
| THBS1 | 0.66888057 | −0.21515608 |
| SOCS3 | 0.71728949 | −0.23035904 |
| STAT4 | 0.73250358 | 0.06969255 |
| COL5A1 | 0.82895474 | 0.02869965 |
| SPRY1 | 0.84793748 | −0.07997049 |
| FOSL1 | 0.85033616 | 0.03958811 |
| WNT10B | 1.04430335 | 0.1033825 |
| CSF2 | 1.21387949 | 0.22876539 |
| BMP4 | 1.30239681 | 0.21301304 |
| LIF | 1.39370879 | −0.06116073 |
| ETV4 | 1.42923832 | 0.17676653 |
| IL6 | 1.68316336 | 0.1815675 |
| IL11 | 1.73407021 | 0.23740715 |
| IL8 | 2.10056954 | 0.1309187 |
| SSX1 | 2.35670991 | 0.66335378 |

REFERENCES

1. Kitagawa, D. et al. Activity-based kinase profiling of approved tyrosine kinase inhibitors. *Genes to Cells* 18, 110-122 (2013).
2. Ku, X., Heinzlmeir, S., Helm, D., Mëdard, G. & Kuster, B. New Affinity Probe Targeting VEGF Receptors for Kinase Inhibitor Selectivity Profiling by Chemical Proteomics. *J. Proteome Res.* 13, 2445-2452 (2014).
3. Kumar, R. et al. Pharmacokinetic-pharmacodynamic correlation from mouse to human with pazopanib, a multikinase angiogenesis inhibitor with potent antitumor and antiangiogenic activity. *Mol. Cancer Ther.* 6, 2012-2021 (2007).
4. Noujaim, J., Payne, L. S., Judson, I., Jones, R. L. & Huang, P. H. Phosphoproteomics in translational research: a sarcoma perspective. *Ann. Oncol.* (2016). doi:10.1093/annonc/mdw030
5. Podar, K. et al. The small-molecule VEGF receptor inhibitor pazopanib (GW786034B) targets both tumor and endothelial cells in multiple myeloma. *Proc. Natl. Acad. Sci.* 103, 19478-19483 (2006).
6. Delea, T. E. et al. Cost-effectiveness of pazopanib in advanced soft-tissue sarcoma in Canada. *Curr. Oncol.* 21, 748 (2014).
7. Amdahl, J. et al. Cost-effectiveness of pazopanib in advanced soft tissue sarcoma in the United kingdom. *Sarcoma* 2014, 481071 (2014).
8. Kasper, B. et al. Long-term responders and survivors on pazopanib for advanced soft tissue sarcomas: subanalysis of two European Organisation for Research and Treatment of Cancer (EORTC) clinical trials 62043 and 62072. *Ann. Oncol.* 25, 719-24 (2014).
9. Sleijfer, S. et al. Pazopanib, a multikinase angiogenesis inhibitor, in patients with relapsed or refractory advanced soft tissue sarcoma: a phase II study from the European organisation for research and treatment of cancer-soft tissue and bone sarcoma group (EORTC study 620. *J. Clin. Oncol.* 27, 3126-32 (2009).
10. Stacchiotti, S. et al. Preclinical and clinical evidence of activity of pazopanib in solitary fibrous tumour. *Eur. J. Cancer* 50, 3021-8 (2014).
11. Maruzzo, M. et al. *Pazopanib as first line treatment for solitary fibrous tumours: the Royal Marsden Hospital experience.* Clin. Sarcoma Res. 5, 5 (2015).
12. Kollar, A. et al. Pazopanib in advanced vascular sarcomas: an EORTC Soft Tissue and Bone Sarcoma Group (STBSG) retrospective analysis. *Acta Oncol.* (Madr). 56, 88-92 (2017).
13. Lipplaa, A., Dijkstra, S. & Gelderblom, H. Efficacy of pazopanib and sunitinib in advanced axial chordoma: a single reference centre case series. *Clin. Sarcoma Res.* 6, 19 (2016).
14. Nakamura, T. et al. The clinical outcome of pazopanib treatment in Japanese patients with relapsed soft tissue sarcoma: A Japanese Musculoskeletal Oncology Group (JMOG) study. *Cancer* 122, 1408-16 (2016).
15. Chibon, F. et al. Validated prediction of clinical outcome in sarcomas and multiple types of cancer on the basis of a gene expression signature related to genome complexity. *Nat. Med.* 16, 781-7 (2010).
16. Guo, X. et al. Clinically Relevant Molecular Subtypes in Leiomyosarcoma. *Clin. Cancer Res.* 21, 3501-11 (2015).
17. Koehler, K., Liebner, D. & Chen, J. L. TP53 mutational status is predictive of pazopanib response in advanced sarcomas. *Ann. Oncol.* 26, 2361-2362 (2015).
18. Fu, S. et al. Phase I study of pazopanib and vorinostat: a therapeutic approach for inhibiting mutant p53-mediated angiogenesis and facilitating mutant p53 degradation. *Ann. Oncol.* 26, 1012-8 (2015).
19. Wong, J. P. et al. Dual Targeting of PDGFRα and FGFR1 Displays Synergistic Efficacy in Malignant Rhabdoid Tumors. *Cell Rep.* 17, 1265-1275 (2016).
20. Altman, D. G. et al. Reporting Recommendations for Tumor Marker Prognostic Studies (REMARK): Explanation and Elaboration. *PLoS Med.* 9, e1001216 (2012).
21. Tusher, V. G., Tibshirani, R. & Chu, G. Significance analysis of microarrays applied to the ionizing radiation response. *Proc. Natl. Acad. Sci. U.S.A* 98, 5116-21 (2001)
22. Tibshirani, R., Hastie, T., Narasimhan, B. & Chu, G. Diagnosis of multiple cancer types by shrunken centroids of gene expression. *Proc. Natl. Acad. Sci.* 99, 6567-6572 (2002).
23. Parker, J. S. et al. Supervised risk predictor of breast cancer based on intrinsic subtypes. *J. Clin. Oncol.* 27, 1160-7 (2009).
24. Velghe, A. I. et al. PDGFRA alterations in cancer: characterization of a gain-of-function V536E transmembrane mutant as well as loss-of-function and passenger mutations. *Oncogene* 33, 2568-2576 (2014).
25. Corless, C. L. et al. PDGFRA Mutations in Gastrointestinal Stromal Tumors: Frequency, Spectrum and In Vitro Sensitivity to Imatinib. *J. Clin. Oncol.* 23, 5357-5364 (2005).
26. Ahmad, I., Iwata, T. & Leung, H. Y. Mechanisms of FGFR-mediated carcinogenesis. *Biochim. Biophys. Acta-Mol. Cell Res.* 1823, 850-860 (2012).
27. Wong, J. P. et al. Dual Targeting of PDGFRα and FGFR1 Displays Synergistic Efficacy in Malignant Rhabdoid Tumors. *Cell Rep.* 17, 1265-1275 (2016).
28. Muller, P. A. J. & Vousden, K. H. Mutant p53 in cancer: new functions and therapeutic opportunities. *Cancer Cell* 25, 304-17 (2014).
29. Segal, N. H. et al. Classification and subtype prediction of adult soft tissue sarcoma by functional genomics. *Am. J. Pathol.* 163, 691-700 (2003).
30. Henderson, S. R. et al. A molecular map of mesenchymal tumors. *Genome Biol.* 6, R76 (2005).
31. Nielsen, T. O. et al. Molecular characterisation of soft tissue tumours: a gene expression study. *Lancet* 359, 1301-1307 (2002).

32. Van der Graaf, W. T. et al. Pazopanib for metastatic soft-tissue sarcoma (PALETTE): a randomised, double-blind, placebo-controlled phase 3 trial. *Lancet* 379, 1879-1886 (2012).
33. Yoo, K. H. et al. Efficacy of pazopanib monotherapy in patients who had been heavily pretreated for metastatic soft tissue sarcoma: a retrospective case series. *BMC Cancer* 15, 154 (2015).
34. Ray-Coquard, I. et al. Treatment patterns and survival in an exhaustive French cohort of pazopanib-eligible patients with metastatic soft tissue sarcoma (STS). *BMC Cancer* 17, 111 (2017).
35. Nakamura, T. et al. The clinical outcome of pazopanib treatment in Japanese patients with relapsed soft tissue sarcoma: A Japanese Musculoskeletal Oncology Group (JMOG) study. *Cancer* 122, 1408-16 (2016).
36. Linch, M., Miah, A. B., Thway, K., Judson, I. R. & Benson, C. Systemic treatment of soft-tissue sarcoma-gold standard and novel therapies. *Nat. Rev. Clin. Oncol.* 11, 187-202 (2014).
37. Lee, A. T. J., Pollack, S. M., Huang, P. & Jones, R. L. Phase III Soft Tissue Sarcoma Trials: Success or Failure? *Curr. Treat. Options Oncol.* 18, 19 (2017).
38. Tap, W. D. et al. Olaratumab and doxorubicin versus doxorubicin alone for treatment of soft-tissue sarcoma: an open-label phase 1b and randomised phase 2 trial. *Lancet* 388, 488-497 (2016).
39. Mir, O. et al. Safety and efficacy of regorafenib in patients with advanced soft tissue sarcoma (REGOSARC): a randomised, double-blind, placebo-controlled, phase 2 trial. *Lancet Oncol.* 0, e20294-711 (2016).
40. Ho, T. H. et al. The impact of FGFR1 and FRS2a expression on sorafenib treatment in metastatic renal cell carcinoma. *BMC Cancer* 15, 304 (2015).

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A method for identifying and treating a cancer patient likely to benefit from tyrosine kinase inhibitor (TKI) therapy, comprising:
   (a) detecting in a biological sample obtained from the patient the expression levels of at least 40 genes selected from ACVR1B, AKT2, ALKBH3, AMH, ARID2, AMER1, ATM, ATR, B2M, BAD, BCL2, BCOR, BID, BIRC3, BMP4, BNIP3, BRAF, CACNA1C, CACNA1E, CACNA1G, CALML6, CARD11, CASP10, CCNB1, CCND1, CCNE1, CCNE2, CCNO, CDC25C, CDC6, CDC7, CDH1, CDK4, CDK6, CDKN2A, CDKN2B, CDKN2C, CDKN2D, CHEK1, CHUK, COL27A1, COL3A1, COL4A4, COL4A6, COL5A1, COL5A2, CREB3L4, CREBBP, CSF2, CXXC4, DAXX, DDB2, DLL1, DLL3, DNMT1, DTX3, DTX4, DUSP4, DUSP6, E2F1, E2F5, EFNA1, EFNA5, ERBB2, ERCC6, ETV4, EZH2, FANCA, FANCB, FANCE, FANCL, FAS, FBXW7, FEN1, FGF12, FGF5, FGF7, FLNA, FLNC, FN1, FOSL1, FUBP1, GADD45A, GLI3, GNA11, GNG12, GRIN2A, GSK3B, GTF2H3, HDAC10, HDAC11, HDAC4, HDAC5, HELLS, HES1, HIST1H3B, HOXA9, HSPB1, IBSP, IDH1, IDH2, IL11, IL11RA, IL12RB2, IL6, IL8, INHBA, IRS1, ITGA6, ITGA7, ITGA8, ITGB3, JAG1, JAK3, KAT2B, KITLG, KMT2C, LAMA3, LAMA5, LAMB3, LAMC3, LEFTY2, LFNG, LIF, LIG4, MAD2L2, MAP2K4, MAP2K6, MAPK10, MAPK8IP1, MCM2, MCM4, MCM5, MDC1, MDM2, MEN1, MET, MFNG, MLF1, MLH1, MLLT3, MLLT4, MMP7, MMP9, MSH2, MSH6, MTOR, MUTYH, MYC, MYD88, NASP, NFKB1, NFKBIZ, NOS3, NOTCH2, NPM1, NTHL1, NUMBL, PAX5, PBX1, PCNA, PDGFC, PDGFRA, PLCB4, PPP2CB, PPP2R2C, PPP3R1, PRKACA, PRKAR1B, PRKAR2A, PRKCB, PRKX, PRLR, PTCH1, PTEN, PTTG2, RAD21, RAD52, RB1, RBX1, RET, RFC4, SF3B1, SHC2, SHC4, SIN3A, SKP1, SKP2, SMAD3, SMAD4, SOCS2, SOCS3, SP1, SPOP, SPRY1, SPRY2, SSX1, STAT4, STK11, SYK, TFDP1, TGFB3, TGFBR2, THBS1, TLR4, TLX1, TNC, TNFRSF10B, TNFRSF10D, TNFSF10, TNR, TP53, TSPAN7, TTK, U2AF1, UBE2T, VEGFA, WEE1, WHSC1L1, WNT10B, WNT6, WT1, ZAK, ZBTB16, and ZIC2, by contacting nucleic acids in the sample with probes or primers, and detecting hybridization or amplification of said nucleic acids encoding said at least 40 genes;
   (b) identifying a patient having expression levels of the at least 40 genes most similar to reference centroid A(3) of Table 6, as compared to any of reference centroids IHC+(1), TP53(2), B(4), C(5) of Table 6 as being associated with longer progression-free survival (PFS) and overall survival (OS); and
   (c) treating the identified patient of step (b) with a TKI, wherein the TKI inhibits at least two targets from: BRAF, CSF1R, DDR1, DDR2, FGFR1, FGFR2, FGFR3, FLT1, FLT4, FRK, KDR, KIT, LCK, LYN, MAP2K6, NTRK1, PDGFRA, PDGFRB, RAF1, RET and TEK, wherein table 6 is:

|  | IHC+ (1) | TP53 (2) | Subgroup A centroid (3) | Subgroup B centroid (4) | Subgroup C centroid (5) |
| --- | --- | --- | --- | --- | --- |
| ACVR1B | −0.15832131 | −0.15832131 | 0.54151057 | −0.15832131 | −0.15832131 |
| AKT2 | −0.30994329 | −0.01919342 | −0.01919342 | −0.01919342 | −0.01919342 |
| ALKBH3 | −0.51139577 | −0.06705258 | −0.06705258 | −0.06705258 | −0.06705258 |
| AMER1 | −0.53544069 | −0.00240749 | −0.00240749 | −0.00240749 | −0.00240749 |
| AMH | −0.15178973 | −0.15178973 | −0.15178973 | −0.15178973 | −1.44283676 |
| ARID2 | −0.01621451 | −0.21931165 | −0.01621451 | −0.01621451 | −0.01621451 |
| ATM | −0.14140818 | −0.14140818 | −0.14140818 | −0.59982807 | −0.14140818 |
| ATR | −0.41755241 | −0.0616667 | −0.0616667 | −0.0616667 | −0.0616667 |
| B2M | 0.03806218 | 0.03806218 | 0.03806218 | 0.03806218 | 0.47297616 |
| BAD | 0.0248534 | 0.27474345 | 0.0248534 | 0.0248534 | 0.0248534 |
| BCL2 | 0.06351095 | 0.06351095 | 0.88344382 | 0.06351095 | 0.06351095 |
| BCOR | 0.05103077 | 0.05103077 | 1.27280929 | 0.05103077 | 0.05103077 |
| BID | 0.58151032 | 0.0455798 | 0.0455798 | 0.0455798 | 0.0455798 |
| BIRC3 | −0.02761286 | −0.02761286 | −1.18099641 | −0.02761286 | −0.02761286 |
| BMP4 | 1.30239681 | 0.21301304 | 0.21301304 | 0.21301304 | 0.21301304 |
| BNIP3 | −0.19708889 | −0.90886955 | −0.19708889 | −0.19708889 | −0.19708889 |
| BRAF | −0.05422312 | −0.05422312 | 0.2484416 | −0.05422312 | −0.05422312 |
| CACNA1C | −0.13582518 | −0.13582518 | −0.13582518 | 0.96758744 | −0.13582518 |
| CACNA1E | 0.17105202 | −0.67762073 | 0.17105202 | 0.17105202 | 0.17105202 |
| CACNA1G | 0.01978593 | 0.99078335 | 0.01978593 | 0.01978593 | 0.01978593 |
| CALML6 | 0.01910958 | 0.01910958 | 0.93075557 | 0.01910958 | 0.01910958 |
| CARD11 | 0.3510245 | 0.3510245 | 0.3510245 | 0.3510245 | 1.54991905 |
| CASP10 | −0.18050625 | −0.18050625 | −0.18050625 | −0.18050625 | 0.39904926 |
| CCNB1 | −0.08780076 | 0.35186891 | −0.08780076 | −0.08780076 | −0.08780076 |
| CCND1 | 0.06716593 | 0.06716593 | 0.06716593 | 0.06716593 | 0.89918266 |
| CCNE1 | 0.03028376 | 0.4673283 | 0.03028376 | 0.03028376 | 0.03028376 |
| CCNE2 | −0.02855095 | −0.02855095 | −0.02855095 | 0.96943946 | −0.02855095 |
| CCNO | −0.74650411 | 0.05814408 | 0.05814408 | 0.05814408 | 0.05814408 |
| CDC25C | −0.20812329 | 0.4321119 | −0.20812329 | −0.20812329 | −0.20812329 |
| CDC6 | −0.13977911 | 0.25507254 | −0.13977911 | −0.13977911 | −0.13977911 |
| CDC7 | −0.0401465 | −0.0401465 | −0.0401465 | −0.0401465 | −0.48566159 |
| CDH1 | 0.5933622 | 0.5933622 | 0.5933622 | 2.70632966 | 0.5933622 |
| CDK4 | 0.02878578 | 0.02878578 | 0.02878578 | 0.02878578 | 0.43127765 |
| CDK6 | −0.09882276 | −0.80702231 | −0.09882276 | −0.09882276 | −0.09882276 |
| CDKN2A | −0.43348608 | 0.40775211 | −0.43348608 | −0.43348608 | −0.43348608 |
| CDKN2B | −0.30199667 | −0.30199667 | −1.13360288 | −0.30199667 | −0.30199667 |
| CDKN2C | −0.0741678 | 0.71842723 | −0.0741678 | −0.0741678 | −0.0741678 |
| CDKN2D | −0.07445202 | −0.07445202 | −0.88415539 | −0.07445202 | −0.07445202 |
| CHEK1 | −0.03670758 | 0.36086714 | −0.03670758 | −0.03670758 | −0.03670758 |
| CHUK | 0.01020521 | 0.01020521 | 0.01020521 | 0.01020521 | 0.3304295 |

-continued

|  | IHC+ (1) | TP53 (2) | Subgroup A centroid (3) | Subgroup B centroid (4) | Subgroup C centroid (5) |
| --- | --- | --- | --- | --- | --- |
| COL27A1 | -0.058947 | -0.058947 | -0.058947 | -1.02899246 | -0.058947 |
| COL3A1 | -0.04583553 | -0.04583553 | -1.12616257 | -0.04583553 | -0.04583553 |
| COL4A4 | -0.19065625 | -0.19065625 | -0.19065625 | -0.19065625 | 0.4691999 |
| COL4A6 | -0.07291156 | -0.07291156 | -0.07291156 | 2.30094864 | -0.07291156 |
| COL5A1 | 0.82895474 | 0.02869965 | 0.02869965 | 0.02869965 | 0.02869965 |
| COL5A2 | -0.10633063 | -0.10633063 | -1.20961533 | -0.10633063 | -0.10633063 |
| CREB3L4 | -0.11547721 | -0.11547721 | -0.11547721 | -0.11547721 | -0.52285762 |
| CREBBP | -0.06115984 | -0.06115984 | 0.41412808 | -0.06115984 | -0.06115984 |
| CSF2 | 1.21387949 | 0.22876539 | 0.22876539 | 0.22876539 | 0.22876539 |
| CXXC4 | 0.1857577 | 0.1857577 | 1.56739048 | 0.1857577 | 0.1857577 |
| DAXX | -0.51598315 | -0.03754511 | -0.03754511 | -0.03754511 | -0.03754511 |
| DDB2 | -0.02877707 | -0.02877707 | 0.73742541 | -0.02877707 | -0.02877707 |
| DLL1 | -0.02445967 | -0.02445967 | 1.38299745 | -0.02445967 | -0.02445967 |
| DLL3 | 0.11550972 | 0.11550972 | 0.11550972 | 0.11550972 | 0.99134018 |
| DNMT1 | -0.06492494 | 0.22828132 | -0.06492494 | -0.06492494 | -0.06492494 |
| DTX3 | -0.00091037 | -0.00091037 | -0.00091037 | 0.57881747 | -0.00091037 |
| DTX4 | -0.13468574 | -0.13468574 | -0.13468574 | -1.34786396 | -0.13468574 |
| DUSP4 | -0.06613786 | -0.06613786 | -0.06613786 | -0.06613786 | 0.79464751 |
| DUSP6 | 0.64607125 | -0.13511565 | -0.13511565 | -0.13511565 | -0.13511565 |
| E2F1 | -0.15690288 | 0.58630128 | -0.15690288 | -0.15690288 | -0.15690288 |
| E2F5 | -0.15133642 | -0.15133642 | -0.15133642 | -0.15133642 | 0.49181536 |
| EFNA1 | -0.11668426 | -0.11668426 | -0.11668426 | -0.11668426 | 0.53773733 |
| EFNA5 | -0.36099156 | -0.36099156 | -2.00486828 | -0.36099156 | -0.36099156 |
| ERBB2 | -0.17090683 | -0.17090683 | 0.56247468 | -0.17090683 | -0.17090683 |
| ERCC6 | -0.03591121 | -0.03591121 | 0.35637641 | -0.03591121 | -0.03591121 |
| ETV4 | 1.42923832 | 0.17676653 | 0.17676653 | 0.17676653 | 0.17676653 |
| EZH2 | -0.13282806 | -0.13282806 | -0.13282806 | -0.13282806 | -0.54806145 |
| FANCA | -0.09874728 | -0.09874728 | -0.09874728 | -0.09874728 | -0.73163501 |
| FANCB | -0.07545182 | 0.28149725 | -0.07545182 | -0.07545182 | -0.07545182 |
| FANCE | 0.03359085 | 0.03359085 | 0.03359085 | 0.82988961 | 0.03359085 |
| FANCL | -0.56516661 | -0.01293858 | -0.01293858 | -0.01293858 | -0.01293858 |
| FAS | -0.11858783 | 0.47425096 | -0.11858783 | -0.11858783 | -0.11858783 |
| FBXW7 | -0.03157043 | -0.03157043 | 0.54732624 | -0.03157043 | -0.03157043 |
| FEN1 | 0.05373816 | 0.05373816 | 0.05373816 | 0.82272386 | 0.05373816 |
| FGF12 | -0.14368413 | -0.91516385 | -0.14368413 | -0.14368413 | -0.14368413 |
| FGF5 | 0.48339559 | 0.48339559 | 0.48339559 | 0.48339559 | 1.59245056 |
| FGF7 | -0.45472135 | -0.45472135 | -0.45472135 | 1.11593826 | -0.45472135 |
| FLNA | 0.13671796 | 0.13671796 | 0.13671796 | 1.69109283 | 0.13671796 |
| FLNC | -0.467287 | -0.467287 | -0.467287 | 0.96770635 | -0.467287 |
| FN1 | -0.04593874 | -0.04593874 | -1.18366565 | -0.04593874 | -0.04593874 |
| FOSL1 | 0.85033616 | 0.03958811 | 0.03958811 | 0.03958811 | 0.03958811 |
| FUBP1 | -0.06703661 | -0.06703661 | 0.36412825 | -0.06703661 | -0.06703661 |
| GADD45A | 0.06766933 | 0.06766933 | 0.06766933 | 0.84508039 | 0.06766933 |
| GLI3 | -0.17664829 | -0.17664829 | -0.17664829 | -0.17664829 | -0.77449891 |
| GNA11 | 0.02755931 | 0.02755931 | 0.02755931 | 0.64967723 | 0.02755931 |
| GNG12 | -0.16995566 | -0.16995566 | -0.85810693 | -0.16995566 | -0.16995566 |
| GRIN2A | 0.36120599 | 1.33705393 | 0.36120599 | 0.36120599 | 0.36120599 |
| GSK3B | -0.3289616 | -0.04260185 | -0.04260185 | -0.04260185 | -0.04260185 |
| GTF2H3 | -0.09051522 | -0.09051522 | 0.33573726 | -0.09051522 | -0.09051522 |
| HDAC10 | -0.12352944 | -0.12352944 | -0.12352944 | -0.12352944 | 0.1647408 |
| HDAC11 | -0.66902718 | -0.09322847 | -0.09322847 | -0.09322847 | -0.09322847 |
| HDAC4 | -0.02614516 | -0.02614516 | 0.6056055 | -0.02614516 | -0.02614516 |
| HDAC5 | -0.44311772 | -0.02343759 | -0.02343759 | -0.02343759 | -0.02343759 |
| HELLS | -0.08627003 | 0.26759075 | -0.08627003 | -0.08627003 | -0.08627003 |
| HES1 | -0.14475643 | -0.14475643 | 1.09720336 | -0.14475643 | -0.14475643 |
| HIST1H3B | -0.02480871 | 0.56445002 | -0.02480871 | -0.02480871 | -0.02480871 |
| HOXA9 | -0.12800919 | 0.60420276 | -0.12800919 | -0.12800919 | -0.12800919 |
| HSPB1 | -0.10464244 | -0.10464244 | -0.10464244 | 0.60254908 | -0.10464244 |
| IBSP | 0.25316339 | 1.48773858 | 0.25316339 | 0.25316339 | 0.25316339 |
| IDH1 | -0.0139642 | -0.0139642 | -0.0139642 | -0.0139642 | 0.35797145 |
| IDH2 | 0.14237266 | 0.14237266 | 0.14237266 | 0.97071118 | 0.14237266 |
| IL11 | 1.73407021 | 0.23740715 | 0.23740715 | 0.23740715 | 0.23740715 |
| IL11RA | -0.01835972 | -0.01835972 | 0.89759852 | -0.01835972 | -0.01835972 |
| IL12RB2 | 0.12363856 | 0.12363856 | 0.12363856 | 0.12363856 | 1.18873886 |
| IL6 | 1.68316336 | 0.1815675 | 0.1815675 | 0.1815675 | 0.1815675 |
| IL8 | 2.10056954 | 0.1309187 | 0.1309187 | 0.1309187 | 0.1309187 |
| INHBA | -0.44395722 | -0.44395722 | -1.93039159 | -0.44395722 | -0.44395722 |
| IRS1 | 0.06052758 | 0.06052758 | 0.06052758 | 1.18660836 | 0.06052758 |
| ITGA6 | 0.0423311 | 0.0423311 | 0.0423311 | 0.0423311 | 0.62988286 |
| ITGA7 | 0.0163744 | 0.0163744 | 0.0163744 | 1.40919398 | 0.0163744 |
| ITGA8 | -0.60196552 | -0.60196552 | -0.60196552 | 1.2401644 | -0.60196552 |
| ITGB3 | -0.03320016 | -0.03320016 | -1.24850492 | -0.03320016 | -0.03320016 |
| JAG1 | 0.16492599 | 0.71120586 | 0.16492599 | 0.16492599 | 0.16492599 |
| JAK3 | -0.20341296 | -0.20341296 | -0.20341296 | -1.06969998 | -0.20341296 |
| KAT2B | -0.04101357 | -0.04101357 | -0.04101357 | -0.04101357 | 0.32993194 |
| KITLG | -0.11534823 | 0.37839946 | -0.11534823 | -0.11534823 | -0.11534823 |

|  | IHC+ (1) | TP53 (2) | Subgroup A centroid (3) | Subgroup B centroid (4) | Subgroup C centroid (5) |
| --- | --- | --- | --- | --- | --- |
| KMT2C | −0.06007021 | −0.06007021 | 0.27599606 | −0.06007021 | −0.06007021 |
| LAMA3 | −0.02993329 | −0.02993329 | −0.02993329 | 1.33919007 | −0.02993329 |
| LAMA5 | 0.22274146 | 0.22274146 | 0.22274146 | 1.55832429 | 0.22274146 |
| LAMB3 | −0.12041485 | −0.12041485 | −0.12041485 | 1.14007598 | −0.12041485 |
| LAMC3 | 0.04945966 | 0.04945966 | 0.04945966 | 0.04945966 | 1.10866665 |
| LEFTY2 | 0.51860941 | 0.51860941 | 0.51860941 | 0.51860941 | −0.56354027 |
| LFNG | 0.10700215 | 0.10700215 | 0.10700215 | −0.67796456 | 0.10700215 |
| LIF | 1.39370879 | −0.06116073 | −0.06116073 | −0.06116073 | −0.06116073 |
| LIG4 | −0.50530259 | −0.04785678 | −0.04785678 | −0.04785678 | −0.04785678 |
| MAD2L2 | 0.03722618 | 0.6081764 | 0.03722618 | 0.03722618 | 0.03722618 |
| MAP2K4 | 0.08248544 | 0.08248544 | 0.08248544 | 0.64727212 | 0.08248544 |
| MAP2K6 | −0.13138211 | −0.13138211 | −0.13138211 | −1.47415459 | −0.13138211 |
| MAPK10 | −0.07793461 | −0.07793461 | −0.07793461 | 1.43393339 | −0.07793461 |
| MAPK8IP1 | −0.00825569 | −0.00825569 | −0.00825569 | −0.00825569 | 0.92651997 |
| MCM2 | −0.07381755 | 0.42160047 | −0.07381755 | −0.07381755 | −0.07381755 |
| MCM4 | −0.04139259 | 0.37963662 | −0.04139259 | −0.04139259 | −0.04139259 |
| MCM5 | −0.13706634 | −0.13706634 | −0.13706634 | 0.29064389 | −0.13706634 |
| MDC1 | −0.37977203 | −0.06129361 | −0.06129361 | −0.06129361 | −0.06129361 |
| MDM2 | 0.0314102 | −0.47856785 | 0.0314102 | 0.0314102 | 0.0314102 |
| MEN1 | −0.10998162 | −0.10998162 | 0.25826164 | −0.10998162 | −0.10998162 |
| MET | 0.03488567 | −0.86253667 | 0.03488567 | 0.03488567 | 0.03488567 |
| MFNG | 0.08194644 | 0.08194644 | 0.08194644 | 0.08194644 | 0.69798176 |
| MLF1 | −0.7380756 | −0.07707883 | −0.07707883 | −0.07707883 | −0.07707883 |
| MLH1 | −0.10111681 | −0.10111681 | 0.31198563 | −0.10111681 | −0.10111681 |
| MLLT3 | −0.15727151 | −0.58592957 | −0.15727151 | −0.15727151 | −0.15727151 |
| MLLT4 | −0.21907125 | −0.68832348 | −0.21907125 | −0.21907125 | −0.21907125 |
| MMP7 | 0.39833697 | 1.54606409 | 0.39833697 | 0.39833697 | 0.39833697 |
| MMP9 | −0.10394205 | 1.60133616 | −0.10394205 | −0.10394205 | −0.10394205 |
| MSH2 | −0.55489979 | −0.03095062 | −0.03095062 | −0.03095062 | −0.03095062 |
| MSH6 | −0.05432838 | −0.05432838 | −0.05432838 | 0.27491694 | −0.05432838 |
| MTOR | −0.06272839 | 0.18781661 | −0.06272839 | −0.06272839 | −0.06272839 |
| MUTYH | −0.50532612 | −0.06272888 | −0.06272888 | −0.06272888 | −0.06272888 |
| MYC | −0.18641001 | −0.18641001 | −0.18641001 | −0.18641001 | 0.74902785 |
| MYD88 | −0.08502077 | −0.08502077 | −0.08502077 | −0.58812129 | −0.08502077 |
| NASP | −0.02523895 | −0.02523895 | −0.02523895 | −0.02523895 | −0.55068349 |
| NFKB1 | −0.1830597 | −0.51522965 | −0.1830597 | −0.1830597 | −0.1830597 |
| NFKBIZ | −0.02574918 | −0.02574918 | −1.18521256 | −0.02574918 | −0.02574918 |
| NOS3 | −0.0004462 | −0.0004462 | −0.0004462 | −0.0004462 | 0.5365944 |
| NOTCH2 | −0.14817229 | −0.14817229 | −0.14817229 | −0.14817229 | −0.72029657 |
| NPM1 | −0.57600022 | 0.00332197 | 0.00332197 | 0.00332197 | 0.00332197 |
| NTHL1 | −0.50778533 | −0.07866785 | −0.07866785 | −0.07866785 | −0.07866785 |
| NUMBL | 0.00052321 | −0.00052321 | 0.59451543 | −0.00052321 | −0.00052321 |
| PAX5 | 0.25809009 | 0.25809009 | 0.25809009 | 0.25809009 | 1.00231025 |
| PBX1 | 0.08501597 | 0.08501597 | 0.08501597 | 0.92159476 | 0.08501597 |
| PCNA | −0.62485093 | −0.01603919 | −0.01603919 | −0.01603919 | −0.01603919 |
| PDGFC | −0.11165439 | −0.11165439 | −0.83987243 | −0.11165439 | −0.11165439 |
| PDGFRA | −0.16915031 | −0.16915031 | −0.16915031 | −1.68249338 | −0.16915031 |
| PLCB4 | −0.35341736 | −0.35341736 | −0.35341736 | 0.81476038 | −0.35341736 |
| PPP2CB | −0.48697106 | 0.0230338 | 0.0230338 | 0.0230338 | 0.0230338 |
| PPP2R2C | −0.68521206 | 0.56494494 | 0.56494494 | 0.56494494 | 0.56494494 |
| PPP3R1 | −0.29772681 | −0.04706913 | −0.04706913 | −0.04706913 | −0.04706913 |
| PRKACA | −0.42317444 | −0.03705625 | −0.03705625 | −0.03705625 | −0.03705625 |
| PRKAR1B | −0.28935676 | −0.28935676 | 0.84966941 | −0.28935676 | −0.28935676 |
| PRKAR2A | −0.00446406 | −0.00446406 | −0.00446406 | 0.37327539 | −0.00446406 |
| PRKCB | −0.04967629 | −0.04967629 | −0.04967629 | −0.04967629 | 0.78745301 |
| PRKX | −0.05123099 | −0.05123099 | −0.05123099 | −0.70281335 | −0.05123099 |
| PRLR | 0.26338038 | −0.55930099 | 0.26338038 | 0.26338038 | 0.26338038 |
| PTCH1 | −0.07195229 | −0.07195229 | 2.15165073 | −0.07195229 | −0.07195229 |
| PTEN | −0.10472757 | −0.10472757 | −0.10472757 | −0.86880722 | −0.10472757 |
| PTTG2 | −0.01924501 | −0.01924501 | −0.59620658 | −0.01924501 | −0.01924501 |
| RAD21 | −0.3994352 | −0.0135588 | −0.0135588 | −0.0135588 | −0.0135588 |
| RAD52 | −0.04587358 | −0.04587358 | 0.38455164 | −0.04587358 | −0.04587358 |
| RB1 | −0.03910675 | −0.6771363 | −0.03910675 | −0.03910675 | −0.03910675 |
| RBX1 | −0.39080421 | −0.04389815 | −0.04389815 | −0.04389815 | −0.04389815 |
| RET | 0.18149733 | 0.18149733 | 0.18149733 | 0.18149733 | 1.43691232 |
| RFC4 | −0.05754212 | −0.05754212 | −0.05754212 | 0.54843713 | −0.05754212 |
| SF3B1 | −0.11220033 | −0.11220033 | 0.23297253 | −0.11220033 | −0.11220033 |
| SHC2 | 0.15686283 | −0.51491502 | 0.15686283 | 0.15686283 | 0.15686283 |
| SHC4 | 0.13709987 | 0.13709987 | 0.13709987 | 0.13709987 | 1.1213424 |
| SIN3A | −0.03351662 | −0.03351662 | −0.03351662 | −0.03351662 | −0.26555161 |
| SKP1 | −0.03003935 | −0.03003935 | 0.30725406 | −0.03003935 | −0.03003935 |
| SKP2 | −0.04245311 | 0.24218446 | −0.04245311 | −0.04245311 | −0.04245311 |
| SMAD3 | −0.02574518 | −0.02574518 | −0.02574518 | −0.02574518 | −0.51213148 |
| SMAD4 | −0.33056479 | 0.00374378 | 0.00374378 | 0.00374378 | 0.00374378 |
| SOCS2 | 0.0433981 | 0.0433981 | 0.0433981 | 1.45120858 | 0.0433981 |
| SOCS3 | 0.71728949 | −0.23035904 | −0.23035904 | −0.23035904 | −0.23035904 |

-continued

| | IHC+ (1) | TP53 (2) | Subgroup A centroid (3) | Subgroup B centroid (4) | Subgroup C centroid (5) |
|---|---|---|---|---|---|
| SP1 | −0.0610679 | 0.152345 | −0.0610679 | −0.0610679 | −0.0610679 |
| SPOP | −0.01412036 | −0.01412036 | −0.01412036 | 0.49523109 | −0.01412036 |
| SPRY1 | 0.84793748 | −0.07997049 | −0.07997049 | −0.07997049 | −0.07997049 |
| SPRY2 | −0.04705577 | −0.04705577 | −0.04705577 | −0.04705577 | 0.47891039 |
| SSX1 | 2.35670991 | 0.66335378 | 0.66335378 | 0.66335378 | 0.66335378 |
| STAT4 | 0.73250358 | 0.06969255 | 0.06969255 | 0.06969255 | 0.06969255 |
| STK11 | −0.33740066 | −0.0326569 | −0.0326569 | −0.0326569 | −0.0326569 |
| SYK | −0.03690692 | −0.03690692 | −0.03690692 | −0.03690692 | 0.40943317 |
| TFDP1 | 0.0962478 | 0.54940854 | 0.0962478 | 0.0962478 | 0.0962478 |
| TGFB3 | 0.07718645 | 0.07718645 | 0.07718645 | 0.07718645 | −0.67517129 |
| TGFBR2 | 0.48530313 | 0.00452876 | 0.00452876 | 0.00452876 | 0.00452876 |
| THBS1 | 0.66888057 | −0.21515608 | −0.21515608 | −0.21515608 | −0.21515608 |
| TLR4 | 0.04571647 | 0.04571647 | 0.04571647 | 0.04571647 | 0.67564346 |
| TLX1 | 0.48484768 | 0.48484768 | 2.37838279 | 0.48484768 | 0.48484768 |
| TNC | −0.02780559 | −0.02780559 | −1.65410027 | −0.02780559 | −0.02780559 |
| TNFRSF10B | −0.01012048 | −0.01012048 | 0.53370864 | −0.01012048 | −0.01012048 |
| TNFRSF10D | −0.02057269 | −0.02057269 | −0.02057269 | −1.20440978 | −0.02057269 |
| TNFSF10 | −0.09580323 | −0.09580323 | −0.09580323 | −0.09580323 | 0.56529496 |
| TNR | 0.11575176 | 0.11575176 | 0.11575176 | 1.38183963 | 0.11575176 |
| TP53 | −0.26722651 | −0.26722651 | −0.26722651 | −1.37187095 | −0.26722651 |
| TSPAN7 | 0.07016174 | 0.07016174 | 1.15874199 | 0.07016174 | 0.07016174 |
| TTK | −0.09832583 | −0.09832583 | −0.09832583 | 0.56938185 | −0.09832583 |
| U2AF1 | −0.00812952 | 0.24625843 | −0.00812952 | −0.00812952 | −0.00812952 |
| UBE2T | −0.02355507 | −0.02355507 | −0.02355507 | −0.02355507 | −0.58524998 |
| VEGFA | −0.03429483 | −0.03429483 | −0.03429483 | −0.03429483 | −0.69022185 |
| WEE1 | −0.6704469 | −0.09453667 | −0.09453667 | −0.09453667 | −0.09453667 |
| WHSC1L1 | 0.00932376 | 0.00932376 | 0.52040958 | 0.00932376 | 0.00932376 |
| WNT10B | 1.04430335 | 0.1033825 | 0.1033825 | 0.1033825 | 0.1033825 |
| WNT6 | −0.03094321 | 0.46879856 | −0.03094321 | −0.03094321 | −0.03094321 |
| WT1 | 0.46923473 | −0.36957191 | 0.46923473 | 0.46923473 | 0.46923473 |
| ZAK | 0.11046378 | 0.11046378 | 0.11046378 | 0.94265393 | 0.11046378 |
| ZBTB16 | −0.16972395 | −0.16972395 | −0.16972395 | −0.16972395 | −1.98760677 |
| ZIC2 | 0.10008527 | 0.10008527 | 1.69354244 | 0.10008527 | 0.10008527. |

2. The method according to claim 1 wherein the expression levels of at least 45, at least 50, at least 60, at least 70, at least 80, at least 90, at least 100, at least 110, at least 120, at least 130, at least 240, at least 150, at least 160, at least 170, at least 180, at least 190, at least 200, at least 210, at least 220 or all 225 of the genes ACVR1B, AKT2, ALKBH3, AMH, ARID2, AMER1, ATM, ATR, B2M, BAD, BCL2, BCOR, BID, BIRC3, BMP4, BNIP3, BRAF, CACNA1C, CACNA1E, CACNA1G, CALML6, CARD11, CASP10, CCNB1, CCND1, CCNE1, CCNE2, CCNO, CDC25C, CDC6, CDC7, CDH1, CDK4, CDK6, CDKN2A, CDKN2B, CDKN2C, CDKN2D, CHEK1, CHUK, COL27A1, COL3A1, COL4A4, COL4A6, COL5A1, COL5A2, CREB3L4, CREBBP, CSF2, CXXC4, DAXX, DDB2, DLL1, DLL3, DNMT1, DTX3, DTX4, DUSP4, DUSP6, E2F1, E2F5, EFNA1, EFNA5, ERBB2, ERCC6, ETV4, EZH2, FANCA, FANCB, FANCE, FANCL, FAS, FBXW7, FEN1, FGF12, FGF5, FGF7, FLNA, FLNC, FN1, FOSL1, FUBP1, GADD45A, GLI3, GNA11, GNG12, GRIN2A, GSK3B, GTF2H3, HDAC10, HDAC11, HDAC4, HDAC5, HELLS, HES1, HIST1H3B, HOXA9, HSPB1, IBSP, IDH1, IDH2, IL11, IL11RA, IL12RB2, IL6, IL8, INHBA, IRS1, ITGA6, ITGA7, ITGA8, ITGB3, JAG1, JAK3, KAT2B, KITLG, KMT2C, LAMA3, LAMA5, LAMB3, LAMC3, LEFTY2, LFNG, LIF, LIG4, MAD2L2, MAP2K4, MAP2K6, MAPK10, MAPK8IP1, MCM2, MCM4, MCM5, MDC1, MDM2, MEN1, MET, MFNG, MLF1, MLH1, MLLT3, MLLT4, MMP7, MMP9, MSH2, MSH6, MTOR, MUTYH, MYC, MYD88, NASP, NFKB1, NFKBIZ, NOS3, NOTCH2, NPM1, NTHL1, NUMBL, PAX5, PBX1, PCNA, PDGFC, PDGFRA, PLCB4, PPP2CB, PPP2R2C, PPP3R1, PRKACA, PRKAR1B, PRKAR2A, PRKCB, PRKX, PRLR, PTCH1, PTEN, PTTG2, RAD21, RAD52, RB1, RBX1, RET, RFC4, SF3B1, SHC2, SHC4, SIN3A, SKP1, SKP2, SMAD3, SMAD4, SOCS2, SOCS3, SP1, SPOP, SPRY1, SPRY2, SSX1, STAT4, STK11, SYK, TFDP1, TGFB3, TGFBR2, THBS1, TLR4, TLX1, TNC, TNFRSF10B, TNFRSF10D, TNFSF10, TNR, TP53, TSPAN7, TTK, U2AF1, UBE2T, VEGFA, WEE1, WHSC1L1, WNT10B, WNT6, WT1, ZAK, ZBTB16, and ZIC2 are determined.

3. The method according to claim 1 wherein the cancer is sarcoma.

4. The method according to claim 3, wherein the expression levels are determined using an RNA microarray, digital counting, RNA-Seq or quantitative PCR.

5. The method according to claim 1 wherein the biological sample is obtained from tissue, cells or fluid from the individual.

6. The method according to claim 1 wherein the cancer is selected from: soft tissue sarcoma (STS), metastatic renal cell carcinoma (mRCC), gastrointestinal stromal tumour (GIST), hepatocellular carcinoma (HCC), neuroendocrine tumour (NET), medullary thyroid cancer (MTC), non-squamous, non-small cell lung cancer (non-squamous NSCLC), and chronic myeloid leukaemia (CML).

7. The method according to claim 6, wherein the cancer is STS or advanced STS.

8. The method according to claim 6 wherein the TKI is selected from: Pazopanib, Regorafenib, Sorafenib, Sunitinib, Lenvatinib, Axitinib, Nintedanib, and Ponatinib, and pharmaceutically acceptable salts thereof.

9. The method according to claim 8 wherein the TKI is Pazopanib.

10. The method according to claim 1 wherein the TKI is Pazopanib and the cancer is soft tissue sarcoma or advanced soft tissue sarcoma.

11. A method for identifying and treating a cancer patient likely to benefit from tyrosine kinase inhibitor (TKI) therapy, comprising:

(a) detecting in a biological sample obtained from the patient the expression levels of at least 40 genes selected from ACVR1B, AKT2, ALKBH3, AMH, ARID2, AMER1, ATM, ATR, B2M, BAD, BCL2, BCOR, BID, BIRC3, BMP4, BNIP3, BRAF, CACNA1C, CACNA1E, CACNA1G, CALML6, CARD11, CASP10, CCNB1, CCND1, CCNE1, CCNE2, CCNO, CDC25C, CDC6, CDC7, CDH1, CDK4, CDK6, CDKN2A, CDKN2B, CDKN2C, CDKN2D, CHEK1, CHUK, COL27A1, COL3A1, COL4A4, COL4A6, COL5A1, COL5A2, CREB3L4, CREBBP, CSF2, CXXC4, DAXX, DDB2, DLL1, DLL3, DNMT1, DTX3, DTX4, DUSP4, DUSP6, E2F1, E2F5, EFNA1, EFNA5, ERBB2, ERCC6, ETV4, EZH2, FANCA, FANCB, FANCE, FANCL, FAS, FBXW7, FEN1, FGF12, FGF5, FGF7, FLNA, FLNC, FN1, FOSL1, FUBP1, GADD45A, GLI3, GNA11, GNG12, GRIN2A, GSK3B, GTF2H3, HDAC10, HDAC11, HDAC4, HDAC5, HELLS, HES1, HIST1H3B, HOXA9, HSPB1, IBSP, IDH1, IDH2, IL11, IL11RA, IL12RB2, IL6, IL8, INHBA, IRS1, ITGA6, ITGA7, ITGA8, ITGB3, JAG1, JAK3, KAT2B, KITLG, KMT2C, LAMA3, LAMA5, LAMB3, LAMC3, LEFTY2, LFNG, LIF, LIG4, MAD2L2, MAP2K4, MAP2K6, MAPK10, MAPK8IP1, MCM2, MCM4, MCM5, MDC1, MDM2, MEN1, MET, MFNG, MLF1, MLH1, MLLT3, MLLT4, MMP7, MMP9, MSH2, MSH6, MTOR, MUTYH, MYC, MYD88, NASP, NFKB1, NFKBIZ, NOS3, NOTCH2, NPM1, NTHL1, NUMBL, PAX5, PBX1, PCNA, PDGFC, PDGFRA, PLCB4, PPP2CB, PPP2R2C, PPP3R1, PRKACA, PRKAR1B, PRKAR2A, PRKCB, PRKX, PRLR, PTCH1, PTEN, PTTG2, RAD21, RAD52, RB1, RBX1, RET, RFC4, SF3B1, SHC2, SHC4, SIN3A, SKP1, SKP2, SMAD3, SMAD4, SOCS2, SOCS3, SP1, SPOP, SPRY1, SPRY2, SSX1, STAT4, STK11, SYK, TFDP1, TGFB3, TGFBR2, THBS1, TLR4, TLX1, TNC, TNFRSF10B, TNFRSF10D, TNFSF10, TNR, TP53, TSPAN7, TTK, U2AF1, UBE2T, VEGFA, WEE1, WHSC1L1, WNT10B, WNT6, WT1, ZAK, ZBTB16, and ZIC2, by contacting nucleic acids in the sample with probes or primers, and detecting hybridization or amplification of said nucleic acids encoding said at least 40 genes, wherein the expression levels of the 40 or more of the genes determined in said step (a) are compared with:

(i) a first reference centroid corresponding to the expression profile of said 40 or more genes determined in a first group of subjects known to have cancer with PDGFRA-Hi/FGFR1-Lo expression;

(ii) a second reference centroid corresponding to the expression profile of said 40 or more genes determined in a second group of subjects known to have cancer with (a) mutant TP53 and (b) PDGFRA/FGFR1 expression that is not PDGFRA-Hi/FGFR1-Lo;

(iii) a third reference centroid corresponding to the expression profile of said 40 or more genes determined in a third group of subjects known to have cancer with (a) a gene expression profile having a closer match to the centroid of subgroup A than subgroups B or C of Table 3, (b) TP53 wildtype, and (c) PDGFRA/FGFR1 expression that is not PDGFRA-Hi/FGFR1-Lo;

(iv) a fourth reference centroid corresponding to the expression profile of said 40 or more genes determined in a fourth group of subjects known to have cancer with (a) a gene expression profile having a closer match to the centroid of subgroup B than subgroups A or C of Table 3, (b) TP53 wildtype, and (c) PDGFRA/FGFR1 expression that is not PDGFRA-Hi/FGFR1-Lo; and (v) a fifth reference centroid corresponding to the expression profile of said 40 or more genes determined in a fifth group of subjects known to have cancer with (a) a gene expression profile having a closer match to the centroid of subgroup C than subgroups A or B of Table 3, (b) TP53 wildtype, and (c) PDGFRA/FGFR1 expression that is not PDGFRA-Hi/FGFR1-Lo;

(b) identifying a patient having expression levels of the at least 40 genes that are most similar to said third reference centroid as compared to any of said first, second, fourth or fifth reference centroids as being associated with longer progression-free survival (PFS) and overall survival (OS); and (c) treating the identified patient of step (b) with a TKI, wherein the TKI inhibits at least two targets from: BRAF, CSF1R, DDR1, DDR2, FGFR1, FGFR2, FGFR3, FLT1, FLT4, FRK, KDR, KIT, LCK, LYN, MAP2K6, NTRK1, PDGFRA, PDGFRB, RAF1, RET and TEK, wherein table 3 is:

| Gene Symbol | Subgroup B centroid | Subgroup A centroid | Subgroup C centroid |
| --- | --- | --- | --- |
| FGF9 | −0.787299586 | 0.684375081 | 0.071127474 |
| NFATC1 | −0.371691666 | 0.704052833 | 0.023044704 |
| FZD10 | −0.440193224 | 0.660391129 | 0.172537497 |
| HMGA2 | −1.323612428 | 0.295732763 | 0.90817728 |
| FZD9 | −1.075145616 | 0.616942772 | 0.410943305 |
| PRKX | −1.153743629 | 0.02023958 | 1.480748471 |
| CCND1 | −0.847605437 | −0.047679935 | 0.844326227 |
| MAP2K6 | −1.186458783 | 0.341738061 | 1.094717343 |
| TP53 | −1.053931167 | 0.276137891 | −0.07221507 |
| FANCF | −2.562689656 | 0.02114079 | 0.285248682 |
| HDAC10 | −0.864986527 | −0.466408988 | 1.358279782 |
| CARD11 | −1.225657695 | 0.031589204 | 1.277944476 |
| FGF5 | −1.030325063 | 0.388725522 | 0.844361302 |
| DUSP4 | −0.851980221 | −0.18231116 | 0.820109581 |
| IL12RB2 | −0.380856163 | −0.42852557 | 0.791789922 |
| E2F5 | −1.194613628 | −0.049929218 | 0.829615055 |
| CCR7 | −0.084056229 | −0.0392025 | 0.836628323 |
| PAX5 | −0.643065022 | 0.250705882 | 0.802373206 |
| NOG | −0.995613082 | 0.777936727 | −0.257207914 |
| PTCH1 | −0.633931616 | 2.131940241 | −0.891766233 |

-continued

| Gene Symbol | Subgroup B centroid | Subgroup A centroid | Subgroup C centroid |
|---|---|---|---|
| ZIC2 | 0.148829172 | 0.771918368 | −0.805607102 |
| CACNA1G | −0.66346841 | 0.911704604 | −0.1016264 |
| SMAD3 | −0.393760319 | 1.018703135 | −0.451762506 |
| CHAD | 0.029259868 | 0.92288135 | 0.235476291 |
| TLX1 | 0.06809746 | 0.867855103 | −0.263254402 |
| BCOR | 0.102427544 | 1.716828147 | −1.525569877 |
| EFNA2 | 0.452825555 | 0.641136053 | −0.36647518 |
| LEFTY2 | 0.779378173 | 0.416545389 | −0.967518679 |
| NOTCH2 | 0.252055478 | 0.336041946 | −0.976488588 |
| ATM | −1.079149788 | −0.154750465 | 0.653606333 |
| TNFRSF10D | −1.120751017 | −0.023301806 | 0.695417144 |
| TGFB1 | −0.899502256 | 0.365260494 | 0.465688467 |
| DKK1 | −0.51629809 | 0.494457312 | 0.681706191 |
| IDH1 | −0.456773483 | 0.280037814 | 1.328340834 |
| COMP | −0.493285797 | 0.819951452 | 0.559484802 |
| PTEN | −0.764885608 | 0.128186717 | 0.825774951 |
| CALML6 | −1.273555604 | 0.849552584 | 0.267196887 |
| ERBB2 | −0.657891493 | 0.868247895 | −0.336671826 |
| IL11RA | −0.574798229 | 0.757662318 | −0.163619158 |
| PDGFD | −1.453013751 | 0.553101435 | 0.342655917 |
| PRKAR1B | −0.861735578 | 0.972622807 | −0.165967303 |
| DDB2 | −1.048250131 | 1.204621227 | 0.153767602 |
| TSPAN7 | −0.586966677 | 1.295666073 | −0.034132673 |
| FBXW7 | −0.551931516 | 0.743952534 | −0.032066214 |
| DLL1 | −0.787054447 | 1.297166278 | −0.028735448 |
| HES1 | −1.350029079 | 1.708702854 | −0.435881651 |
| COL27A1 | −0.678678331 | 0.932985532 | −0.06990641 |
| PDGFRA | −0.631137099 | 0.771453391 | 0.002225072 |
| CCND2 | −0.962072017 | 0.560935922 | 0.380438596 |
| CXXC4 | −1.135455693 | 0.927997254 | 0.168080612 |
| ACVR1B | −0.715425503 | 1.035669748 | −0.098350604 |
| DTX4 | −0.980772905 | 1.188830049 | 0.344156922 |
| TGFB3 | 0.779010809 | 0.453512809 | −1.151684947 |
| ZBTB16 | 0.744144038 | 0.300340307 | −1.501842069 |
| MAPK10 | 0.746376668 | −0.429814494 | −0.788117541 |
| SPOP | 1.211367282 | −0.57725145 | −0.550759513 |
| CASP7 | 0.943717067 | −1.042835031 | 0.467273755 |
| FGF21 | 0.616732498 | −1.397117511 | −0.041120318 |
| BAD | 0.606883027 | −1.201194407 | 0.232550134 |
| GSK3B | 0.885705342 | −1.39075106 | 0.610667114 |
| RBX1 | 0.166483538 | −1.055858889 | 0.71029212 |
| RELA | 0.611208315 | −0.869112536 | 0.201460338 |
| NUPR1 | 0.939785066 | −0.614213269 | −0.451309641 |
| DDIT3 | 1.18240637 | −1.318487563 | 0.223796918 |
| LAMB3 | 1.552616212 | −0.901993606 | 0.038750971 |
| TSHR | 0.452978334 | −1.281483556 | 0.321335827 |
| BCL2L1 | 0.490231758 | −0.792877145 | 0.85930403 |
| PIM1 | 1.163851083 | −0.58387838 | 0.43760126 |
| PRKCB | −0.220213795 | −0.44819218 | 0.693162357 |
| PLD1 | 0.078761527 | −0.747955173 | 0.330941788 |
| WNT3 | 0.443885608 | −0.810662403 | 0.009175691 |
| EIF4EBP1 | −0.070945866 | −0.897973905 | 0.010952684 |
| IRAK2 | 1.48428277 | −1.194483728 | −0.40789912 |
| PRKAA2 | 1.381125373 | −0.775485013 | −0.577567956 |
| DUSP5 | 0.327417325 | −1.005227809 | 0.322905127 |
| IL8 | 0.47273382 | −1.183932351 | 0.413001976 |
| MAP2K1 | 0.630232347 | −1.253785345 | −0.076450981 |
| BIRC3 | 0.718062464 | −1.255101549 | 0.237248246 |
| PLA2G4C | 1.496594473 | −1.346242957 | −0.15784499 |
| PPP3CC | 0.664650863 | −1.36423635 | 0.256830574 |
| CAPN2 | 0.643376276 | −1.155868131 | 0.247414615 |
| GZMB | 0.675014406 | −1.142799947 | 0.722529353 |
| CLCF1 | 0.716776379 | −0.847605107 | 0.342471593 |
| HGF | 0.290481662 | −0.610592648 | 0.50255412 |
| ITGA3 | 0.656718626 | −2.639015229 | 0.467661891 |
| IL6R | 1.25332586 | −1.599829447 | −0.032175941 |
| POLD4 | 0.672053389 | −1.147721365 | 0.210396896 |
| AMH | 0.288540555 | 0.250910932 | −0.994093078 |
| CACNA1C | 1.676167163 | −0.351229666 | −0.670030512 |
| CACNA1H | 0.850490171 | 0.252197083 | −0.853900562 |
| GNA11 | 1.124323404 | −0.745622387 | −0.153580798 |
| ITGA7 | 1.042754581 | −0.659327019 | −0.17332686 |
| JAG1 | 0.728317828 | −0.512594469 | −0.375946652 |
| LAMA5 | 1.622724844 | −1.060012408 | 0.072913031 |
| IDH2 | 1.478046247 | −0.923619017 | 0.358613769 |
| PLA2G10 | 0.931837184 | −0.102139226 | 0.135420614 |

-continued

| Gene Symbol | Subgroup B centroid | Subgroup A centroid | Subgroup C centroid |
|---|---|---|---|
| HSPB1 | 1.258279601 | −1.731442887 | 0.471013239 |
| LAMC2 | 1.16859924 | −1.360857477 | 0.005444094 |
| FLNC | 1.839552557 | −1.255013658 | 0.013631778 |
| NFKBIZ | 2.315727502 | −1.292126131 | 0.197458225 |
| FN1 | 0.660402717 | −1.171486781 | 0.234728184 |
| GNG12 | 0.867571726 | −0.981276666 | 0.471261377 |
| PDGFC | 1.196009475 | −1.133981891 | 0.004647767 |
| GAS1 | 0.779622888 | −0.752350475 | 0.219109788 |
| CDKN2D | 1.442455149 | −2.288021107 | 0.432605996 |
| TNC | 2.489192272 | −1.589168535 | −0.18592867 |
| CDKN2A | 1.509085425 | −0.73385756 | −0.063471162 |
| CDKN2B | 1.969916123 | −1.427909465 | 0.040850212 |
| INHBA | 1.701129382 | −1.951616488 | 0.011540028 |
| PTPRR | 1.451595841 | −1.532015885 | 0.509429781 |
| NOTCH3 | 0.896323229 | −0.97089252 | 0.204819781 |
| FLNA | 3.352606408 | −1.630559407 | 0.110599618 |
| ITGB3 | 2.029627821 | −1.363726479 | 0.172308131 |
| CDH1 | 1.417579351 | −0.563519168 | −0.012000775 |
| IL22RA1 | 0.677423648 | −0.861368018 | −0.084338277 |
| PRKAR2A | 0.954173113 | −1.411559699 | −0.110220662 |
| DTX3 | 0.836185822 | −0.362975758 | −0.481378145 |
| GRIN2A | 1.367454914 | −0.535776184 | −0.271174006 |
| POLE2 | 0.797767805 | −0.686659307 | −0.015103545 |
| CDKN2C | 1.659187221 | −0.368692467 | −0.280435804 |
| CCNE2 | 2.322615612 | −0.285274237 | −0.620886998 |
| FANCE | 1.739950882 | −0.174523797 | −1.115444165 |
| CDC25C | 0.885753996 | −0.614233996 | −0.633132809 |
| FANCA | 0.843349767 | −0.327032636 | −0.853923908 |
| CCNA2 | 1.709739605 | −0.762854153 | −0.151256005 |
| DNMT1 | 1.087975952 | −0.772201927 | −0.139753541 |
| WHSC1 | 1.011227482 | −0.710351274 | 0.184213773 |
| E2F1 | 1.066547328 | −0.894977636 | −0.186057173 |
| PTTG2 | 0.995372679 | −1.454954386 | 0.043486443 |
| RFC4 | 1.730057786 | −0.638599876 | −0.508480338 |
| MCM2 | 1.529183146 | −0.36493793 | −0.479749297 |
| MCM4 | 1.070557299 | −0.628650321 | 0.140545393 |
| BRCA2 | 1.292667438 | −0.897838271 | 0.100241908 |
| TTK | 2.388139352 | −0.618834387 | −0.128012393 |
| CCNB1 | 1.451881304 | −0.619865956 | −0.079524277 |
| MSH6 | 1.499274067 | −0.5013127 | −0.336590614 |
| MCM5 | 1.98081102 | −0.697209461 | −0.578660576 |
| UBE2T | 1.85858348 | −0.105697652 | −0.665881982 |
| FEN1 | 1.86125434 | −0.646411517 | −0.576062555 |
| CHEK1 | 1.448005524 | −0.836815017 | −0.357022212 |
| BRIP1 | 1.969177489 | −0.504861708 | −0.218232737 |
| CDC7 | 1.699141198 | −0.915926744 | −0.522885786 |
| ITGA8 | 1.543535453 | −0.238387103 | −1.639134229 |
| ETS2 | 0.779810809 | 0.198093282 | −0.575997412 |
| COL4A6 | 1.658235267 | −0.282608549 | −1.56570051 |
| LAMA3 | 2.083772989 | −0.709274494 | −0.584584899 |
| GADD45G | 1.022032515 | −0.43766438 | −0.202119219 |
| ID2 | 0.62903887 | −0.510034449 | 0.119602389 |
| CACNB2 | 0.981132087 | −0.865116096 | 0.038963893 |
| NKD1 | 2.691019394 | −0.322986548 | −0.744692386 |
| SOCS2 | 0.834990812 | −0.655453649 | −0.071526563 |
| PLCB4 | 0.508382694 | −1.029629816 | −0.727123493 |
| RASGRP2 | 1.415707148 | −0.84422873 | −0.216800183 |
| IRS1 | 1.47181196 | −0.40396467 | 0.227234957 |
| TNR | 1.180868996 | −0.840068366 | −0.092317008 |
| GADD45A | 1.287113277 | −1.517075592 | 0.011215464 |
| ZAK | 1.643122992 | −0.497654428 | −0.637329531 |
| FGF7 | 1.698227137 | −1.240536774 | −0.522181449 |
| PBX1 | 1.467757304 | −0.234263903 | −0.375071496 |
| PPARG | 0.138766121 | −0.932222796 | 0.483262572 |
| THBS1 | 0.254930123 | −0.997056609 | 0.173708474 |
| TNFAIP3 | 0.145328112 | −1.051965129 | 0.524290309 |
| EYA1 | 0.2928126 | −1.028756263 | 0.071321766 |
| EFNA5 | 0.001526286 | −1.149909284 | 0.044343314 |
| MYC | 0.001204978 | −1.246321996 | 0.792535029 |
| NFKB1 | −0.04492968 | −1.203821974 | 0.563903708 |
| RUNX1 | −0.29660105 | −0.587183221 | 0.975896848 |
| COL3A1 | −0.05310455 | −0.938619869 | 0.330406692 |
| COL5A2 | 0.066324157 | −1.298836749 | 0.702791004 |
| SPRY1 | −0.261396451 | −0.572573824 | 0.808702985 |
| VEGFC | 0.277920507 | −0.584003317 | 0.583459169 |
| COL4A4 | −0.215428822 | −0.865628696 | 0.850231366 |

-continued

| Gene Symbol | Subgroup B centroid | Subgroup A centroid | Subgroup C centroid |
| --- | --- | --- | --- |
| SOCS3 | 0.190162345 | −0.966843307 | 1.157732644 |
| ETV1 | −0.483944692 | −0.472162475 | 0.667492018 |
| NRAS | −0.40205324 | −0.741671466 | 0.618482163 |
| LIF | −0.427738236 | −0.89005586 | 0.65285878 |
| APC | −0.41323835 | −1.145962291 | 0.569063763 |
| PLAT | 0.255086414 | −0.897781696 | 0.652706703 |
| KAT2B | 0.169588215 | −0.715561144 | 0.808610693 |
| MET | −0.487219685 | −0.569517119 | 0.528969462 |
| DUSP10 | 1.162440885 | −1.43248128 | 0.453731599 |
| PPARGC1A | 1.101127687 | −0.885265217 | 0.209763192 |
| WNT16 | 0.569244222 | −1.353938971 | 0.786026088 |
| CALML5 | −0.254803322 | −1.202570257 | 0.868342334 |
| GATA3 | −0.095593162 | −1.173998403 | 0.559141534 |
| IL15 | 0.185965654 | −0.529551785 | 0.811668987 |
| IL2RB | 0.867636615 | −0.725722192 | 0.404721588 |
| IL7R | 0.500044032 | −1.04018038 | 0.461856038 |
| IL3RA | 0.322997508 | −0.744100389 | 0.710771403 |
| NOS3 | 0.031965527 | −0.55997275 | 1.008066472 |
| IL6 | 0.25202091 | −1.057818045 | 0.521808798 |
| MAP3K8 | 0.525534565 | −0.629689865 | 0.558661012 |
| BCL2A1 | −0.118492282 | −1.248060312 | 0.535233973 |
| SHC1 | 0.432448249 | −1.095032147 | 0.793300777 |
| TNFRSF10A | −0.469698881 | −0.657359638 | 0.525516546 |
| CASP10 | −0.489827618 | −0.346416482 | 1.154981817 |
| TLR4 | −0.502549677 | −0.321086708 | 0.889080653 |
| GRB2 | −0.437187727 | −0.814409187 | 2.119019854 |
| RAC2 | −0.813796838 | −0.558222741 | 0.746175214 |
| CSF1R | −0.763822741 | −0.332235482 | 1.156562363 |
| PIK3R5 | −0.422120799 | −0.424025806 | 1.087625971 |
| TLR2 | −0.457895575 | −0.566882875 | 1.200496741 |
| PIK3CG | −0.498928755 | −0.404086965 | 1.099985115 |
| SYK | −0.471120916 | −0.497930912 | 1.929710234 |
| IL2RA | −0.030524763 | −0.840989014 | 0.663049508 |
| MFNG | −0.384916371 | −0.481471138 | 1.033405111 |
| BID | 0.088886574 | −0.575331123 | 0.818429222 |
| PIK3CD | −0.17143245 | 0.010877708 | 1.174375031 |
| RASGRF2 | −0.455902975 | −0.189934532 | 0.843247694 |
| TNFSF10 | −0.475279967 | −0.931256638 | 1.231408832 |
| ITGA6 | −0.832468699 | −0.251085473 | 0.693305201 |
| MMP9 | −0.182247094 | −0.647025881 | 1.303500224 |
| IGF1 | −1.319084701 | 0.348703024 | 0.801157409 |
| JAK3 | −1.313284985 | 0.162243618 | 0.887569963 |
| TGFBR2 | −0.576704709 | −0.33857086 | 0.682451581 |
| SPRY2 | −0.648697274 | −0.11309924 | 0.649505825 |
| LFNG | −0.644681481 | −0.098858024 | 0.709630093 |
| MPL | −0.067370728 | −0.6571279 | 0.612307561 |
| LAMC3 | −0.133458348 | −0.185543739 | 1.057434835 |
| RET | −0.205916792 | −0.027391926 | 0.770810755 |
| FOS | −0.494262419 | −0.199625214 | 0.643536599 |
| MAPK8IP1 | −0.239136578 | −0.505341384 | 0.517286908 |
| B2M | 0.234106651 | −0.551781156 | 1.211511026 |
| MYD88 | −1.01250718 | −0.955275251 | 1.683288678 |
| CHUK | 0.031111998 | −0.563848617 | 1.112479518 |
| MAP2K2 | 0.297626549 | −1.301076449 | 0.810353045 |
| IL19 | 0.114049756 | −1.237506873 | 0.753586963 |
| COL1A1 | −0.295920059 | −0.715165274 | 0.638320928 |
| PLAU | 0.011625842 | −0.971909393 | 0.821172402. |

12. The method of claim 11, wherein PDGFRA/FGFR1 expression is PDGFRA-Hi/FGFR1-Hi or PDGFRA-Lo/FGFR1-Lo or PDGFRA-Lo/FGFR1-Hi.

13. A method of determining a prognosis following tyrosine kinase inhibitor (TKI) treatment in an individual with cancer, the method comprising:
(a) treating the individual with a TKI, wherein the TKI inhibits at least two targets from: BRAF, CSF1R, DDR1, DDR2, FGFR1, FGFR2, FGFR3, FLT1, FLT4, FRK, KDR, KIT, LCK, LYN, MAP2K6, NTRK1, PDGFRA, PDGFRB, RAF1, RET and TEK; and
(b) determining in a biological sample obtained from the individual the expression levels of each of 40 or more of genes ACVR1B, AKT2, ALKBH3, AMH, ARID2, AMER1, ATM, ATR, B2M, BAD, BCL2, BCOR, BID, BIRC3, BMP4, BNIP3, BRAF, CACNA1C, CACNA1E, CACNA1G, CALML6, CARD11, CASP10, CCNB1, CCND1, CCNE1, CCNE2, CCNO, CDC25C, CDC6, CDC7, CDH1, CDK4, CDK6, CDKN2A, CDKN2B, CDKN2C, CDKN2D, CHEK1, CHUK, COL27A1, COL3A1, COL4A4, COL4A6, COL5A1, COL5A2, CREB3L4, CREBBP, CSF2, CXXC4, DAXX, DDB2, DLL1, DLL3, DNMT1, DTX3, DTX4, DUSP4, DUSP6, E2F1, E2F5, EFNA1, EFNA5, ERBB2, ERCC6, ETV4, EZH2, FANCA, FANCB, FANCE, FANCL, FAS, FBXW7, FEN1, FGF12, FGF5, FGF7, FLNA, FLNC, FN1, FOSL1, FUBP1, GADD45A, GLI3, GNA11, GNG12, GRIN2A, GSK3B, GTF2H3, HDAC10, HDAC11, HDAC4, HDAC5, HELLS, HES1, HIST1H3B, HOXA9, HSPB1, IBSP, IDH1, IDH2, IL11, IL11RA, IL12RB2, IL6, IL8, INHBA, IRS1, ITGA6, ITGA7, ITGA8, ITGB3, JAG1, JAK3, KAT2B, KITLG, KMT2C, LAMA3, LAMA5, LAMB3, LAMC3, LEFTY2, LFNG, LIF, LIG4, MAD2L2, MAP2K4, MAP2K6, MAPK10, MAPK8IP1, MCM2, MCM4, MCM5, MDC1, MDM2, MEN1, MET, MFNG, MLF1, MLH1, MLLT3, MLLT4, MMP7, MMP9, MSH2, MSH6, MTOR, MUTYH, MYC, MYD88, NASP, NFKB1, NFKBIZ, NOS3, NOTCH2, NPM1, NTHL1, NUMBL, PAX5, PBX1, PCNA, PDGFC, PDGFRA, PLCB4, PPP2CB, PPP2R2C, PPP3R1, PRKACA, PRKAR1B, PRKAR2A, PRKCB, PRKX, PRLR, PTCH1, PTEN, PTTG2, RAD21, RAD52, RB1, RBX1, RET, RFC4, SF3B1, SHC2, SHC4, SIN3A, SKP1, SKP2, SMAD3, SMAD4, SOCS2, SOCS3, SP1, SPOP, SPRY1, SPRY2, SSX1, STAT4, STK11, SYK, TFDP1, TGFB3, TGFBR2, THBS1, TLR4, TLX1, TNC, TNFRSF10B, TNFRSF10D, TNFSF10, TNR, TP53, TSPAN7, TTK, U2AF1, UBE2T, VEGFA, WEE1, WHSC1L1, WNT10B, WNT6, WT1, ZAK, ZBTB16, and ZIC2 by contacting nucleic acids in the sample with probes or primers, and detecting hybridization or amplification of said nucleic acids encoding said at least 40 genes, (c) identifying the individual having expression levels of the 40 or more of genes determined in step (b) are most similar to a third reference centroid as compared to a first, second, fourth or fifth reference centroids, as having a good prognosis; and (d) continuing TKI treatment;
wherein the reference centroids are:
(i) a first reference centroid corresponding to the expression profile of said 40 or more genes determined in a first group of subjects known to have cancer with PDGFRA-Hi/FGFR1-Lo expression;
(ii) a second reference centroid corresponding to the expression profile of said 40 or more genes determined in a second group of subjects known to have cancer with mutated TP53 and PDGFRA/FGFR1 expression that is not PDGFRA-Hi/FGFR1-Lo expression;
(iii) a third reference centroid corresponding to the expression profile of said 40 or more genes determined in a third group of subjects known to have cancer with (a) a gene expression profile having a closer match to the centroid of subgroup A than subgroups B or C of Table 3, (b) TP53 wild-type, and (c) PDGFRA/FGFR1 expression that is not PDGFRA-Hi/FGFR1-Lo expression;
(iv) a fourth reference centroid corresponding to the expression profile of said 40 or more genes determined in a fourth group of subjects known to have cancer with (a) a gene expression profile having a closer match to the centroid of subgroup B than subgroups A or C of Table 3, (b) TP53 wild-type, and (c) PDGFRA/FGFR1 expression that is not PDGFRA-Hi/FGFR1-Lo expression; and
(v) a fifth reference centroid corresponding to the expression profile of said 40 or more genes determined in a fifth group of subjects known to have cancer with (a) a gene expression profile having a closer match to the centroid of subgroup C than subgroups A or B of Table 3, (b) TP53 wild-type, and (c) PDGFRA/FGFR1 expression that is not PDGFRA-Hi/FGFR1-Lo expression;
and wherein table 3 is:

| Gene Symbol | Subgroup B centroid | Subgroup A centroid | Subgroup C centroid |
| --- | --- | --- | --- |
| FGF9 | −0.787299586 | 0.684375081 | 0.071127474 |
| NFATC1 | −0.371691666 | 0.704052833 | 0.023044704 |
| FZD10 | −0.440193224 | 0.660391129 | 0.172537497 |
| HMGA2 | −1.323612428 | 0.295732763 | 0.90817728 |
| FZD9 | −1.075145616 | 0.616942772 | 0.410943305 |
| PRKX | −1.153743629 | 0.02023958 | 1.480748471 |
| CCND1 | −0.847605437 | −0.047679935 | 0.844326227 |
| MAP2K6 | −1.186458783 | 0.341738061 | 1.094717343 |
| TP53 | −1.053931167 | 0.276137891 | −0.07221507 |
| FANCF | −2.562689656 | 0.02114079 | 0.285248682 |
| HDAC10 | −0.864986527 | −0.466408988 | 1.358279782 |
| CARD11 | −1.225657695 | 0.031589204 | 1.277944476 |
| FGF5 | −1.030325063 | 0.388725522 | 0.844361302 |
| DUSP4 | −0.851980221 | −0.18231116 | 0.820109581 |
| IL12RB2 | −0.380856163 | −0.42852557 | 0.791789922 |
| E2F5 | −1.194613628 | −0.049929218 | 0.829615055 |
| CCR7 | −0.084056229 | −0.0392025 | 0.836628323 |
| PAX5 | −0.643065022 | 0.250705882 | 0.802373206 |
| NOG | −0.995613082 | 0.777936727 | −0.257207914 |
| PTCH1 | −0.633931616 | 2.131940241 | −0.891766233 |
| ZIC2 | 0.148829172 | 0.771918368 | −0.805607102 |
| CACNA1G | −0.66346841 | 0.911704604 | −0.1016264 |
| SMAD3 | −0.393760319 | 1.018703135 | −0.451762506 |
| CHAD | 0.029259868 | 0.92288135 | 0.235476291 |
| TLX1 | 0.06809746 | 0.867855103 | −0.263254402 |
| BCOR | 0.102427544 | 1.716828147 | −1.525569877 |
| EFNA2 | 0.452825555 | 0.641136053 | −0.36647518 |
| LEFTY2 | 0.779378173 | 0.416545389 | −0.967518679 |
| NOTCH2 | 0.252055478 | 0.336041946 | −0.976488588 |
| ATM | −1.079149788 | −0.154750465 | 0.653606333 |
| TNFRSF10D | −1.120751017 | −0.023301806 | 0.695417144 |
| TGFB1 | −0.899502256 | 0.365260494 | 0.465688467 |
| DKK1 | −0.51629809 | 0.494457312 | 0.681706191 |

-continued

| Gene Symbol | Subgroup B centroid | Subgroup A centroid | Subgroup C centroid |
|---|---|---|---|
| IDH1 | −0.456773483 | 0.280037814 | 1.328340834 |
| COMP | −0.493285797 | 0.819951452 | 0.559484802 |
| PTEN | −0.764885608 | 0.128186717 | 0.825774951 |
| CALML6 | −1.273555604 | 0.849552584 | 0.267196887 |
| ERBB2 | −0.657891493 | 0.868247895 | −0.336671826 |
| IL11RA | −0.574798229 | 0.757662318 | −0.163619158 |
| PDGFD | −1.453013751 | 0.553101435 | 0.342655917 |
| PRKAR1B | −0.861735578 | 0.972622807 | −0.165967303 |
| DDB2 | −1.048250131 | 1.204621227 | 0.153767602 |
| TSPAN7 | −0.586966677 | 1.295666073 | −0.034132673 |
| FBXW7 | −0.551931516 | 0.743952534 | −0.032066214 |
| DLL1 | −0.787054447 | 1.297166278 | −0.028735448 |
| HES1 | −1.350029079 | 1.708702854 | −0.435881651 |
| COL27A1 | −0.678678331 | 0.932985532 | −0.06990641 |
| PDGFRA | −0.631137099 | 0.771453391 | 0.002225072 |
| CCND2 | −0.962072017 | 0.560935922 | 0.380438596 |
| CXXC4 | −1.135455693 | 0.927997254 | 0.168080612 |
| ACVR1B | −0.715425503 | 1.035669748 | −0.098350604 |
| DTX4 | −0.980772905 | 1.188830049 | 0.344156922 |
| TGFB3 | 0.779010809 | 0.453512809 | −1.151684947 |
| ZBTB16 | 0.744144038 | 0.300340307 | −1.501842069 |
| MAPK10 | 0.746376668 | −0.429814494 | −0.788117541 |
| SPOP | 1.211367282 | −0.57725145 | −0.550759513 |
| CASP7 | 0.943717067 | −1.042835031 | 0.467273755 |
| FGF21 | 0.616732498 | −1.397117511 | −0.041120318 |
| BAD | 0.606883027 | −1.201194407 | 0.232550134 |
| GSK3B | 0.885705342 | −1.39075076 | 0.610667114 |
| RBX1 | 0.166483538 | −1.055858889 | 0.71029212 |
| RELA | 0.611208315 | −0.869112536 | 0.201460338 |
| NUPR1 | 0.939785066 | −0.614213269 | −0.451309641 |
| DDIT3 | 1.18240637 | −1.318487563 | 0.223796918 |
| LAMB3 | 1.552616212 | −0.901993606 | 0.038750971 |
| TSHR | 0.452978334 | −1.281483556 | 0.321335827 |
| BCL2L1 | 0.490231758 | −0.792877145 | 0.85930403 |
| PIM1 | 1.163851083 | −0.58387838 | 0.43760126 |
| PRKCB | −0.220213795 | −0.44819218 | 0.693162357 |
| PLD1 | 0.078761527 | −0.747955173 | 0.330941788 |
| WNT3 | 0.443885608 | −0.810662403 | 0.009175691 |
| EIF4EBP1 | −0.070945866 | −0.897973905 | 0.010952684 |
| IRAK2 | 1.48428277 | −1.194483728 | −0.40789912 |
| PRKAA2 | 1.381125373 | −0.775485013 | −0.577567956 |
| DUSP5 | 0.327417325 | −1.005227809 | 0.322905127 |
| IL8 | 0.47273382 | −1.183932351 | 0.413001976 |
| MAP2K1 | 0.630232347 | −1.253785345 | −0.076450981 |
| BIRC3 | 0.718062464 | −1.255101549 | 0.237248246 |
| PLA2G4C | 1.496594473 | −1.346242957 | −0.15784499 |
| PPP3CC | 0.664650863 | −1.36423635 | 0.256830574 |
| CAPN2 | 0.643376276 | −1.155868131 | 0.247414615 |
| GZMB | 0.675014406 | −1.142799947 | 0.722529353 |
| CLCF1 | 0.716776379 | −0.847605107 | 0.342471593 |
| HGF | 0.290481662 | −0.610592648 | 0.50255412 |
| ITGA3 | 0.656718626 | −2.639015229 | 0.467661891 |
| IL6R | 1.25332586 | −1.599829447 | −0.032175941 |
| POLD4 | 0.672053389 | −1.147721365 | 0.210396896 |
| AMH | 0.288540555 | 0.250910932 | −0.994093078 |
| CACNA1C | 1.676167163 | −0.351229666 | −0.670030512 |
| CACNA1H | 0.850490171 | 0.252197083 | −0.853900562 |
| GNA11 | 1.124323404 | −0.745622387 | −0.153580798 |
| ITGA7 | 1.042754581 | −0.659327019 | −0.17332686 |
| JAG1 | 0.728317828 | −0.512594469 | −0.375946652 |
| LAMA5 | 1.622724844 | −1.060012408 | 0.072913031 |
| IDH2 | 1.478046247 | −0.923619017 | 0.358613769 |
| PLA2G10 | 0.931837184 | −0.102139226 | 0.135420614 |
| HSPB1 | 1.258279601 | −1.731442887 | 0.471013239 |
| LAMC2 | 1.16859924 | −1.360857477 | 0.005444094 |
| FLNC | 1.839552557 | −1.255013658 | 0.013631778 |
| NFKBIZ | 2.315727502 | −1.292126131 | 0.197458225 |
| FN1 | 0.660402717 | −1.171486781 | 0.234728184 |
| GNG12 | 0.867571726 | −0.981276666 | 0.471261377 |
| PDGFC | 1.196009475 | −1.133981891 | 0.004647767 |
| GAS1 | 0.779622888 | −0.752350475 | 0.219109788 |
| CDKN2D | 1.442455149 | −2.288021107 | 0.432605996 |
| TNC | 2.489192272 | −1.589168535 | −0.18592867 |
| CDKN2A | 1.509085425 | −0.73385756 | −0.063471162 |
| CDKN2B | 1.969916123 | −1.427909465 | 0.040850212 |
| INHBA | 1.701129382 | −1.951616488 | 0.011540028 |

-continued

| Gene Symbol | Subgroup B centroid | Subgroup A centroid | Subgroup C centroid |
|---|---|---|---|
| PTPRR | 1.451595841 | −1.532015885 | 0.509429781 |
| NOTCH3 | 0.896323229 | −0.97089252 | 0.204819781 |
| FLNA | 3.352606408 | −1.630559407 | 0.110599618 |
| ITGB3 | 2.029627821 | −1.363726479 | 0.172308131 |
| CDH1 | 1.417579351 | −0.563519168 | −0.012000775 |
| IL22RA1 | 0.677423648 | −0.861368018 | −0.084338277 |
| PRKAR2A | 0.954173113 | −1.411559699 | −0.110220662 |
| DTX3 | 0.836185822 | −0.362975758 | −0.481378145 |
| GRIN2A | 1.367454914 | −0.535776184 | −0.271174006 |
| POLE2 | 0.797767805 | −0.686659307 | −0.015103545 |
| CDKN2C | 1.659187221 | −0.368692467 | −0.280435804 |
| CCNE2 | 2.322615612 | −0.285274237 | −0.620886998 |
| FANCE | 1.739950882 | −0.174523797 | −1.115444165 |
| CDC25C | 0.885753996 | −0.614233996 | −0.633132809 |
| FANCA | 0.843349767 | −0.327032636 | −0.853923908 |
| CCNA2 | 1.709739605 | −0.762854153 | −0.151256005 |
| DNMT1 | 1.087975952 | −0.772201927 | −0.139753541 |
| WHSC1 | 1.011227482 | −0.710351274 | 0.184213773 |
| E2F1 | 1.066547328 | −0.894977636 | −0.186057173 |
| PTTG2 | 0.995372679 | −1.454954386 | 0.043486443 |
| RFC4 | 1.730057786 | −0.638599876 | −0.508480338 |
| MCM2 | 1.529183146 | −0.36493793 | −0.479749297 |
| MCM4 | 1.070557299 | −0.628650321 | 0.140545393 |
| BRCA2 | 1.292667438 | −0.897838271 | 0.100241908 |
| TTK | 2.388139352 | −0.618834387 | −0.128012393 |
| CCNB1 | 1.451881304 | −0.619865956 | −0.079524277 |
| MSH6 | 1.499274067 | −0.5013127 | −0.336590614 |
| MCM5 | 1.98081102 | −0.697209461 | −0.578660576 |
| UBE2T | 1.85858348 | −0.105697652 | −0.665881982 |
| FEN1 | 1.86125434 | −0.646411517 | −0.576062555 |
| CHEK1 | 1.448005524 | −0.836815017 | −0.357022212 |
| BRIP1 | 1.969177489 | −0.504861708 | −0.218232737 |
| CDC7 | 1.699141198 | −0.915926744 | −0.522885786 |
| ITGA8 | 1.543535453 | −0.238387103 | −1.639134229 |
| ETS2 | 0.779810809 | 0.198093282 | −0.575997412 |
| COL4A6 | 1.658235267 | −0.282608549 | −1.56570051 |
| LAMA3 | 2.083772989 | −0.709274494 | −0.584584899 |
| GADD45G | 1.022032515 | −0.43766438 | −0.202119219 |
| ID2 | 0.62903887 | −0.510034449 | 0.119602389 |
| CACNB2 | 0.981132087 | −0.865116096 | 0.038963893 |
| NKD1 | 2.691019394 | −0.322986548 | −0.744692386 |
| SOCS2 | 0.834990812 | −0.655453649 | −0.071526563 |
| PLCB4 | 0.508382694 | −1.029629816 | −0.727123493 |
| RASGRP2 | 1.415707148 | −0.84422873 | −0.216800183 |
| IRS1 | 1.47181196 | −0.40396467 | 0.227234957 |
| TNR | 1.180868996 | −0.840068366 | −0.092317008 |
| GADD45A | 1.287113277 | −1.517075592 | 0.011215464 |
| ZAK | 1.643122992 | −0.497654428 | −0.637329531 |
| FGF7 | 1.698227137 | −1.240536774 | −0.522181449 |
| PBX1 | 1.467757304 | −0.234263903 | −0.375071496 |
| PPARG | 0.138766121 | −0.932222796 | 0.483262572 |
| THBS1 | 0.254930123 | −0.997056609 | 0.173708474 |
| TNFAIP3 | 0.145328112 | −1.051965129 | 0.524290309 |
| EYA1 | 0.2928126 | −1.028756263 | 0.071321766 |
| EFNA5 | 0.001526286 | −1.149909284 | 0.044343314 |
| MYC | 0.001204978 | −1.246321996 | 0.792535029 |
| NFKB1 | −0.04492968 | −1.203821974 | 0.563903708 |
| RUNX1 | −0.29660105 | −0.587183221 | 0.975896848 |
| COL3A1 | −0.05310455 | −0.938619869 | 0.330406692 |
| COL5A2 | 0.066324157 | −1.298836749 | 0.702791004 |
| SPRY1 | −0.261396451 | −0.572573824 | 0.808702985 |
| VEGFC | 0.277920507 | −0.584003317 | 0.583459169 |
| COL4A4 | −0.215428822 | −0.865628696 | 0.850231366 |
| SOCS3 | 0.190162345 | −0.966843307 | 1.157732644 |
| ETV1 | −0.483944692 | −0.472162475 | 0.667492018 |
| NRAS | −0.40205324 | −0.741671466 | 0.618482163 |
| LIF | −0.427738236 | −0.89005586 | 0.65285878 |
| APC | −0.41323835 | −1.145962291 | 0.569063763 |
| PLAT | 0.255086414 | −0.897781696 | 0.652706703 |
| KAT2B | 0.169588215 | −0.715561144 | 0.808610693 |
| MET | −0.487219685 | −0.569517119 | 0.528969462 |
| DUSP10 | 1.162440885 | −1.43248128 | 0.453731599 |
| PPARGCIA | 1.101127687 | −0.885265217 | 0.209763192 |
| WNT16 | 0.569244222 | −1.353938971 | 0.786026088 |
| CALML5 | −0.254803322 | −1.202570257 | 0.868342334 |
| GATA3 | −0.095593162 | −1.173998403 | 0.559141534 |

| Gene Symbol | Subgroup B centroid | Subgroup A centroid | Subgroup C centroid |
|---|---|---|---|
| IL15 | 0.185965654 | −0.529551785 | 0.811668987 |
| IL2RB | 0.867636615 | −0.725722192 | 0.404721588 |
| IL7R | 0.500044032 | −1.04018038 | 0.461856038 |
| IL3RA | 0.322997508 | −0.744100389 | 0.710771403 |
| NOS3 | 0.031965527 | −0.55997275 | 1.008066472 |
| IL6 | 0.25202091 | −1.057818045 | 0.521808798 |
| MAP3K8 | 0.525534565 | −0.629689865 | 0.558661012 |
| BCL2A1 | −0.118492282 | −1.248060312 | 0.535233973 |
| SHC1 | 0.432448249 | −1.095032147 | 0.793300777 |
| TNFRSF10A | −0.469698881 | −0.657359638 | 0.525516546 |
| CASP10 | −0.489827618 | −0.346416482 | 1.154981817 |
| TLR4 | −0.502549677 | −0.321086708 | 0.889080653 |
| GRB2 | −0.437187727 | −0.814409187 | 2.119019854 |
| RAC2 | −0.813796838 | −0.558222741 | 0.746175214 |
| CSF1R | −0.763822741 | −0.332235482 | 1.156562363 |
| PIK3R5 | −0.422120799 | −0.424025806 | 1.087625971 |
| TLR2 | −0.457895575 | −0.566882875 | 1.200496741 |
| PIK3CG | −0.498928755 | −0.404086965 | 1.099985115 |
| SYK | −0.471120916 | −0.497930912 | 1.929710234 |
| IL2RA | −0.030524763 | −0.840989014 | 0.663049508 |
| MFNG | −0.384916371 | −0.481471138 | 1.033405111 |
| BID | 0.088886574 | −0.575331123 | 0.818429222 |
| PIK3CD | −0.17143245 | 0.010877708 | 1.174375031 |
| RASGRF2 | −0.455902975 | −0.189934532 | 0.843247694 |
| TNFSF10 | −0.475279967 | −0.931256638 | 1.231408832 |
| ITGA6 | −0.832468699 | −0.251085473 | 0.693305201 |
| MMP9 | −0.182247094 | −0.647025881 | 1.303500224 |
| IGF1 | −1.319084701 | 0.348703024 | 0.801157409 |
| JAK3 | −1.313284985 | 0.162243618 | 0.887569963 |
| TGFBR2 | −0.576704709 | −0.33857086 | 0.682451581 |
| SPRY2 | −0.648697274 | −0.11309924 | 0.649505825 |
| LFNG | −0.644681481 | −0.098858024 | 0.709630093 |
| MPL | −0.067370728 | −0.6571279 | 0.612307561 |
| LAMC3 | −0.133458348 | −0.185543739 | 1.057434835 |
| RET | −0.205916792 | −0.027391926 | 0.770810755 |
| FOS | −0.494262419 | −0.199625214 | 0.643536599 |
| MAPK8IP1 | −0.239136578 | −0.505341384 | 0.517286908 |
| B2M | 0.234106651 | −0.551781156 | 1.211511026 |
| MYD88 | −1.01250718 | −0.955275251 | 1.683288678 |
| CHUK | 0.031111998 | −0.563848617 | 1.112479518 |
| MAP2K2 | 0.297626549 | −1.301076449 | 0.810353045 |
| IL19 | 0.114049756 | −1.237506873 | 0.753586963 |
| COL1A1 | −0.295920059 | −0.715165274 | 0.638320928 |
| PLAU | 0.011625842 | −0.971909393 | 0.821172402. |

14. The method of claim 13 wherein said cancer is sarcoma or soft tissue sarcoma.

15. A method of determining a prognosis following tyrosine kinase inhibitor (TKI) treatment in an individual with a cancer, the method comprising:
 (a) treating the individual with a TKI, wherein the TKI inhibits at least two targets from: BRAF, CSF1R, DDR1, DDR2, FGFR1, FGFR2, FGFR3, FLT1, FLT4, FRK, KDR, KIT, LCK, LYN, MAP2K6, NTRK1, PDGFRA, PDGFRB, RAF1, RET and TEK; and
 (b) determining in a biological sample obtained from the individual, expression levels of each of 40 or more of genes ACVR1B, AKT2, ALKBH3, AMH, ARID2, AMER1, ATM, ATR, B2M, BAD, BCL2, BCOR, BID, BIRC3, BMP4, BNIP3, BRAF, CACNA1C, CACNA1E, CACNA1G, CALML6, CARD11, CASP10, CCNB1, CCND1, CCNE1, CCNE2, CCNO, CDC25C, CDC6, CDC7, CDH1, CDK4, CDK6, CDKN2A, CDKN2B, CDKN2C, CDKN2D, CHEK1, CHUK, COL27A1, COL3A1, COL4A4, COL4A6, COL5A1, COL5A2, CREB3L4, CREBBP, CSF2, CXXC4, DAXX, DDB2, DLL1, DLL3, DNMT1, DTX3, DTX4, DUSP4, DUSP6, E2F1, E2F5, EFNA1, EFNA5, ERBB2, ERCC6, ETV4, EZH2, FANCA, FANCB, FANCE, FANCL, FAS, FBXW7, FEN1, FGF12, FGF5, FGF7, FLNA, FLNC, FN1, FOSL1, FUBP1, GADD45A, GLI3, GNA11, GNG12, GRIN2A, GSK3B, GTF2H3, HDAC10, HDAC11, HDAC4, HDAC5, HELLS, HES1, HIST1H3B, HOXA9, HSPB1, IBSP, IDH1, IDH2, IL11, IL11RA, IL12RB2, IL6, IL8, INHBA, IRS1, ITGA6, ITGA7, ITGA8, ITGB3, JAG1, JAK3, KAT2B, KITLG, KMT2C, LAMA3, LAMA5, LAMB3, LAMC3, LEFTY2, LFNG, LIF, LIG4, MAD2L2, MAP2K4, MAP2K6, MAPK10, MAPK8IP1, MCM2, MCM4, MCM5, MDC1, MDM2, MEN1, MET, MFNG, MLF1, MLH1, MLLT3, MLLT4, MMP7, MMP9, MSH2, MSH6, MTOR, MUTYH, MYC, MYD88, NASP, NFKB1, NFKBIZ, NOS3, NOTCH2, NPM1, NTHL1, NUMBL, PAX5, PBX1, PCNA, PDGFC, PDGFRA, PLCB4, PPP2CB, PPP2R2C, PPP3R1, PRKACA, PRKAR1B, PRKAR2A, PRKCB, PRKX, PRLR, PTCH1, PTEN, PTTG2, RAD21, RAD52, RB1, RBX1, RET, RFC4, SF3B1, SHC2, SHC4, SIN3A, SKP1, SKP2, SMAD3, SMAD4, SOCS2, SOCS3, SP1, SPOP, SPRY1, SPRY2, SSX1, STAT4, STK11, SYK, TFDP1, TGFB3, TGFBR2, THBS1, TLR4, TLX1, TNC, TNFRSF10B, TNFRSF10D, TNFSF10, TNR, TP53, TSPAN7, TTK, U2AF1, UBE2T, VEGFA, WEE1, WHSC1L1, WNT10B, WNT6, WT1, ZAK, ZBTB16, and ZIC2 by contacting nucleic acids in the sample with probes or primers, and detecting hybridization or amplification of said nucleic acids encoding said at least 40 genes,
(c) identifying the individual having expression levels of the 40 or more of genes determined in step (b) most similar to a first, second, fourth or fifth reference centroid as compared to a third reference centroid as having a poor prognosis, and
(d) treating the identified individual with an alternative therapy to said TKI selected from at least one of radiotherapy and chemotherapy;
wherein the reference centroids are:
(i) a first reference centroid corresponding to the expression profile of said 40 or more genes determined in a first group of subjects known to have cancer with PDGFRA-Hi/FGFR1-Lo expression;
(ii) a second reference centroid corresponding to the expression profile of said 40 or more genes determined in a second group of subjects known to have cancer with mutated TP53 and PDGFRA/FGFR1 expression that is not PDGFRA-Hi/FGFR1-Lo expression;
(iii) a third reference centroid corresponding to the expression profile of said 40 or more genes determined in a third group of subjects known to have cancer with (a) a gene expression profile having a closer match to the centroid of subgroup A than subgroups B or C of Table 3, (b) TP53 wild-type, and (c) PDGFRA/FGFR1 expression that is not PDGFRA-Hi/FGFR1-Lo expression;
(iv) a fourth reference centroid corresponding to the expression profile of said 40 or more genes determined in a fourth group of subjects known to have cancer with (a) a gene expression profile having a closer match to the centroid of subgroup B than subgroups A or C of Table 3, (b) TP53 wild-type, and (c) PDGFRA/FGFR1 expression that is not PDGFRA-Hi/FGFR1-Lo expression; and
(v) a fifth reference centroid corresponding to the expression profile of said 40 or more genes determined in a fifth group of subjects known to have cancer with (a) a gene expression profile having a closer match to the centroid of subgroup C than subgroups A or B of Table 3, (b) TP53 wild-type, and (c) PDGFRA/FGFR1 expression that is not PDGFRA-Hi/FGFR1-Lo expression
and wherein table 3 is:

| Gene Symbol | Subgroup B centroid | Subgroup A centroid | Subgroup C centroid |
| --- | --- | --- | --- |
| FGF9 | −0.787299586 | 0.684375081 | 0.071127474 |
| NFATC1 | −0.371691666 | 0.704052833 | 0.023044704 |
| FZD10 | −0.440193224 | 0.660391129 | 0.172537497 |
| HMGA2 | −1.323612428 | 0.295732763 | 0.90817728 |
| FZD9 | −1.075145616 | 0.616942772 | 0.410943305 |
| PRKX | −1.153743629 | 0.02023958 | 1.480748471 |
| CCND1 | −0.847605437 | −0.047679935 | 0.844326227 |
| MAP2K6 | −1.186458783 | 0.341738061 | 1.094717343 |
| TP53 | −1.053931167 | 0.276137891 | −0.07221507 |
| FANCF | −2.562689656 | 0.02114079 | 0.285248682 |
| HDAC10 | −0.864986527 | −0.466408988 | 1.358279782 |
| CARD11 | −1.225657695 | 0.031589204 | 1.277944476 |
| FGF5 | −1.030325063 | 0.388725522 | 0.844361302 |
| DUSP4 | −0.851980221 | −0.18231116 | 0.820109581 |
| IL12RB2 | −0.380856163 | −0.42852557 | 0.791789922 |
| E2F5 | −1.194613628 | −0.049929218 | 0.829615055 |
| CCR7 | −0.084056229 | −0.0392025 | 0.836628323 |
| PAX5 | −0.643065022 | 0.250705882 | 0.802373206 |
| NOG | −0.995613082 | 0.777936727 | −0.257207914 |
| PTCH1 | −0.633931616 | 2.131940241 | −0.891766233 |
| ZIC2 | 0.148829172 | 0.771918368 | −0.805607102 |
| CACNA1G | −0.66346841 | 0.911704604 | −0.1016264 |
| SMAD3 | −0.393760319 | 1.018703135 | −0.451762506 |
| CHAD | 0.029259868 | 0.92288135 | 0.235476291 |
| TLX1 | 0.06809746 | 0.867855103 | −0.263254402 |
| BCOR | 0.102427544 | 1.716828147 | −1.525569877 |
| EFNA2 | 0.452825555 | 0.641136053 | −0.36647518 |
| LEFTY2 | 0.779378173 | 0.416545389 | −0.967518679 |
| NOTCH2 | 0.252055478 | 0.336041946 | −0.976488588 |
| ATM | −1.079149788 | −0.154750465 | 0.653606333 |
| TNFRSF10D | −1.120751017 | −0.023301806 | 0.695417144 |
| TGFB1 | −0.899502256 | 0.365260494 | 0.465688467 |
| DKK1 | −0.51629809 | 0.494457312 | 0.681706191 |
| IDH1 | −0.456773483 | 0.280037814 | 1.328340834 |
| COMP | −0.493285797 | 0.819951452 | 0.559484802 |
| PTEN | −0.764885608 | 0.128186717 | 0.825774951 |
| CALML6 | −1.273555604 | 0.849552584 | 0.267196887 |
| ERBB2 | −0.657891493 | 0.868247895 | −0.336671826 |
| IL11RA | −0.574798229 | 0.757662318 | −0.163619158 |
| PDGFD | −1.453013751 | 0.553101435 | 0.342655917 |
| PRKAR1B | −0.861735578 | 0.972622807 | −0.165967303 |
| DDB2 | −1.048250131 | 1.204621227 | 0.153767602 |
| TSPAN7 | −0.586966677 | 1.295666073 | −0.034132673 |
| FBXW7 | −0.551931516 | 0.743952534 | −0.032066214 |
| DLL1 | −0.787054447 | 1.297166278 | −0.028735448 |
| HES1 | −1.350029079 | 1.708702854 | −0.435881651 |
| COL27A1 | −0.678678331 | 0.932985532 | −0.06990641 |

-continued

| Gene Symbol | Subgroup B centroid | Subgroup A centroid | Subgroup C centroid |
|---|---|---|---|
| PDGFRA | −0.631137099 | 0.771453391 | 0.002225072 |
| CCND2 | −0.962072017 | 0.560935922 | 0.380438596 |
| CXXC4 | −1.135455693 | 0.927997254 | 0.168080612 |
| ACVR1B | −0.715425503 | 1.035669748 | −0.098350604 |
| DTX4 | −0.980772905 | 1.188830049 | 0.344156922 |
| TGFB3 | 0.779010809 | 0.453512809 | −1.151684947 |
| ZBTB16 | 0.744144038 | 0.300340307 | −1.501842069 |
| MAPK10 | 0.746376668 | −0.429814494 | −0.788117541 |
| SPOP | 1.211367282 | −0.57725145 | −0.550759513 |
| CASP7 | 0.943717067 | −1.042835031 | 0.467273755 |
| FGF21 | 0.616732498 | −1.397117511 | −0.041120318 |
| BAD | 0.606883027 | −1.201194407 | 0.232550134 |
| GSK3B | 0.885705342 | −1.39075106 | 0.610667114 |
| RBX1 | 0.166483538 | −1.055858889 | 0.71029212 |
| RELA | 0.611208315 | −0.869112536 | 0.201460338 |
| NUPR1 | 0.939785066 | −0.614213269 | −0.451309641 |
| DDIT3 | 1.18240637 | −1.318487563 | 0.223796918 |
| LAMB3 | 1.552616212 | −0.901993606 | 0.038750971 |
| TSHR | 0.452978334 | −1.281483556 | 0.321335827 |
| BCL2L1 | 0.490231758 | −0.792877145 | 0.85930403 |
| PIM1 | 1.163851083 | −0.58387838 | 0.43760126 |
| PRKCB | −0.220213795 | −0.44819218 | 0.693162357 |
| PLD1 | 0.078761527 | −0.747955173 | 0.330941788 |
| WNT3 | 0.443885608 | −0.810662403 | 0.009175691 |
| EIF4EBP1 | −0.070945866 | −0.897973905 | 0.010952684 |
| IRAK2 | 1.48428277 | −1.194483728 | −0.40789912 |
| PRKAA2 | 1.381125373 | −0.775485013 | −0.577567956 |
| DUSP5 | 0.327417325 | −1.005227809 | 0.322905127 |
| IL8 | 0.47273382 | −1.183932351 | 0.413001976 |
| MAP2K1 | 0.630232347 | −1.253785345 | −0.076450981 |
| BIRC3 | 0.718062464 | −1.255101549 | 0.237248246 |
| PLA2G4C | 1.496594473 | −1.346242957 | −0.15784499 |
| PPP3CC | 0.664650863 | −1.36423635 | 0.256830574 |
| CAPN2 | 0.643376276 | −1.155868131 | 0.247414615 |
| GZMB | 0.675014406 | −1.142799947 | 0.722529353 |
| CLCF1 | 0.716776379 | −0.847605107 | 0.342471593 |
| HGF | 0.290481662 | −0.610592648 | 0.50255412 |
| ITGA3 | 0.656718626 | −2.639015229 | 0.467661891 |
| IL6R | 1.25332586 | −1.599829447 | −0.032175941 |
| POLD4 | 0.672053389 | −1.147721365 | 0.210396896 |
| AMH | 0.288540555 | 0.250910932 | −0.994093078 |
| CACNAIC | 1.676167163 | −0.351229666 | −0.670030512 |
| CACNA1H | 0.850490171 | 0.252197083 | −0.853900562 |
| GNA11 | 1.124323404 | −0.745622387 | −0.153580798 |
| ITGA7 | 1.042754581 | −0.659327019 | −0.17332686 |
| JAG1 | 0.728317828 | −0.512594469 | −0.375946652 |
| LAMA5 | 1.622724844 | −1.060012408 | 0.072913031 |
| IDH2 | 1.478046247 | −0.923619017 | 0.358613769 |
| PLA2G10 | 0.931837184 | −0.102139226 | 0.135420614 |
| HSPB1 | 1.258279601 | −1.731442887 | 0.471013239 |
| LAMC2 | 1.16859924 | −1.360857477 | 0.005444094 |
| FLNC | 1.839552557 | −1.255013658 | 0.013631778 |
| NFKBIZ | 2.315727502 | −1.292126131 | 0.197458225 |
| FN1 | 0.660402717 | −1.171486781 | 0.234728184 |
| GNG12 | 0.867571726 | −0.981276666 | 0.471261377 |
| PDGFC | 1.196009475 | −1.133981891 | 0.004647767 |
| GAS1 | 0.779622888 | −0.752350475 | 0.219109788 |
| CDKN2D | 1.442455149 | −2.288021107 | 0.432605996 |
| TNC | 2.489192272 | −1.589168535 | −0.18592867 |
| CDKN2A | 1.509085425 | −0.73385756 | −0.063471162 |
| CDKN2B | 1.969916123 | −1.427909465 | 0.040850212 |
| INHBA | 1.701129382 | −1.951616488 | 0.011540028 |
| PTPRR | 1.451595841 | −1.532015885 | 0.509429781 |
| NOTCH3 | 0.896323229 | −0.97089252 | 0.204819781 |
| FLNA | 3.352606408 | −1.630559407 | 0.110599618 |
| ITGB3 | 2.029627821 | −1.363726479 | 0.172308131 |
| CDH1 | 1.417579351 | −0.563519168 | −0.012000775 |
| IL22RA1 | 0.677423648 | −0.861368018 | −0.084338277 |
| PRKAR2A | 0.954173113 | −1.411559699 | −0.110220662 |
| DTX3 | 0.836185822 | −0.362975758 | −0.481378145 |
| GRIN2A | 1.367454914 | −0.535776184 | −0.271174006 |
| POLE2 | 0.797767805 | −0.686659307 | −0.015103545 |
| CDKN2C | 1.659187221 | −0.368692467 | −0.280435804 |
| CCNE2 | 2.322615612 | −0.285274237 | −0.620886998 |
| FANCE | 1.739950882 | −0.174523797 | −1.115444165 |
| CDC25C | 0.885753996 | −0.614233996 | −0.633132809 |

-continued

| Gene Symbol | Subgroup B centroid | Subgroup A centroid | Subgroup C centroid |
|---|---|---|---|
| FANCA | 0.843349767 | −0.327032636 | −0.853923908 |
| CCNA2 | 1.709739605 | −0.762854153 | −0.151256005 |
| DNMT1 | 1.087975952 | −0.772201927 | −0.139753541 |
| WHSC1 | 1.011227482 | −0.710351274 | 0.184213773 |
| E2F1 | 1.066547328 | −0.894977636 | −0.186057173 |
| PTTG2 | 0.995372679 | −1.454954386 | 0.043486443 |
| RFC4 | 1.730057786 | −0.638599876 | −0.508480338 |
| MCM2 | 1.529183146 | −0.36493793 | −0.479749297 |
| MCM4 | 1.070557299 | −0.628650321 | 0.140545393 |
| BRCA2 | 1.292667438 | −0.897838271 | 0.100241908 |
| TTK | 2.388139352 | −0.618834387 | −0.128012393 |
| CCNB1 | 1.451881304 | −0.619865956 | −0.079524277 |
| MSH6 | 1.499274067 | −0.5013127 | −0.336590614 |
| MCM5 | 1.98081102 | −0.697209461 | −0.578660576 |
| UBE2T | 1.85858348 | −0.105697652 | −0.665881982 |
| FEN1 | 1.86125434 | −0.646411517 | −0.576062555 |
| CHEK1 | 1.448005524 | −0.836815017 | −0.357022212 |
| BRIP1 | 1.969177489 | −0.504861708 | −0.218232737 |
| CDC7 | 1.699141198 | −0.915926744 | −0.522885786 |
| ITGA8 | 1.543535453 | −0.238387103 | −1.639134229 |
| ETS2 | 0.779810809 | 0.198093282 | −0.575997412 |
| COL4A6 | 1.658235267 | −0.282608549 | −1.56570051 |
| LAMA3 | 2.083772989 | −0.709274494 | −0.584584899 |
| GADD45G | 1.022032515 | −0.43766438 | −0.202119219 |
| ID2 | 0.62903887 | −0.510034449 | 0.119602389 |
| CACNB2 | 0.981132087 | −0.865116096 | 0.038963893 |
| NKD1 | 2.691019394 | −0.322986548 | −0.744692386 |
| SOCS2 | 0.834990812 | −0.655453649 | −0.071526563 |
| PLCB4 | 0.508382694 | −1.029629816 | −0.727123493 |
| RASGRP2 | 1.415707148 | −0.84422873 | −0.216800183 |
| IRS1 | 1.47181196 | −0.40396467 | 0.227234957 |
| TNR | 1.180868996 | −0.840068366 | −0.092317008 |
| GADD45A | 1.287113277 | −1.517075592 | 0.011215464 |
| ZAK | 1.643122992 | −0.497654428 | −0.637329531 |
| FGF7 | 1.698227137 | −1.240536774 | −0.522181449 |
| PBX1 | 1.467757304 | −0.234263903 | −0.375071496 |
| PPARG | 0.138766121 | −0.932222796 | 0.483262572 |
| THBS1 | 0.254930123 | −0.997056609 | 0.173708474 |
| TNFAIP3 | 0.145328112 | −1.051965129 | 0.524290309 |
| EYA1 | 0.2928126 | −1.028756263 | 0.071321766 |
| EFNA5 | 0.001526286 | −1.149909284 | 0.044343314 |
| MYC | 0.001204978 | −1.246321996 | 0.792535029 |
| NFKB1 | −0.04492968 | −1.203821974 | 0.563903708 |
| RUNX1 | −0.29660105 | −0.587183221 | 0.975896848 |
| COL3A1 | −0.05310455 | −0.938619869 | 0.330406692 |
| COL5A2 | 0.066324157 | −1.298836749 | 0.702791004 |
| SPRY1 | −0.261396451 | −0.572573824 | 0.808702985 |
| VEGFC | 0.277920507 | −0.584003317 | 0.583459169 |
| COL4A4 | −0.215428822 | −0.865628696 | 0.850231366 |
| SOCS3 | 0.190162345 | −0.966843307 | 1.157732644 |
| ETV1 | −0.483944692 | −0.472162475 | 0.667492018 |
| NRAS | −0.40205324 | −0.741671466 | 0.618482163 |
| LIF | −0.427738236 | −0.89005586 | 0.65285878 |
| APC | −0.41323835 | −1.145962291 | 0.569063763 |
| PLAT | 0.255086414 | −0.897781696 | 0.652706703 |
| KAT2B | 0.169588215 | −0.715561144 | 0.808610693 |
| MET | −0.487219685 | −0.569517119 | 0.528969462 |
| DUSP10 | 1.162440885 | −1.43248128 | 0.453731599 |
| PPARGC1A | 1.101127687 | −0.885265217 | 0.209763192 |
| WNT16 | 0.569244222 | −1.353938971 | 0.786026088 |
| CALML5 | −0.254803322 | −1.202570257 | 0.868342334 |
| GATA3 | −0.095593162 | −1.173998403 | 0.559141534 |
| IL15 | 0.185965654 | −0.529551785 | 0.811668987 |
| IL2RB | 0.867636615 | −0.725722192 | 0.404721588 |
| IL7R | 0.500044032 | −1.04018038 | 0.461856038 |
| IL3RA | 0.322997508 | −0.744100389 | 0.710771403 |
| NOS3 | 0.031965527 | −0.55997275 | 1.008066472 |
| IL6 | 0.25202091 | −1.057818045 | 0.521808798 |
| MAP3K8 | 0.525534565 | −0.629689865 | 0.558661012 |
| BCL2A1 | −0.118492282 | −1.248060312 | 0.535233973 |
| SHC1 | 0.432448249 | −1.095032147 | 0.793300777 |
| TNFRSF10A | −0.469698881 | −0.657359638 | 0.525516546 |
| CASP10 | −0.489827618 | −0.346416482 | 1.154981817 |
| TLR4 | −0.502549677 | −0.321086708 | 0.889080653 |
| GRB2 | −0.437187727 | −0.814409187 | 2.119019854 |
| RAC2 | −0.813796838 | −0.558222741 | 0.746175214 |

-continued

| Gene Symbol | Subgroup B centroid | Subgroup A centroid | Subgroup C centroid |
|---|---|---|---|
| CSF1R | −0.763822741 | −0.332235482 | 1.156562363 |
| PIK3R5 | −0.422120799 | −0.424025806 | 1.087625971 |
| TLR2 | −0.457895575 | −0.566882875 | 1.200496741 |
| PIK3CG | −0.498928755 | −0.404086965 | 1.099985115 |
| SYK | −0.471120916 | −0.497930912 | 1.929710234 |
| IL2RA | −0.030524763 | −0.840989014 | 0.663049508 |
| MFNG | −0.384916371 | −0.481471138 | 1.033405111 |
| BID | 0.088886574 | −0.575331123 | 0.818429222 |
| PIK3CD | −0.17143245 | 0.010877708 | 1.174375031 |
| RASGRF2 | −0.455902975 | −0.189934532 | 0.843247694 |
| TNFSF10 | −0.475279967 | −0.931256638 | 1.231408832 |
| ITGA6 | −0.832468699 | −0.251085473 | 0.693305201 |
| MMP9 | −0.182247094 | −0.647025881 | 1.303500224 |
| IGF1 | −1.319084701 | 0.348703024 | 0.801157409 |
| JAK3 | −1.313284985 | 0.162243618 | 0.887569963 |
| TGFBR2 | −0.576704709 | −0.33857086 | 0.682451581 |
| SPRY2 | −0.648697274 | −0.11309924 | 0.649505825 |
| LFNG | −0.644681481 | −0.098858024 | 0.709630093 |
| MPL | −0.067370728 | −0.6571279 | 0.612307561 |
| LAMC3 | −0.133458348 | −0.185543739 | 1.057434835 |
| RET | −0.205916792 | −0.027391926 | 0.770810755 |
| FOS | −0.494262419 | −0.199625214 | 0.643536599 |
| MAPK8IP1 | −0.239136578 | −0.505341384 | 0.517286908 |
| B2M | 0.234106651 | −0.551781156 | 1.211511026 |
| MYD88 | −1.01250718 | −0.955275251 | 1.683288678 |
| CHUK | 0.031111998 | −0.563848617 | 1.112479518 |
| MAP2K2 | 0.297626549 | −1.301076449 | 0.810353045 |
| IL19 | 0.114049756 | −1.237506873 | 0.753586963 |
| COL1A1 | −0.295920059 | −0.715165274 | 0.638320928 |
| PLAU | 0.011625842 | −0.971909393 | 0.821172402 |

16. A method of determining a prognosis following tyrosine kinase inhibitor (TKI) treatment in an individual with cancer, the method comprising:

(a) treating the individual with a TKI, wherein the TKI inhibits at least two targets from: BRAF, CSF1R, DDR1, DDR2, FGFR1, FGFR2, FGFR3, FLT1, FLT4, FRK, KDR, KIT, LCK, LYN, MAP2K6, NTRK1, PDGFRA, PDGFRB, RAF1, RET and TEK; and (b) determining in a biological sample obtained from the individual the expression levels of each of 40 or more of genes ACVR1B, AKT2, ALKBH3, AMH, ARID2, AMER1, ATM, ATR, B2M, BAD, BCL2, BCOR, BID, BIRC3, BMP4, BNIP3, BRAF, CACNA1C, CACNA1E, CACNA1G, CALML6, CARD11, CASP10, CCNB1, CCND1, CCNE1, CCNE2, CCNO, CDC25C, CDC6, CDC7, CDH1, CDK4, CDK6, CDKN2A, CDKN2B, CDKN2C, CDKN2D, CHEK1, CHUK, COL27A1, COL3A1, COL4A4, COL4A6, COL5A1, COL5A2, CREB3L4, CREBBP, CSF2, CXXC4, DAXX, DDB2, DLL1, DLL3, DNMT1, DTX3, DTX4, DUSP4, DUSP6, E2F1, E2F5, EFNA1, EFNA5, ERBB2, ERCC6, ETV4, EZH2, FANCA, FANCB, FANCE, FANCL, FAS, FBXW7, FEN1, FGF12, FGF5, FGF7, FLNA, FLNC, FN1, FOSL1, FUBP1, GADD45A, GLI3, GNA11, GNG12, GRIN2A, GSK3B, GTF2H3, HDAC10, HDAC11, HDAC4, HDAC5, HELLS, HES1, HIST1H3B, HOXA9, HSPB1, IBSP, IDH1, IDH2, IL11, IL11RA, IL12RB2, IL6, IL8, INHBA, IRS1, ITGA6, ITGA7, ITGA8, ITGB3, JAG1, JAK3, KAT2B, KITLG, KMT2C, LAMA3, LAMA5, LAMB3, LAMC3, LEFTY2, LFNG, LIF, LIG4, MAD2L2, MAP2K4, MAP2K6, MAPK10, MAPK8IP1, MCM2, MCM4, MCM5, MDC1, MDM2, MEN1, MET, MFNG, MLF1, MLH1, MLLT3, MLLT4, MMP7, MMP9, MSH2, MSH6, MTOR, MUTYH, MYC, MYD88, NASP, NFKB1, NFKBIZ, NOS3, NOTCH2, NPM1, NTHL1, NUMBL, PAX5, PBX1, PCNA, PDGFC, PDGFRA, PLCB4, PPP2CB, PPP2R2C, PPP3R1, PRKACA, PRKAR1B, PRKAR2A, PRKCB, PRKX, PRLR, PTCH1, PTEN, PTTG2, RAD21, RAD52, RB1, RBX1, RET, RFC4, SF3B1, SHC2, SHC4, SIN3A, SKP1, SKP2, SMAD3, SMAD4, SOCS2, SOCS3, SP1, SPOP, SPRY1, SPRY2, SSX1, STAT4, STK11, SYK, TFDP1, TGFB3, TGFBR2, THBS1, TLR4, TLX1, TNC, TNFRSF10B, TNFRSF10D, TNFSF10, TNR, TP53, TSPAN7, TTK, U2AF1, UBE2T, VEGFA, WEE1, WHSC1L1, WNT10B, WNT6, WT1, ZAK, ZBTB16, and ZIC2 by contacting nucleic acids in the sample with probes or primers, and detecting hybridization or amplification of said nucleic acids encoding said at least 40 genes, (c) identifying the individual (i) having expression levels of the 40 or more of genes determined in step (b) most similar to the reference centroid A(3) of Table 6, as compared to any of reference centroids IHC+(1), TP53(2), B(4), C(5) listed in Table 6; as having a good prognosis; or (ii) having expression levels of the 40 or more of genes determined in step (b) most similar to the reference centroid IHC+(1), TP53(2), B(4) or C(5) of Table 6 than centroid A(3) of Table 6; as having a poor prognosis, and (d) continuing to treat the identified individual in step (c)(i) with said TKI, or treating the identified individual in step (c)(ii) with an alternative therapy to said TKI selected from at least one of radiotherapy and chemotherapy, wherein table 6 is:

|  | IHC+ (1) | TP53 (2) | Subgroup A centroid (3) | Subgroup B centroid (4) | Subgroup C centroid (5) |
|---|---|---|---|---|---|
| ACVR1B | −0.15832131 | −0.15832131 | 0.54151057 | −0.15832131 | −0.15832131 |
| AKT2 | −0.30994329 | −0.01919342 | −0.01919342 | −0.01919342 | −0.01919342 |
| ALKBH3 | −0.51139577 | −0.06705258 | −0.06705258 | −0.06705258 | −0.06705258 |
| AMER1 | −0.53544069 | −0.00240749 | −0.00240749 | −0.00240749 | −0.00240749 |
| AMH | −0.15178973 | −0.15178973 | −0.15178973 | −0.15178973 | −1.44283676 |
| ARID2 | −0.01621451 | −0.21931165 | −0.01621451 | −0.01621451 | −0.01621451 |
| ATM | −0.14140818 | −0.14140818 | −0.14140818 | −0.59982807 | −0.14140818 |
| ATR | −0.41755241 | −0.0616667 | −0.0616667 | −0.0616667 | −0.0616667 |
| B2M | 0.03806218 | 0.03806218 | 0.03806218 | 0.03806218 | 0.47297616 |
| BAD | 0.0248534 | 0.27474345 | 0.0248534 | 0.0248534 | 0.0248534 |
| BCL2 | 0.06351095 | 0.06351095 | 0.88344382 | 0.06351095 | 0.06351095 |
| BCOR | 0.05103077 | 0.05103077 | 1.27280929 | 0.05103077 | 0.05103077 |
| BID | 0.58151032 | 0.0455798 | 0.0455798 | 0.0455798 | 0.0455798 |
| BIRC3 | −0.02761286 | −0.02761286 | −1.18099641 | −0.02761286 | −0.02761286 |
| BMP4 | 1.30239681 | 0.21301304 | 0.21301304 | 0.21301304 | 0.21301304 |
| BNIP3 | −0.19708889 | −0.90886955 | −0.19708889 | −0.19708889 | −0.19708889 |
| BRAF | −0.05422312 | −0.05422312 | 0.2484416 | −0.05422312 | −0.05422312 |
| CACNAIC | −0.13582518 | −0.13582518 | −0.13582518 | 0.96758744 | −0.13582518 |
| CACNA1E | 0.17105202 | −0.67762073 | 0.17105202 | 0.17105202 | 0.17105202 |
| CACNA1G | 0.01978593 | 0.99078335 | 0.01978593 | 0.01978593 | 0.01978593 |
| CALML6 | 0.01910958 | 0.01910958 | 0.93075557 | 0.01910958 | 0.01910958 |
| CARD11 | 0.3510245 | 0.3510245 | 0.3510245 | 0.3510245 | 1.54991905 |
| CASP10 | −0.18050625 | −0.18050625 | −0.18050625 | −0.18050625 | 0.39904926 |
| CCNB1 | −0.08780076 | 0.35186891 | −0.08780076 | −0.08780076 | −0.08780076 |
| CCND1 | 0.06716593 | 0.06716593 | 0.06716593 | 0.06716593 | 0.89918266 |
| CCNE1 | 0.03028376 | 0.4673283 | 0.03028376 | 0.03028376 | 0.03028376 |
| CCNE2 | −0.02855095 | −0.02855095 | −0.02855095 | 0.96943946 | −0.02855095 |
| CCNO | −0.74650411 | 0.05814408 | 0.05814408 | 0.05814408 | 0.05814408 |
| CDC25C | −0.20812329 | 0.4321119 | −0.20812329 | −0.20812329 | −0.20812329 |
| CDC6 | −0.13977911 | 0.25507254 | −0.13977911 | −0.13977911 | −0.13977911 |
| CDC7 | −0.0401465 | −0.0401465 | −0.0401465 | −0.0401465 | −0.48566159 |
| CDH1 | 0.5933622 | 0.5933622 | 0.5933622 | 2.70632966 | 0.5933622 |
| CDK4 | 0.02878578 | 0.02878578 | 0.02878578 | 0.02878578 | 0.43127765 |
| CDK6 | −0.09882276 | −0.80702231 | −0.09882276 | −0.09882276 | −0.09882276 |
| CDKN2A | −0.43348608 | 0.40775211 | −0.43348608 | −0.43348608 | −0.43348608 |
| CDKN2B | −0.30199667 | −0.30199667 | −1.13360288 | −0.30199667 | −0.30199667 |
| CDKN2C | −0.0741678 | 0.71842723 | −0.0741678 | −0.0741678 | −0.0741678 |
| CDKN2D | −0.07445202 | −0.07445202 | −0.88415539 | −0.07445202 | −0.07445202 |
| CHEK1 | −0.03670758 | 0.36086714 | −0.03670758 | −0.03670758 | −0.03670758 |
| CHUK | 0.01020521 | 0.01020521 | 0.01020521 | 0.01020521 | 0.3304295 |
| COL27A1 | −0.058947 | −0.058947 | −0.058947 | −1.02899246 | −0.058947 |
| COL3A1 | −0.04583553 | −0.04583553 | −1.12616257 | −0.04583553 | −0.04583553 |
| COL4A4 | −0.19065625 | −0.19065625 | −0.19065625 | −0.19065625 | 0.4691999 |
| COL4A6 | −0.07291156 | −0.07291156 | −0.07291156 | 2.30094864 | −0.07291156 |
| COL5A1 | 0.82895474 | 0.02869965 | 0.02869965 | 0.02869965 | 0.02869965 |
| COL5A2 | −0.10633063 | −0.10633063 | −1.20961533 | −0.10633063 | −0.10633063 |
| CREB3L4 | −0.11547721 | −0.11547721 | −0.11547721 | −0.11547721 | −0.52285762 |
| CREBBP | −0.06115984 | −0.06115984 | 0.41412808 | −0.06115984 | −0.06115984 |
| CSF2 | 1.21387949 | 0.22876539 | 0.22876539 | 0.22876539 | 0.22876539 |
| CXXC4 | 0.1857577 | 0.1857577 | 1.56739048 | 0.1857577 | 0.1857577 |
| DAXX | −0.51598315 | −0.03754511 | −0.03754511 | −0.03754511 | −0.03754511 |
| DDB2 | −0.02877707 | −0.02877707 | 0.73742507 | −0.02877707 | −0.02877707 |
| DLL1 | −0.02445967 | −0.02445967 | 1.38299745 | −0.02445967 | −0.02445967 |
| DLL3 | 0.11550972 | 0.11550972 | 0.11550972 | 0.11550972 | 0.99134018 |
| DNMT1 | −0.06492494 | 0.22828132 | −0.06492494 | −0.06492494 | −0.06492494 |
| DTX3 | −0.00091037 | −0.00091037 | −0.00091037 | 0.57881747 | −0.00091037 |
| DTX4 | −0.13468574 | −0.13468574 | −0.13468574 | −1.34786396 | −0.13468574 |
| DUSP4 | −0.06613786 | −0.06613786 | −0.06613786 | −0.06613786 | 0.79464751 |
| DUSP6 | 0.64607125 | −0.13511565 | −0.13511565 | −0.13511565 | −0.13511565 |
| E2F1 | −0.15690288 | 0.58630128 | −0.15690288 | −0.15690288 | −0.15690288 |
| E2F5 | −0.15133642 | −0.15133642 | −0.15133642 | −0.15133642 | 0.49181536 |
| EFNA1 | −0.11668426 | −0.11668426 | −0.11668426 | −0.11668426 | 0.53773733 |
| EFNA5 | −0.36099156 | −0.36099156 | −2.00486828 | −0.36099156 | −0.36099156 |
| ERBB2 | −0.17090683 | −0.17090683 | 0.56247468 | −0.17090683 | −0.17090683 |
| ERCC6 | −0.03591121 | −0.03591121 | 0.35767641 | −0.03591121 | −0.03591121 |
| ETV4 | 1.42923832 | 0.17676653 | 0.17676653 | 0.17676653 | 0.17676653 |
| EZH2 | −0.13282806 | −0.13282806 | −0.13282806 | −0.13282806 | −0.54806145 |
| FANCA | −0.09874728 | −0.09874728 | −0.09874728 | −0.09874728 | −0.73163501 |
| FANCB | −0.07545182 | 0.28149725 | −0.07545182 | −0.07545182 | −0.07545182 |
| FANCE | 0.03359085 | 0.03359085 | 0.03359085 | 0.82988961 | 0.03359085 |
| FANCL | −0.56516661 | −0.01293858 | −0.01293858 | −0.01293858 | −0.01293858 |
| FAS | −0.11858783 | 0.47425096 | −0.11858783 | −0.11858783 | −0.11858783 |
| FBXW7 | −0.03157043 | −0.03157043 | 0.54732624 | −0.03157043 | −0.03157043 |
| FEN1 | 0.05373816 | 0.05373816 | 0.05373816 | 0.82272386 | 0.05373816 |
| FGF12 | −0.14368413 | −0.91516385 | −0.14368413 | −0.14368413 | −0.14368413 |
| FGF5 | 0.48339559 | 0.48339559 | 0.48339559 | 0.48339559 | 1.59245056 |
| FGF7 | −0.45472135 | −0.45472135 | −0.45472135 | 1.11593826 | −0.45472135 |
| FLNA | 0.13671796 | 0.13671796 | 0.13671796 | 1.69109283 | 0.13671796 |

-continued

|  | IHC+ (1) | TP53 (2) | Subgroup A centroid (3) | Subgroup B centroid (4) | Subgroup C centroid (5) |
| --- | --- | --- | --- | --- | --- |
| FLNC | −0.467287 | −0.467287 | −0.467287 | 0.96770635 | −0.467287 |
| FN1 | −0.04593874 | −0.04593874 | −1.18366565 | −0.04593874 | −0.04593874 |
| FOSL1 | 0.85033616 | 0.03958811 | 0.03958811 | 0.03958811 | 0.03958811 |
| FUBP1 | −0.06703661 | −0.06703661 | 0.36412825 | −0.06703661 | −0.06703661 |
| GADD45A | 0.06766933 | 0.06766933 | 0.06766933 | 0.84508039 | 0.06766933 |
| GLI3 | −0.17664829 | −0.17664829 | −0.17664829 | −0.17664829 | −0.77449891 |
| GNA11 | 0.02755931 | 0.02755931 | 0.02755931 | 0.64967723 | 0.02755931 |
| GNG12 | −0.16995566 | −0.16995566 | −0.85810693 | −0.16995566 | −0.16995566 |
| GRIN2A | 0.36120599 | 1.33705393 | 0.36120599 | 0.36120599 | 0.36120599 |
| GSK3B | −0.3289616 | −0.04260185 | −0.04260185 | −0.04260185 | −0.04260185 |
| GTF2H3 | −0.09051522 | −0.09051522 | 0.33573726 | −0.09051522 | −0.09051522 |
| HDAC10 | −0.12352944 | −0.12352944 | −0.12352944 | −0.12352944 | 0.1647408 |
| HDAC11 | −0.66902718 | −0.09322847 | −0.09322847 | −0.09322847 | −0.09322847 |
| HDAC4 | −0.02614516 | −0.02614516 | 0.6056055 | −0.02614516 | −0.02614516 |
| HDAC5 | −0.44311772 | −0.02343759 | −0.02343759 | −0.02343759 | −0.02343759 |
| HELLS | −0.08627003 | 0.26759075 | −0.08627003 | −0.08627003 | −0.08627003 |
| HES1 | −0.14475643 | −0.14475643 | 1.09720336 | −0.14475643 | −0.14475643 |
| HIST1H3B | −0.02480871 | 0.56445002 | −0.02480871 | −0.02480871 | −0.02480871 |
| HOXA9 | −0.12800919 | 0.60420276 | −0.12800919 | −0.12800919 | −0.12800919 |
| HSPB1 | −0.10464244 | −0.10464244 | −0.10464244 | 0.60254908 | −0.10464244 |
| IBSP | 0.25316339 | 1.48773858 | 0.25316339 | 0.25316339 | 0.25316339 |
| IDH1 | −0.0139642 | −0.0139642 | −0.0139642 | −0.0139642 | 0.35797145 |
| IDH2 | 0.14237266 | 0.14237266 | 0.14237266 | 0.97071118 | 0.14237266 |
| IL11 | 1.73407021 | 0.23740715 | 0.23740715 | 0.23740715 | 0.23740715 |
| IL11RA | −0.01835972 | −0.01835972 | 0.89759852 | −0.01835972 | −0.01835972 |
| IL12RB2 | 0.12363856 | 0.12363856 | 0.12363856 | 0.12363856 | 1.18873886 |
| IL6 | 1.68316336 | 0.1815675 | 0.1815675 | 0.1815675 | 0.1815675 |
| IL8 | 2.10056954 | 0.1309187 | 0.1309187 | 0.1309187 | 0.1309187 |
| INHBA | −0.44395722 | −0.44395722 | −1.93039159 | −0.44395722 | −0.44395722 |
| IRS1 | 0.06052758 | 0.06052758 | 0.06052758 | 1.18660836 | 0.06052758 |
| ITGA6 | 0.0423311 | 0.0423311 | 0.0423311 | 0.0423311 | 0.62988286 |
| ITGA7 | 0.0163744 | 0.0163744 | 0.0163744 | 1.40919398 | 0.0163744 |
| ITGA8 | −0.60196552 | −0.60196552 | −0.60196552 | 1.2401644 | −0.60196552 |
| ITGB3 | −0.03320016 | −0.03320016 | −1.24850492 | −0.03320016 | −0.03320016 |
| JAG1 | 0.16492599 | 0.71120586 | 0.16492599 | 0.16492599 | 0.16492599 |
| JAK3 | −0.20341296 | −0.20341296 | −0.20341296 | −1.06969998 | −0.20341296 |
| KAT2B | −0.04101357 | −0.04101357 | −0.04101357 | −0.04101357 | 0.32993194 |
| KITLG | −0.11534823 | 0.37839946 | −0.11534823 | −0.11534823 | −0.11534823 |
| KMT2C | −0.06007021 | −0.06007021 | 0.27599606 | −0.06007021 | −0.06007021 |
| LAMA3 | −0.02993329 | −0.02993329 | −0.02993329 | 1.33919007 | −0.02993329 |
| LAMA5 | 0.22274146 | 0.22274146 | 0.22274146 | 1.55832429 | 0.22274146 |
| LAMB3 | −0.12041485 | −0.12041485 | −0.12041485 | 1.14007598 | −0.12041485 |
| LAMC3 | 0.04945966 | 0.04945966 | 0.04945966 | 0.04945966 | 1.10866665 |
| LEFTY2 | 0.51860941 | 0.51860941 | 0.51860941 | 0.51860941 | −0.56354027 |
| LFNG | 0.10700215 | 0.10700215 | 0.10700215 | −0.67796456 | 0.10700215 |
| LIF | 1.39370879 | −0.06116073 | −0.06116073 | −0.06116073 | −0.06116073 |
| LIG4 | −0.50530259 | −0.04785678 | −0.04785678 | −0.04785678 | −0.04785678 |
| MAD2L2 | 0.03722618 | 0.6081764 | 0.03722618 | 0.03722618 | 0.03722618 |
| MAP2K4 | 0.08248544 | 0.08248544 | 0.08248544 | 0.64727212 | 0.08248544 |
| MAP2K6 | −0.13138211 | −0.13138211 | −0.13138211 | −1.47415459 | −0.13138211 |
| MAPK10 | −0.07793461 | −0.07793461 | −0.07793461 | 1.43393339 | −0.07793461 |
| MAPK8IP1 | −0.00825569 | −0.00825569 | −0.00825569 | −0.00825569 | 0.92651997 |
| MCM2 | −0.07381755 | 0.42160047 | −0.07381755 | −0.07381755 | −0.07381755 |
| MCM4 | −0.04139259 | 0.37963662 | −0.04139259 | −0.04139259 | −0.04139259 |
| MCM5 | −0.13706634 | −0.13706634 | −0.13706634 | 0.29064389 | −0.13706634 |
| MDC1 | −0.37977203 | −0.06129361 | −0.06129361 | −0.06129361 | −0.06129361 |
| MDM2 | 0.0314102 | −0.47856785 | 0.0314102 | 0.0314102 | 0.0314102 |
| MEN1 | −0.10998162 | −0.10998162 | 0.25826164 | −0.10998162 | −0.10998162 |
| MET | 0.03488567 | −0.86253667 | 0.03488567 | 0.03488567 | 0.03488567 |
| MFNG | 0.08194644 | 0.08194644 | 0.08194644 | 0.08194644 | 0.69796176 |
| MLF1 | −0.7380756 | −0.07707883 | −0.07707883 | −0.07707883 | −0.07707883 |
| MLH1 | −0.10111681 | −0.10111681 | 0.31198563 | −0.10111681 | −0.10111681 |
| MLLT3 | −0.15727151 | −0.58592957 | −0.15727151 | −0.15727151 | −0.15727151 |
| MLLT4 | −0.21907125 | −0.68832348 | −0.21907125 | −0.21907125 | −0.21907125 |
| MMP7 | 0.39833697 | 1.54606409 | 0.39833697 | 0.39833697 | 0.39833697 |
| MMP9 | −0.10394205 | 1.60133616 | −0.10394205 | −0.10394205 | −0.10394205 |
| MSH2 | −0.55489979 | −0.03095062 | −0.03095062 | −0.03095062 | −0.03095062 |
| MSH6 | −0.05432838 | −0.05432838 | −0.05432838 | 0.27491694 | −0.05432838 |
| MTOR | −0.06272839 | 0.18781661 | −0.06272839 | −0.06272839 | −0.06272839 |
| MUTYH | −0.50532612 | −0.06272888 | −0.06272888 | −0.06272888 | −0.06272888 |
| MYC | −0.18641001 | −0.18641001 | −0.18641001 | −0.18641001 | 0.74902785 |
| MYD88 | −0.08502077 | −0.08502077 | −0.08502077 | −0.58812129 | −0.08502077 |
| NASP | −0.02523895 | −0.02523895 | −0.02523895 | −0.02523895 | −0.55068349 |
| NFKB1 | 0.1830597 | −0.51522965 | −0.1830597 | −0.1830597 | −0.1830597 |
| NFKBIZ | −0.02574918 | −0.02574918 | −1.18521256 | −0.02574918 | −0.02574918 |
| NOS3 | −0.0004462 | −0.0004462 | −0.0004462 | −0.0004462 | 0.5365944 |

-continued

|  | IHC+ (1) | TP53 (2) | Subgroup A centroid (3) | Subgroup B centroid (4) | Subgroup C centroid (5) |
| --- | --- | --- | --- | --- | --- |
| NOTCH2 | −0.14817229 | −0.14817229 | −0.14817229 | −0.14817229 | −0.72029657 |
| NPM1 | −0.57600022 | 0.00332197 | 0.00332197 | 0.00332197 | 0.00332197 |
| NTHL1 | −0.50778533 | −0.07866785 | −0.07866785 | −0.07866785 | −0.07866785 |
| NUMBL | −0.00052321 | −0.00052321 | 0.59451543 | −0.00052321 | −0.00052321 |
| PAX5 | 0.25809009 | 0.25809009 | 0.25809009 | 0.25809009 | 1.00231025 |
| PBX1 | 0.08501597 | 0.08501597 | 0.08501597 | 0.92159476 | 0.08501597 |
| PCNA | −0.62485093 | −0.01603919 | −0.01603919 | −0.01603919 | −0.01603919 |
| PDGFC | −0.11165439 | −0.11165439 | −0.83987243 | −0.11165439 | −0.11165439 |
| PDGFRA | −0.16915031 | −0.16915031 | −0.16915031 | −1.68249338 | −0.16915031 |
| PLCB4 | −0.35341736 | −0.35341736 | −0.35341736 | 0.81476038 | −0.35341736 |
| PPP2CB | −0.48697106 | 0.0230338 | 0.0230338 | 0.0230338 | 0.0230338 |
| PPP2R2C | −0.68521206 | 0.56494494 | 0.56494494 | 0.56494494 | 0.56494494 |
| PPP3R1 | −0.29772681 | −0.04706913 | −0.04706913 | −0.04706913 | −0.04706913 |
| PRKACA | −0.42317444 | −0.03705625 | −0.03705625 | −0.03705625 | −0.03705625 |
| PRKAR1B | −0.28935676 | −0.28935676 | 0.84966941 | −0.28935676 | −0.28935676 |
| PRKAR2A | −0.00446406 | −0.00446406 | −0.00446406 | 0.37327539 | −0.00446406 |
| PRKCB | −0.04967629 | −0.04967629 | −0.04967629 | −0.04967629 | 0.78745301 |
| PRKX | −0.05123099 | −0.05123099 | −0.05123099 | −0.70281335 | −0.05123099 |
| PRLR | 0.26338038 | −0.55930099 | 0.26338038 | 0.26338038 | 0.26338038 |
| PTCH1 | −0.07195229 | −0.07195229 | 2.15165073 | −0.07195229 | −0.07195229 |
| PTEN | −0.10472757 | −0.10472757 | −0.10472757 | −0.86880722 | −0.10472757 |
| PTTG2 | −0.01924501 | −0.01924501 | −0.59690658 | −0.01924501 | −0.01924501 |
| RAD21 | −0.3994352 | −0.0135588 | −0.0135588 | −0.0135588 | −0.0135588 |
| RAD52 | −0.04587358 | −0.04587358 | 0.38455164 | −0.04587358 | −0.04587358 |
| RB1 | −0.03910675 | −0.6771363 | −0.03910675 | −0.03910675 | −0.03910675 |
| RBX1 | −0.39080421 | −0.04389815 | −0.04389815 | −0.04389815 | −0.04389815 |
| RET | 0.18149733 | 0.18149733 | 0.18149733 | 0.18149733 | 1.43631232 |
| RFC4 | −0.05754212 | −0.05754212 | −0.05754212 | 0.54843713 | −0.05754212 |
| SF3B1 | −0.11220033 | −0.11220033 | 0.23297253 | −0.11220033 | −0.11220033 |
| SHC2 | 0.15686283 | −0.51491502 | 0.15686283 | 0.15686283 | 0.15686283 |
| SHC4 | 0.13709987 | 0.13709987 | 0.13709987 | 0.13709987 | 1.1213424 |
| SIN3A | −0.03351662 | −0.03351662 | −0.03351662 | −0.03351662 | −0.26555161 |
| SKP1 | −0.03003935 | −0.03003935 | 0.30725406 | −0.03003935 | −0.03003935 |
| SKP2 | −0.04245311 | 0.24218446 | −0.04245311 | −0.04245311 | −0.04245311 |
| SMAD3 | −0.02574518 | −0.02574518 | −0.02574518 | −0.02574518 | −0.51213148 |
| SMAD4 | −0.33056479 | 0.00374378 | 0.00374378 | 0.00374378 | 0.00374378 |
| SOCS2 | 0.0433981 | 0.0433981 | 0.0433981 | 1.45120858 | 0.0433981 |
| SOCS3 | 0.71728949 | −0.23035904 | −0.23035904 | −0.23035904 | −0.23035904 |
| SP1 | −0.0610679 | 0.152345 | −0.0610679 | −0.0610679 | −0.0610679 |
| SPOP | −0.01412036 | −0.01412036 | −0.01412036 | 0.49523109 | −0.01412036 |
| SPRY1 | 0.84793748 | −0.07997049 | −0.07997049 | −0.07997049 | −0.07997049 |
| SPRY2 | −0.04705577 | −0.04705577 | −0.04705577 | −0.04705577 | 0.47891039 |
| SSX1 | 2.35670991 | 0.66335378 | 0.66335378 | 0.66335378 | 0.66335378 |
| STAT4 | 0.73250358 | 0.06969255 | 0.06969255 | 0.06969255 | 0.06969255 |
| STK11 | −0.33740066 | −0.0326569 | −0.0326569 | −0.0326569 | −0.0326569 |
| SYK | −0.03690692 | −0.03690692 | −0.03690692 | −0.03690692 | 0.40943317 |
| TFDP1 | 0.0962478 | 0.54940854 | 0.0962478 | 0.0962478 | 0.0962478 |
| TGFB3 | 0.07718645 | 0.07718645 | 0.07718645 | 0.07718645 | −0.67517129 |
| TGFBR2 | 0.48530313 | 0.00452876 | 0.00452876 | 0.00452876 | 0.00452876 |
| THBS1 | 0.66888057 | −0.21515608 | −0.21515608 | −0.21515608 | −0.21515608 |
| TLR4 | 0.04571647 | 0.04571647 | 0.04571647 | 0.04571647 | 0.67564346 |
| TLX1 | 0.48484768 | 0.48484768 | 2.37838279 | 0.48484768 | 0.48484768 |
| TNC | −0.02780559 | −0.02780559 | −1.65410027 | −0.02780559 | −0.02780559 |
| TNFRSF10B | −0.01012048 | −0.01012048 | 0.53370864 | −0.01012048 | −0.01012048 |
| TNFRSF10D | −0.02057269 | −0.02057269 | −0.02057269 | −1.20440978 | −0.02057269 |
| TNFSF10 | −0.09580323 | −0.09580323 | −0.09580323 | −0.09580323 | 0.56520496 |
| TNR | 0.11575176 | 0.11575176 | 0.11575176 | 1.38183963 | 0.11575176 |
| TP53 | −0.26722651 | −0.26722651 | −0.26722651 | −1.37187095 | −0.26722651 |
| TSPAN7 | 0.07016174 | 0.07016174 | 1.15874199 | 0.07016174 | 0.07016174 |
| TTK | −0.09832583 | −0.09832583 | −0.09832583 | 0.56938185 | −0.09832583 |
| U2AF1 | −0.00812952 | 0.24625843 | −0.00812952 | −0.00812952 | −0.00812952 |
| UBE2T | −0.02355507 | −0.02355507 | −0.02355507 | −0.02355507 | −0.58524998 |
| VEGFA | −0.03429483 | −0.03429483 | −0.03429483 | −0.03429483 | −0.69022185 |
| WEE1 | −0.6704469 | −0.09453667 | −0.09453667 | −0.09453667 | −0.09453667 |
| WHSC1L1 | 0.00932376 | 0.00932376 | 0.52040958 | 0.00932376 | 0.00932376 |
| WNT10B | 1.04430335 | 0.1033825 | 0.1033825 | 0.1033825 | 0.1033825 |
| WNT6 | −0.03094321 | 0.46879856 | −0.03094321 | −0.03094321 | −0.03094321 |
| WT1 | 0.46923473 | −0.36957191 | 0.46923473 | 0.46923473 | 0.46923473 |
| ZAK | 0.11046378 | 0.11046378 | 0.11046378 | 0.94265393 | 0.11046378 |
| ZBTB16 | −0.16972395 | −0.16972395 | −0.16972395 | −0.16972395 | −1.98760677 |
| ZIC2 | 0.10008527 | 0.10008527 | 1.69354244 | 0.10008527 | 0.10008527. |

\* \* \* \* \*